United States Patent
Lubelski et al.

(10) Patent No.: US 10,837,027 B2
(45) Date of Patent: Nov. 17, 2020

(54) FURTHER IMPROVED AAV VECTORS PRODUCED IN INSECT CELLS

(71) Applicant: UniQure IP B.V., Amsterdam (NL)

(72) Inventors: Jacek Lubelski, Amsterdam (NL); Sebastiaan Menno Bosma, Amsterdam (NL); Harald Peter Albert Petry, Amsterdam (NL); Wilhelmus Theodorus Johannes Maria Christiaan Hermens, Amsterdam (NL)

(73) Assignee: UNIQURE IP B.V., Amsterdam (NL)

( * ) Notice: Subject to any disclaimer, the term of this patent is extended or adjusted under 35 U.S.C. 154(b) by 90 days.

(21) Appl. No.: 15/124,139

(22) PCT Filed: Mar. 10, 2015

(86) PCT No.: PCT/NL2015/050149
§ 371 (c)(1),
(2) Date: Sep. 7, 2016

(87) PCT Pub. No.: WO2015/137802
PCT Pub. Date: Sep. 17, 2015

(65) Prior Publication Data
US 2017/0356008 A1      Dec. 14, 2017

(30) Foreign Application Priority Data
Mar. 10, 2014  (EP) .................................. 14158610

(51) Int. Cl.
*C12N 15/86*      (2006.01)
*C07K 14/005*     (2006.01)
*C12N 7/00*       (2006.01)

(52) U.S. Cl.
CPC ............ *C12N 15/86* (2013.01); *C07K 14/005* (2013.01); *C12N 7/00* (2013.01); *C12N 2710/14043* (2013.01); *C12N 2750/14121* (2013.01); *C12N 2750/14122* (2013.01); *C12N 2750/14143* (2013.01); *C12N 2750/14152* (2013.01); *C12N 2799/026* (2013.01); *C12N 2830/008* (2013.01)

(58) Field of Classification Search
None
See application file for complete search history.

(56) References Cited

FOREIGN PATENT DOCUMENTS

| WO | 03042361 A2 | 5/2003 |
|----|-------------|--------|
| WO | 2007046703 A2 | 4/2007 |

OTHER PUBLICATIONS

Accession No. AY58160, WO 9961601, May 28, 1999.*
Urabe, Masashi et al., "Scalable generation of high-titer recombinant adeno-associated virus type 5 in insect cells", Journal of Virology, 80(4)1874-1885 (Feb. 2006).
Urabe, M. et al., "Insect cells as a factory to produce adeno-associated virus type 2 vectors", Human Gene Therapy, 13(16)1935-1943 (Nov. 2002).

* cited by examiner

*Primary Examiner* — Celine X Qian
(74) *Attorney, Agent, or Firm* — Foley & Lardner LLP

(57) ABSTRACT

The present invention relates to the production of adeno-associated viral vectors in insect cells. The insect cells therefore comprise a first nucleotide sequence encoding the adeno-associated virus (AAV) capsid proteins, whereby the initiation codon for translation of the AAV VP1 capsid protein is a non-ATG, suboptimal initiation codon and wherein the coding sequence for one or more amino acid residues have been inserted between the suboptimal translation initiation codon and the codon encoding the amino acid residue that corresponds to the amino acid residue at position 2 of the wild type capsid amino acid sequence of which the first amino acid residue is alanine, glycine valine, aspartic acid or glutamic acid. The insect cell further comprises a second nucleotide sequence comprising at least one AAV inverted terminal repeat (ITR) nucleotide sequence; a third nucleotide sequence comprising a Rep52 or a Rep40 coding sequence operably linked to expression control sequences for expression in an insect cell; and, a fourth nucleotide sequence comprising a Rep78 or a Rep68 coding sequence operably linked to expression control sequences for expression in an insect cell. The invention further relates to adeno-associated viral vectors with an altered ratio of the viral capsid proteins.

21 Claims, 7 Drawing Sheets

Specification includes a Sequence Listing.

AAV5 capsid mutants

AAV5 capsid mutants

FURTHER IMPROVED AAV VECTORS PRODUCED IN INSECT CELLS

FIELD OF THE INVENTION

The present invention relates to the production of adeno-associated virus in insect cells and to adeno-associated virus that provides improved infectivity.

BACKGROUND OF THE INVENTION

Adeno-associated virus (AAV) may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) is being evaluated in gene therapy clinical trials for hemophilia B, malignant melanoma, cystic fibrosis, and other diseases. Numerous clinical trials and recent approval of a first gene therapy medicine in Europe, Alipogene tiparvovec (Glybera®, uniQure), holds a promise for AAV to become main stay of clinical practice.

In general, there are two main types of production systems for recombinant AAV. On the one hand there are conventional production systems in mammalian cell types (such as 293 cells, COS cells, HeLa cells, KB cells) and on the other hand more recently, production systems using insect cells have been developed.

The mammalian production system suffers from several drawbacks, of which the most important one for therapeutic use is the limited number of rAAV particles generated per cell (order of $10^4$ particles (reviewed in Clark, 2002. Kidney Int. 61(Suppl. 1). 9-15). For a clinical study, more than $10^{15}$ particles of rAAV may be required. To produce this number of rAAV particles, transfection and culture with approximately $10^{11}$ cultured human 293 cells, the equivalent of 5,000 175-cm² flasks of cells, would be required, which means transfecting up to $10^{11}$ 293 cells. Therefore, large scale production of rAAV using mammalian cell culture systems to obtain material for clinical trials has already proven to be problematic, production at commercial scale may not even be feasible. Furthermore there is always the risk, that a vector for clinical use that is produced in a mammalian cell culture will be contaminated with undesirable, perhaps pathogenic, material present in the mammalian host cell.

To overcome these problems of mammalian productions systems, an AAV production system has been developed using insect cells (Urabe et al., 2002, Hum. Gene Ther. 13: 1935-1943, US 20030148506 and US 20040197895). For production of AAV in insect cells some modifications were necessary in order to achieve the correct stoichiometry of the three AAV capsid proteins (VP1, VP2 and VP3), which relies on a combination of alternate usage of two splice acceptor sites and the suboptimal utilization of an ACG initiation codon for VP2 that is not accurately reproduced by insect cells. To mimic the correct stoichiometry of the capsid proteins in insect cells Urabe et al. (2002, supra) use a construct that is transcribed into a single polycistronic messenger that is able to express all three VP proteins without requiring splicing and wherein the most upstream initiator codon is replaced by the suboptimal initiator codon ACG.

WO2007/046703 discloses the further improvement of the infectivity of baculovirus-produced rAAV vectors based production by optimisation of the stoichiometry of AAV capsid proteins in insect cells.

Kohlbrenner et al. (2005, Mol. Ther. 12: 1217-25) reported that the baculovirus construct for expression of the two Rep protein, as used by Urabe et al., suffers from an inherent instability. By splitting the palindromic orientation of the two Rep genes in Urabe's original vector and designing two separate baculovirus vectors for expressing Rep52 and Rep78, Kohlbrenner et al. (2005, supra) increased the passaging stability of the vector. However, despite the consistent expression of Rep78 and Rep52 from the two independent baculovirus-Rep constructs in insect cells over at least 5 passages, rAAV vector yield is 5 to 10-fold lower as compared to the original baculovirus-Rep construct designed by Urabe et al. (2002, supra).

WO2009/014445 provides an alternative for improving the stability during of baculovirus-based rAAV vector production by using repeated coding sequences with differential codon biases.

Urabe et al. (J Virol., 2006, 80(4):1874-1885) report that AAV5 particles produced in the baculovirus system using ACG as initiation codon of the VP1 capsid protein have a poor infectivity and that—in contrast to AAV2 with VP1 expressed from an ACG initiation codon—mutating the +4 position to a G-residue in the AAV5 VP1 coding sequence did not improve infectivity. Urabe et al. addressed this problem by constructing chimeric AAV2/5 VP1 proteins, wherein a N-terminal portion of at least 49 amino acids of AAV5 VP1 is replaced with the corresponding part of AAV2 VP1 in order to improve the infectivity of the virions. There is thus still a need in the art for an AAV5 VP1 expressed from an ACG initiation codon that retains infectivity without extensive modifications.

The present inventors have, however, found that AAV vectors, in particular AAV5 vectors, such as non-chimeric AAV5 vectors which have been modified according to Urabe (Urabe et al., 2002. Hum. Gene Ther. 13: 1935-1943), WO2007/046703 or WO2009/014445, produced in the baculovirus system show a reduced infectivity in in vitro and in vivo studies in mice as compared to e.g. corresponding AAV vectors produced in conventional mammalian 293 cells. Hence, there is still a need for a baculovirus-based production system for rAAV vectors with improved infectivity.

DESCRIPTION OF THE INVENTION

Brief Description of the Invention

In a first aspect, the present invention relates to a nucleic acid molecule having a nucleotide sequence comprising an open reading frame, wherein the reading frame in 5' to 3' order comprises, or consists of:
  (i) a first codon, which is a suboptimal translation initiation codon selected from the group consisting of CTG, ACG, TTG and GTG;
  (ii) a second codon encoding an amino acid residue selected from the group consisting of alanine, glycine, valine, aspartic acid and glutamic acid;
  (iii) optionally, one or more codons encoding additional amino acid residues following the second codon; and,
  (iv) a sequence encoding adeno-associated virus (AAV) capsid proteins, whereby the sequence lacks only the VP1 translation initiation codon.

In a preferred embodiment, the AAV capsid proteins are AAV serotype 5, AAV serotype 8, or AAV serotype 9 capsid proteins, more preferably the AAV capsid proteins have an amino acid sequence selected from the group consisting of: SEQ ID NO: 22, 28, 30, 71 and 73.

Alternatively or in combination with any previous embodiments, in a further preferred embodiment the second codon encodes alanine.

Alternatively or in combination with any previous embodiments, in a further preferred embodiment the second codon is selected from the group consisting of GCT, GCC, GCA, GCG and GGU, preferably wherein the codon is GCT.

In a second aspect, the present invention relates to a nucleic acid construct comprising a nucleic acid molecule according to the invention, wherein the nucleotide sequence of the reading frame encoding the adeno-associated virus (AAV) capsid proteins is operably linked to expression control sequences for expression in an insect cell.

Alternatively or in combination with any previous embodiments, in a further preferred embodiment the nucleotide sequence of the reading frame is operably linked to a promoter selected from the group consisting of: polyhedron promoter, p10 promoter, 4xHsp27 EcRE+minimal Hsp70 promoter, deltaE1 promoter. E1 promoter. In a preferred embodiment of the present invention, the construct is an insect-compatible vector, preferably a baculoviral vector.

Alternatively or in combination with any previous embodiments, the nucleic acid molecule comprises an open reading frame selected from the group consisting of: SEQ ID NO: 51, 69, 42, 47, 48 and 50, preferably SEQ ID NO:51 or SEQ ID NO:69, more preferably SEQ ID NO:51.

In a third aspect, the present invention relates to an insect cell comprising a nucleic acid construct according to the invention.

Alternatively or in combination with any previous embodiments, in a further preferred embodiment the insect cell further comprises: (a) a second nucleotide sequence comprising at least one AAV inverted terminal repeat (ITR) nucleotide sequence; (b) a third nucleotide sequence comprising a Rep78 or a Rep68 coding sequence operably linked to expression control sequences for expression in an insect cell; (c) optionally, a fourth nucleotide sequence comprising a Rep52 or a Rep40 coding sequence operably linked to expression control sequences for expression in an insect cell.

Alternatively or in combination with any previous embodiments, in a further preferred embodiment the insect cell comprises: (a) a first nucleic acid construct according to the invention, whereby the first nucleic acid construct further comprises the third and fourth nucleotide sequences as defined above, and, (b) a second nucleic acid construct comprising the second nucleotide sequence as defined above, wherein the second nucleic acid construct preferably is an insect cell-compatible vector, more preferably a baculoviral vector.

Alternatively or in combination with any previous embodiments, in a further preferred embodiment the second nucleotide sequence further comprises at least one nucleotide sequence encoding a gene product of interest (for expression in a mammalian cell) and whereby the at least one nucleotide sequence encoding a gene product of interest becomes incorporated into the genome of an AAV serotype 5 produced in the insect cell.

Alternatively or in combination with any previous embodiments, in a further preferred embodiment the second nucleotide sequence comprises two AAV ITR nucleotide sequences and wherein the at least one nucleotide sequence encoding a gene product of interest is located between the two AAV ITR nucleotide sequences.

Alternatively or in combination with any previous embodiments, in a further preferred embodiment the first nucleotide sequence, second nucleotide sequence, third nucleotide sequence and optionally fourth nucleotide sequence are stably integrated in the genome of the insect cell.

In a fourth aspect, the present invention relates to an AAV virion, comprising in its genome at least one nucleotide sequence encoding a gene product of interest, whereby the at least one nucleotide sequence preferably is not a native AAV nucleotide sequence, and wherein the AAV VP1 capsid protein comprises, or consists of, from N terminus to C terminus:

(i) a first amino acid residue, which is encoded by a translation initiation codon, preferably by a suboptimal translation initiation codon selected from the group consisting of CTG, ACG, TTG and GTG;

(ii) a second amino acid residue selected from the group consisting of alanine, glycine, valine, aspartic acid and glutamic acid;

(iii) optionally, one or more additional amino acid residues following the second amino acid residue; and, (iv) an amino acid sequence of the AAV VP1 capsid protein, whereby the sequence lacks only the amino acid residue that is encoded by the VP1 translation initiation codon.

Preferably, an AAV virion according to the invention comprises a gene product of interest that encodes a Factor IX or a Factor VIII protein.

In a fifth aspect, the present invention relates to a method for producing an AAV in an insect cell, comprising the steps of: (a) culturing an insect cell according to the invention under conditions such that AAV is produced; and optionally (b) recovery of the AAV.

Definitions

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein.

GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Nucleotide sequences encoding parvoviral Rep proteins of the invention may also be defined by their capability to hybridise with the nucleotide sequence of SEQ ID NO:1, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 500/sequence identity. The person skilled in the art will be able to modify these hybridisation conditions in order to specifically identify sequences varying in identity between 50% and 90%.

DETAILED DESCRIPTION OF THE INVENTION

The present invention relates to the use of animal parvoviruses, in particular dependoviruses such as infectious human or simian AAV, and the components thereof (e.g., an animal parvovirus genome) for use as vectors for introduction and/or expression of nucleic acids in mammalian cells. In particular, the invention relates to improvements in infectivity of such parvoviral vectors when produced in insect cells.

Viruses of the Parvoviridae family are small DNA animal viruses. Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, 6, 7, 8, 9, 10, 11, 12, 13) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production. The three capsid proteins, VP1, VP2 and VP3 are expressed from a single VP reading frame from the p40 promoter, wtAAV infection in mammalian cells relies for the capsid proteins production on a combination of alternate usage of two splice acceptor sites and the suboptimal utilization of an ACG initiation codon for VP2. This is however not accurately reproduced in insect cells, thus requiring further features to obtain the correct stoichiometry of the AAV capsid proteins.

In a first aspect the invention relates to a nucleic acid molecule having a nucleotide sequence comprising an open reading frame encoding adeno-associated virus (AAV) capsid proteins. Preferably, the reading frame encoding the capsid proteins is modified, compared to a wild type open reading frame encoding AAV capsid proteins, by at least: (i) replacement of the ATG initiation codon for a suboptimal translation initiation codon selected from the group consisting of CTG, ACG, TTG and GTG; and (ii) the insertion of codons for one or more amino acid residues inserted between the suboptimal translation initiation codon and the codon encoding the amino acid residue that corresponds to the amino acid residue at position 2 of a capsid protein amino acid sequence, preferably the amino acid residue at position 2 of a wild type capsid protein amino acid sequence. It is understood that position 2 of a (wild type) capsid protein amino acid sequence preferably refers to position 2 of the amino acid sequence of a (wild type) AAV VP1 capsid protein. Preferably, the suboptimal translation initiation codon is immediately followed at its 3'-end by a codon for an amino acid residue selected from the group consisting of alanine, glycine, valine, aspartic acid and glutamic acid.

Alternatively, in this aspect the invention relates to a nucleic acid molecule having a nucleotide sequence comprising an open reading frame, wherein the open reading frame in 5' to 3' order comprises, or consists of:

(i) a first codon, which is a suboptimal translation initiation codon selected from the group consisting of CTG, ACG, TTG and GTG;

(ii) a second codon selected from the group consisting of alanine, glycine, valine, aspartic acid and glutamic acid;

(iii) optionally, one or more codons for additional amino acid residues following the second codon; and, (iv) a sequence encoding AAV capsid proteins, whereby the sequence lacks the VP1 translation initiation codon, preferably whereby the sequence lacks only the VP1 translation initiation codon or, alternatively said, whereby the sequence lacks no more than the VP1 translation initiation codon.

Thus, in (iv) the sequence preferably comprises, or consists of: the remainder of an open reading frame encoding AAV capsid proteins whereby the remainder starts at the position corresponding to the second amino acid position in a wild type open reading frame encoding the capsid proteins.

A nucleic acid molecule having a nucleotide sequence comprising an open reading frame encoding adeno-associated virus (AAV) capsid proteins is herein understood to comprise nucleotide sequences encoding, preferably all three, VP1, VP2, and VP3 capsid proteins of animal parvoviruses.

The phrase "starts with a suboptimal translation initiation codon selected from the group consisting of CTG, ACG, TTG and GTG" or "first codon, which is a suboptimal translation initiation codon selected from the group consisting of CTG, ACG, TTG and GTG" is herein understood to mean that the initiation codon of the open reading frame encoding the adeno-associated virus (AAV) capsid proteins at the position encoding the amino terminus of the VP1 capsid protein is a suboptimal translation initiation codon selected from the group consisting of CTG, ACG, TTG and GTG Suboptimal is herein understood to mean that the codon is less efficient in the initiation of translation in an otherwise identical context as compared to the normal ATG codon. Preferably the initiation codon for translation of the AAV VP1 capsid protein is selected from ACG, TTG, GTG, and CTG, more preferably the initiation codon for translation of the AAV VP1 capsid protein is selected from CTG and ACG and most preferably the initiation codon for translation of the AAV VP1 capsid protein is CTG. The animal parvovirus preferably is a dependovirus, more preferably a human or simian adeno-associated virus (AAV).

In a particularly preferred embodiment, the suboptimal initiation codon of VP1 is CTG, one additional codon is introduced immediately adjacent to the suboptimal initiation codon at its 3' end, the additional codon coding for alanine. Preferably the capsid proteins are AAV5 capsid proteins. This results in improved potency of the AAV5 virions. The term "potency" is herein used to mean the ability of a vector to drive the expression of its genetic material.

The open reading frame further comprises a second codon encoding an amino acid residue selected from the group consisting of alanine, glycine, valine, aspartic acid and glutamic acid, preferably encoding alanine. More preferably, the second codon is selected from the group consisting of GCT, GCC, GCA, GCG and GGU, preferably wherein the codon is GCT. The open reading frame optionally comprises one or more codons encoding further additional amino acid residues following the second codon, for example codons for 1, 2, 3, 4, 5, 6, 7, 8, 9, 10, 11, 12, 13, 14, 15, 16, 17, 18, 19 or 20 additional amino acids, but preferably less than 60, 50, 40, 35, 30, 25, 20, 19, 18, 17, 16, 15 or 14 additional amino acid residues. As will be readily understood, the codons encoding the additional amino acid residues are to be in frame with the open reading frame of the capsid proteins.

In an embodiment, if the open reading frame is compared with a wild-type capsid protein, the open reading frame encoding the capsid proteins further comprises codons that encode for one or more amino acid residues inserted between the suboptimal translation initiation codon of VP1 and the codon that encodes for the amino acid residue immediately adjacent to the initiation codon on its 3' end in the corresponding wild-type capsid protein. For example, the open reading frame comprises codons for 1, 2, 3, 4, 5, 6, 7, 8, 9, 10, 11, 12, 13, 14, 15, 16, 17, 18, 19 or 20 additional amino acid residues as compared to the corresponding wild-type capsid protein. Preferably, the open reading frame comprises codons for less than 60, 50, 40, 35, 30, 25, 20, 19, 18, 17, 16, 15 or 14 additional amino acid residues as compared to the corresponding wild-type capsid protein. As will be readily understood, the codons encoding the additional amino acid residues are to be in frame with the open reading frame of the capsid proteins. Of these codons that encode the additional amino acid residues as compared to the corresponding wild-type capsid proteins, the first codon, i.e. the codon that is immediately adjacent to the suboptimal translation initiation codon at its 3' end, encodes for an amino acid residue selected from the group consisting of alanine, glycine, valine, aspartic acid and glutamic acid. Thus, if there is only one additional codon between the translation initiation codon and the codon that encodes for the amino acid residue that corresponds to residue 2 of the wild-type sequence, that additional codon encodes an amino acid residue selected from the group consisting of alanine, glycine, valine, aspartic acid and glutamic acid. If there are more than one additional codon between the translation initiation codon and the codon that encodes for amino acid residue 2 of the wild-type sequence, then the codon immediately following the translation initiation codon encodes an amino acid residue selected from the group consisting of alanine, glycine, valine, aspartic acid and glutamic acid. Preferably, the additional amino acid residue immediately following the suboptimal translation initiation codon (i.e. at its 3' end) is alanine, glycine or valine, more preferably alanine. In other words, in a preferred embodiment of the present invention, the codon immediately following the suboptimal translation initiation codon encodes alanine.

In a preferred embodiment of the present invention, the codon immediately following the suboptimal translation initiation codon, i.e. the second codon, is selected from the group consisting of GCT, GCC, GCA, GCG, GGU, GGC, GGA, GGG, GUU, GUC, GUA, GUG, GAU, GAC, GAA and GAG, preferably from the group consisting of GCT, GCC, GCA, GCG and GGU, even more preferably the codon is GCT.

The sequence encoding AAV capsid proteins in step (iv) can be a capsid sequence as found in nature such as for example of AAV1-AAV13 of which the nucleotide and amino acid sequences are shown in SEQ ID NO: 13-38 and SEQ TD NO. 70-73. Hence, the sequence encoding AAV capsid proteins in step (iv) can for example be a capsid sequence selected from the group consisting of: AAV1, AAV2, AAV3, AAV4, AAV5, AAV6, AAV7, AAV8, AAV9, AAV10, AAV11, AAV12 and AAV13. Alternatively, the sequence is man-made, for example, the sequence may be a hybrid form or may be codon optimized, such as for example by codon usage of AcmNPv or *Spodoptera frugiperda*. For example, the capsid sequence may be composed of the VP2 and VP3 sequences of AAV1 whereas the remainder of the VP1 sequence is of AAV5. A preferred capsid protein is AAV5, preferably as provided in SEQ ID NO: 22, AAV8, preferably as provided in SEQ ID NO: 28 or AAV9, preferably as provided in SEQ ID NO: 30, SEQ ID NO 71 or SEQ ID NO:73. Thus, in a preferred embodiment, the AAV capsid proteins are AAV serotype 5, AAV serotype 8, or AAV serotype 9 capsid proteins that have been modified according to the invention. If the capsid protein is AAV9, it is preferred that the capsid protein has a sequence such as for example disclosed in WO 03/052052 or in WO 05/033321 or as provided in SEQ ID NO: 29, 30, 70, 71, 72, 73 or 74. More preferably, if the capsid protein is AAV9 the capsid protein has a sequence as provided in SEQ ID NO: 72 and 73. More preferably, the AAV capsid proteins are AAV serotype 5 capsid proteins that have been modified according to the invention. It is understood that the exact molecular weights of the capsid proteins, as well as the exact positions of the translation initiation codons may differ between different parvoviruses. However, the skilled person will know how to identify the corresponding position in nucleotide sequence from other parvoviruses than AAV-5. Alternatively, the sequence encoding AAV capsid proteins is a man-made sequence, for example as a result of directed evolution experiments. This can include generation of capsid libraries via DNA shuffling, error prone PCR, bioinformatic rational design, site saturated mutagenesis. Resulting capsids are based on the existing serotypes but contain various amino acid or nucleotide changes that improve the features of such capsids. The resulting capsids can be a combination of various parts of existing serotypes, "shuffled capsids" or contain completely novel changes, i.e. additions, deletions or substitutions of one or more amino acids or nucleotides, organized in groups or spread over the whole length of gene or protein. See for example Schaffer and Maheshri; Proceedings of the 26th Annual International Conference of the IEEE EMBS San Francisco, Calif., USA; Sep. 1-5, 2004, pages 3520-3523; Asuri et al (2012) Molecular Therapy 20(2)329-3389; Lisowski et al (2014) Nature 506(7488):382-386, herein incorporated by reference.

In a preferred embodiment of the invention, the open reading frame encoding VP3 capsid protein starts with non-canonical translation initiation codon selected from the group consisting of: ACG, ATT, ATA, AGA, AGG, AAA, CTG, CTT, CTC, CTA, CGA, CGC, TTG, TAG and GTG. Preferably, the non-canonical translation initiation codon is selected from the group consisting of GTG, CTG, ACG, TTG, more preferably the non-canonical translation initiation codon is CTG.

A preferred nucleotide sequence of the invention for the expression of the AAV capsid proteins is a nucleotide sequence comprising an expression control sequence comprising a VP2 initiator context. A VP2 initiator context is herein understood to mean a number of nucleotides preceding the non-canonical translational imitation start of VP2. In a preferred embodiment, the VP initiator context is a nine nucleotide sequence of SEQ. ID NO: 3 or a nucleotide sequence substantially homologous to SEQ. ID NO: 3, upstream of the suboptimal translation initiation codon of the nucleotide sequence encoding the AAV VP1 capsid protein, preferably immediately upstream of the suboptimal translation initiation codon, i.e. immediately adjacent to the suboptimal translation initiation codon at its 5' end. A sequence with substantial identity to the nucleotide sequence of SEQ. ID NO: 3 and that will help increase expression of VP1 is e.g. a sequence which has at least 60%, 70%, 80% or 90% identity, preferably 100% identity, to the nine nucleotide sequence of SEQ ID NO: 3.

A further preferred nucleotide sequence of the invention for the expression of the AAV capsid proteins is a nucleotide sequence comprising an expression control sequence comprising a Kozak consensus sequence around the initiation codon of the nucleotide sequence encoding the AAV VP1 capsid protein. The Kozak consensus sequence is herein defined as GCCRCC(NNN)G (SEQ. ID NO: 4), wherein R is a purine (i.e. A or G) and wherein (NNN) stands for any of the suboptimal initiation codons as defined herein above. Preferably, in the Kozak consensus sequence in the nucleotide sequence of the invention, the R is a G. The nucleotide sequence of the invention for the expression of the AAV capsid proteins comprising a Kozak consensus sequence is thus preferably selected from GCCACC(ACG)G (SEQ ID NO: 5), GCCGCC(ACG)G (SEQ ID NO: 6), GCCACC(TG)G (SEQ ID NO: 7), GCCGCC(TTG)G (SEQ ID NO:

8), GCCACC(GTG)G (SEQ ID NO: 9), GCCGCC(GTG)G (SEQ ID NO. 10), GCCACC(CTG)G (SEQ ID NO. 11) and GCCGCC(CTG)G (SEQ ID NO: 12), more preferably the nucleotide sequence comprising the Kozak consensus sequence is selected from GCCACC(CTG)G (SEQ ID NO: 11) and GCCGCC(CTG)G (SEQ ID NO: 12), most preferably, the nucleotide sequence comprising the Kozak consensus sequence is GCCGCC(CTG)G (SEQ ID NO: 12). The nucleotides in brackets herein indicate the position of the initiation codon of the VP1 protein.

The nucleotide sequence of the invention for expression of the AAV capsid proteins further preferably comprises at least one modification of the nucleotide sequence encoding AAV VP1 capsid protein selected from among a G at nucleotide position 12, an A at nucleotide position 21, and a C at nucleotide position 24, wherein the nucleotide positions correspond to the nucleotide positions of the wild-type nucleotide sequences, for example as shown in SEQ ID NO:21. A "potential/possible false start site" or "potential/possible false translation initiation codon" is herein understood to mean an in-frame ATG codon located in the coding sequence of the capsid protein(s). Elimination of possible false start sites for translation of VP1 of other serotypes will be well understood by an artisan of skill in the art, as will be the the elimination of putative splice sites that may be recognized in insect cells. For example, the modification of the nucleotide at position 12 is not required for recombinant AAV5, since the nucleotide T is not giving rise to a false ATG codon. For example, the further modification of the nucleotide sequence for AAV5 can be as presented in SEQ ID NO:39. The various modifications of the wild-type AAV sequences for proper expression in insect cells is achieved by application of well-known genetic engineering techniques such as described e.g. in Sambrook and Russell (2001) "Molecular Cloning: A Laboratory Manual (3$^{rd}$ edition), Cold Spring Harbor Laboratory, Cold Spring Harbor Laboratory Press, New York. Various further modifications of VP coding regions are known to the skilled artisan which could either increase yield of VP and virion or have other desired effects, such as altered tropism or reduce antigenicity of the virion. These modifications are within the scope of the present invention.

In a preferred embodiment, the nucleic acid molecule according to the present invention comprises or consists of an open reading frame selected from the group consisting of: SEQ ID NO: 51, 69, 41, 42, 43, 44, 45, 46, 47, 48, 50 and 52, more preferably the nucleic acid molecule according to the present invention comprises or consists of an open reading frame selected from the group consisting of: SEQ ID NO-51, 69, 42, 43, 47, 48 and 50, and even more preferably it comprises or consists of SEQ ID NO: 69 or 51, and still more preferably it comprises or consists of SEQ ID NO:51.

Preferably the nucleotide sequence of the invention encoding the AAV capsid proteins is operably linked to expression control sequences for expression in an insect cell. Thus, in a second aspect, the present invention relates to a nucleic acid construct comprising a nucleic acid molecule according to the invention, wherein the nucleotide sequence of the open reading frame encoding the adeno-associated virus (AAV) capsid proteins is operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex., Luckow. 1991. In Prokop et al., Cloning and Expression of Heterologous Genes in Insect Cells with Baculovirus Vectors' Recombinant DNA Technology and Applications, 97-152; King, L. A. and R. D Possee, 1992, The baculovirus expression system, Chapman and Hall, United Kingdom, O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of the nucleotide sequence of the invention encoding of the AAV capsid proteins is e.g. the polyhedron (polH) promoter, such as the polH promoter provided in SEQ ID NO:53 and the short polH promoter provided in SEQ ID NO:54. However, other promoters that are active in insect cells are known in the art, e.g. a polyhedrin (polH) promoter, p10 promoter, p35 promoter, 4×Hsp27 EcRE+minimal Hsp70 promoter, deltaE1 promoter, E1 promoter or IE-1 promoter and further promoters described in the above references.

Preferably the nucleic acid construct for expression of the AAV capsid proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

In a preferred embodiment, the nucleic acid molecule comprised in the nucleic acid construct according to the present invention, comprises or consists of an open reading frame selected from the group consisting of SEQ ID NO: 51, 69, 42, 43, 47, 48 and 50, more preferably it comprises or consists of SEQ ID NO:51 or SEQ ID NO:69, even more preferably it comprises or consists of SEQ ID NO:51.

In a third aspect the invention relates to an insect cell comprising a nucleic acid construct of the invention as defined above. Any insect cell which allows for replication of AAV and which can be maintained in culture can be used in accordance with the present invention. For example, the cell line used can be from Spodoptera frugiperda, drosophila cell lines, or mosquito cell lines, e.g., Aedes albopictus derived cell lines. Preferred insect cells or cell lines are cells from the insect species which are susceptible to baculovirus infection, including e.g. expresSF+®, Drosophila Schneider 2 (S2) Cells, Se301, SelZD2109, SeUCR1, Sf9, Sf900+, Sf21, BTI-TN-5B1-4, MG-1, Tn368, HzAm1, Ha2302, Hz2E5 and High Five from Invitrogen.

A preferred insect cell according to the invention further comprises: (a) a second nucleotide sequence comprising at least one AAV inverted terminal repeat (ITR) nucleotide sequence; (b) a third nucleotide sequence comprising a Rep52 or a Rep40 coding sequence operably linked to expression control sequences for expression in an insect cell; and, (c) a fourth nucleotide sequence comprising a Rep78 or a Rep68 coding sequence operably linked to expression control sequences for expression in an insect cell.

In the context of the invention "at least one AAV ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins (e.g., Rep 78 or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An AAV replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for AAV replication of a circular vector. Thus, one ITR nucleotide sequence can be used in the context of the present invention. Preferably, however, two or another even number of regular ITRs are used. Most preferably, two ITR sequences are used. In view of the safety of viral vectors it may be desirable to construct a viral vector that is unable to further propagate after initial introduction into a cell. Such a safety mechanism for limiting undesirable vector propagation in a recipient may be provided by using rAAV with a chimeric ITR as described in US2003148506. In a preferred embodiment, the nucleotide sequence encoding the parvoviral VP1, VP2 and VP3 capsid proteins comprises at least one in frame insertion of a sequence coding for an immune evasion repeat, such as described in WO 2009/154452. This results in formation of a so-called self-complementary or monomeric duplex parvoviral virion, which has the advantage that it shows a reduced immune response. In a preferred embodiment, the sequence encoding the parvoviral VP1, VP2 and VP3 capsid proteins comprises a monomeric duplex or self complementary genome. For the preparation of a monomeric duplex AAV vector, AAV Rep proteins and AAV capsid proteins are expressed in insect cells according to the present invention and in the presence of a vector genome comprising at least one AAV ITR, wherein Rep52 and/or Rep40 protein expression is increased relative to Rep78 and/or Rep68 protein expression. Monomeric duplex AAV vectors, can also be prepared by expressing in insect cells AAV Rep proteins and AAV Cap proteins in the presence of a vector genome construct flanked by at least one AAV ITR, wherein the nicking activity of Rep78 and/or Rep 60 is reduced relative to the helicase/encapsidation activity of Rep52 and/or Rep 40, as for example described in WO2011/122950.

The number of vectors or nucleic acid constructs employed is not limiting in the invention. For example, one, two, three, four, five, six, or more vectors can be employed to produce AAV in insect cells in accordance with the present invention. If six vectors are employed, one vector encodes AAV VP1, another vector encodes AAV VP2, yet another vector encodes AAV VP3, still yet another vector encodes Rep52 or Rep40, while Rep78 or Rep 68 is encoded by another vector and a final vector comprises at least one AAV ITR. Additional vectors might be employed to express, for example, Rep52 and Rep40, and Rep78 and Rep 68. If fewer than six vectors are used, the vectors can comprise various combinations of the at least one AAV ITR and the VP1, VP2, VP3, Rep52/Rep40, and Rep78/Rep68 coding sequences. Preferably, two vectors or three vectors are used, with two vectors being more preferred as described above. If two vectors are used, preferably the insect cell comprises: (a) a first nucleic acid construct for expression of the AAV capsid proteins as defined above, which construct further comprises the third and fourth nucleotide sequences as defined in (b) and (c) above, the third nucleotide sequence comprising a Rep52 or a Rep40 coding sequence operably linked to at least one expression control sequence for expression in an insect cell, and the fourth nucleotide sequence comprising a Rep78 or a Rep68 coding sequence operably linked to at least one expression control sequence for expression in an insect cell; and (b) a second nucleic acid construct comprising the second nucleotide sequence as defined in (a) above, comprising at least one AAV ITR nucleotide sequence. If three vectors are used, preferably the same configuration as used for two vectors is used except that separate vectors are used for expression of the capsid proteins and for expression of the Rep52, Rep40 Rep78 and Rep68 proteins. The sequences on each vector can be in any order relative to each other. For example, if one vector comprises ITRs and an ORF comprising nucleotide sequences encoding VP capsid proteins, the VP ORF can be located on the vector such that, upon replication of the DNA between ITR sequences, the VP ORF is replicated or not replicated. For another example, the Rep coding sequences and/or the ORF comprising nucleotide sequences encoding VP capsid proteins can be in any order on a vector. In is understood that also the second, third and further nucleic acid construct(s) preferably are an insect cell-compatible vectors, preferably a baculoviral vectors as described above. Alternatively, in the insect cell of the invention, one or more of the first nucleotide sequence, second nucleotide sequence, third nucleotide sequence, and fourth nucleotide sequence and optional further nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

Thus, in a preferred embodiment, an insect cell according to the invention comprises: (a) a first nucleic acid construct according to the invention, whereby the first nucleic acid construct further comprises the third and fourth nucleotide sequences as defined above; and, (b) a second nucleic acid construct comprising the second nucleotide sequence as defined above, wherein the second nucleic acid construct preferably is an insect cell-compatible vector, more preferably a baculoviral vector.

The a preferred embodiment of the invention, the second nucleotide sequence present in the insect cells of the invention, i.e. the sequence comprising at least one AAV ITR, further comprises at least one nucleotide sequence encoding a gene product of interest (preferably for expression in a mammalian cell), whereby preferably the at least one nucleotide sequence encoding a gene product of interest becomes incorporated into the genome of an AAV produced in the insect cell. Preferably, at least one nucleotide sequence encoding a gene product of interest is a sequence for expression in a mammalian cell. Preferably, the second nucleotide sequence comprises two AAV ITR nucleotide sequences and wherein the at least one nucleotide sequence encoding a gene product of interest is located between the two AAV ITR nucleotide sequences. Preferably, the nucleotide sequence encoding a gene product of interest (for expression in the mammalian cell) will be incorporated into the AAV genome produced in the insect cell if it is located between two regular ITRs, or is located on either side of an ITR engineered with two D regions. Thus, in a preferred embodiment, the invention provides an insect cell according the invention, wherein the second nucleotide sequence comprises two AAV ITR nucleotide sequences and wherein the at least one nucleotide sequence encoding a gene product of interest is located between the two AAV ITR nucleotide sequences.

Typically, the gene product of interest, including ITRs, is 5,000 nucleotides (nt) or less in length. In another embodiment an oversize DNA, i.e. more than 5,000 nt in length, can be expressed in vitro or in vivo by using AAV vector described by the present invention. An oversized DNA is here understood as a DNA exceeding the maximum AAV packaging limit of 5 kbp. Therefore, the generation of AAV vectors able to produce recombinant proteins that are usually encoded by larger genomes than 5.0 kb is also feasible. For instance, the present inventors have generated rAAV5 vectors containing partially, uni-directionally packaged fragments of hFVIII in insect cells. The total size of vector genome encompassing at least 5.6 kb packaged into two populations of FVIII fragment-containing AAV5 particles. These variant AAV5-FVIII vectors were shown to be actively secreting FVIII. This was confirmed in vitro, where the AAV vector comprising a gene product of interest encoding Factor VIII after infection of Huh7 cells resulted in production of active FVIII protein. Similarly, tail vein delivery of rAAV.FVIII in mice resulted in production of active FVIII protein. The molecular analysis of the encapsidation products unequivocally showed that the 5.6 kbp FVIII expression cassette is not entirely encapsidated in AAV particle. Without wishing to be bound by any theory, we hypothesize that + and − DNA strands of the encapsidated molecules revealed missing 5' ends. This is consistent with a previously reported unidirectional (starting at 3' end) packaging mechanism operating according to "head-full principia" with 4.7-4.9 kbp limit (see for example Wu et al. [2010] Molecular Therapy 18(1):80-86; Dong et al. [2010] Molecular Therapy 18(1):87-92; Kapranov et al. [2012] Human Gene Therapy 23:46-55; and in particular Lai et al. [2010] Molecular Therapy 18(1):75-79. Although only approximately 5 kb of the whole 5.6 kb vector genome was encapsidated, the vector was potent and lead to expression of active FVIII. We have shown that the correct template for production of FVIII was assembled in the target cell based on partial complementation of + and − DNA strains followed by second strand synthesis.

The second nucleotide sequence defined herein above may thus comprise a nucleotide sequence encoding at least one "gene product of interest" for expression in a mammalian cell, located such that it will be incorporated into an AAV genome replicated in the insect cell. Any nucleotide sequence can be incorporated for later expression in a mammalian cell transfected with the AAV produced in accordance with the present invention, as long as the constructs remain within the packaging capacity of the AAV virion. The nucleotide sequence may e.g. encode a protein it may express an RNAi agent, i.e. an RNA molecule that is capable of RNA interference such as e.g. a shRNA (short hairpin RNA) or an siRNA (short interfering RNA). "siRNA" means a small interfering RNA that is a short-length double-stranded RNA that are not toxic in mammalian cells (Elbashir et al., 2001, Nature 411: 494-98; Caplen et al., 2001, Proc. Natl. Acad. Sci USA 98: 9742-47). In a preferred embodiment, the second nucleotide sequence may comprise two nucleotide sequences and each encodes one gene product of interest for expression in a mammalian cell. Each of the two nucleotide sequences encoding a product of interest is located such that it will be incorporated into a rAAV genome replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), cytokines or interleukins like e.g. IL-10, dystrophin, PBGD, NaGLU, Treg167, Treg289, EPO, IGF, IFN, GDNF, FOXP3, Factor VIII, VEGF, AGXT and insulin. Alternatively, or in addition as a second gene product, second nucleotide sequence defined herein above may comprise a nucleotide sequence encoding a polypeptide that serve as marker proteins to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York. Furthermore, second nucleotide sequence defined herein above may comprise a nucleotide sequence encoding a polypeptide that may serve as a fail-safe mechanism that allows to cure a subject from cells transduced with the rAAV of the invention, if deemed necessary. Such a nucleotide sequence, often referred to as a suicide gene, encodes a protein that is capable of convening a prodrug into a toxic substance that is capable of killing the transgenic cells in which the protein is expressed. Suitable examples of such suicide genes include e.g. the E. coli cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob Agents Chemother. 31: 844-849).

In another embodiment the gene product of interest can be an AAV protein. In particular, a Rep protein, such as Rep78 or Rep68, or a functional fragment thereof. A nucleotide sequence encoding a Rep78 and/or a Rep68, if present on the rAAV genome of the invention and expressed in a mammalian cell transduced with the rAAV of the invention, allows for integration of the rAAV into the genome of the transduced mammalian cell. Expression of Rep78 and/or Rep68 in an rAAV-transduced or infected mammalian cell can provide an advantage for certain uses of the rAAV, by allowing long term or permanent expression of any other gene product of interest introduced in the cell by the rAAV.

In the rAAV vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an al-anti-trypsin promoter, a thyroid hormone-binding globulin promoter, an albumin promoter, LPS (thyroxine-binding globlin) promoter, HCR-ApoCII hybrid promoter, HCR-hAAT hybrid promoter and an apolipoprotein E promoter, LPI, HLP, minimal TTR promoter, FVIII promoter, hyperon enhancer, ealb-hAAT. Other examples include the E2F promoter for tumor-selective, and, in particular, neurological cell tumor-selective expression (Parr et al., 1997, Nat. Med. 3:1145-9) or the 11-2 promoter for use in mononuclear blood cells (Hagenbaugh et al., 1997, J Exp Med; 185: 2101-10).

AAV is able to infect a number of mammalian cells. See, e.g., Tratschin et al., Mol. Cell Biol., 5(11):3251-3260 (1985) and Grimm et al., Hum. Gene Ther., 10(15):2445-2450 (1999). However, AAV transduction of human synovial fibroblasts is significantly more efficient than in similar murine cells, Jennings et al., Arthritis Res, 3:1 (2001), and the cellular tropicity of AAV differs among serotypes See, e.g., Davidson et al., Proc. Natl. Acad. Sci. USA, 97(7): 3428-3432 (2000) (discussing differences among AAV2, AAV4, and AAV5 with respect to mammalian CNS cell tropism and transduction efficiency).

AAV sequences that may be used in the present invention for the production of AAV in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901: GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). Human or simian adeno-associated virus (AAV) serotypes are preferred sources of AAV nucleotide sequences for use in the context of the present invention, more preferably AAV serotypes which normally infects humans (e.g., serotypes 1, 2, 3A, 3B, 4, 5, 6, 7, 8, 9, 10, 11, 12 and 13) or primates (e.g., serotypes 1 and 4).

Preferably the AAV ITR sequences for use in the context of the present invention are derived from AAV1, AAV2, AAV5 and/or AAV4. Likewise, the Rep52, Rep40, Rep78 and/or Rep68 coding sequences are preferably derived from AAV1, AAV2, and/or AAV4. The sequences coding for the VP1, VP2, and VP3 capsid proteins for use in the context of the present invention may be taken from any of the known 42 serotypes, more preferably from AAV1, AAV2. AAV3, AAV4, AAV5, AAV6, AAV7, AAV8 or AAV9 or newly developed AAV-like particles obtained by e.g. capsid shuffling techniques and AAV capsid libraries. In a preferred embodiment, the sequences coding for the VP1, VP2, and VP3 capsid proteins are from AAV5 or AAV8, more preferably from AAV5.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability Rep and ITR sequences to cross-complement corresponding sequences of other serotypes allows for the production of pseudotyped AAV particles comprising the capsid proteins of a serotype (e.g., AAV3) and the Rep and/or ITR sequences of another AAV serotype (e.g., AAV2). Such pseudotyped AAV particles are a part of the present invention Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of AAV5 can differ from production of other serotypes in insect cells. Where methods of the invention are employed produce rAAV5, it is preferred that one or more vectors comprising, collectively in the case of more than one vector, a nucleotide sequence comprising an AAV5 ITR, a nucleotide sequence comprises an AAV5 Rep52 and/or Rep40 coding sequence, and a nucleotide sequence comprises an AAV5 Rep78 and/or Rep68 coding sequence. Such ITR and Rep sequences can be modified as desired to obtain efficient production of rAAV5 or pseudotyped rAAV5 vectors in insect cells. E.g., the start codon of the Rep sequences can be modified.

In a preferred embodiment, the first nucleotide sequence, second nucleotide sequence, third nucleotide sequence and optionally fourth nucleotide sequence are stably integrated in the genome of the insect cell.

In a further aspect the invention relates to an AAV virion. Preferably, the AAV virion comprises in its genome at least one nucleotide sequence encoding a gene product of interest, whereby the at least one nucleotide sequence preferably is not a native AAV nucleotide sequence, and wherein the AAV VP1 capsid protein comprises or consists of, from the N-terminal end to the C-terminal end:
  (i) a first amino acid residue, which is encoded by a translation initiation codon, preferably by a suboptimal translation initiation codon selected from the group consisting of CTG. ACG, TTG and GTG;
  (ii) a second amino acid residue selected from the group consisting of alanine, glycine, valine, aspartic acid and glutamic acid;
  (iii) optionally, one or more additional amino acid residues following the second amino acid residue; and,
  (iv) an amino acid sequence of the AAV VP1 capsid protein, whereby the sequence lacks the amino acid residue that is encoded by the VP1 translation initiation codon. Preferably whereby the sequence lacks only the amino acid residue encoded by the VP1 translation initiation codon or, alternatively said, whereby the sequence lacks no more than the amino acid residue encoded by VP1 translation initiation codon.

Preferably, the amino acid sequence of the AAV VP1 capsid protein lacking only the amino acid residue encoded by the VP1 translation initiation codon is a naturally occurring amino acid sequence of a AAV VP1 capsid protein only lacking the amino acid residue encoded by the naturally occurring VP1 translation initiation codon. The first amino acid residue, which is encoded by a suboptimal translation initiation codon, typically is a methionine residue.

Alternatively, in this aspect the invention relates to an AAV virion, wherein the AAV virion comprises in its genome at least one nucleotide sequence encoding a gene product of interest, whereby the at least one nucleotide sequence preferably is not a native AAV nucleotide sequence, and wherein the AAV VP1 capsid has one or more additional amino acid residues inserted between the initiation codon and the amino acid residue that corresponds to the amino acid residue at position 2 of the wild type capsid protein, wherein the additional amino acid residue immediately following the initiation codon is selected from the group consisting of alanine, glycine, valine, aspartic acid and glutamic acid.

Preferably, in a virion according to the invention the stoichiometry of the AAV VP1, VP2, and VP3 capsid proteins is as follows; the amount of VP1: (a) is at least 100, 105, 110, 120, 150, 200 or 4000/% of the amount of VP2; or (b) is at least 8, 10, 10.5, 11, 12, 15, 20 or 40% of the amount of VP3; or (c) is at least as defined in both (a) and (b). Preferably, the amount of VP1, VP2 and VP3 is determined using an antibody recognizing an epitope that is common to each of VP1, VP2 and VP3. Various immunoassays are available in the art that will allow quantify the relative amounts of VP1, VP2 and/or VP3 (see e.g. Using Antibodies, E. Harlow and D. Lane, 1999, Cold Spring Harbor Laboratory Press, New York). A suitable antibody recognizing an epitope that is common to each of the three capsid proteins is e.g. the mouse anti-Cap B1 antibody (as is commercially available from Progen, Germany).

A preferred AAV according to the invention is a virion comprising in its genome at least one nucleotide sequence encoding a gene product of interest, whereby the at least one nucleotide sequence preferably is not a native AAV nucleotide sequence, and whereby the AAV virion comprises a VP1 capsid protein that comprises a methionine, a threonine, a leucine or a valine at amino acid position 1. A more preferred AAV virion according to the invention has the ratio's of capsid proteins as defined above and comprises a VP1 capsid protein comprises a leucine or a valine at amino acid position 1. Even more preferred is an AAV virion that is obtainable from an insect cell as defined above in e.g. a method as defined herein below. Still more preferred is an AAV virion that comprises a threonine or a leucine at position 1 of the VP1 capsid protein, even more preferably a threonine residue.

An advantage of the AAV virions of the invention is their improved infectivity Without wishing to be bound by any theory, it seems that in particular the infectivity increases with an increase of the amount of VP1 protein in the capsid in relation to the amounts of VP2 and/or VP3 in the capsid. The infectivity of an AAV virion is herein understood to mean the efficiency of transduction of the transgene comprised in the virion, as may be deduced from the expression rate of the transgene and the amount or activity of the product expressed from the transgene.

Preferably, an AAV virion of the invention comprises a gene product of interest that encodes a polypeptide gene product selected from the group consisting of: CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), cytokines or interleukins like e.g. IL-10, dystrophin, PBGD, NaGLU, Treg167, Treg289, EPO, IGF, IFN, GDNF, FOXP3, Factor VIII, VEGF, AGXT and insulin. More preferably, the gene product of interest encodes a Factor IX or a Factor VIII protein.

In another aspect the invention thus relates to a method for producing an AAV in an insect cell. Preferably the method comprises the steps of: (a) culturing an insect cell as defined in herein above under conditions such that AAV is produced; and, optionally, (b) recovery of the AAV. Growing conditions for insect cells in culture, and production of heterologous products in insect cells in culture are well-known in the art and described e.g. in the above cited references on molecular engineering of insects cells.

Preferably the method further comprises the step of affinity-purification of the AAV using an anti-AAV antibody, preferably an immobilized antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of AAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

1. Introduction

Figure 1:
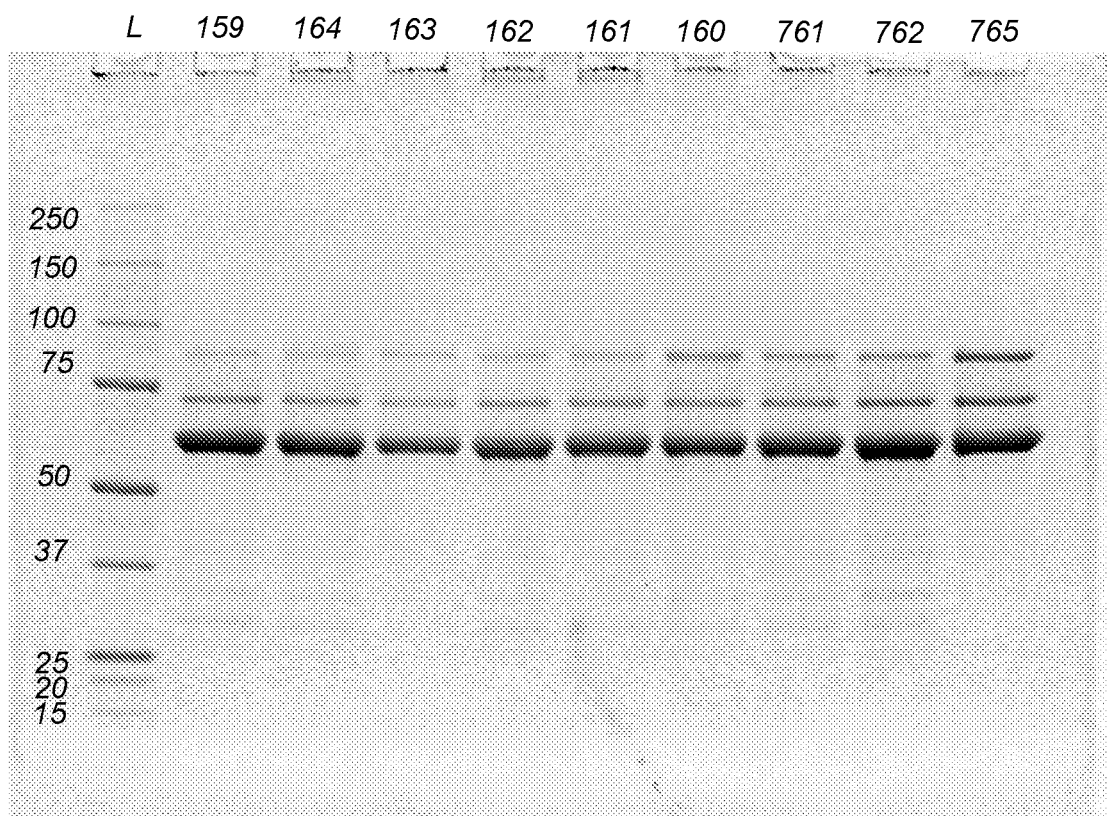
FIG. 1: Various mutant capsids harbouring reporter transgene SEAP were purified and resolved on an NuPage gel. Three capsid proteins, VP1 (87 kDa), VP2 (72 kDa) and VP3 (62 kDa) are shown.

The initial baculovirus system for production of rAAV was described by Urabe et al (Urabe et al. [2002] Human Gene Therapy 13(16):1935-1943) and consists of three baculoviruses, namely Bac-Rep, Bac-cap and Bac-vec, co-infection of which into insect cells e.g. SF9 resulted in generation of rAAV. The properties of such produced rAAV, i.e. physical and molecular characteristic including potency, did not differ significantly from the rAAV generated in mammalian cells (Urabe [2002] supra). In order to accomplish efficient generation of rAAV vectors in insect cells the AAV proteins needed for the process had to be expressed at appropriate levels. This required a number of adaptations of operons encoding for Rep and Cap proteins. Wild type AAV expresses large Rep78 to small Rep52 from two distinct promoters p5 and p19 respectively and splicing of the two messengers results in generation of Rep68 and Rep52 variants. This operon organization results in limited expression of Rep78 and relatively higher expression of Rep52. In order to mimic the low 78 to 52 ratio Urabe and colleagues constructed a DNA cassette in which expression of Rep78 was driven by the partially deleted promoter for the immediate-early 1 gene (ΔIE-1) whereas Rep52 expression was controlled by a strong polyhedrin promoter (polh). The spliced variants of large and small Reps were not observed in insect cells which likely relates to the difference in splicing processes between mammalian and insect cells. Another technical challenge to be overcome was related to the expression of the three major viral proteins (VP's). Wild type AAV expresses VP1, 2 and 3 from p40 promoter. Arising messenger RNA is spliced into two species: one responsible for VP1 expression whereas the second expresses both VP2 and VP3 via a "leaky ribosomal scanning mechanism" where the protein is initiated from non-canonical start i.e. ACG, is occasionally missed by the ribosome complex which than proceeds further until it finds the canonical start of VP3. Due to the differences in splicing machinery between vertebrate and insect cells the above described mechanism did not result in generation of proper capsids in insect cells. Urabe et al., decided to introduce a modification of translational start of VP1 which was similar to these found in the VP2 in such a way that the translational start of VP1 was changed to ACG and the initiation context, which consists of 9 nucleotides preceeding VP1, was changed to those preceeding VP2. These genetic alterations resulted in expression of the three VPs in the correct stoichiometry that could properly assemble into capsids from a single polycistronic mRNA. The transgene cassette on the other hand was similar to what was previously described for mammalian based systems, flanked by ITRs as the only in trans required elements for replication and packaging.

With the growing number of newly discovered AAV serotypes that hold different desired properties, there is a need for generation of these capsids in the BEV system. Although a successful production of AAV2 in the insect cells has been shown, not all serotypes perform equally well in the system adapted for AAV2. it seems that adapting a new serotype for optimum production and potency is not a trivial task and will require a tailor made approach. Previous attempts to adapt the rAAV5 sequence for production by BEVS in insect cells met a limited success, resulting in low incorporation of VP1 to the capsid (Kohlbrenner et al. (2005) Molecular Therapy 12 (6):1217-1225, Urabe et al. (2006) Journal of Virology 80(4):1874-1885). To circumvent this problem, Urabe et al. generated a chimeric type 2/5 virus which contains the N-terminal 136 amino acid residues from AAV type 2 and the remainder sequence from AAV serotype 5. Such virus was reported to produce well and to display similar potency to that of the wild type AAV5 (Urabe et al. (2006) supra). However, the resulting virion was a chimera and it does not represent the "true" rAAV5 serotype.

In order to generate genuine rAAV5 in insect cells with improved infectivity and/or potency, we designed several capsid protein 5 mutants. It seems important for the infectivity that the stoichiometry of the three viral proteins is balanced. For example, as previously reported we noticed that the lack of VP1 synthesis drastically influences the potency of the vector. Furthermore, we observed that the potency of the vectors was negatively correlated with the high incorporation of VP3 as compared to VP1 and VP2. Viral preparations with an excessive amount of VP3 were poor in transducing cells in vitro and in vitro. Finally we have constructed a genuine (or "true") rAAV5 capsid which displays superior potency to the chimeric rAAV5 generated by Urabe et al (2006, supra). This new capsid was found to have balanced VP stoichiometry, and similar or superior potency as compared to the chimeric AAV2/5.

2. Methods 2.1. Generation of rAAV5 Vectors rAAV5 batches were generated by co-infecting expresSF+® insect cell line (Protein Sciences Corporation)

with three different baculoviruses, which comprised expression cassettes for the capsid (rAAV5 variant library), replicase and transgene (Seap or Factor IX) under the control of a CMV and LP 1 promoter, respectively. Capsid expression cassettes were under the control of a polyhedron promoter. Rep expression cassettes were as described in WO 2009/14445 (BACVD183) and under control of a deltaE1 and polyhedron promoter driving expression of Rep78 and Rep52, respectively. ExpresSF+® cells were infected at a 5:1:1 (Rep:Cap:Transgene) volumetric ratio using freshly amplified baculovirus stocks. After a 72 hour incubation at 28° C., cells were lysed with 10× lysis buffer (1.5M NaCl, 0.5M Tris-HCl, 1 mM $MgCl_2$, 1% Triton X-100, pH=8.5) for 1 hour at 28° C. Genomic DNA was digested by Benzonase treatment for 1 hour at 37'C. Cell debris was removed by centrifugation for 15 minutes at 1900×g after which the supernatant containing the rAAV5 particles was stored at 4° C. Vector titers were determined in this so-called crude cell lysate with a specific Q-PCR directed against the promoter region of the transgene. Briefly, affinity purified vectors were analysed by Q-PCR AAVs were treated with DNAse at 37° C. to degrade extraneous DNA. AAV DNA was then released from the particles by 1M NaOH treatment. Following a short heat treatment (30 minutes at 37-C) the alkaline environment was neutralized with an equal volume of 1M HCl. The neutralized samples contained the AAV DNA that was used in the Taqman Q-PCR. Q-PCR was performed according to standard procedures using primers and probes listed in Table 1 below.

2.2. Purification of rAAV5 Vectors rAAV5 particles were purified from crude lysates by a batch binding protocol using AVB sepharose (affinity resin, GE healthcare). rAAV5 crude cell lysates were added to washed (with 0.2M $HPO_4$ pH=7.5 buffer) resin. Subsequently, samples were incubated for 2 hours at room temperature under gentle mixing. Following the incubation the resin was washed in 0.2M $HPO_4$ pH=7.5 buffer and bound vectors were eluted by the addition of 0.2M Glycine pH=2.5. The pH of the eluted vectors was immediately neutralized by the addition of 0.5M Tris-HCl pH=8.5. Purified rAAV5 batches were stored at −20° C. Purified vectors were titered by a specific Q-PCR.

In order to generate higher vector amounts for in vivo study a modified purification protocol was used. Briefly, following the harvest, the clarified lysate was passed over a 0.22 μm filter (Millipak 60, 0.22 μm). Next, vector particles were affinity purified by means of a 8 ml AVB sepharose column (GE Healthcare) on a AKTA explorer (FPLC chromatography system, GE healthcare). Bound rAAV5 particles were eluted from the column with 0.2M Glycine pH=2.5. The eluate was immediately neutralized by 60 mM Tris HCl pH=7.5. The buffer of the neutralized eluates was exchanged to PBS 5% Sucrose with the help of 100 KDa ultrafiltration (Millipore) filter. The final product was then filtered on a 0.22 μm filter (Millex GP), aliquoted and stored at −20° C. until further use. Following the purification virus titers were determined with a specific Q-PCR

TABLE 1

TAQMAN Q-PCR primers

|  |  | Description | SEQ ID NO: |
|---|---|---|---|
| primers used for detection of Seap transgene |  |  |  |
| pr59 | AATGGGCGGTAGGCGTGTA | CMV promotor fwd | 55 |
| pr60 | AGGCGATCTGACGGTTCACTAA | CMV promotor rev | 56 |
| pb12 | TGGGAGGTCTATATAAGCAG | CMV promotor probe Fam-MGB | 57 |
| primers used for detection of Factor IX transgene |  |  |  |
| pr1103 | CAAGTATGGCATCTACACCAAAGTCT | FIX fwd | 58 |
| pr1104 | GCAATAGCATCACAAATTTCACAAA | FIX rev | 59 |
| pb25 | TGTGAACTGGATCAAGGAGAAGACCAAGC | FIX probe Fam-Tamra | 60 |

2.3. VP Protein Composition of rAAV5 Variants

VP protein composition of purified rAAV5 variants was determined on Bis-tris polyacrylamide gels (Nupage, Life technologies) stained with Sypro Ruby. Briefly, 15 μl of purified rAAV5 was mixed with 5 μl 4×LDS loading buffer (Life technologies) and loaded on a Bis-Tris polyacrylamide gel. The samples were electrophoretically separated for 2 hours at 100 Volts. Following electrophoresis the proteins were fixed for 30 minutes with 10% NaAC/7% EtOH and stained with Sypro Ruby (Life technologies) for 2 hours VP proteins were then visualized under UV light on an ImageQuant system (GE Healthcare).

2.4. In Vitro Potency

To investigate in vitro potency of the different serotype 5 capsid variants, two continuous cell lines were used. Here, $1 \times 10^5$ Hela and Huh7 were infected with rAAV5 variants at various multiplicity of infection. The experiments were performed in a 24-well plate with approximately 80% confluency at 1e5 cells/well. In both experiments wild type adenovirus was used at a multiplicity of infection of 30. This addition of wild type adenovirus is only applied in in vitro potency tests, in order to accelerate the process of second strand synthesis to within about 24 hours, thereby allowing the assay to be performed in a relatively shorter period of time and avoiding the need of cell passages. 48 hours after the start of the infection Seap expression was measured in the supernatant using the Seap reporter assay kit (Roche). Luminescence was measured on a Spectramax L luminometer (Molecular devices) at 470 nm with an integration time of 1 second.

2.5. In Vivo Potency

To investigate in vivo potency of the different serotype 5 capsid variants, two different experiments were performed. Briefly, the potency of rAAV5 vectors constructs 159-164 harbouring Seap reporter gene was investigated in C57BL/6 mice. Different vectors were injected intramuscularly in mice at a dose of 5×10$^{12}$ gc/kg. Groups consisted of 5 mice each, 7 groups in total including a PBS group. Mice plasma was obtained 2, 4 and 6 weeks after the injection after which the mice were sacrificed. Seap activity was measured in the plasma using the Seap reporter assay kit from Roche. Luminescence was measured on a Spectramax L luminometer (Molecular devices) at 470 nm with an integration time of 1 second.

Next, the in vivo potency of variant AAV5(765) was compared to that of AAV5(160) and AAV5(92). AAV5(92) was a kind gift received from laboratory of dr. Kotin (Urabe et al, 2006) C57BL/6 mice were injected intravenously at doses of 2×10$^{12}$ gc/kg and 2×10$^{13}$ gc/kg with 765 or 160 both harbouring FIX as a reporter gene. In total seven groups of five mice each were injected including a PBS group Plasma was collected 1, 2 and 4 weeks following injection after which the mice were sacrificed. Factor IX protein present in the plasma was measured with a factor IX specific ELISA (VisuLize FIX antigen kit, Kordia). Optical density was measured at 450 nm on a Versamax ELISA plate reader (Molecular devices).

3. Results 3.1. Generation of rAAV5 in RBEVS

AAV is a mammalian virus that uses its host's machinery to express its genes, among which a cap gene. The mechanism by which a correct stoichiometry of VP1:VP2:VP3 is achieved in a mammalian host are not present or are not optimal in insect cells. Therefore, Urabe et al., developed a strategy of genetic adjustments to organization of cap polycistronic mRNA which resulted in production of three VP's of AAV2 in insect cells at the correct stoichiometry (Urabe et al. (2002) supra). The attempts to establish similar methods to produce rAAV5 in BEVS proved to be unsuccessful to achieve sufficient infectious particles. Without wishing to be bound by any theory, this seems to be caused by a low incorporation of VP1 into the capsids (Urabe et al. (2006) supra). Thereby, Urabe et al., building on the previous success with the type 2 serotype, replaced the N-terminal portion of the type 5 VP1 with that of the type 2, to produce infectious AAV5 particles (Urabe et al. (2006) supra). Although successful, the chimeric AAV2/5 chimeric capsid does not comprise bonafide type 5 particles and as such may have altered properties as compared to AAV5, which could represent the combination of the two capsids rather than those from the type 5.

In order to allow for AAV5 virion production in insect cells with an improved infectivity and potency, in the present invention a series of genetic alteration to cap5 expression cassette of AAV5 were made (Table 2). As previously noted (Urabe et al. (2006) supra) the wild type cap5 gene (here clone number 763) did not support generation of rAAV. Lack of recognition of native AAV splicing signals in insect cells most likely resulted in low expression of separate VP's and lack of vector production. Due to the fact that eukaryotic ribosomes read mRNA unidirectional from 5' to 3', the first translation initiation start (here VP1) of polycistronic cap5 mRNA is detrimental for expression of all three proteins. The wild type initiation start is composed of ATG, a so-called strong translation initiation codon, that does not allow for ribosomal read through and thereby blocks the expression of other two VPs, which leads to lack of rAAV production. Due to the fact that wild type AAV uses ribosomal read through to express VP2 (non-canonical translation initiation start, ACG) and VP3 (ATG), lead us to investigate the translational start of VP1 and its immediate surroundings to alter the expression and/or assembly of three VP's.

It has been reported before that the nucleotide context of the translational start have an influence on the strength of the translational initiation (Kozak (1987) Nucleic Acid Research 15(20):8125-8148; WO2007/046703). The preferred nucleotides seem to be A at the position (−3) and G at the position (+4) with AUG counting +1, +2 and +13 respectively (Kozak supra; WO2007/046703). Table 2 details the specific changes that were introduced to the translational initiation start, its upstream and downstream context to tune the expression of three VPs. We have investigated the upstream initiation context that originally surrounds VP2 translational start; various non-canonical start codons (ACG, CTG, TTG, GTG), various mutagenic changes to the +2 wild type triplet and insertion between the +1 initiation triplet and the +2 wild type triplet. The expression cassettes encompassing combination of these features were used for generation of rAAV.

TABLE 2

Description of AAV5 capsid variants. A number of different mutations surrounding the translational start of VP1 were generated to improve the stoichiometry of three VPs expressed in insect cells. Nucleotides and amino residues changed as compared to the wild type serotype 5 capsid sequence are indicated in bold.

| Bac. VD No. | VP2 initiator context-upstream | Start codon | Amino acid additions(s) | 5' part of capsid sequence | SEQ ID NO: |
|---|---|---|---|---|---|
| AAV5 wild type | — | ATG | — | TCT TTT GTT GAT CAC CCT CCA GAT TGG T ... <br> S   F   V   D   H   P   P   D   W | 39 |
| | | Changes surrounding the CP1 translation start | | | |
| 159 | CCTGTTAAG | ACG | — | TCT TTT GTT GAT CAC CCA CCC GAT TGG T ... <br> S   F   V   D   H   P   P   D   W | 41 |
| 160 | CCTGTTAAG | ACG | GCTA | TCT TTT GTT GAT CAC CCA CCC GAT TGG T ... <br> S   F   V   D   H   P   P   D   W | 42 |
| 161 | CCTGTTAAG | ACG | — | GCT TTT GTT GAT CAC CCA CCC GAT TGG T ... <br> A   F   V   D   H   P   P   D   W | 43 |
| 162 | CCTGTTAAG | CTG | — | ACT TTT GTT GAT CAC CCA CCC GAT TGG T ... <br> T   F   V   D   H   P   P   D   W | 44 |

TABLE 2-continued

Description of AAV5 capsid variants. A number of different mutations surrounding the translational start of VP1 were generated to improve the stoichiometry of three VPs expressed in insect cells. Nucleotides and amino residues changed as compared to the wild type serotype 5 capsid sequence are indicated in bold.

| Bac. VD No. | VP2 initiator context-upstream | Start codon | Amino acid additions(s) | 5' part of capsid sequence | SEQ ID NO: |
|---|---|---|---|---|---|
| 163 | CCTGTTAAG | CTG | ACTT | AGC TTT GTT GAT CAC CCA CCC GAT TGG T ... <br> S   F   V   D   H   P   P   D   W | 45 |
| 164 | CCTGTTAAG | CTG | — | AGT TTT GTT GAT CAC CCA CCC GAT TGG T ... <br> S   F   V   D   H   P   P   D   W | 46 |
| 761 | CCTGTTAAG | ACG | GCTA | TCT TTT GTT GAT CAC CCA CCC GAT TGG T ... <br> S   F   V   D   H   P   P   D   W | 47 |
| 762 | — | ACG | GCTA | TCT TTT GTT GAT CAC CCA CCC GAT TGG T ... <br> S   F   V   D   H   P   P   D   W | 48 |
| 763 (wild type AAV5) | — | ATG | — | TCT TTT GTT GAT CAC CCT CCA GAT TGG T ... <br> S   F   V   D   H   P   P   D   W | 49 |
| 764 | — | TTG | GCTA | TCT TTT GTT GAT CAC CCA CCC GAT TGG T ... <br> S   F   V   D   H   P   P   D   W | 50 |
| 765 | — | CTG | GCTA | TCT TTT GTT GAT CAC CCA CCC GAT TGG T ... <br> S   F   V   D   H   P   P   D   W | 51 |
| 766 | — | GTG | GCTA | TCT TTT GTT GAT CAC CCA CCC GAT TGG T ... <br> S   F   V   D   H   P   P   D   W | 52 |
| 43 | CCTGTTAAG | CTG | GCTA | TCT TTT GTT GAT CAC CCA CCC GAT TGG T ... <br> S   F   V   D   H   P   P   D   W | 69 |

Bac. VD No's 159-164 and 43 are operably linked to a polH promoter (SEQ ID NO: 53)
Bac. VD No's 761-766 are operably linked to a short polH promoter (SEQ ID NO: 54)

3.2. Small Nucleotide Changes Surrounding the Translation Initiation Start of VP1 have Profound Effects on the Potency of the Vector Baculovirus constructs harbouring all variants of cap5 expression cassettes listed in table 2 were successfully generated. Subsequently, these baculovirus constructs in combination with baculoviruses harbouring Rep(s) and transgene (reporter gene e.g. SEAP or FIX) were used for generation of rAAV. Some of the tested constructs irrespectively of multiple attempts did not support generation of rAAV production. This included wild type AAV5 (construct 763) and some of the constructs harbouring non-canonical starts, TTG (construct 764), GTG (construct 766). All the other constructs listed in table 2 resulted in successful generation of rAAV.

Figure 6:
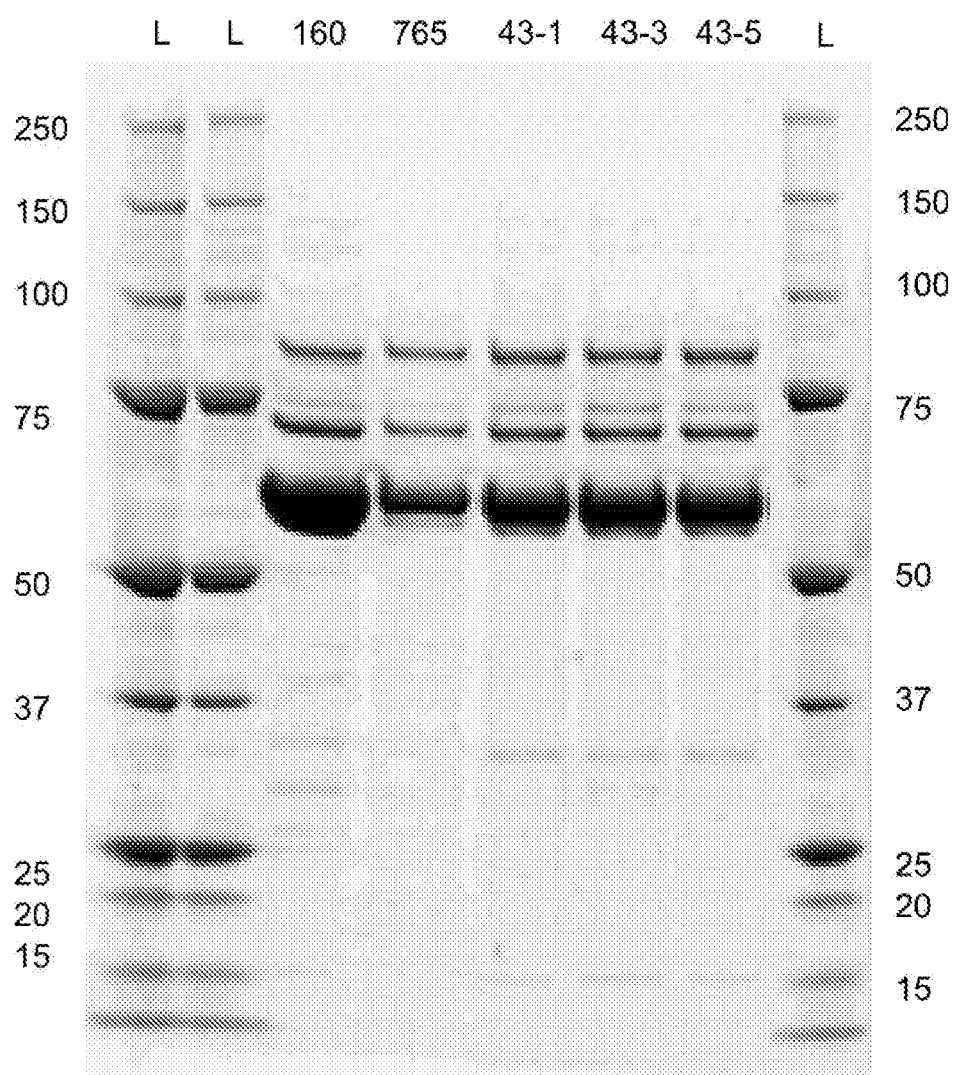
FIG. 6: Mutant capsids harbouring reporter transgene SEAP were purified and resolved on an NuPage gel to show the three capsid proteins VP1, VP2 and VP3. Three clones of construct 43 are shown.

The three viral proteins (VPs) of successfully produced rAAV type 5 variants were isolated. The stoichiometry of the three VPs was investigated by electrophoretic separation (SDS-PAGE) of purified vectors (FIGS. 1 and 6). It appears that the small modifications introduced to the expression cassette of cap5 gene have a profound influence on the expression and/or assembly of the three VP proteins which is reflected in the composition of the capsids. We have noted that the adaptation of serotype 5 capsid to the insect cells by introducing non-canonical start codon (ACG) and the nine nucleotide upstream context CCTGTTAAG, which was reported by Urabe et al., as a modification allowing for insect cell production of serotype 2, resulted in low incorporation of VP1 (low VP1/VP2 ratio) and incorporation of excessive levels of VP3 into the capsid (high VP3/VP1 ratio) resulting in aberrant stoichiometry of the three VPs (FIG. 1, construct 159). Similarly, modification of nucleotide +4 to constitute G and to resemble closer canonical Kozak sequence, which resulted in exchange of serine at position +2 for alanine (construct 161), resulted in low incorporation of VP1 and high incorporation of VP3 (low VP1/VP2 high VP3/VP1). Use of different non-canonical codon CTG in combination with upstream CCTGTTAAG and downstream modification, i.e. change +4 nucleotide to A (construct 162), or +4-5 to AG (construct 164) or insertion of ACT as a second triplet with the modification of original +2 triplet to AGC (construct 163) did not improve VP1 incorporation to the capsid resulting in low VP1/VP2 high VP3/VP1. One of the constructs that showed a VP1/VP2 ratio close to 1 was construct 160 which encompasses direct upstream insertion of CCTGTTAAG, non-canonical ACG and insertion of an additional alanine in position +2 encoded by GCT as compared to the wild-type sequence, although the incorporation of VP3 was still in excess (equal VP1/VP2 high VP2/VP1). Subsequently, the promoter sequence in the construct 160 was mutated such that it resembles more precisely the wild type polyhedrin promoter. This generated the mutant 761. The VP2 initiation context was removed creating mutant 762. In both cases (761 and 762) there was a slight negative influence on the stoichiometry of the virus (lower VP1 incorporation) as compared to construct 160 (FIG. 1) Next, translation initiation start site of VP1 in construct 160 (to preserve the beneficial GCT directly downstream from the translation start codon) was altered to wild type ATG (mutant 763), TTG (mutant 764), CTG (mutant 765), GTG (mutant 766). All but the 765 mutant resulted in lack of detectable production of rAAV. Interestingly, combination of CTG as a non-canonical VP1 initiation start and addition of GCT triplet (encoding extra alanine) immediately following the translational start (765) resulted in higher incorporation of VP1 than VP2 and strong attenuation of VP3 ultimately resulting in balanced wild type AAV like VP stoichiometry (high VP1/VP2 moderate VP3/VP1) Finally, construct 43, which is like construct 160 with CTG as VP1 initiation codon instead of ACG, resulted in VP1 production with an almost native VP ratio (FIG. 6).

3.3. Superfluous Expression of P3 is Responsible for a Low Potency of True Type 5 AAV Mutants in BEVS.

Figure 2:
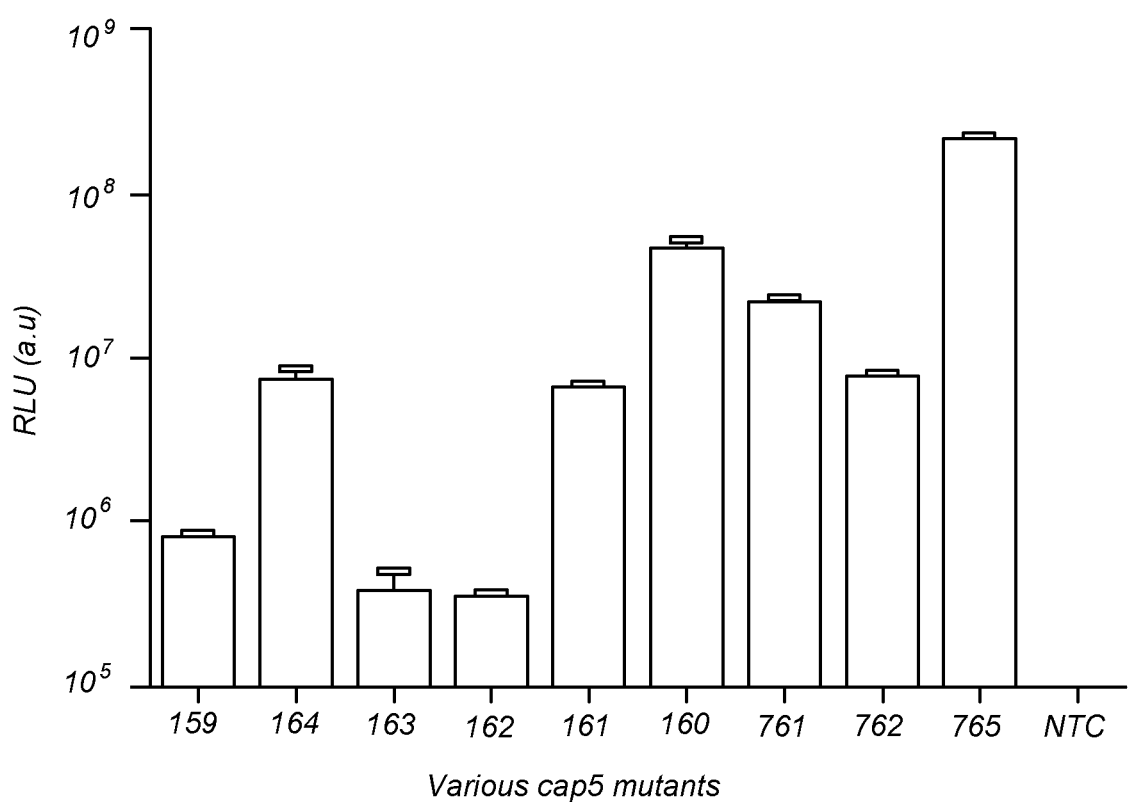
FIG. 2: In vitro potency assay with various AAV5 capsid mutants carrying seap expression cassette in Hela cells. The activity of the reporter gene is measured indirectly as emission of light and is expressed in RLU (relative light units). NTC=negative control.
Figure 3:
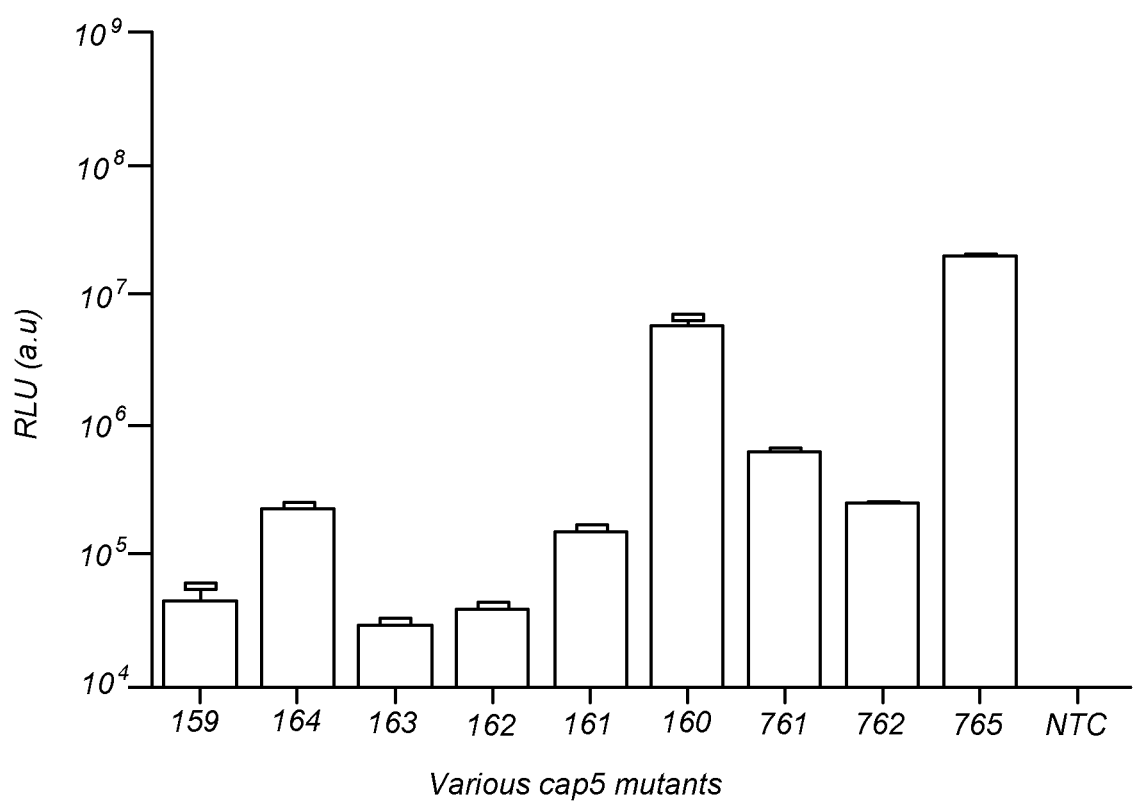
FIG. 3: In vitro potency assay with various AAV5 capsid mutants carrying seap expression cassette in Huh7 cells. The activity of the reporter gene is measured indirectly as emission of light and is expressed in RLU (relative light units). NTC=negative control.
Figure 7A:
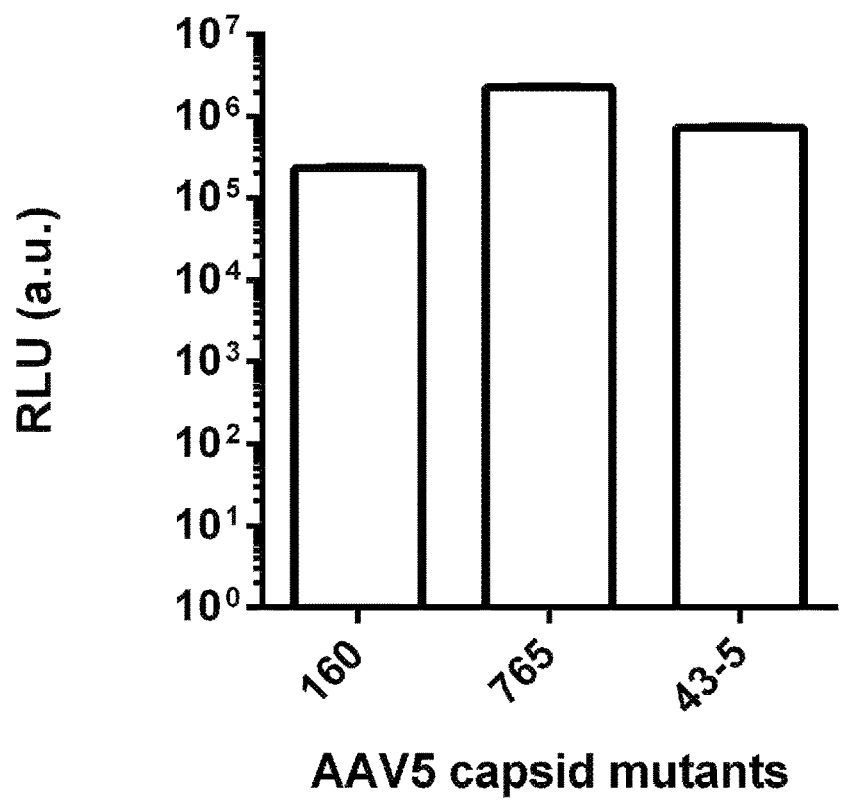
FIG. 7: In vitro potency assay with various AAV5 capsid mutants carrying seap expression cassette in HeLa cells (A) and in Huh7 cells (B). The activity of the reporter gene is measured indirectly as emission of light and is expressed in RLU (relative light units) (a.u.: arbitrary units).
Figure 7B:
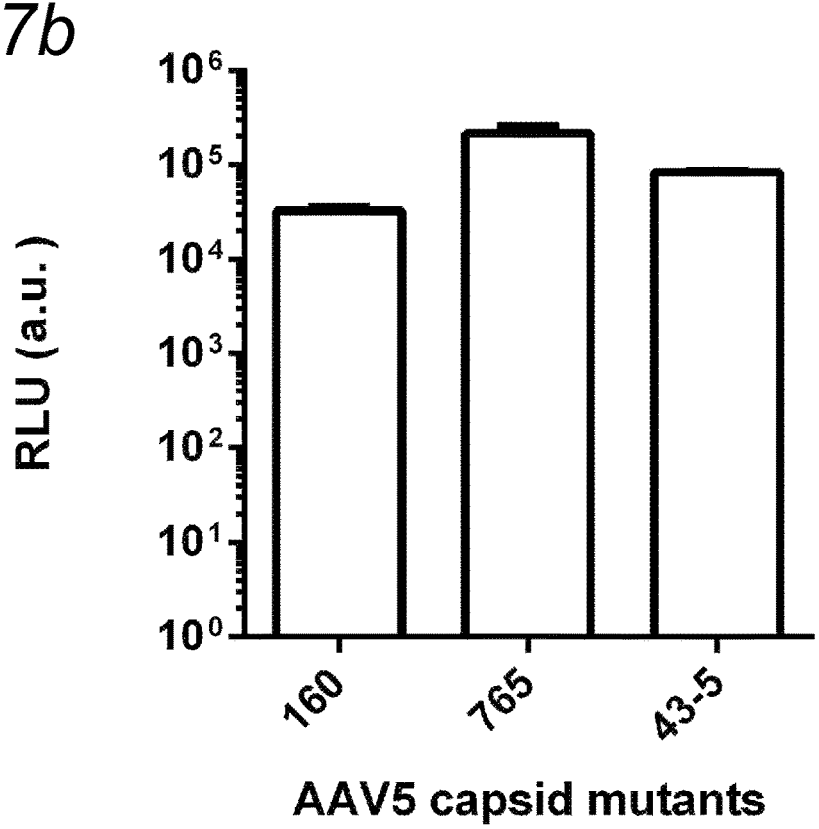

In order to study the potency of the library of serotype 5 capsids, i.e., the ability of the vector to drive the expression of its genetic material, that have different VP stoichiometry in vitro and in vivo study where performed. Two different continuous cell lines were used i.e. Hela (FIG. 2 and FIG. 7A) and Huh7 (FIG. 3 and FIG. 7B). In both cases the set of mutants which showed incorporation of VP1 below that of VP2 and excessive incorporation of VP3 (constructs 159, 161-164) showed very reduced potency (FIG. 2-3). The potency of the vector was much improved by balancing VP1 and VP2 incorporation (construct 160). Shortening of the promoter (construct 761) and removal of the initiator constructs (construct 762) had a negative effect on the vector potency. The most potent vector, construct 765 (FIG. 2-3) showed VP1 to VP2 ratio in favour of the former and significantly decreased VP3 incorporation. Finally, the polH promoter (not shortened) in combination with the initiator construct, the CTG initiation codon and additional GCT triplet (encoding extra alanine) (construct 43) showed a good potency, albeit somewhat less than the potency of construct 765 (FIGS. 7A and B).

Figure 4:
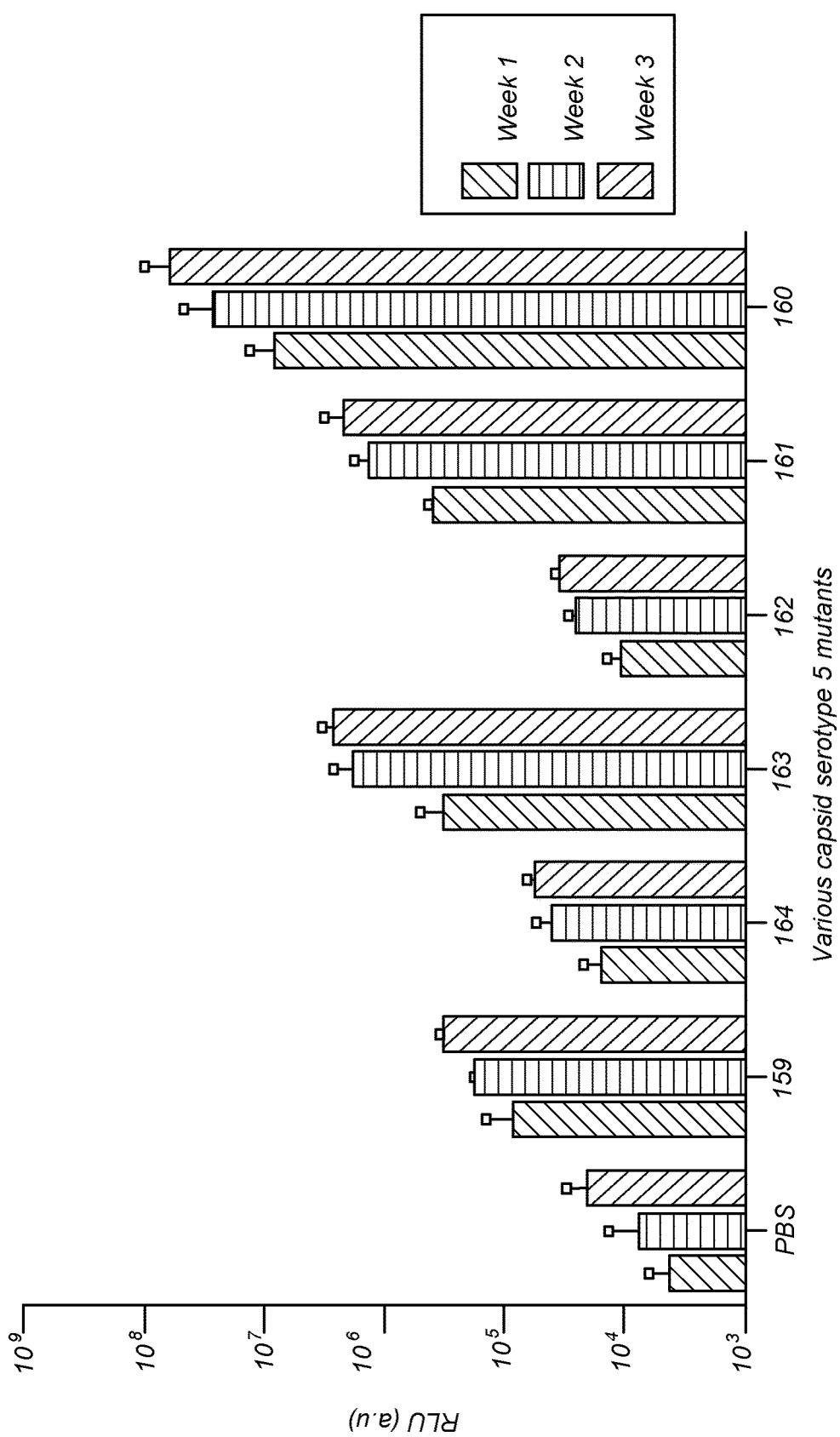
FIG. 4: In vivo potency assay of various capsid mutants carrying seap expression cassette in C57BL/6 mice. The activity of the reporter gene is measured indirectly as emission of light and is expressed in RLU (relative light units).

A subset of mutants (constructs 159-164) was tested in vivo (C57BL/6 mice) for potency. The vectors carried a reporter gene SEAP. Mice were injected with capsid 5 variants at a dose 5e12 gc/kg and monitored in time. In line with in vitro observation, variant that showed the best potency out of the tested set (160) also had VP1/VP2 in equimolar amounts (FIG. 4).

Figure 5:
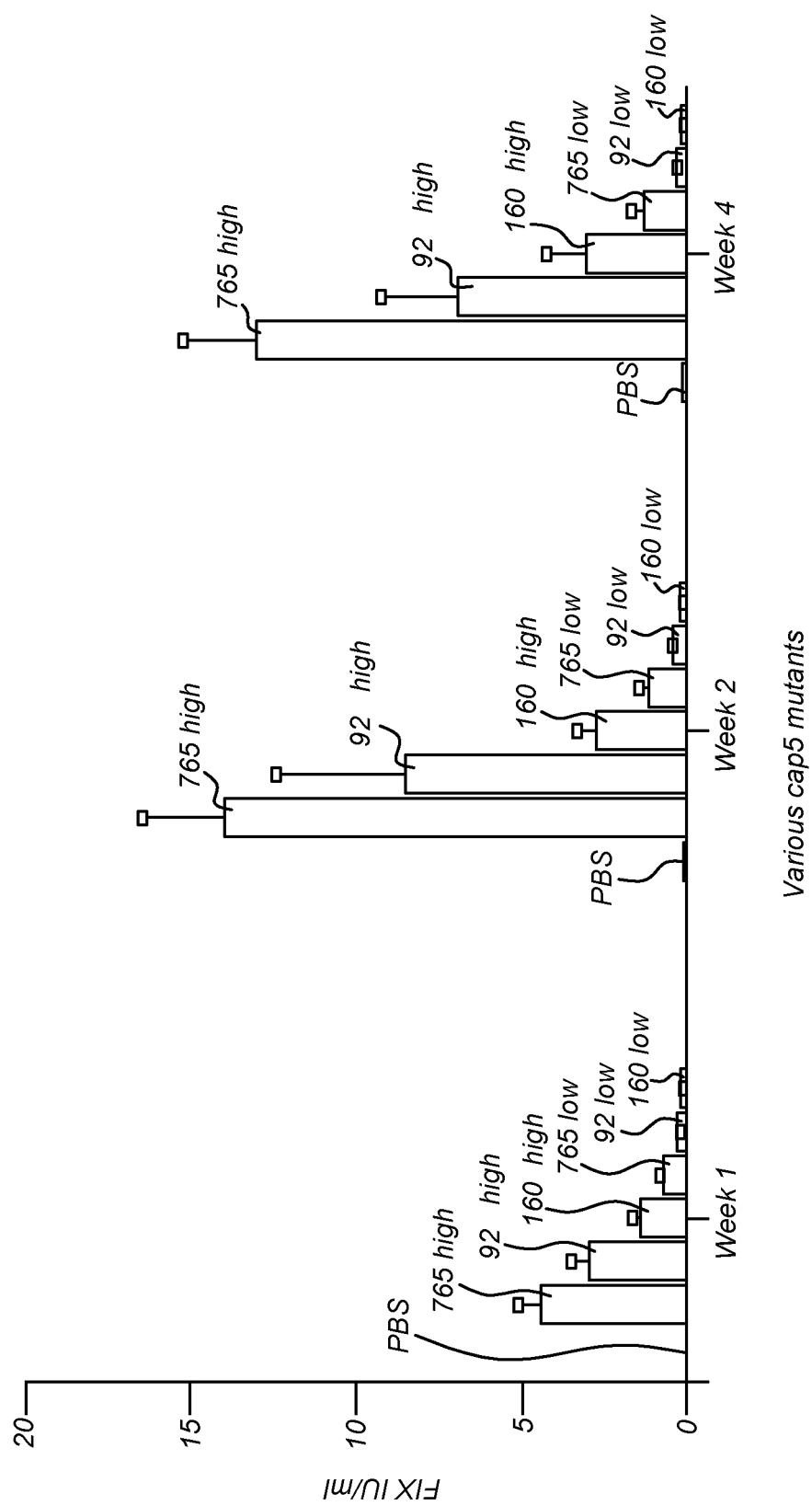
FIG. 5: In vivo potency assay of various AAV5 capsid mutants carrying FIX expression cassette in C57BL/6 mice. FIX expression was monitored in mice upon administration of two different vectors i.e. capsid variant 160 and 765. Both capsids carry FIX expression cassette. FIX is measured in plasma at week 1, 2 and 4 post injections by means of specific ELISA. IU/ml represents international units of FIX protein found in 1 ml of plasma. PBS—phosphate buffered saline.

3.4. Insect Cell Produced Gemuine AAV5 (765) Performs Superior to the Chimeric Type 2/5 Mutant In Vivo In order to investigate the potency of the AAV5 (765) in vivo three vector batches were prepared. These included the chimeric type 2/5 (92) (Urabe et al. (2006) supra), the genuine type AAV5 that contains excessive amounts of VP3 (160) and the best in vitro performing genuine type 5 AAV with wild type stoichiometry of VP's (765). All batches were produced under the same conditions using baculovirus constructs harbouring Rep proteins and FIX expression cassette (as described in WO 2006/36502). In order to compare the potency of the three vector preparations black 6 mice were injected with two different doses of the vectors, i.e. low dose 2e12 gc/kg and a high dose 2e13 gc/kg. In total seven groups including the vehicle group consisting of 5 animals each, were included in the experiment. Following the start of the experiment, blood was collected at week 1, 2 and 4. The expression of FIX was monitored in the blood by means of specific ELISA. The results corroborated the previous in vitro findings were newly generated 765 mutant displayed significant improved potency over 160 construct. Interestingly, 765 construct was also significantly better that the type 2/5 chimera (construct 92) published by Urabe et al. (2006) (supra) (FIG. 5). Unpaired t test was used to investigate the differences between 765 vs. 160 and 765 vs. 92. In all cases i.e. week 1, 2 and 4 there was a statistical significant difference with a p value <0.05.

4. Discussion

Generation of rAAV in insect cells requires a number of adjustments in the genetic organization of the cap gene. In mammalian cells AAV expresses its VP proteins from a single open reading frame by utilizing alternative splicing and the poorly utilized ACG initiator start for VP2. This results in a VP1:VP2:VP3 stoichiometry of 1:1:10. In insect cell these mechanisms failed to produce AAV vectors with a correct VP stoichiometry (Urabe et al. (2002) supra). This is a known problem which has previously been circumvented by Urabe et al., to generate rAAV2 serotype by changing the VP1 initiator triplet to ACG and by mutating the 9 nucleotides upstream from the translation initiation start site. These changes resulted in production of all three rAAV2 VP's in a correct stoichiometry. Similar genetic alteration in rAAV5 expression cassette resulted in low VP1 production and low potency of produced virus Building upon the success of the genetic adaptation to rAAV2, Urabe et al. decided to: make a series of six domain swap mutants where, rAAV5 received various length of N-terminal portion of VP1 from AAV2 (ranging from 7 amino acids up until 136 amino acids). This approach resulted in the production of a chimeric rAAV5 that showed a correct stoichiometry of VP's. Moreover, the domain swap mutants, resulted in a potency that was similar or superior to that of rAAV5 produced in 293T cells (Urabe et al. (2006) supra). Although, Urabe et al., demonstrated that chimeric rAAV5 can be generated in insect cells the obtained vector does not comprise bona fide AAV5 particles and as such may differ in various aspects such as susceptibility to pre-existing neutralizing antibodies, intracellular trafficking, bio-distribution and/or targeting from the true AAV5 serotype. At the same time the Urabe et al., reported that the attempts to produce infectious genuine rAAV5 failed due to low synthesis of VP1 polypeptide (Urabe et al. (2006) supra).

Here we have constructed a library of cap5 mutants objected at understanding the determinants underlying low potency of genuine rAAV5 produced in insect cells First, we have examined a mutant (159) that incorporated a number of adaptations which were previously used for successful generation of rAAV2 in insect cells (Urabe et al. (2002) supra). This mutant contains 9 nucleotide upstream VP2 initiator context placed upstream of VP1 translational start and non-canonical translation initiation start ACG. These 9 nucleotides were previously used by Urabe et al., to express serotype 2 gene in insect cells (Urabe et al. (2002) supra). This particular sequence naturally flanks non-canonical start codon (ACG) of VP2. Next, the wild type ATG was change to either ACG or CTG and in order to provide optimal downstream context from the start codon various mutations were introduced. Most of the mutants showed aberrant VPs stoichiometry with low incorporation of VP1 and excessive presence of VP3 (low VP1/VP2 and high VP3/VP1 ratio). The ratio VP1/VP2 was much improved in the genetic design 160, which still however showed excessive incorporation of VP3 into the vector particles. Finally, one of the genetic designs i.e. 765 showed high incorporation of VP1 (high VP1/VP2 ratio) and reduced incorporation of VP3 as compared to other tested variants (balanced VP3/VP2 ratio).

The low ratio of VP1/VP2 proteins has been postulated before to be responsible for the low vector potency (Hermonat et al. (1984) Journal of Virology 51(2):329-339; Tratschin et al (1984) Journal of Virology 51(3):611-619). Unique VP1 part of AAV is buried inside the capsid and becomes exposed during intracellular trafficking of virus to the nucleus. It first becomes exposed as a response to lowering pH in the lumen of endosome. Free N-terminal part of VP1 contains phospholipase domain which upon exposure to the outside of capsid becomes available to hydrolase specifically the 2-acyl ester (sn-2) bond of phospholipid substrates, resulting in release of lysophospholipids and free fatty acid allowing, in turn, endosomal escape of AAV. Unique portion of VP1 contains nucleus localization signals (clusters of basic amino acids) and was implicated in nucleus targeting of AAV. Finally, some authors suggest that unique portion of VP1 may play a role in virus uncoating in the nucleus. Low VP1/VP2 ratio and excessive incorporation of VP3 into viral particles (high VP3/VP1 ratio) may result in either 1) decreased incorporation of VP1 into the assembled particles on average or 2) generation of two particle populations A) correctly assembled particles (having close to wild type stoichiometry 1:1:10, i.e. 5 VP1 molecules per vector particle) B) VP3/VP2 only particles. In both situations (1 and 2) such vector preparation may have altered potency. The excessive amounts of VP3 proteins (as compared to VP1 or VP2) present in the vector preparation likely results in impaired trafficking of the vector to the nucleus due to disturbed endosomal escape. In order to test the hypothesis that the VP stoichiometry is detrimental for vector potency and to generate more potent vector the library of mutants of serotype 5 capsid was tested in vitro and in vivo.

It appeared that the VP's stoichiometry correlated well with the potency of the vector. As shown before (Hermonat et al. (1984) supra; Tratschin et al. (1984) supra; WO2007046703A2) low VP1N/VP2 ratio has strong influence on the potency of the virus. The mutants 159, 161-164 all have shown low VP1/VP2 ration and drastically reduced potency. Improved ratio between VP1/VP2 had significant impact on the potency of the vector (160). Interestingly further improvement in the VP1/VP2 ratio and decreasing the incorporation of VP3 to vector particles (decreasing VP3/VP1 ratio) resulted in generation of improved vector 43 and of the most potent vector (construct 765) among the tested set. This data clearly indicate that the molecular make-up of the vector particle is detrimental for its potency. Improving incorporation of VP1 and at the same time decreasing that of VP3 seems to give the best results in terms of the vector potency. The influence of low VP1/VP2 ratio of particles generated in BEVS has been reported previously to have negative impact on vector potency. The ratio of VP2/VP3 was not considered so far, mainly due to the fact that its genetic design for production in BEVS is the same as in the wild type AAV virus. Thereby, it is not expected that it lead to altered VP2/VP3 ratio. However, with all but one mutant presented here, we observed excessive incorporation of VP3 into the vector particles (high VP3/VP1 ratio) indicating that alteration of VP1 translational start surroundings has strong effects on expression of VP2 and VP3. Only the mutant 765 showed balance stoichiometry with high VP1/VP2 ratio and decreased incorporation of VP3, which resulted in increased potency as compared to other tested variants. Furthermore, the potency of 765 variant was compared in vivo (mice) to AAV5 like vector produced in REVS (construct 92). The 92 construct is chimera of AAV serotype 5 with the N-terminal 136 amino acid portion of serotype 2 (Urabe et al. (2006) supra). Although construct 92 does not comprise a true AAV5 it is the only alternative currently available for generation of AAV5 like particles in BEVS. The 765 construct showed statistically significant superiority to the 92 construct.

We hypothesize that the strong influence on expression of downstream VP2 and VP3 by mutagenic changes of VP1 translational reason is related to the translational process itself. Translation is unidirectional in eukaryotes and starts with mRNA 5'. Ribosomes, once engaged with mRNA, proceed until they find translational ATG start in appropriate context to initiate protein synthesis. Sometimes a week initiation starts e.g. ACG or CTG, if surrounded by appropriate nucleotide context may initiate protein synthesis in a non-canonical manner. This mechanism is called leaky ribosomal scanning. The strength of the leaky ribosomal scanning at VP1 will determine the portion of ribosomes "leakage" to VP2 and VP3 and strength of protein expression from the latter two. In turn the expressions of all three components will determine their presence in the final assembled capsid.

The invention claimed is:

1. A nucleic acid molecule comprising a first nucleotide sequence comprising an open reading frame (ORF), wherein the ORF in 5' to 3' order comprises: (i) a suboptimal translation initiation codon consisting of CTG or ACG; (ii) an inserted codon encoding alanine; and (iii) a sequence encoding a wild-type adeno-associated virus (AAV) serotype 5 capsid protein VP1 starting at position 2 of the protein and lacking the wild-type translation initiation codon.

2. The nucleic acid molecule according to claim 1, wherein the capsid proteins have the amino acid sequence of SEQ ID NO; 22.

3. The nucleic acid molecule according to claim 1, wherein the inserted codon encoding an amino acid residue is selected from the group consisting of GCT, GCC, GCA and GCG.

4. The nucleic acid molecule according to claim 3, wherein the inserted codon encoding an amino acid residue is GCT.

5. A first nucleic acid construct comprising the nucleic acid molecule according to claim 1, wherein the first nucleotide sequence encoding the AAV capsid proteins is operably linked to an expression control sequence for expression in an insect cell.

6. The nucleic acid construct according to claim 5, wherein the nucleotide sequence of the ORF is operably linked to a promoter selected from the group consisting of polyhedron promoter, p10 promoter, Hsp27 EcRE+minimal Hsp70 promoter, deltaE1 promoter and E1 promoter.

7. The nucleic acid construct according to claim 5, wherein the construct is an insect-compatible vector.

8. The nucleic acid construct according to claim 7, wherein the vector is a baculoviral vector.

9. The nucleic acid construct according to claim 5, wherein the nucleic acid molecule comprises an ORF selected from the group consisting of: SEQ ID NO:51, SEQ ID NO:69, SEQ ID NO:42, SEQ ID NO:47 and SEQ ID NO:48.

10. The nucleic acid construct according to claim 9, wherein the ORF is SEQ ID NO:51.

11. An insect cell comprising the first nucleic acid construct according to claim 5.

12. The insect cell according to claim 11, wherein the insect cell further comprises: (a) a second nucleotide sequence comprising at least one AAV inverted terminal repeat (ITR) nucleotide sequence; (b) a third nucleotide sequence comprising a Rep78 or a Rep68 coding sequence operably linked to an expression control sequence for expression in an insect cell.

13. The insect cell according to claim 12, wherein the second nucleotide sequence further comprises at least one nucleotide sequence that encodes a gene product of interest for expression in a mammalian cell.

14. The insect cell according to claim 13, wherein the second nucleotide sequence comprising said at least one nucleotide sequence encoding said gene product of interest comprises two AAV ITR nucleotide sequences between which the sequence encoding the gene product of interest is located.

15. An AAV virion comprising a VP1 capsid protein and comprising in its genome at least one nucleotide sequence encoding a gene product of interest, wherein: (a) the at least one nucleotide sequence encoding the gene product of interest is not a native AAV nucleotide sequence, (b) the AAV VP1 capsid protein comprises, from N terminus to C terminus: (i) a first amino acid residue encoded by a translation initiation codon consisting of CTG or ACG; (ii) an inserted alanine residue; (iii) an amino acid sequence of an AAV serotype 5 VP1 capsid protein starting at position 2 of the protein and lacking the amino acid residue that is encoded by the VP1 translation initiation codon.

16. The AAV virion according to claim 15, wherein the gene product of interest encodes a Factor IX or a Factor VIII protein.

17. The AAV virion according to claim 16, wherein the Factor IX or Factor VIII protein is a human Factor IX or Factor VIII protein.

18. A method for producing AAV virions in an insect cell, comprising the steps of: (a) culturing the insect cell of claim 11 under conditions such that AAV virions are produced; and (b) optionally recovering the AAV virions.

19. The insect cell according to claim 12, wherein the insect cell further comprises a fourth nucleotide sequence comprising a Rep52 or Rep40 coding sequence operably linked to an expression control sequence for expression in an insect cell.

20. The insect cell according to claim 19, wherein the first nucleic acid construct comprises the third and fourth nucleotide sequences; and the insect cell further comprises a second nucleic acid construct comprising the second nucleotide sequence.

21. The insect cell according to claim 20, wherein the second nucleic construct is a baculoviral vector.

\* \* \* \* \*

SEQUENCE LISTING

```
<160> NUMBER OF SEQ ID NOS: 73

<210> SEQ ID NO 1
<211> LENGTH: 1876
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 2
<220> FEATURE:
<221> NAME/KEY: CDS
<222> LOCATION: (11)..(1876)
<223> OTHER INFORMATION: Rep78 coding sequence
<220> FEATURE:
<221> NAME/KEY: misc_feature
<222> LOCATION: (683)..(1876)

<400> SEQUENCE: 1
cgcagccgcc atg ccg ggg ttt tac gag att gtg att aag gtc ccc agc        49
            Met Pro Gly Phe Tyr Glu Ile Val Ile Lys Val Pro Ser
            1               5                   10 gac ctt gac gag cat ctg ccc ggc att tct gac agc ttt gtg aac tgg        97
Asp Leu Asp Glu His Leu Pro Gly Ile Ser Asp Ser Phe Val Asn Trp
    15                  20                  25
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtg | gcc | gag | aag | gaa | tgg | gag | ttg | ccg | cca | gat | tct | gac | atg | gat | ctg | 145  |
| Val | Ala | Glu | Lys | Glu | Trp | Glu | Leu | Pro | Pro | Asp | Ser | Asp | Met | Asp | Leu |      |
| 30  |     |     |     | 35  |     |     |     | 40  |     |     |     | 45  |     |     |     |      |

| aat | ctg | att | gag | cag | gca | ccc | ctg | acc | gtg | gcc | gag | aag | ctg | cag | cgc | 193 |
|-----|-----|-----|-----|-----|-----|-----|-----|-----|-----|-----|-----|-----|-----|-----|-----|-----|
| Asn | Leu | Ile | Glu | Gln | Ala | Pro | Leu | Thr | Val | Ala | Glu | Lys | Leu | Gln | Arg |     |
|     |     |     | 50  |     |     |     |     | 55  |     |     |     |     | 60  |     |     |     |

| gac | ttt | ctg | acg | gaa | tgg | cgc | cgt | gtg | agt | aag | gcc | ccg | gag | gcc | ctt | 241 |
|-----|-----|-----|-----|-----|-----|-----|-----|-----|-----|-----|-----|-----|-----|-----|-----|-----|
| Asp | Phe | Leu | Thr | Glu | Trp | Arg | Arg | Val | Ser | Lys | Ala | Pro | Glu | Ala | Leu |     |
|     |     |     | 65  |     |     |     |     | 70  |     |     |     |     | 75  |     |     |     |

| ttc | ttt | gtg | caa | ttt | gag | aag | gga | gag | agc | tac | ttc | cac | atg | cac | gtg | 289 |
|-----|-----|-----|-----|-----|-----|-----|-----|-----|-----|-----|-----|-----|-----|-----|-----|-----|
| Phe | Phe | Val | Gln | Phe | Glu | Lys | Gly | Glu | Ser | Tyr | Phe | His | Met | His | Val |     |
|     |     | 80  |     |     |     |     | 85  |     |     |     |     | 90  |     |     |     |     |

| ctc | gtg | gaa | acc | acc | ggg | gtg | aaa | tcc | atg | gtt | ttg | gga | cgt | ttc | ctg | 337 |
|-----|-----|-----|-----|-----|-----|-----|-----|-----|-----|-----|-----|-----|-----|-----|-----|-----|
| Leu | Val | Glu | Thr | Thr | Gly | Val | Lys | Ser | Met | Val | Leu | Gly | Arg | Phe | Leu |     |
|     | 95  |     |     |     |     | 100 |     |     |     |     | 105 |     |     |     |     |     |

| agt | cag | att | cgc | gaa | aaa | ctg | att | cag | aga | att | tac | cgc | ggg | atc | gag | 385 |
|-----|-----|-----|-----|-----|-----|-----|-----|-----|-----|-----|-----|-----|-----|-----|-----|-----|
| Ser | Gln | Ile | Arg | Glu | Lys | Leu | Ile | Gln | Arg | Ile | Tyr | Arg | Gly | Ile | Glu |     |
| 110 |     |     |     |     | 115 |     |     |     |     | 120 |     |     |     |     | 125 |     |

| ccg | act | ttg | cca | aac | tgg | ttc | gcg | gtc | aca | aag | acc | aga | aat | ggc | gcc | 433 |
|-----|-----|-----|-----|-----|-----|-----|-----|-----|-----|-----|-----|-----|-----|-----|-----|-----|
| Pro | Thr | Leu | Pro | Asn | Trp | Phe | Ala | Val | Thr | Lys | Thr | Arg | Asn | Gly | Ala |     |
|     |     |     |     | 130 |     |     |     |     | 135 |     |     |     |     | 140 |     |     |

| gga | ggc | ggg | aac | aag | gtg | gtg | gat | gag | tgc | tac | atc | ccc | aat | tac | ttg | 481 |
|-----|-----|-----|-----|-----|-----|-----|-----|-----|-----|-----|-----|-----|-----|-----|-----|-----|
| Gly | Gly | Gly | Asn | Lys | Val | Val | Asp | Glu | Cys | Tyr | Ile | Pro | Asn | Tyr | Leu |     |
|     |     | 145 |     |     |     |     | 150 |     |     |     |     | 155 |     |     |     |     |

| ctc | ccc | aaa | acc | cag | cct | gag | ctc | cag | tgg | gcg | tgg | act | aat | atg | gaa | 529 |
|-----|-----|-----|-----|-----|-----|-----|-----|-----|-----|-----|-----|-----|-----|-----|-----|-----|
| Leu | Pro | Lys | Thr | Gln | Pro | Glu | Leu | Gln | Trp | Ala | Trp | Thr | Asn | Met | Glu |     |
|     |     | 160 |     |     |     |     | 165 |     |     |     |     | 170 |     |     |     |     |

| cag | tat | tta | agc | gcc | tgt | ttg | aat | ctc | acg | gag | cgt | aaa | cgg | ttg | gtg | 577 |
|-----|-----|-----|-----|-----|-----|-----|-----|-----|-----|-----|-----|-----|-----|-----|-----|-----|
| Gln | Tyr | Leu | Ser | Ala | Cys | Leu | Asn | Leu | Thr | Glu | Arg | Lys | Arg | Leu | Val |     |
|     | 175 |     |     |     |     | 180 |     |     |     |     | 185 |     |     |     |     |     |

| gcg | cag | cat | ctg | acg | cac | gtg | tcg | cag | acg | cag | gag | cag | aac | aaa | gag | 625 |
|-----|-----|-----|-----|-----|-----|-----|-----|-----|-----|-----|-----|-----|-----|-----|-----|-----|
| Ala | Gln | His | Leu | Thr | His | Val | Ser | Gln | Thr | Gln | Glu | Gln | Asn | Lys | Glu |     |
| 190 |     |     |     |     | 195 |     |     |     |     | 200 |     |     |     |     | 205 |     |

| aat | cag | aat | ccc | aat | tct | gat | gcg | ccg | gtg | atc | aga | tca | aaa | act | tca | 673 |
|-----|-----|-----|-----|-----|-----|-----|-----|-----|-----|-----|-----|-----|-----|-----|-----|-----|
| Asn | Gln | Asn | Pro | Asn | Ser | Asp | Ala | Pro | Val | Ile | Arg | Ser | Lys | Thr | Ser |     |
|     |     |     |     | 210 |     |     |     |     | 215 |     |     |     |     | 220 |     |     |

| gcc | agg | tac | atg | gag | ctg | gtc | ggg | tgg | ctc | gtg | gac | aag | ggg | att | acc | 721 |
|-----|-----|-----|-----|-----|-----|-----|-----|-----|-----|-----|-----|-----|-----|-----|-----|-----|
| Ala | Arg | Tyr | Met | Glu | Leu | Val | Gly | Trp | Leu | Val | Asp | Lys | Gly | Ile | Thr |     |
|     |     |     | 225 |     |     |     |     | 230 |     |     |     |     | 235 |     |     |     |

| tcg | gag | aag | cag | tgg | atc | cag | gag | gac | cag | gcc | tca | tac | atc | tcc | ttc | 769 |
|-----|-----|-----|-----|-----|-----|-----|-----|-----|-----|-----|-----|-----|-----|-----|-----|-----|
| Ser | Glu | Lys | Gln | Trp | Ile | Gln | Glu | Asp | Gln | Ala | Ser | Tyr | Ile | Ser | Phe |     |
|     |     | 240 |     |     |     |     | 245 |     |     |     |     | 250 |     |     |     |     |

| aat | gcg | gcc | tcc | aac | tcg | cgg | tcc | caa | atc | aag | gct | gcc | ttg | gac | aat | 817 |
|-----|-----|-----|-----|-----|-----|-----|-----|-----|-----|-----|-----|-----|-----|-----|-----|-----|
| Asn | Ala | Ala | Ser | Asn | Ser | Arg | Ser | Gln | Ile | Lys | Ala | Ala | Leu | Asp | Asn |     |
| 255 |     |     |     |     | 260 |     |     |     |     | 265 |     |     |     |     |     |     |

| gcg | gga | aag | att | atg | agc | ctg | act | aaa | acc | gcc | ccc | gac | tac | ctg | gtg | 865 |
|-----|-----|-----|-----|-----|-----|-----|-----|-----|-----|-----|-----|-----|-----|-----|-----|-----|
| Ala | Gly | Lys | Ile | Met | Ser | Leu | Thr | Lys | Thr | Ala | Pro | Asp | Tyr | Leu | Val |     |
| 270 |     |     |     |     | 275 |     |     |     |     | 280 |     |     |     |     | 285 |     |

| ggc | cag | cag | ccc | gtg | gag | gac | att | tcc | agc | aat | cgg | att | tat | aaa | att | 913 |
|-----|-----|-----|-----|-----|-----|-----|-----|-----|-----|-----|-----|-----|-----|-----|-----|-----|
| Gly | Gln | Gln | Pro | Val | Glu | Asp | Ile | Ser | Ser | Asn | Arg | Ile | Tyr | Lys | Ile |     |
|     |     |     |     | 290 |     |     |     |     | 295 |     |     |     |     | 300 |     |     |

| ttg | gaa | cta | aac | ggg | tac | gat | ccc | caa | tat | gcg | gct | tcc | gtc | ttt | ctg | 961 |
|-----|-----|-----|-----|-----|-----|-----|-----|-----|-----|-----|-----|-----|-----|-----|-----|-----|
| Leu | Glu | Leu | Asn | Gly | Tyr | Asp | Pro | Gln | Tyr | Ala | Ala | Ser | Val | Phe | Leu |     |
|     |     |     | 305 |     |     |     |     | 310 |     |     |     |     | 315 |     |     |     |

| gga | tgg | gcc | acg | aaa | aag | ttc | ggc | aag | agg | aac | acc | atc | tgg | ctg | ttt | 1009 |
|-----|-----|-----|-----|-----|-----|-----|-----|-----|-----|-----|-----|-----|-----|-----|-----|------|
| Gly | Trp | Ala | Thr | Lys | Lys | Phe | Gly | Lys | Arg | Asn | Thr | Ile | Trp | Leu | Phe |      |
|     |     | 320 |     |     |     |     | 325 |     |     |     |     | 330 |     |     |     |      |

| ggg | cct | gca | act | acc | ggg | aag | acc | aac | atc | gcg | gag | gcc | ata | gcc | cac | 1057 |
|-----|-----|-----|-----|-----|-----|-----|-----|-----|-----|-----|-----|-----|-----|-----|-----|------|
| Gly | Pro | Ala | Thr | Thr | Gly | Lys | Thr | Asn | Ile | Ala | Glu | Ala | Ile | Ala | His |      |
|     |     |     | 335 |     |     |     |     | 340 |     |     |     |     | 345 |     |     |      |

```
act gtg ccc ttc tac ggg tgc gta aac tgg acc aat gag aac ttt ccc    1105
Thr Val Pro Phe Tyr Gly Cys Val Asn Trp Thr Asn Glu Asn Phe Pro
350             355                 360                 365 ttc aac gac tgt gtc gac aag atg gtg atc tgg tgg gag gag ggg aag    1153
Phe Asn Asp Cys Val Asp Lys Met Val Ile Trp Trp Glu Glu Gly Lys
                370                 375                 380 atg acc gcc aag gtc gtg gag tcg gcc aaa gcc att ctc gga gga agc    1201
Met Thr Ala Lys Val Val Glu Ser Ala Lys Ala Ile Leu Gly Gly Ser
            385                 390                 395 aag gtg cgc gtg gac cag aaa tgc aag tcc tcg gcc cag ata gac ccg    1249
Lys Val Arg Val Asp Gln Lys Cys Lys Ser Ser Ala Gln Ile Asp Pro
        400                 405                 410 act ccc gtg atc gtc acc tcc aac acc aac atg tgc gcc gtg att gac    1297
Thr Pro Val Ile Val Thr Ser Asn Thr Asn Met Cys Ala Val Ile Asp
    415                 420                 425 ggg aac tca acg acc ttc gaa cac cag cag ccg ttg caa gac cgg atg    1345
Gly Asn Ser Thr Thr Phe Glu His Gln Gln Pro Leu Gln Asp Arg Met
430                 435                 440                 445 ttc aaa ttt gaa ctc acc cgc cgt ctg gat cat gac ttt ggg aag gtc    1393
Phe Lys Phe Glu Leu Thr Arg Arg Leu Asp His Asp Phe Gly Lys Val
                450                 455                 460 acc aag cag gaa gtc aaa gac ttt ttc cgg tgg gca aag gat cac gtg    1441
Thr Lys Gln Glu Val Lys Asp Phe Phe Arg Trp Ala Lys Asp His Val
                465                 470                 475 gtt gag gtg gag cat gaa ttc tac gtc aaa aag ggt gga gcc aag aaa    1489
Val Glu Val Glu His Glu Phe Tyr Val Lys Lys Gly Gly Ala Lys Lys
            480                 485                 490 aga ccc gcc ccc agt gac gca gat ata agt gag ccc aaa cgg gtg cgc    1537
Arg Pro Ala Pro Ser Asp Ala Asp Ile Ser Glu Pro Lys Arg Val Arg
        495                 500                 505 gag tca gtt gcg cag cca tcg acg tca gac gcg gaa gct tcg atc aac    1585
Glu Ser Val Ala Gln Pro Ser Thr Ser Asp Ala Glu Ala Ser Ile Asn
    510                 515                 520                 525 tac gca gac agg tac caa aac aaa tgt tct cgt cac gtg ggc atg aat    1633
Tyr Ala Asp Arg Tyr Gln Asn Lys Cys Ser Arg His Val Gly Met Asn
                530                 535                 540 ctg atg ctg ttt ccc tgc aga caa tgc gag aga atg aat cag aat tca    1681
Leu Met Leu Phe Pro Cys Arg Gln Cys Glu Arg Met Asn Gln Asn Ser
                545                 550                 555 aat atc tgc ttc act cac gga cag aaa gac tgt tta gag tgc ttt ccc    1729
Asn Ile Cys Phe Thr His Gly Gln Lys Asp Cys Leu Glu Cys Phe Pro
            560                 565                 570 gtg tca gaa tct caa ccc gtt tct gtc gtc aaa aag gcg tat cag aaa    1777
Val Ser Glu Ser Gln Pro Val Ser Val Val Lys Lys Ala Tyr Gln Lys
575                 580                 585 ctg tgc tac att cat cat atc atg gga aag gtg cca gac gct tgc act    1825
Leu Cys Tyr Ile His His Ile Met Gly Lys Val Pro Asp Ala Cys Thr
590                 595                 600                 605 gcc tgc gat ctg gtc aat gtg gat ttg gat gac tgc atc ttt gaa caa    1873
Ala Cys Asp Leu Val Asn Val Asp Leu Asp Asp Cys Ile Phe Glu Gln
                610                 615                 620 taa                                                                 1876

<210> SEQ ID NO 2
<211> LENGTH: 621
<212> TYPE: PRT
<213> ORGANISM: Artificial Sequence
<220> FEATURE:
<223> OTHER INFORMATION: Synthetic construct
```

```
<400> SEQUENCE: 2

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415
```

-continued

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
610                 615                 620

<210> SEQ ID NO 3
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 2 fragment

<400> SEQUENCE: 3 cctgttaag                                                                9

<210> SEQ ID NO 4
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak
<220> FEATURE:
<221> NAME/KEY: misc_feature
<222> LOCATION: (4)..(4)
<223> OTHER INFORMATION: r=purine = A or G
<220> FEATURE:
<221> NAME/KEY: misc_feature
<222> LOCATION: (7)..(9)
<223> OTHER INFORMATION: n is a, c, g, or t

<400> SEQUENCE: 4 gccrccnnng                                                              10

```
<210> SEQ ID NO 5
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 5
gccaccacgg                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 6
gccgccacgg                                                          10

<210> SEQ ID NO 7
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 7
gccaccttgg                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 8
gccgccttgg                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 9
gccaccgtgg                                                          10

<210> SEQ ID NO 10
<211> LENGTH: 10
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 10
gccgccgtgg                                                            10

<210> SEQ ID NO 11
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 11
gccaccctgg                                                            10

<210> SEQ ID NO 12
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: kozak sequence

<400> SEQUENCE: 12
gccgccctgg                                                            10

<210> SEQ ID NO 13
<211> LENGTH: 4718
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 1
<220> FEATURE:
<221> NAME/KEY: CDS
<222> LOCATION: (2223)..(4433)
<223> OTHER INFORMATION: VP1
<220> FEATURE:
<221> NAME/KEY: misc_feature
<222> LOCATION: (2634)..(4433)
<223> OTHER INFORMATION: AAV1 VP2
<220> FEATURE:
<221> NAME/KEY: misc_feature
<222> LOCATION: (2829)..(4433)
<223> OTHER INFORMATION: AAV1 VP3

<400> SEQUENCE: 13
ttgcccactc cctctctgcg cgctcgctcg ctcggtgggg cctgcggacc aaaggtccgc     60
agacggcaga gctctgctct gccggcccca ccgagcgagc gagcgcgcag agagggagtg    120
ggcaactcca tcactagggg taatcgcgaa gcgcctccca cgctgccgcg tcagcgctga    180
cgtaaattac gtcatagggg agtggtcctg tattagctgt cacgtgagtg cttttgcgac    240
attttgcgac accacgtggc catttagggt atatatggcc gagtgagcga gcaggatctc    300
cattttgacc gcgaaatttg aacgagcagc agccatgccg gcttctacg agatcgtgat    360 caaggtgccg agcgacctgg acgagcacct gccgggcatt tctgactcgt tgtgagctg    420
```

```
ggtggccgag aaggaatggg agctgccccc ggattctgac atggatctga atctgattga    480
gcaggcaccc ctgaccgtgg ccgagaagct gcagcgcgac ttcctggtcc aatggcgccg    540
cgtgagtaag gccccggagg ccctcttctt tgttcagttc gagaagggcg agtcctactt    600
ccacctccat attctggtgg agaccacggg ggtcaaatcc atggtgctgg ccgcttcct    660
gagtcagatt agggacaagc tggtgcagac catctaccgc gggatcgagc cgaccctgcc    720
caactggttc gcggtgacca agacgcgtaa tggcgccgga gggggaaca aggtggtgga    780
cgagtgctac atccccaact acctcctgcc caagactcag cccgagctgc agtgggcgtg    840
gactaacatg gaggagtata taagcgcctg tttgaacctg gccgagcgca aacggctcgt    900
ggcgcagcac ctgacccacg tcagccagac ccaggagcag aacaaggaga atctgaaccc    960
caattctgac gcgcctgtca tccggtcaaa aacctccgcg cgctacatgg agctggtcgg   1020
gtggctggtg gaccggggca tcacctccga gaagcagtgg atccaggagg accaggcctc   1080
gtacatctcc ttcaacgccg cttccaactc gcggtcccag atcaaggccg ctctggacaa   1140
tgccggcaag atcatggcgc tgaccaaatc cgcgcccgac tacctggtag gccccgctcc   1200
gcccgcggac attaaaacca accgcatcta ccgcatcctg gagctgaacg gctacgaacc   1260
tgcctacgcc ggctccgtct ttctcggctg ggcccagaaa aggttcggga agcgcaacac   1320
catctggctg tttgggccgg ccaccacggg caagaccaac atcgcggaag ccatcgccca   1380
cgccgtgccc ttctacggct gcgtcaactg gaccaatgag aactttccct tcaatgattg   1440
cgtcgacaag atggtgatct ggtgggagga gggcaagatg acggccaagg tcgtggagtc   1500
cgccaaggcc attctcggcg gcagcaaggt gcgcgtggca caaaagtgca agtcgtccgc   1560
ccagatcgac cccaccccg tgatcgtcac ctccaacacc aacatgtgcg ccgtgattga   1620
cgggaacagc accaccttcg agcaccagca gccgttgcag gaccggatgt tcaaatttga   1680
actcacccgc cgtctggagc atgactttgg caaggtgaca aagcaggaag tcaaagagtt   1740
cttccgctgg gcgcaggatc acgtgaccga ggtggcgcat gagttctacg tcagaaaggg   1800
tggagccaac aaaagacccg ccccgatga cgcggataaa agcgagccca gcgggcctg   1860
cccctcagtc gcggatccat cgacgtcaga gcgcgaagga gctccggtgg actttgccga   1920
caggtaccaa aacaaatgtt ctcgtcacgc gggcatgctt cagatgctgt ttccctgcaa   1980
gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gt atg gct gcc gat ggt tat ctt cca gat tgg ctc gag gac aac ctc    2267
   Met Ala Ala Asp Gly Tyr Leu Pro Asp Trp Leu Glu Asp Asn Leu
   1               5                   10                  15 tct gag ggc att cgc gag tgg tgg gac ttg aaa cct gga gcc ccg aag    2315
Ser Glu Gly Ile Arg Glu Trp Trp Asp Leu Lys Pro Gly Ala Pro Lys
                20                  25                  30 ccc aaa gcc aac cag caa aag cag gac gac ggc cgg ggt ctg gtg ctt    2363
Pro Lys Ala Asn Gln Gln Lys Gln Asp Asp Gly Arg Gly Leu Val Leu
            35                  40                  45 cct ggc tac aag tac ctc gga ccc ttc aac gga ctc gac aag ggg gag    2411
Pro Gly Tyr Lys Tyr Leu Gly Pro Phe Asn Gly Leu Asp Lys Gly Glu
        50                  55                  60 ccc gtc aac gcg gcg gac gca gcg gcc ctc gag cac gac aag gcc tac    2459
Pro Val Asn Ala Ala Asp Ala Ala Ala Leu Glu His Asp Lys Ala Tyr
65                  70                  75
```

-continued

```
gac cag cag ctc aaa gcg ggt gac aat ccg tac ctg cgg tat aac cac      2507
Asp Gln Gln Leu Lys Ala Gly Asp Asn Pro Tyr Leu Arg Tyr Asn His
 80              85                  90                  95 gcc gac gcc gag ttt cag gag cgt ctg caa gaa gat acg tct ttt ggg      2555
Ala Asp Ala Glu Phe Gln Glu Arg Leu Gln Glu Asp Thr Ser Phe Gly
                100                 105                 110 ggc aac ctc ggg cga gca gtc ttc cag gcc aag aag cgg gtt ctc gaa      2603
Gly Asn Leu Gly Arg Ala Val Phe Gln Ala Lys Lys Arg Val Leu Glu
            115                 120                 125 cct ctc ggt ctg gtt gag gaa ggc gct aag acg gct cct gga aag aaa      2651
Pro Leu Gly Leu Val Glu Glu Gly Ala Lys Thr Ala Pro Gly Lys Lys
        130                 135                 140 cgt ccg gta gag cag tcg cca caa gag cca gac tcc tcc tcg ggc atc      2699
Arg Pro Val Glu Gln Ser Pro Gln Glu Pro Asp Ser Ser Ser Gly Ile
    145                 150                 155 ggc aag aca ggc cag cag ccc gct aaa aag aga ctc aat ttt ggt cag      2747
Gly Lys Thr Gly Gln Gln Pro Ala Lys Lys Arg Leu Asn Phe Gly Gln
160                 165                 170                 175 act ggc gac tca gag tca gtc ccc gat cca caa cct ctc gga gaa cct      2795
Thr Gly Asp Ser Glu Ser Val Pro Asp Pro Gln Pro Leu Gly Glu Pro
                180                 185                 190 cca gca acc ccc gct gct gtg gga cct act aca atg gct tca ggc ggt      2843
Pro Ala Thr Pro Ala Ala Val Gly Pro Thr Thr Met Ala Ser Gly Gly
            195                 200                 205 ggc gca cca atg gca gac aat aac gaa ggc gcc gac gga gtg ggt aat      2891
Gly Ala Pro Met Ala Asp Asn Asn Glu Gly Ala Asp Gly Val Gly Asn
        210                 215                 220 gcc tca gga aat tgg cat tgc gat tcc aca tgg ctg ggc gac aga gtc      2939
Ala Ser Gly Asn Trp His Cys Asp Ser Thr Trp Leu Gly Asp Arg Val
    225                 230                 235 atc acc acc agc acc cgc acc tgg gcc ttg ccc acc tac aat aac cac      2987
Ile Thr Thr Ser Thr Arg Thr Trp Ala Leu Pro Thr Tyr Asn Asn His
240                 245                 250                 255 ctc tac aag caa atc tcc agt gct tca acg ggg gcc agc aac gac aac      3035
Leu Tyr Lys Gln Ile Ser Ser Ala Ser Thr Gly Ala Ser Asn Asp Asn
                260                 265                 270 cac tac ttc ggc tac agc acc ccc tgg ggg tat ttt gat ttc aac aga      3083
His Tyr Phe Gly Tyr Ser Thr Pro Trp Gly Tyr Phe Asp Phe Asn Arg
            275                 280                 285 ttc cac tgc cac ttt tca cca cgt gac tgg cag cga ctc atc aac aac      3131
Phe His Cys His Phe Ser Pro Arg Asp Trp Gln Arg Leu Ile Asn Asn
        290                 295                 300 aat tgg gga ttc cgg ccc aag aga ctc aac ttc aaa ctc ttc aac atc      3179
Asn Trp Gly Phe Arg Pro Lys Arg Leu Asn Phe Lys Leu Phe Asn Ile
    305                 310                 315 caa gtc aag gag gtc acg acg aat gat ggc gtc aca acc atc gct aat      3227
Gln Val Lys Glu Val Thr Thr Asn Asp Gly Val Thr Thr Ile Ala Asn
320                 325                 330                 335 aac ctt acc agc acg gtt caa gtc ttc tcg gac tcg gag tac cag ctt      3275
Asn Leu Thr Ser Thr Val Gln Val Phe Ser Asp Ser Glu Tyr Gln Leu
                340                 345                 350 ccg tac gtc ctc ggc tct gcg cac cag ggc tgc ctc cct ccg ttc ccg      3323
Pro Tyr Val Leu Gly Ser Ala His Gln Gly Cys Leu Pro Pro Phe Pro
            355                 360                 365 gcg gac gtg ttc atg att ccg caa tac ggc tac ctg acg ctc aac aat      3371
Ala Asp Val Phe Met Ile Pro Gln Tyr Gly Tyr Leu Thr Leu Asn Asn
        370                 375                 380 ggc agc caa gcc gtg gga cgt tca tcc ttt tac tgc ctg gaa tat ttc      3419
Gly Ser Gln Ala Val Gly Arg Ser Ser Phe Tyr Cys Leu Glu Tyr Phe
```

-continued

|  | 385 |  |  | 390 |  |  | 395 |  |  |  |  |  |  |  |  |  |
|---|---|---|---|---|---|---|---|---|---|---|---|---|---|---|---|---|

```
cct tct cag atg ctg aga acg ggc aac aac ttt acc ttc agc tac acc    3467
Pro Ser Gln Met Leu Arg Thr Gly Asn Asn Phe Thr Phe Ser Tyr Thr
400             405                 410                 415 ttt gag gaa gtg cct ttc cac agc agc tac gcg cac agc cag agc ctg    3515
Phe Glu Glu Val Pro Phe His Ser Ser Tyr Ala His Ser Gln Ser Leu
                420                 425                 430 gac cgg ctg atg aat cct ctc atc gac caa tac ctg tat tac ctg aac    3563
Asp Arg Leu Met Asn Pro Leu Ile Asp Gln Tyr Leu Tyr Tyr Leu Asn
            435                 440                 445 aga act caa aat cag tcc gga agt gcc caa aac aag gac ttg ctg ttt    3611
Arg Thr Gln Asn Gln Ser Gly Ser Ala Gln Asn Lys Asp Leu Leu Phe
        450                 455                 460 agc cgt ggg tct cca gct ggc atg tct gtt cag ccc aaa aac tgg cta    3659
Ser Arg Gly Ser Pro Ala Gly Met Ser Val Gln Pro Lys Asn Trp Leu
    465                 470                 475 cct gga ccc tgt tat cgg cag cag cgc gtt tct aaa aca aaa aca gac    3707
Pro Gly Pro Cys Tyr Arg Gln Gln Arg Val Ser Lys Thr Lys Thr Asp
480                 485                 490                 495 aac aac aac agc aat ttt acc tgg act ggt gct tca aaa tat aac ctc    3755
Asn Asn Asn Ser Asn Phe Thr Trp Thr Gly Ala Ser Lys Tyr Asn Leu
                500                 505                 510 aat ggg cgt gaa tcc atc atc aac cct ggc act gct atg gcc tca cac    3803
Asn Gly Arg Glu Ser Ile Ile Asn Pro Gly Thr Ala Met Ala Ser His
            515                 520                 525 aaa gac gac gaa gac aag ttc ttt ccc atg agc ggt gtc atg att ttt    3851
Lys Asp Asp Glu Asp Lys Phe Phe Pro Met Ser Gly Val Met Ile Phe
        530                 535                 540 gga aaa gag agc gcc gga gct tca aac act gca ttg gac aat gtc atg    3899
Gly Lys Glu Ser Ala Gly Ala Ser Asn Thr Ala Leu Asp Asn Val Met
    545                 550                 555 att aca gac gaa gag gaa att aaa gcc act aac cct gtg gcc acc gaa    3947
Ile Thr Asp Glu Glu Glu Ile Lys Ala Thr Asn Pro Val Ala Thr Glu
560                 565                 570                 575 aga ttt ggg acc gtg gca gtc aat ttc cag agc agc agc aca gac cct    3995
Arg Phe Gly Thr Val Ala Val Asn Phe Gln Ser Ser Ser Thr Asp Pro
                580                 585                 590 gcg acc gga gat gtg cat gct atg gga gca tta cct ggc atg gtg tgg    4043
Ala Thr Gly Asp Val His Ala Met Gly Ala Leu Pro Gly Met Val Trp
            595                 600                 605 caa gat aga gac gtg tac ctg cag ggt ccc att tgg gcc aaa att cct    4091
Gln Asp Arg Asp Val Tyr Leu Gln Gly Pro Ile Trp Ala Lys Ile Pro
        610                 615                 620 cac aca gat gga cac ttt cac ccg tct cct ctt atg ggc ggc ttt gga    4139
His Thr Asp Gly His Phe His Pro Ser Pro Leu Met Gly Gly Phe Gly
    625                 630                 635 ctc aag aac ccg cct cct cag atc ctc atc aaa aac acg cct gtt cct    4187
Leu Lys Asn Pro Pro Pro Gln Ile Leu Ile Lys Asn Thr Pro Val Pro
640                 645                 650                 655 gcg aat cct ccg gcg gag ttt tca gct aca aag ttt gct tca ttc atc    4235
Ala Asn Pro Pro Ala Glu Phe Ser Ala Thr Lys Phe Ala Ser Phe Ile
                660                 665                 670 acc caa tac tcc aca gga caa gtg agt gtg gaa att gaa tgg gag ctg    4283
Thr Gln Tyr Ser Thr Gly Gln Val Ser Val Glu Ile Glu Trp Glu Leu
            675                 680                 685 cag aaa gaa aac agc aag cgc tgg aat ccc gaa gtg cag tac aca tcc    4331
Gln Lys Glu Asn Ser Lys Arg Trp Asn Pro Glu Val Gln Tyr Thr Ser
        690                 695                 700 aat tat gca aaa tct gcc aac gtt gat ttt act gtg gac aac aat gga    4379
```

```
                Asn Tyr Ala Lys Ser Ala Asn Val Asp Phe Thr Val Asp Asn Asn Gly
                    705                 710                 715 ctt tat act gag cct cgc ccc att ggc acc cgt tac ctt acc cgt ccc              4427
Leu Tyr Thr Glu Pro Arg Pro Ile Gly Thr Arg Tyr Leu Thr Arg Pro
720                 725                 730                 735 ctg taa ttacgtgtta atcaataaac cggttgattc gtttcagttg aactttggtc               4483
Leu tcctgtcctt cttatcttat cggttaccat ggtatagct tacacattaa ctgcttggtt            4543
gcgcttcgcg ataaaagact tacgtcatcg ggttacccct agtgatggag ttgcccactc            4603
cctctctgcg cgctcgctcg ctcggtgggg cctgcggacc aaaggtccgc agacggcaga            4663
gctctgctct gccggcccca ccgagcgagc gagcgcgcag agagggagtg ggcaa                 4718
```

<210> SEQ ID NO 14
<211> LENGTH: 736
<212> TYPE: PRT
<213> ORGANISM: Artificial Sequence
<220> FEATURE:
<223> OTHER INFORMATION: Synthetic Construct

<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270
```

```
Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
```

690                 695                 700
Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 15
<211> LENGTH: 4679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 2
<220> FEATURE:
<221> NAME/KEY: CDS
<222> LOCATION: (2203)..(4410)
<223> OTHER INFORMATION: AAV2 VP1
<220> FEATURE:
<221> NAME/KEY: misc_feature
<222> LOCATION: (2614)..(4410)
<223> OTHER INFORMATION: AAV2 VP2
<220> FEATURE:
<221> NAME/KEY: misc_feature
<222> LOCATION: (2809)..(4410)
<223> OTHER INFORMATION: AAV2 VP3

<400> SEQUENCE: 15
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat    240
gtggtcacgc tgggtattta gcccgagtg agcacgcagg gtctccattt tgaagcggga    300
ggtttgaacg cgcagccgcc atgccggggt tttacgagat tgtgattaag gtccccagcg    360
accttgacga gcatctgccc ggcatttctg acagctttgt gaactgggtg gccgagaagg    420
aatgggagtt gccgccagat tctgacatgg atctgaatct gattgagcag caccccctga    480
ccgtggccga gaagctgcag cgcgactttc tgacggaatg cgccgtgtg agtaaggccc    540 cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg gaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca agagaatca gaatcccaat tctgatgcgc    960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagccccgtg gaggacattt    1200 ccagcaatcg gatttataaa attttggaac taaacgggta cgatcccaa tatgcggctt    1260 ccgtcttctct gggatgggcc acgaaaaagt tcggcaagag gaacaccatc tggctgtttg    1320
ggcctgcaac taccgggaag accaacatcg cggaggccat agcccacact gtgcccttct    1380

```
acgggtgcgt aaactggacc aatgagaact ttcccttcaa cgactgtgtc gacaagatgg    1440
tgatctggtg ggaggagggg aagatgaccg ccaaggtcgt ggagtcggcc aaagccattc    1500
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa    1740 aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gt atg gct gcc gat       2214
                                              Met Ala Ala Asp
                                              1 ggt tat ctt cca gat tgg ctc gag gac act ctc tct gaa gga ata aga     2262
Gly Tyr Leu Pro Asp Trp Leu Glu Asp Thr Leu Ser Glu Gly Ile Arg
5                  10                  15                  20 cag tgg tgg aag ctc aaa cct ggc cca cca cca aag ccc gca gag          2310
Gln Trp Trp Lys Leu Lys Pro Gly Pro Pro Pro Lys Pro Ala Glu
            25                  30                  35 cgg cat aag gac gac agc agg ggt ctt gtg ctt cct ggg tac aag tac     2358
Arg His Lys Asp Asp Ser Arg Gly Leu Val Leu Pro Gly Tyr Lys Tyr
                40                  45                  50 ctc gga ccc ttc aac gga ctc gac aag gga gag ccg gtc aac gag gca     2406
Leu Gly Pro Phe Asn Gly Leu Asp Lys Gly Glu Pro Val Asn Glu Ala
            55                  60                  65 gac gcc gcg gcc ctc gag cac gac aaa gcc tac gac cgg cag ctc gac     2454
Asp Ala Ala Ala Leu Glu His Asp Lys Ala Tyr Asp Arg Gln Leu Asp
        70                  75                  80 agc gga gac aac ccg tac ctc aag tac aac cac gcc gac gcg gag ttt     2502
Ser Gly Asp Asn Pro Tyr Leu Lys Tyr Asn His Ala Asp Ala Glu Phe
85                  90                  95                  100 cag gag cgc ctt aaa gaa gat acg tct ttt ggg ggc aac ctc gga cga     2550
Gln Glu Arg Leu Lys Glu Asp Thr Ser Phe Gly Gly Asn Leu Gly Arg
                105                 110                 115 gca gtc ttc cag gcg aaa aag agg gtt ctt gaa cct ctg ggc ctg gtt     2598
Ala Val Phe Gln Ala Lys Lys Arg Val Leu Glu Pro Leu Gly Leu Val
            120                 125                 130 gag gaa cct gtt aag acg gct ccg gga aaa aag agg ccg gta gag cac     2646
Glu Glu Pro Val Lys Thr Ala Pro Gly Lys Lys Arg Pro Val Glu His
        135                 140                 145 tct cct gtg gag cca gac tcc tcc tcg gga acc gga aag gcg ggc cag     2694
Ser Pro Val Glu Pro Asp Ser Ser Ser Gly Thr Gly Lys Ala Gly Gln
    150                 155                 160 cag cct gca aga aaa aga ttg aat ttt ggt cag act gga gac gca gac     2742
Gln Pro Ala Arg Lys Arg Leu Asn Phe Gly Gln Thr Gly Asp Ala Asp
165                 170                 175                 180 tca gta cct gac ccc cag cct ctc gga cag cca cca gca gcc ccc tct     2790
Ser Val Pro Asp Pro Gln Pro Leu Gly Gln Pro Pro Ala Ala Pro Ser
                185                 190                 195 ggt ctg gga act aat acg atg gct aca ggc agt ggc gca cca atg gca     2838
```

|   |   |   |   |   |   |   |   |   |   |   |   |   |   |
|---|---|---|---|---|---|---|---|---|---|---|---|---|---|
| Gly | Leu | Gly | Thr | Asn | Thr | Met | Ala | Thr | Gly | Ser | Gly | Ala | Pro | Met | Ala |
|     |     |     | 200 |     |     |     | 205 |     |     |     | 210 |     |     |

```
gac aat aac gag ggc gcc gac gga gtg ggt aat tcc tcg gga aat tgg        2886
Asp Asn Asn Glu Gly Ala Asp Gly Val Gly Asn Ser Ser Gly Asn Trp
            215                 220                 225 cat tgc gat tcc aca tgg atg ggc gac aga gtc atc acc acc agc acc        2934
His Cys Asp Ser Thr Trp Met Gly Asp Arg Val Ile Thr Thr Ser Thr
230                 235                 240 cga acc tgg gcc ctg ccc acc tac aac aac cac ctc tac aaa caa att        2982
Arg Thr Trp Ala Leu Pro Thr Tyr Asn Asn His Leu Tyr Lys Gln Ile
245                 250                 255                 260 tcc agc caa tca gga gcc tcg aac gac aat cac tac ttt ggc tac agc        3030
Ser Ser Gln Ser Gly Ala Ser Asn Asp Asn His Tyr Phe Gly Tyr Ser
            265                 270                 275 acc cct tgg ggg tat ttt gac ttc aac aga ttc cac tgc cac ttt tca        3078
Thr Pro Trp Gly Tyr Phe Asp Phe Asn Arg Phe His Cys His Phe Ser
            280                 285                 290 cca cgt gac tgg caa aga ctc atc aac aac aac tgg gga ttc cga ccc        3126
Pro Arg Asp Trp Gln Arg Leu Ile Asn Asn Asn Trp Gly Phe Arg Pro
            295                 300                 305 aag aga ctc aac ttc aag ctc ttt aac att caa gtc aaa gag gtc acg        3174
Lys Arg Leu Asn Phe Lys Leu Phe Asn Ile Gln Val Lys Glu Val Thr
310                 315                 320 cag aat gac ggt acg acg acg att gcc aat aac ctt acc agc acg gtt        3222
Gln Asn Asp Gly Thr Thr Thr Ile Ala Asn Asn Leu Thr Ser Thr Val
325                 330                 335                 340 cag gtg ttt act gac tcg gag tac cag ctc ccg tac gtc ctc ggc tcg        3270
Gln Val Phe Thr Asp Ser Glu Tyr Gln Leu Pro Tyr Val Leu Gly Ser
            345                 350                 355 gcg cat caa gga tgc ctc ccg ccg ttc cca gca gac gtc ttc atg gtg        3318
Ala His Gln Gly Cys Leu Pro Pro Phe Pro Ala Asp Val Phe Met Val
            360                 365                 370 cca cag tat gga tac ctc acc ctg aac aac ggg agt cag gca gta gga        3366
Pro Gln Tyr Gly Tyr Leu Thr Leu Asn Asn Gly Ser Gln Ala Val Gly
            375                 380                 385 cgc tct tca ttt tac tgc ctg gag tac ttt cct tct cag atg ctg cgt        3414
Arg Ser Ser Phe Tyr Cys Leu Glu Tyr Phe Pro Ser Gln Met Leu Arg
390                 395                 400 acc gga aac aac ttt acc ttc agc tac act ttt gag gac gtt cct ttc        3462
Thr Gly Asn Asn Phe Thr Phe Ser Tyr Thr Phe Glu Asp Val Pro Phe
405                 410                 415                 420 cac agc agc tac gct cac agc cag agt ctg gac cgt ctc atg aat cct        3510
His Ser Ser Tyr Ala His Ser Gln Ser Leu Asp Arg Leu Met Asn Pro
                425                 430                 435 ctc atc gac cag tac ctg tat tac ttg agc aga aca aac act cca agt        3558
Leu Ile Asp Gln Tyr Leu Tyr Tyr Leu Ser Arg Thr Asn Thr Pro Ser
            440                 445                 450 gga acc acc acg cag tca agg ctt cag ttt tct cag gcc gga gcg agt        3606
Gly Thr Thr Thr Gln Ser Arg Leu Gln Phe Ser Gln Ala Gly Ala Ser
            455                 460                 465 gac att cgg gac cag tct agg aac tgg ctt cct gga ccc tgt tac cgc        3654
Asp Ile Arg Asp Gln Ser Arg Asn Trp Leu Pro Gly Pro Cys Tyr Arg
470                 475                 480 cag cag cga gta tca aag aca tct gcg gat aac aac aac agt gaa tac        3702
Gln Gln Arg Val Ser Lys Thr Ser Ala Asp Asn Asn Asn Ser Glu Tyr
485                 490                 495                 500 tcg tgg act gga gct acc aag tac cac ctc aat ggc aga gac tct ctg        3750
Ser Trp Thr Gly Ala Thr Lys Tyr His Leu Asn Gly Arg Asp Ser Leu
            505                 510                 515
```

| | | | | | | | | | | | | | | | |
|---|---|---|---|---|---|---|---|---|---|---|---|---|---|---|---|
| gtg | aat | ccg | ggc | ccg | gcc | atg | gca | agc | cac | aag | gac | gat | gaa | gaa | aag | 3798 |
| Val | Asn | Pro | Gly | Pro | Ala | Met | Ala | Ser | His | Lys | Asp | Asp | Glu | Glu | Lys | |
| | | | 520 | | | | 525 | | | | | 530 | | | | |

| ttt | ttt | cct | cag | agc | ggg | gtt | ctc | atc | ttt | ggg | aag | caa | ggc | tca | gag | 3846 |
|---|---|---|---|---|---|---|---|---|---|---|---|---|---|---|---|---|
| Phe | Phe | Pro | Gln | Ser | Gly | Val | Leu | Ile | Phe | Gly | Lys | Gln | Gly | Ser | Glu | |
| | | | 535 | | | | | 540 | | | | | 545 | | | |

| aaa | aca | aat | gtg | gac | att | gaa | aag | gtc | atg | att | aca | gac | gaa | gag | gaa | 3894 |
|---|---|---|---|---|---|---|---|---|---|---|---|---|---|---|---|---|
| Lys | Thr | Asn | Val | Asp | Ile | Glu | Lys | Val | Met | Ile | Thr | Asp | Glu | Glu | Glu | |
| | 550 | | | | | 555 | | | | | 560 | | | | | |

| atc | agg | aca | acc | aat | ccc | gtg | gct | acg | gag | cag | tat | ggt | tct | gta | tct | 3942 |
|---|---|---|---|---|---|---|---|---|---|---|---|---|---|---|---|---|
| Ile | Arg | Thr | Thr | Asn | Pro | Val | Ala | Thr | Glu | Gln | Tyr | Gly | Ser | Val | Ser | |
| 565 | | | | | 570 | | | | | 575 | | | | | 580 | |

| acc | aac | ctc | cag | aga | ggc | aac | aga | caa | gca | gct | acc | gca | gat | gtc | aac | 3990 |
|---|---|---|---|---|---|---|---|---|---|---|---|---|---|---|---|---|
| Thr | Asn | Leu | Gln | Arg | Gly | Asn | Arg | Gln | Ala | Ala | Thr | Ala | Asp | Val | Asn | |
| | | | | | 585 | | | | | 590 | | | | | 595 | |

| aca | caa | ggc | gtt | ctt | cca | ggc | atg | gtc | tgg | cag | gac | aga | gat | gtg | tac | 4038 |
|---|---|---|---|---|---|---|---|---|---|---|---|---|---|---|---|---|
| Thr | Gln | Gly | Val | Leu | Pro | Gly | Met | Val | Trp | Gln | Asp | Arg | Asp | Val | Tyr | |
| | | | 600 | | | | | 605 | | | | | 610 | | | |

| ctt | cag | ggg | ccc | atc | tgg | gca | aag | att | cca | cac | acg | gac | gga | cat | ttt | 4086 |
|---|---|---|---|---|---|---|---|---|---|---|---|---|---|---|---|---|
| Leu | Gln | Gly | Pro | Ile | Trp | Ala | Lys | Ile | Pro | His | Thr | Asp | Gly | His | Phe | |
| | | | 615 | | | | | 620 | | | | | 625 | | | |

| cac | ccc | tct | ccc | ctc | atg | ggt | gga | ttc | gga | ctt | aaa | cac | cct | cct | cca | 4134 |
|---|---|---|---|---|---|---|---|---|---|---|---|---|---|---|---|---|
| His | Pro | Ser | Pro | Leu | Met | Gly | Gly | Phe | Gly | Leu | Lys | His | Pro | Pro | Pro | |
| | 630 | | | | | 635 | | | | | 640 | | | | | |

| cag | att | ctc | atc | aag | aac | acc | ccg | gta | cct | gcg | aat | cct | tcg | acc | acc | 4182 |
|---|---|---|---|---|---|---|---|---|---|---|---|---|---|---|---|---|
| Gln | Ile | Leu | Ile | Lys | Asn | Thr | Pro | Val | Pro | Ala | Asn | Pro | Ser | Thr | Thr | |
| 645 | | | | | 650 | | | | | 655 | | | | | 660 | |

| ttc | agt | gcg | gca | aag | ttt | gct | tcc | ttc | atc | aca | cag | tac | tcc | acg | gga | 4230 |
|---|---|---|---|---|---|---|---|---|---|---|---|---|---|---|---|---|
| Phe | Ser | Ala | Ala | Lys | Phe | Ala | Ser | Phe | Ile | Thr | Gln | Tyr | Ser | Thr | Gly | |
| | | | | 665 | | | | | 670 | | | | | 675 | | |

| cag | gtc | agc | gtg | gag | atc | gag | tgg | gag | ctg | cag | aag | gaa | aac | agc | aaa | 4278 |
|---|---|---|---|---|---|---|---|---|---|---|---|---|---|---|---|---|
| Gln | Val | Ser | Val | Glu | Ile | Glu | Trp | Glu | Leu | Gln | Lys | Glu | Asn | Ser | Lys | |
| | | | 680 | | | | | 685 | | | | | 690 | | | |

| cgc | tgg | aat | ccc | gaa | att | cag | tac | act | tcc | aac | tac | aac | aag | tct | gtt | 4326 |
|---|---|---|---|---|---|---|---|---|---|---|---|---|---|---|---|---|
| Arg | Trp | Asn | Pro | Glu | Ile | Gln | Tyr | Thr | Ser | Asn | Tyr | Asn | Lys | Ser | Val | |
| | | | 695 | | | | | 700 | | | | | 705 | | | |

| aat | gtg | gac | ttt | act | gtg | gac | act | aat | ggc | gtg | tat | tca | gag | cct | cgc | 4374 |
|---|---|---|---|---|---|---|---|---|---|---|---|---|---|---|---|---|
| Asn | Val | Asp | Phe | Thr | Val | Asp | Thr | Asn | Gly | Val | Tyr | Ser | Glu | Pro | Arg | |
| | 710 | | | | | 715 | | | | | 720 | | | | | |

| ccc | att | ggc | acc | aga | tac | ctg | act | cgt | aat | ctg | taa | ttgcttgtta | | | | 4420 |
|---|---|---|---|---|---|---|---|---|---|---|---|---|---|---|---|---|
| Pro | Ile | Gly | Thr | Arg | Tyr | Leu | Thr | Arg | Asn | Leu | | | | | | |
| 725 | | | | | 730 | | | | | 735 | | | | | | |

| | |
|---|---|
| atcaataaac cgtttaattc gtttcagttg aactttggtc tctgcgtatt tctttcttat | 4480 |
| ctagtttcca tggctacgta gataagtagc atggcgggtt aatcattaac tacaaggaac | 4540 |
| ccctagtgat ggagttggcc actccctctc tgcgcgctcg ctcgctcact gaggccgggc | 4600 |
| gaccaaaggt cgcccgacgc ccgggctttg cccgggcggc ctcagtgagc gagcgagcgc | 4660 |
| gcagagaggg agtggccaa | 4679 |

<210> SEQ ID NO 16
<211> LENGTH: 735
<212> TYPE: PRT
<213> ORGANISM: Artificial Sequence
<220> FEATURE:
<223> OTHER INFORMATION: Synthetic Construct

<400> SEQUENCE: 16

Met Ala Ala Asp Gly Tyr Leu Pro Asp Trp Leu Glu Asp Thr Leu Ser
1               5                   10                  15

-continued

Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr

```
                    435                 440                 445
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 17
<211> LENGTH: 4726
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 3
<220> FEATURE:
<221> NAME/KEY: CDS
<222> LOCATION: (2209)..(4419)
<223> OTHER INFORMATION: AAV3 VP1
<220> FEATURE:
<221> NAME/KEY: misc_feature
<222> LOCATION: (2620)..(4419)
<223> OTHER INFORMATION: AAV3 VP2
<220> FEATURE:
<221> NAME/KEY: misc_feature
<222> LOCATION: (2815)..(4419)
<223> OTHER INFORMATION: AAV3 VP3
```

-continued

<400> SEQUENCE: 17

```
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaactcca tcactagagg tatggcagtg acgtaacgcg aagcgcgcga agcgagacca     180
cgcctaccag ctgcgtcagc agtcaggtga ccctttttgcg acagtttgcg acaccacgtg    240
gccgctgagg gtatatattc tcgagtgagc gaaccaggag ctccattttg accgcgaaat     300
ttgaacgagc agcagccatg ccggggttct acgagattgt cctgaaggtc ccgagtgacc     360
tggacgagcg cctgccgggc atttctaact cgtttgttaa ctgggtggcc gagaaggaat     420
gggacgtgcc gccggattct gacatggatc cgaatctgat tgagcaggca ccctgaccg      480
tggccgaaaa gcttcagcgc gagttcctgg tggagtggcg ccgcgtgagt aaggccccgg     540
aggccctctt ttttgtccag ttcgaaaagg gggagaccta cttccacctg cacgtgctga     600
ttgagaccat cggggtcaaa tccatggtgg tcggccgcta cgtgagccag attaaagaga     660
agctggtgac ccgcatctac cgcggggtcg agccgcagct tccgaactgg ttcgcggtga     720
ccaaaacgcg aaatggcgcc gggggcggga acaaggtggt ggacgactgc tacatcccca     780
actacctgct ccccaagacc cagcccgagc tccagtgggc gtggactaac atggaccagt     840
atttaagcgc ctgtttgaat ctcgcggagc gtaaacggct ggtggcgcag catctgacgc     900
acgtgtcgca gacgcaggag cagaacaaag agaatcagaa ccccaattct gacgcgccgg     960
tcatcaggtc aaaaacctca gccaggtaca tggagctggt cgggtggctg gtggaccgcg    1020
ggatcacgtc agaaaagcaa tggattcagg aggaccaggc ctcgtacatc tccttcaacg    1080
ccgcctccaa ctcgcggtcc cagatcaagg ccgcgctgga caatgcctcc aagatcatga    1140
gcctgacaaa gacggctccg gactacctgg tgggcagcaa cccgccggag gacattacca    1200
aaaatcggat ctaccaaatc ctggagctga acgggtacga tccgcagtac gcggcctccg    1260
tcttcctggg ctgggcgcaa aagaagttcg ggaagaggaa caccatctgg ctctttgggc    1320
cggccacgac gggtaaaaac aacatcgcgg aagccatcgc ccacgccgtg cccttctacg    1380
gctgcgtaaa ctggaccaat gagaactttc ccttcaacga ttgcgtcgac aagatggtga    1440
tctggtggga ggagggcaag atgacggcca aggtcgtgga gagcgccaag gccattctgg    1500
gcggaagcaa ggtgcgcgtg gaccaaaagt gcaagtcatc ggcccagatc gaacccactc    1560
ccgtgatcgt cacctccaac accaacatgt gcgccgtgat tgacgggaac agcaccacct    1620
tcgagcatca gcagccgctg caggaccgga tgtttgaatt tgaacttacc cgccgtttgg    1680
accatgactt tgggaaggtc accaaacagg aagtaaagga ctttttccgg tgggcttccg    1740
atcacgtgac tgacgtggct catgagttct acgtcagaaa gggtggagct aagaaacgcc    1800
ccgcctccaa tgacgcggat gtaagcgagc aaaacggga gtgcacgtca cttgcgcagc    1860
cgacaacgtc agacgcggaa gcaccggcgg actacgcgga caggtaccaa aacaaatgtt    1920
ctcgtcacgt gggcatgaat ctgatgcttt ttccctgtaa acatgcgag agaatgaatc     1980
aaatttccaa tgtctgtttt acgcatggtc aaagagactg tggggaatgc ttccctggaa    2040
tgtcagaatc tcaacccgtt tctgtcgtca aaagaagac ttatcagaaa ctgtgtccaa     2100
ttcatcatat cctgggaagg gcacccgaga ttgcctgttc ggcctgcgat ttggccaatg    2160
tggacttgga tgactgtgtt tctgagcaat aaatgactta accaggt atg gct gct     2217
                                                    Met Ala Ala
                                                     1
gac ggt tat ctt cca gat tgg ctc gag gac aac ctt tct gaa ggc att      2265
```

```
Asp Gly Tyr Leu Pro Asp Trp Leu Glu Asp Asn Leu Ser Glu Gly Ile
  5              10                  15 cgt gag tgg tgg gct ctg aaa cct gga gtc cct caa ccc aaa gcg aac    2313
Arg Glu Trp Trp Ala Leu Lys Pro Gly Val Pro Gln Pro Lys Ala Asn
 20              25                  30                  35 caa caa cac cag gac aac cgt cgg ggt ctt gtg ctt ccg ggt tac aaa    2361
Gln Gln His Gln Asp Asn Arg Arg Gly Leu Val Leu Pro Gly Tyr Lys
             40                  45                  50 tac ctc gga ccc ggt aac gga ctc gac aaa gga gag ccg gtc aac gag    2409
Tyr Leu Gly Pro Gly Asn Gly Leu Asp Lys Gly Glu Pro Val Asn Glu
             55                  60                  65 gcg gac gcg gca gcc ctc gaa cac gac aaa gct tac gac cag cag ctc    2457
Ala Asp Ala Ala Ala Leu Glu His Asp Lys Ala Tyr Asp Gln Gln Leu
         70                  75                  80 aag gcc ggt gac aac ccg tac ctc aag tac aac cac gcc gac gcc gag    2505
Lys Ala Gly Asp Asn Pro Tyr Leu Lys Tyr Asn His Ala Asp Ala Glu
 85                  90                  95 ttt cag gag cgt ctt caa gaa gat acg tct ttt ggg ggc aac ctt ggc    2553
Phe Gln Glu Arg Leu Gln Glu Asp Thr Ser Phe Gly Gly Asn Leu Gly
100                 105                 110                 115 aga gca gtc ttc cag gcc aaa aag agg atc ctt gag cct ctt ggt ctg    2601
Arg Ala Val Phe Gln Ala Lys Lys Arg Ile Leu Glu Pro Leu Gly Leu
                120                 125                 130 gtt gag gaa gca gct aaa acg gct cct gga aag aag ggg gct gta gat    2649
Val Glu Glu Ala Ala Lys Thr Ala Pro Gly Lys Lys Gly Ala Val Asp
                135                 140                 145 cag tct cct cag gaa ccg gac tca tca tct ggt gtt ggc aaa tcg ggc    2697
Gln Ser Pro Gln Glu Pro Asp Ser Ser Ser Gly Val Gly Lys Ser Gly
        150                 155                 160 aaa cag cct gcc aga aaa aga cta aat ttc ggt cag act gga gac tca    2745
Lys Gln Pro Ala Arg Lys Arg Leu Asn Phe Gly Gln Thr Gly Asp Ser
165                 170                 175 gag tca gtc cca gac cct caa cct ctc gga gaa cca cca gca gcc ccc    2793
Glu Ser Val Pro Asp Pro Gln Pro Leu Gly Glu Pro Pro Ala Ala Pro
180                 185                 190                 195 aca agt ttg gga tct aat aca atg gct tca ggc ggt ggc gca cca atg    2841
Thr Ser Leu Gly Ser Asn Thr Met Ala Ser Gly Gly Gly Ala Pro Met
                200                 205                 210 gca gac aat aac gag ggt gcc gat gga gtg ggt aat tcc tca gga aat    2889
Ala Asp Asn Asn Glu Gly Ala Asp Gly Val Gly Asn Ser Ser Gly Asn
                215                 220                 225 tgg cat tgc gat tcc caa tgg ctg ggc gac aga gtc atc acc acc agc    2937
Trp His Cys Asp Ser Gln Trp Leu Gly Asp Arg Val Ile Thr Thr Ser
        230                 235                 240 acc aga acc tgg gcc ctg ccc act tac aac aac cat ctc tac aag caa    2985
Thr Arg Thr Trp Ala Leu Pro Thr Tyr Asn Asn His Leu Tyr Lys Gln
245                 250                 255 atc tcc agc caa tca gga gct tca aac gac aac cac tac ttt ggc tac    3033
Ile Ser Ser Gln Ser Gly Ala Ser Asn Asp Asn His Tyr Phe Gly Tyr
260                 265                 270                 275 agc acc cct tgg ggg tat ttt gac ttt aac aga ttc cac tgc cac ttc    3081
Ser Thr Pro Trp Gly Tyr Phe Asp Phe Asn Arg Phe His Cys His Phe
                280                 285                 290 tca cca cgt gac tgg cag cga ctc att aac aac aac tgg gga ttc cgg    3129
Ser Pro Arg Asp Trp Gln Arg Leu Ile Asn Asn Asn Trp Gly Phe Arg
                295                 300                 305 ccc aag aaa ctc agc ttc aag ctc ttc aac atc caa gtt aga ggg gtc    3177
Pro Lys Lys Leu Ser Phe Lys Leu Phe Asn Ile Gln Val Arg Gly Val
                310                 315                 320
```

```
acg cag aac gat ggc acg acg act att gcc aat aac ctt acc agc acg   3225
Thr Gln Asn Asp Gly Thr Thr Thr Ile Ala Asn Asn Leu Thr Ser Thr
325                 330                 335 gtt caa gtg ttt acg gac tcg gag tat cag ctc ccg tac gtg ctc ggg   3273
Val Gln Val Phe Thr Asp Ser Glu Tyr Gln Leu Pro Tyr Val Leu Gly
340                 345                 350                 355 tcg gcg cac caa ggc tgt ctc ccg ccg ttt cca gcg gac gtc ttc atg   3321
Ser Ala His Gln Gly Cys Leu Pro Pro Phe Pro Ala Asp Val Phe Met
                360                 365                 370 gtc cct cag tat gga tac ctc acc ctg aac aac gga agt caa gcg gtg   3369
Val Pro Gln Tyr Gly Tyr Leu Thr Leu Asn Asn Gly Ser Gln Ala Val
            375                 380                 385 gga cgc tca tcc ttt tac tgc ctg gag tac ttc cct tcg cag atg cta   3417
Gly Arg Ser Ser Phe Tyr Cys Leu Glu Tyr Phe Pro Ser Gln Met Leu
        390                 395                 400 agg act gga aat aac ttc caa ttc agc tat acc ttc gag gat gta cct   3465
Arg Thr Gly Asn Asn Phe Gln Phe Ser Tyr Thr Phe Glu Asp Val Pro
    405                 410                 415 ttt cac agc agc tac gct cac agc cag agt ttg gat cgc ttg atg aat   3513
Phe His Ser Ser Tyr Ala His Ser Gln Ser Leu Asp Arg Leu Met Asn
420                 425                 430                 435 cct ctt att gat cag tat ctg tac tac ctg aac aga acg caa gga aca   3561
Pro Leu Ile Asp Gln Tyr Leu Tyr Tyr Leu Asn Arg Thr Gln Gly Thr
                440                 445                 450 acc tct gga aca acc aac caa tca cgg ctg ctt ttt agc cag gct ggg   3609
Thr Ser Gly Thr Thr Asn Gln Ser Arg Leu Leu Phe Ser Gln Ala Gly
            455                 460                 465 cct cag tct atg tct ttg cag gcc aga aat tgg cta cct ggg ccc tgc   3657
Pro Gln Ser Met Ser Leu Gln Ala Arg Asn Trp Leu Pro Gly Pro Cys
        470                 475                 480 tac cgg caa cag aga ctt tca aag act gct aac gac aac aac aac agt   3705
Tyr Arg Gln Gln Arg Leu Ser Lys Thr Ala Asn Asp Asn Asn Asn Ser
    485                 490                 495 aac ttt cct tgg aca gcg gcc agc aaa tat cat ctc aat ggc cgc gac   3753
Asn Phe Pro Trp Thr Ala Ala Ser Lys Tyr His Leu Asn Gly Arg Asp
500                 505                 510                 515 tcg ctg gtg aat cca gga cca gct atg gcc agt cac aag gac gat gaa   3801
Ser Leu Val Asn Pro Gly Pro Ala Met Ala Ser His Lys Asp Asp Glu
                520                 525                 530 gaa aaa ttt ttc cct atg cac ggc aat cta ata ttt ggc aaa gaa ggg   3849
Glu Lys Phe Phe Pro Met His Gly Asn Leu Ile Phe Gly Lys Glu Gly
            535                 540                 545 aca acg gca agt aac gca gaa tta gat aat gta atg att acg gat gaa   3897
Thr Thr Ala Ser Asn Ala Glu Leu Asp Asn Val Met Ile Thr Asp Glu
        550                 555                 560 gaa gag att cgt acc acc aat cct gtg gca aca gag cag tat gga act   3945
Glu Glu Ile Arg Thr Thr Asn Pro Val Ala Thr Glu Gln Tyr Gly Thr
    565                 570                 575 gtg gca aat aac ttg cag agc tca aat aca gct ccc acg act gga act   3993
Val Ala Asn Asn Leu Gln Ser Ser Asn Thr Ala Pro Thr Thr Gly Thr
580                 585                 590                 595 gtc aat cat cag ggg gcc tta cct ggc atg gtg tgg caa gat cgt gac   4041
Val Asn His Gln Gly Ala Leu Pro Gly Met Val Trp Gln Asp Arg Asp
                600                 605                 610 gtg tac ctt caa gga cct atc tgg gca aag att cct cac acg gat gga   4089
Val Tyr Leu Gln Gly Pro Ile Trp Ala Lys Ile Pro His Thr Asp Gly
            615                 620                 625 cac ttt cat cct tct cct ctg atg gga ggc ttt gga ctg aaa cat ccg   4137
His Phe His Pro Ser Pro Leu Met Gly Gly Phe Gly Leu Lys His Pro
        630                 635                 640
```

```
cct cct caa atc atg atc aaa aat act ccg gta ccg gca aat cct ccg      4185
Pro Pro Gln Ile Met Ile Lys Asn Thr Pro Val Pro Ala Asn Pro Pro
645                 650                 655 acg act ttc agc ccg gcc aag ttt gct tca ttt atc act cag tac tcc      4233
Thr Thr Phe Ser Pro Ala Lys Phe Ala Ser Phe Ile Thr Gln Tyr Ser
660                 665                 670                 675 act gga cag gtc agc gtg gaa att gag tgg gag cta cag aaa gaa aac      4281
Thr Gly Gln Val Ser Val Glu Ile Glu Trp Glu Leu Gln Lys Glu Asn
                680                 685                 690 agc aaa cgt tgg aat cca gag att cag tac act tcc aac tac aac aag      4329
Ser Lys Arg Trp Asn Pro Glu Ile Gln Tyr Thr Ser Asn Tyr Asn Lys
            695                 700                 705 tct gtt aat gtg gac ttt act gta gac act aat ggt gtt tat agt gaa      4377
Ser Val Asn Val Asp Phe Thr Val Asp Thr Asn Gly Val Tyr Ser Glu
        710                 715                 720 cct cgc cct att gga acc cgg tat ctc aca cga aac ttg tga              4419
Pro Arg Pro Ile Gly Thr Arg Tyr Leu Thr Arg Asn Leu
    725                 730                 735 atcctggtta atcaataaac cgtttaattc gtttcagttg aactttggct cttgtgcact    4479
tctttatctt tatcttgttt ccatggctac tgcgtagata agcagcggcc tgcggcgctt    4539
gcgcttcgcg gtttacaact gctggttaat atttaactct cgccatacct ctagtgatgg    4599
agttggccac tccctctatg cgcactcgct cgctcggtgg ggcctggcga ccaaaggtcg    4659
ccagacggac gtgctttgca cgtccggccc caccgagcga gcgagtgcgc atagagggag    4719
tggccaa                                                              4726

<210> SEQ ID NO 18
<211> LENGTH: 736
<212> TYPE: PRT
<213> ORGANISM: Artificial Sequence
<220> FEATURE:
<223> OTHER INFORMATION: Synthetic Construct

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175
```

```
Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590
```

```
Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 19
<211> LENGTH: 4767
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 4
<220> FEATURE:
<221> NAME/KEY: CDS
<222> LOCATION: (2260)..(4464)
<223> OTHER INFORMATION: AAV4 VP1
<220> FEATURE:
<221> NAME/KEY: misc_feature
<222> LOCATION: (2668)..(4464)
<223> OTHER INFORMATION: AAV4 VP2
<220> FEATURE:
<221> NAME/KEY: misc_feature
<222> LOCATION: (2848)..(4464)
<223> OTHER INFORMATION: AAV4 VP3

<400> SEQUENCE: 19
ttggccactc cctctatgcg cgctcgctca ctcactcggc cctggagacc aaaggtctcc    60
agactgccgg cctctggccg gcagggccga gtgagtgagc gagcgcgcat agagggagtg   120
gccaactcca tcatctaggt ttgcccactg acgtcaatgt gacgtcctag ggttagggag   180
gtccctgtat tagcagtcac gtgagtgtcg tatttcgcgg agcgtagcgg agcgcatacc   240
aagctgccac gtcacagcca cgtggtccgt ttgcgacagt ttgcgacacc atgtggtcag   300
gagggtatat aaccgcgagt gagccagcga ggagctccat tttgcccgcg aattttgaac   360
gagcagcagc catgccgggg ttctacgaga tcgtgctgaa ggtgcccagc gacctggacg   420
agcacctgcc cggcatttct gactcttttg tgagctgggt ggccgagaag gaatgggagc   480
tgccgccgga ttctgacatg gacttgaatc tgattgagca ggcacccctg accgtggccg   540
aaaagctgca acgcgagttc ctggtcgagt ggcgccgcgt gagtaaggcc ccggaggccc   600
tcttctttgt ccagttcgag aagggggaca gctacttcca cctgcacatc ctggtggaga   660
ccgtgggcgt caaatccatg gtggtgggcg gctacgtgag ccagattaaa gagaagctgg   720
tgaccccgca ctaccgcggg gtcgagccgc agcttccgaa ctggttcgcg gtgaccaaga   780
cgcgtaatgg cgccggaggc gggaacaagg tggtggacga ctgctacatc cccaactacc   840
```

```
tgctccccaa gacccagccc gagctccagt gggcgtggac taacatggac cagtatataa    900
gcgcctgttt gaatctcgcg gagcgtaaac ggctggtggc gcagcatctg acgcacgtgt    960
cgcagacgca ggagcagaac aaggaaaacc agaaccccaa ttctgacgcg ccggtcatca   1020
ggtcaaaaac ctccgccagg tacatggagc tggtcgggtg gctggtggac cgcgggatca   1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
caaagacggc tccggactac ctggtgggcc agaacccgcc ggaggacatt ccagcaacc    1260
gcatctaccg aatcctcgag atgaacgggt acgatccgca gtacgcggcc tccgtcttcc   1320
tgggctgggc gcaaaagaag ttcgggaaga ggaacaccat ctggctcttt gggccggcca   1380
cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca aagacttttt ccggtgggcg tcagatcacg   1800
tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg cttttccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagat atg act gac ggt tac     2274
                                             Met Thr Asp Gly Tyr
                                              1               5
ctt cca gat tgg cta gag gac aac ctc tct gaa ggc gtt cga gag tgg    2322
Leu Pro Asp Trp Leu Glu Asp Asn Leu Ser Glu Gly Val Arg Glu Trp
            10                  15                  20
tgg gcg ctg caa cct gga gcc cct aaa ccc aag gca aat caa caa cat    2370
Trp Ala Leu Gln Pro Gly Ala Pro Lys Pro Lys Ala Asn Gln Gln His
        25                  30                  35
cag gac aac gct cgg ggt ctt gtg ctt ccg ggt tac aaa tac ctc gga    2418
Gln Asp Asn Ala Arg Gly Leu Val Leu Pro Gly Tyr Lys Tyr Leu Gly
    40                  45                  50
ccc ggc aac gga ctc gac aag ggg gaa ccc gtc aac gca gcg gac gcg    2466
Pro Gly Asn Gly Leu Asp Lys Gly Glu Pro Val Asn Ala Ala Asp Ala
55                  60                  65
gca gcc ctc gag cac gac aag gcc tac gac cag cag ctc aag gcc ggt    2514
Ala Ala Leu Glu His Asp Lys Ala Tyr Asp Gln Gln Leu Lys Ala Gly
70                  75                  80                  85
gac aac ccc tac ctc aag tac aac cac gcc gac gcg gag ttc cag cag    2562
Asp Asn Pro Tyr Leu Lys Tyr Asn His Ala Asp Ala Glu Phe Gln Gln
                90                  95                  100
cgg ctt cag ggc gac aca tcg ttt ggg ggc aac ctc ggc aga gca gtc    2610
Arg Leu Gln Gly Asp Thr Ser Phe Gly Gly Asn Leu Gly Arg Ala Val
        105                 110                 115
```

-continued

| | | |
|---|---|---|
| ttc cag gcc aaa aag agg gtt ctt gaa cct ctt ggt ctg gtt gag caa<br>Phe Gln Ala Lys Lys Arg Val Leu Glu Pro Leu Gly Leu Val Glu Gln<br>120                 125                    130 | 2658 |
| gcg ggt gag acg gct cct gga aag aag aga ccg ttg att gaa tcc ccc<br>Ala Gly Glu Thr Ala Pro Gly Lys Lys Arg Pro Leu Ile Glu Ser Pro<br>135                 140                  145 | 2706 |
| cag cag ccc gac tcc tcc acg ggt atc ggc aaa aaa ggc aag cag ccg<br>Gln Gln Pro Asp Ser Ser Thr Gly Ile Gly Lys Lys Gly Lys Gln Pro<br>150                 155                160                165 | 2754 |
| gct aaa aag aag ctc gtt ttc gaa gac gaa act gga gca ggc gac gga<br>Ala Lys Lys Lys Leu Val Phe Glu Asp Glu Thr Gly Ala Gly Asp Gly<br>               170                175                  180 | 2802 |
| ccc cct gag gga tca act tcc gga gcc atg tct gat gac agt gag atg<br>Pro Pro Glu Gly Ser Thr Ser Gly Ala Met Ser Asp Asp Ser Glu Met<br>185                 190                195 | 2850 |
| cgt gca gca gct ggc gga gct gca gtc gag ggc gga caa ggt gcc gat<br>Arg Ala Ala Ala Gly Gly Ala Ala Val Glu Gly Gly Gln Gly Ala Asp<br>               200                205                  210 | 2898 |
| gga gtg ggt aat gcc tcg ggt gat tgg cat tgc gat tcc acc tgg tct<br>Gly Val Gly Asn Ala Ser Gly Asp Trp His Cys Asp Ser Thr Trp Ser<br>215                 220                225 | 2946 |
| gag ggc cac gtc acg acc acc agc acc aga acc tgg gtc ttg ccc acc<br>Glu Gly His Val Thr Thr Thr Ser Thr Arg Thr Trp Val Leu Pro Thr<br>230                 235                240                245 | 2994 |
| tac aac aac cac ctc tac aag cga ctc gga gag agc ctg cag tcc aac<br>Tyr Asn Asn His Leu Tyr Lys Arg Leu Gly Glu Ser Leu Gln Ser Asn<br>               250                255                  260 | 3042 |
| acc tac aac gga ttc tcc acc ccc tgg gga tac ttt gac ttc aac cgc<br>Thr Tyr Asn Gly Phe Ser Thr Pro Trp Gly Tyr Phe Asp Phe Asn Arg<br>265                 270                275 | 3090 |
| ttc cac tgc cac ttc tca cca cgt gac tgg cag cga ctc atc aac aac<br>Phe His Cys His Phe Ser Pro Arg Asp Trp Gln Arg Leu Ile Asn Asn<br>280                 285                290 | 3138 |
| aac tgg ggc atg cga ccc aaa gcc atg cgg gtc aaa atc ttc aac atc<br>Asn Trp Gly Met Arg Pro Lys Ala Met Arg Val Lys Ile Phe Asn Ile<br>295                 300                305 | 3186 |
| cag gtc aag gag gtc acg acg tcg aac ggc gag aca acg gtg gct aat<br>Gln Val Lys Glu Val Thr Thr Ser Asn Gly Glu Thr Thr Val Ala Asn<br>310                 315                320                325 | 3234 |
| aac ctt acc agc acg gtt cag atc ttt gcg gac tcg tcg tac gaa ctg<br>Asn Leu Thr Ser Thr Val Gln Ile Phe Ala Asp Ser Ser Tyr Glu Leu<br>               330                335                  340 | 3282 |
| ccg tac gtg atg gat gcg ggt caa gag ggc agc ctg cct cct ttt ccc<br>Pro Tyr Val Met Asp Ala Gly Gln Glu Gly Ser Leu Pro Pro Phe Pro<br>               345                350                  355 | 3330 |
| aac gac gtc ttt atg gtg ccc cag tac ggc tac tgt gga ctg gtg acc<br>Asn Asp Val Phe Met Val Pro Gln Tyr Gly Tyr Cys Gly Leu Val Thr<br>               360                365                  370 | 3378 |
| ggc aac act tcg cag caa cag act gac aga aat gcc ttc tac tgc ctg<br>Gly Asn Thr Ser Gln Gln Gln Thr Asp Arg Asn Ala Phe Tyr Cys Leu<br>375                 380                385 | 3426 |
| gag tac ttt cct tcg cag atg ctg cgg act ggc aac aac ttt gaa att<br>Glu Tyr Phe Pro Ser Gln Met Leu Arg Thr Gly Asn Asn Phe Glu Ile<br>390                 395                400                405 | 3474 |
| acg tac agt ttt gag aag gtg cct ttc cac tcg atg tac gcg cac agc<br>Thr Tyr Ser Phe Glu Lys Val Pro Phe His Ser Met Tyr Ala His Ser<br>               410                415                  420 | 3522 |
| cag agc ctg gac cgg ctg atg aac cct ctc atc gac cag tac ctg tgg<br>Gln Ser Leu Asp Arg Leu Met Asn Pro Leu Ile Asp Gln Tyr Leu Trp<br>               425                430                  435 | 3570 |

```
gga ctg caa tcg acc acc acc gga acc acc ctg aat gcc ggg act gcc    3618
Gly Leu Gln Ser Thr Thr Thr Gly Thr Thr Leu Asn Ala Gly Thr Ala
        440             445                 450 acc acc aac ttt acc aag ctg cgg cct acc aac ttt tcc aac ttt aaa    3666
Thr Thr Asn Phe Thr Lys Leu Arg Pro Thr Asn Phe Ser Asn Phe Lys
455                 460                 465 aag aac tgg ctg ccc ggg cct tca atc aag cag cag ggc ttc tca aag    3714
Lys Asn Trp Leu Pro Gly Pro Ser Ile Lys Gln Gln Gly Phe Ser Lys
470                 475                 480                 485 act gcc aat caa aac tac aag atc cct gcc acc ggg tca gac agt ctc    3762
Thr Ala Asn Gln Asn Tyr Lys Ile Pro Ala Thr Gly Ser Asp Ser Leu
            490                 495                 500 atc aaa tac gag acg cac agc act ctg gac gga aga tgg agt gcc ctg    3810
Ile Lys Tyr Glu Thr His Ser Thr Leu Asp Gly Arg Trp Ser Ala Leu
        505                 510                 515 acc ccc gga cct cca atg gcc acg gct gga cct gcg gac agc aag ttc    3858
Thr Pro Gly Pro Pro Met Ala Thr Ala Gly Pro Ala Asp Ser Lys Phe
        520                 525                 530 agc aac agc cag ctc atc ttt gcg ggg cct aaa cag aac ggc aac acg    3906
Ser Asn Ser Gln Leu Ile Phe Ala Gly Pro Lys Gln Asn Gly Asn Thr
    535                 540                 545 gcc acc gta ccc ggg act ctg atc ttc acc tct gag gag gag ctg gca    3954
Ala Thr Val Pro Gly Thr Leu Ile Phe Thr Ser Glu Glu Glu Leu Ala
550                 555                 560                 565 gcc acc aac gcc acc gat acg gac atg tgg ggc aac cta cct ggc ggt    4002
Ala Thr Asn Ala Thr Asp Thr Asp Met Trp Gly Asn Leu Pro Gly Gly
                570                 575                 580 gac cag agc aac agc aac ctg ccg acc gtg gac aga ctg aca gcc ttg    4050
Asp Gln Ser Asn Ser Asn Leu Pro Thr Val Asp Arg Leu Thr Ala Leu
            585                 590                 595 gga gcc gtg cct gga atg gtc tgg caa aac aga gac att tac tac cag    4098
Gly Ala Val Pro Gly Met Val Trp Gln Asn Arg Asp Ile Tyr Tyr Gln
        600                 605                 610 ggt ccc att tgg gcc aag att cct cat acc gat gga cac ttt cac ccc    4146
Gly Pro Ile Trp Ala Lys Ile Pro His Thr Asp Gly His Phe His Pro
    615                 620                 625 tca ccg ctg att ggt ggg ttt ggg ctg aaa cac ccg cct cct caa att    4194
Ser Pro Leu Ile Gly Gly Phe Gly Leu Lys His Pro Pro Pro Gln Ile
630                 635                 640                 645 ttt atc aag aac acc ccg gta cct gcg aat cct gca acg acc ttc agc    4242
Phe Ile Lys Asn Thr Pro Val Pro Ala Asn Pro Ala Thr Thr Phe Ser
                650                 655                 660 tct act ccg gta aac tcc ttc att act cag tac agc act ggc cag gtg    4290
Ser Thr Pro Val Asn Ser Phe Ile Thr Gln Tyr Ser Thr Gly Gln Val
            665                 670                 675 tcg gtg cag att gac tgg gag atc cag aag gag cgg tcc aaa cgc tgg    4338
Ser Val Gln Ile Asp Trp Glu Ile Gln Lys Glu Arg Ser Lys Arg Trp
        680                 685                 690 aac ccc gag gtc cag ttt acc tcc aac tac gga cag caa aac tct ctg    4386
Asn Pro Glu Val Gln Phe Thr Ser Asn Tyr Gly Gln Gln Asn Ser Leu
    695                 700                 705 ttg tgg gct ccc gat gcg gct ggg aaa tac act gag cct agg gct atc    4434
Leu Trp Ala Pro Asp Ala Ala Gly Lys Tyr Thr Glu Pro Arg Ala Ile
710                 715                 720                 725 ggt acc cgc tac ctc acc cac cac ctg taa taacctgtta atcaataaac     4484
Gly Thr Arg Tyr Leu Thr His His Leu
                730 cggtttattc gtttcagttg aactttggtc tccgtgtcct tcttatctta tctcgtttcc  4544
```

```
atggctactg cgtacataag cagcggcctg cggcgcttgc gcttcgcggt ttacaactgc    4604
cggttaatca gtaacttctg caaaccaga tgatggagtt ggccacatta gctatgcgcg     4664
ctcgctcact cactcggccc tggagaccaa aggtctccag actgccggcc tctggccggc    4724
agggccgagt gagtgagcga gcgcgcatag agggagtggc caa                       4767
```

<210> SEQ ID NO 20
<211> LENGTH: 734
<212> TYPE: PRT
<213> ORGANISM: Artificial Sequence
<220> FEATURE:
<223> OTHER INFORMATION: Synthetic Construct

<400> SEQUENCE: 20

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
```

```
              325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
            355                 360                 365
Cys Gly Leu Val Thr Gly Asn Thr Ser Gln Gln Thr Asp Arg Asn
370                 375                 380
Ala Phe Tyr Cys Leu Glu Tyr Phe Pro Ser Gln Met Leu Arg Thr Gly
385                 390                 395                 400
Asn Asn Phe Glu Ile Thr Tyr Ser Phe Glu Lys Val Pro Phe His Ser
                405                 410                 415
Met Tyr Ala His Ser Gln Ser Leu Asp Arg Leu Met Asn Pro Leu Ile
                420                 425                 430
Asp Gln Tyr Leu Trp Gly Leu Gln Ser Thr Thr Gly Thr Thr Leu
            435                 440                 445
Asn Ala Gly Thr Ala Thr Thr Asn Phe Thr Lys Leu Arg Pro Thr Asn
450                 455                 460
Phe Ser Asn Phe Lys Lys Asn Trp Leu Pro Gly Pro Ser Ile Lys Gln
465                 470                 475                 480
Gln Gly Phe Ser Lys Thr Ala Asn Gln Asn Tyr Lys Ile Pro Ala Thr
                485                 490                 495
Gly Ser Asp Ser Leu Ile Lys Tyr Glu Thr His Ser Thr Leu Asp Gly
                500                 505                 510
Arg Trp Ser Ala Leu Thr Pro Gly Pro Pro Met Ala Thr Ala Gly Pro
            515                 520                 525
Ala Asp Ser Lys Phe Ser Asn Ser Gln Leu Ile Phe Ala Gly Pro Lys
            530                 535                 540
Gln Asn Gly Asn Thr Ala Thr Val Pro Gly Thr Leu Ile Phe Thr Ser
545                 550                 555                 560
Glu Glu Glu Leu Ala Ala Thr Asn Ala Thr Asp Thr Asp Met Trp Gly
                565                 570                 575
Asn Leu Pro Gly Gly Asp Gln Ser Asn Ser Asn Leu Pro Thr Val Asp
            580                 585                 590
Arg Leu Thr Ala Leu Gly Ala Val Pro Gly Met Val Trp Gln Asn Arg
            595                 600                 605
Asp Ile Tyr Tyr Gln Gly Pro Ile Trp Ala Lys Ile Pro His Thr Asp
            610                 615                 620
Gly His Phe His Pro Ser Pro Leu Ile Gly Gly Phe Gly Leu Lys His
625                 630                 635                 640
Pro Pro Pro Gln Ile Phe Ile Lys Asn Thr Pro Val Pro Ala Asn Pro
                645                 650                 655
Ala Thr Thr Phe Ser Ser Thr Pro Val Asn Ser Phe Ile Thr Gln Tyr
                660                 665                 670
Ser Thr Gly Gln Val Ser Val Gln Ile Asp Trp Glu Ile Gln Lys Glu
            675                 680                 685
Arg Ser Lys Arg Trp Asn Pro Glu Val Gln Phe Thr Ser Asn Tyr Gly
            690                 695                 700
Gln Gln Asn Ser Leu Leu Trp Ala Pro Asp Ala Ala Gly Lys Tyr Thr
705                 710                 715                 720
Glu Pro Arg Ala Ile Gly Thr Arg Tyr Leu Thr His His Leu
                725                 730

<210> SEQ ID NO 21
```

```
<211> LENGTH: 4642
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 5
<220> FEATURE:
<221> NAME/KEY: CDS
<222> LOCATION: (2207)..(4381)
<223> OTHER INFORMATION: AAV5 VP1
<220> FEATURE:
<221> NAME/KEY: misc_feature
<222> LOCATION: (2615)..(4381)
<223> OTHER INFORMATION: AAV5 VP2
<220> FEATURE:
<221> NAME/KEY: misc_feature
<222> LOCATION: (2783)..(4381)
<223> OTHER INFORMATION: AAV5 VP3

<400> SEQUENCE: 21
ctctcccccc tgtcgcgttc gctcgctcgc tggctcgttt ggggggggtgg cagctcaaag      60 agctgccaga cgacggccct ctggccgtcg ccccccaaa  cgagccagcg agcgagcgaa     120
cgcgacaggg gggagagtgc cacactctca agcaagggg  ttttgtaagc agtgatgtca     180
taatgatgta atgcttattg tcacgcgata gttaatgatt aacagtcatg tgatgtgttt     240
tatccaatag gaagaaagcg cgcgtatgag ttctcgcgag acttccgggg tataaaagac     300
cgagtgaacg agcccgccgc cattctttgc tctggactgc tagaggaccc tcgctgccat     360
ggctaccttc tatgaagtca ttgttcgcgt cccatttgac gtggaggaac atctgcctgg     420
aatttctgac agctttgtgg actgggtaac tggtcaaatt gggagctgc  tccagagtc     480 agatttaaat ttgactctgg ttgaacagcc tcagttgacg gtggctgata gaattcgccg     540
cgtgttcctg tacgagtgga caaattttc  caagcaggag tccaaattct tgtgcagtt     600 tgaaaaggga tctgaatatt ttcatctgca cacgcttgtg gagacctccg gcatctcttc     660
catggtcctc ggccgctacg tgagtcagat tcgcgcccag ctggtgaaag tggtcttcca     720
gggaattgaa ccccagatca acgactgggt cgccatcacc aaggtaaaga agggcggagc     780
caataaggtg gtggattctg gtatattcc  cgcctacctg ctgccgaagg tccaaccgga     840
gcttcagtgg gcgtggacaa acctggacga gtataaattg gccgccctga atctggagga     900
gcgcaaacgg ctcgtcgcgc agtttctggc agaatcctcg cagcgctcgc aggaggcggc     960
ttcgcagcgt gagttctcgg ctgacccggt catcaaaagc aagacttccc agaaatacat    1020
ggcgctcgtc aactggctcg tggagcacgg catcacttcc gagaagcagt ggatccagga    1080
aaatcaggag agctacctct ccttcaactc caccggcaac tctcggagcc agatcaaggc    1140
cgcgctcgac aacgcgacca aaattatgag tctgacaaaa agcgcggtgg actacctcgt    1200
ggggagctcc gttcccgagg acatttcaaa aaacagaatc tggcaaattt ttgagatgaa    1260
tggctacgac ccggctacg  cgggatccat cctctacggc tggtgtcagc gctccttcaa    1320
caagaggaac accgtctggc tctacggacc cgccacgacc ggcaagacca acatcgcgga    1380
ggccatcgcc cacactgtgc ccttttacgg ctgcgtgaac tggaccaatg aaaactttcc    1440
ctttaatgac tgtgtggaca aaatgctcat ttggtgggag gagggaaaga tgaccaacaa    1500
ggtggttgaa tccgccaagg ccatcctggg gggctcaaag gtgcgggtcg atcagaaatg    1560
taaatcctct gttcaaattg attctacccc tgtcattgta acttccaata caaacatgtg    1620
tgtggtggtg gatgggaatt ccacgacctt tgaacaccag cagccgctgg aggaccgcat    1680
```

-continued

```
gttcaaattt gaactgacta agcggctccc gccagatttt ggcaagatta ctaagcagga    1740
agtcaaggac ttttttgctt gggcaaaggt caatcaggtg ccggtgactc acgagtttaa    1800
agttcccagg gaattggcgg gaactaaagg ggcggagaaa tctctaaaac gcccactggg    1860
tgacgtcacc aatactagct ataaaagtct ggagaagcgg gccaggctct catttgttcc    1920
cgagacgcct cgcagttcag acgtgactgt tgatcccgct cctctgcgac cgctcaattg    1980
gaattcaagg tatgattgca aatgtgacta tcatgctcaa tttgacaaca tttctaacaa    2040
atgtgatgaa tgtgaatatt tgaatcgggg caaaaatgga tgtatctgtc acaatgtaac    2100
tcactgtcaa atttgtcatg ggattccccc ctgggaaaag gaaaacttgt cagattttgg    2160
ggattttgac gatgccaata agaacagta ataaagcga gtagtc atg tct ttt        2215
                                                 Met Ser Phe
                                                  1
```

| | | | | | | | | | | | | | | | | |
|---|---|---|---|---|---|---|---|---|---|---|---|---|---|---|---|---|
| gtt | gat | cac | cct | cca | gat | tgg | ttg | gaa | gaa | gtt | ggt | gaa | ggt | ctt | cgc | 2263 |
| Val | Asp | His | Pro | Pro | Asp | Trp | Leu | Glu | Glu | Val | Gly | Glu | Gly | Leu | Arg | |
| 5 | | | | | 10 | | | | | 15 | | | | | | |

| | | | | | | | | | | | | | | | | |
|---|---|---|---|---|---|---|---|---|---|---|---|---|---|---|---|---|
| gag | ttt | ttg | ggc | ctt | gaa | gcg | ggc | cca | ccg | aaa | cca | aaa | ccc | aat | cag | 2311 |
| Glu | Phe | Leu | Gly | Leu | Glu | Ala | Gly | Pro | Pro | Lys | Pro | Lys | Pro | Asn | Gln | |
| 20 | | | | | 25 | | | | | 30 | | | | | 35 | |

| | | | | | | | | | | | | | | | | |
|---|---|---|---|---|---|---|---|---|---|---|---|---|---|---|---|---|
| cag | cat | caa | gat | caa | gcc | cgt | ggt | ctt | gtg | ctg | cct | ggt | tat | aac | tat | 2359 |
| Gln | His | Gln | Asp | Gln | Ala | Arg | Gly | Leu | Val | Leu | Pro | Gly | Tyr | Asn | Tyr | |
| | | | | 40 | | | | | 45 | | | | | 50 | | |

| | | | | | | | | | | | | | | | | |
|---|---|---|---|---|---|---|---|---|---|---|---|---|---|---|---|---|
| ctc | gga | ccc | gga | aac | ggt | ctc | gat | cga | gga | gag | cct | gtc | aac | agg | gca | 2407 |
| Leu | Gly | Pro | Gly | Asn | Gly | Leu | Asp | Arg | Gly | Glu | Pro | Val | Asn | Arg | Ala | |
| | | | 55 | | | | | 60 | | | | | 65 | | | |

| | | | | | | | | | | | | | | | | |
|---|---|---|---|---|---|---|---|---|---|---|---|---|---|---|---|---|
| gac | gag | gtc | gcg | cga | gag | cac | gac | atc | tcg | tac | aac | gag | cag | ctt | gag | 2455 |
| Asp | Glu | Val | Ala | Arg | Glu | His | Asp | Ile | Ser | Tyr | Asn | Glu | Gln | Leu | Glu | |
| | | 70 | | | | | 75 | | | | | 80 | | | | |

| | | | | | | | | | | | | | | | | |
|---|---|---|---|---|---|---|---|---|---|---|---|---|---|---|---|---|
| gcg | gga | gac | aac | ccc | tac | ctc | aag | tac | aac | cac | gcg | gac | gcc | gag | ttt | 2503 |
| Ala | Gly | Asp | Asn | Pro | Tyr | Leu | Lys | Tyr | Asn | His | Ala | Asp | Ala | Glu | Phe | |
| | 85 | | | | | 90 | | | | | 95 | | | | | |

| | | | | | | | | | | | | | | | | |
|---|---|---|---|---|---|---|---|---|---|---|---|---|---|---|---|---|
| cag | gag | aag | ctc | gcc | gac | gac | aca | tcc | ttc | ggg | gga | aac | ctc | gga | aag | 2551 |
| Gln | Glu | Lys | Leu | Ala | Asp | Asp | Thr | Ser | Phe | Gly | Gly | Asn | Leu | Gly | Lys | |
| 100 | | | | | 105 | | | | | 110 | | | | | 115 | |

| | | | | | | | | | | | | | | | | |
|---|---|---|---|---|---|---|---|---|---|---|---|---|---|---|---|---|
| gca | gtc | ttt | cag | gcc | aag | aaa | agg | gtt | ctc | gaa | cct | ttt | ggc | ctg | gtt | 2599 |
| Ala | Val | Phe | Gln | Ala | Lys | Lys | Arg | Val | Leu | Glu | Pro | Phe | Gly | Leu | Val | |
| | | | 120 | | | | | 125 | | | | | 130 | | | |

| | | | | | | | | | | | | | | | | |
|---|---|---|---|---|---|---|---|---|---|---|---|---|---|---|---|---|
| gaa | gag | ggt | gct | aag | acg | gcc | cct | acc | gga | aag | cgg | ata | gac | gac | cac | 2647 |
| Glu | Glu | Gly | Ala | Lys | Thr | Ala | Pro | Thr | Gly | Lys | Arg | Ile | Asp | Asp | His | |
| | | | 135 | | | | | 140 | | | | | 145 | | | |

| | | | | | | | | | | | | | | | | |
|---|---|---|---|---|---|---|---|---|---|---|---|---|---|---|---|---|
| ttt | cca | aaa | aga | aag | aag | gct | cgg | acc | gaa | gag | gac | tcc | aag | cct | tcc | 2695 |
| Phe | Pro | Lys | Arg | Lys | Lys | Ala | Arg | Thr | Glu | Glu | Asp | Ser | Lys | Pro | Ser | |
| | | 150 | | | | | 155 | | | | | 160 | | | | |

| | | | | | | | | | | | | | | | | |
|---|---|---|---|---|---|---|---|---|---|---|---|---|---|---|---|---|
| acc | tcg | tca | gac | gcc | gaa | gct | gga | ccc | agc | gga | tcc | cag | cag | ctg | caa | 2743 |
| Thr | Ser | Ser | Asp | Ala | Glu | Ala | Gly | Pro | Ser | Gly | Ser | Gln | Gln | Leu | Gln | |
| | 165 | | | | | 170 | | | | | 175 | | | | | |

| | | | | | | | | | | | | | | | | |
|---|---|---|---|---|---|---|---|---|---|---|---|---|---|---|---|---|
| atc | cca | gcc | caa | cca | gcc | tca | agt | ttg | gga | gct | gat | aca | atg | tct | gcg | 2791 |
| Ile | Pro | Ala | Gln | Pro | Ala | Ser | Ser | Leu | Gly | Ala | Asp | Thr | Met | Ser | Ala | |
| 180 | | | | | 185 | | | | | 190 | | | | | 195 | |

| | | | | | | | | | | | | | | | | |
|---|---|---|---|---|---|---|---|---|---|---|---|---|---|---|---|---|
| gga | ggt | ggc | ggc | cca | ttg | ggc | gac | aat | aac | caa | ggt | gcc | gat | gga | gtg | 2839 |
| Gly | Gly | Gly | Gly | Pro | Leu | Gly | Asp | Asn | Asn | Gln | Gly | Ala | Asp | Gly | Val | |
| | | | | 200 | | | | | 205 | | | | | 210 | | |

| | | | | | | | | | | | | | | | | |
|---|---|---|---|---|---|---|---|---|---|---|---|---|---|---|---|---|
| ggc | aat | gcc | tcg | gga | gat | tgg | cat | tgc | gat | tcc | acg | tgg | atg | ggg | gac | 2887 |
| Gly | Asn | Ala | Ser | Gly | Asp | Trp | His | Cys | Asp | Ser | Thr | Trp | Met | Gly | Asp | |
| | | | 215 | | | | | 220 | | | | | 225 | | | |

| | | | | | | | | | | | | | | | | |
|---|---|---|---|---|---|---|---|---|---|---|---|---|---|---|---|---|
| aga | gtc | gtc | acc | aag | tcc | acc | cga | acc | tgg | gtg | ctg | ccc | agc | tac | aac | 2935 |
| Arg | Val | Val | Thr | Lys | Ser | Thr | Arg | Thr | Trp | Val | Leu | Pro | Ser | Tyr | Asn | |
| | | 230 | | | | | 235 | | | | | 240 | | | | |

-continued

| | | |
|---|---|---|
| aac cac cag tac cga gag atc aaa agc ggc tcc gtc gac gga agc aac<br>Asn His Gln Tyr Arg Glu Ile Lys Ser Gly Ser Val Asp Gly Ser Asn<br>245                     250                       255 | 2983 |
| gcc aac gcc tac ttt gga tac agc acc ccc tgg ggg tac ttt gac ttt<br>Ala Asn Ala Tyr Phe Gly Tyr Ser Thr Pro Trp Gly Tyr Phe Asp Phe<br>260                     265                     270                     275 | 3031 |
| aac cgc ttc cac agc cac tgg agc ccc cga gac tgg caa aga ctc atc<br>Asn Arg Phe His Ser His Trp Ser Pro Arg Asp Trp Gln Arg Leu Ile<br>                     280                     285                     290 | 3079 |
| aac aac tac tgg ggc ttc aga ccc cgg tcc ctc aga gtc aaa atc ttc<br>Asn Asn Tyr Trp Gly Phe Arg Pro Arg Ser Leu Arg Val Lys Ile Phe<br>                     295                     300                     305 | 3127 |
| aac att caa gtc aaa gag gtc acg gtg cag gac tcc acc acc acc atc<br>Asn Ile Gln Val Lys Glu Val Thr Val Gln Asp Ser Thr Thr Thr Ile<br>310                     315                     320 | 3175 |
| gcc aac aac ctc acc tcc acc gtc caa gtg ttt acg gac gac gac tac<br>Ala Asn Asn Leu Thr Ser Thr Val Gln Val Phe Thr Asp Asp Asp Tyr<br>325                     330                     335 | 3223 |
| cag ctg ccc tac gtc gtc ggc aac ggg acc gag gga tgc ctg ccg gcc<br>Gln Leu Pro Tyr Val Val Gly Asn Gly Thr Glu Gly Cys Leu Pro Ala<br>340                     345                     350                     355 | 3271 |
| ttc cct ccg cag gtc ttt acg ctg ccg cag tac ggt tac gcg acg ctg<br>Phe Pro Pro Gln Val Phe Thr Leu Pro Gln Tyr Gly Tyr Ala Thr Leu<br>                     360                     365                     370 | 3319 |
| aac cgc gac aac aca gaa aat ccc acc gag agg agc agc ttc ttc tgc<br>Asn Arg Asp Asn Thr Glu Asn Pro Thr Glu Arg Ser Ser Phe Phe Cys<br>                     375                     380                     385 | 3367 |
| cta gag tac ttt ccc agc aag atg ctg aga acg ggc aac aac ttt gag<br>Leu Glu Tyr Phe Pro Ser Lys Met Leu Arg Thr Gly Asn Asn Phe Glu<br>390                     395                     400 | 3415 |
| ttt acc tac aac ttt gag gag gtg ccc ttc cac tcc agc ttc gct ccc<br>Phe Thr Tyr Asn Phe Glu Glu Val Pro Phe His Ser Ser Phe Ala Pro<br>405                     410                     415 | 3463 |
| agt cag aac ctg ttc aag ctg gcc aac ccg ctg gtg gac cag tac ttg<br>Ser Gln Asn Leu Phe Lys Leu Ala Asn Pro Leu Val Asp Gln Tyr Leu<br>420                     425                     430                     435 | 3511 |
| tac cgc ttc gtg agc aca aat aac act ggc gga gtc cag ttc aac aag<br>Tyr Arg Phe Val Ser Thr Asn Asn Thr Gly Gly Val Gln Phe Asn Lys<br>                     440                     445                     450 | 3559 |
| aac ctg gcc ggg aga tac gcc aac acc tac aaa aac tgg ttc ccg ggg<br>Asn Leu Ala Gly Arg Tyr Ala Asn Thr Tyr Lys Asn Trp Phe Pro Gly<br>                     455                     460                     465 | 3607 |
| ccc atg ggc cga acc cag ggc tgg aac ctg ggc tcc ggg gtc aac cgc<br>Pro Met Gly Arg Thr Gln Gly Trp Asn Leu Gly Ser Gly Val Asn Arg<br>                     470                     475                     480 | 3655 |
| gcc agt gtc agc gcc ttc gcc acg acc aat agg atg gag ctc gag ggc<br>Ala Ser Val Ser Ala Phe Ala Thr Thr Asn Arg Met Glu Leu Glu Gly<br>485                     490                     495 | 3703 |
| gcg agt tac cag gtg ccc ccg cag ccg aac ggc atg acc aac aac ctc<br>Ala Ser Tyr Gln Val Pro Pro Gln Pro Asn Gly Met Thr Asn Asn Leu<br>500                     505                     510                     515 | 3751 |
| cag ggc agc aac acc tat gcc ctg gag aac act atg atc ttc aac agc<br>Gln Gly Ser Asn Thr Tyr Ala Leu Glu Asn Thr Met Ile Phe Asn Ser<br>                     520                     525                     530 | 3799 |
| cag ccg gcg aac ccg ggc acc acc gcc acg tac ctc gag ggc aac atg<br>Gln Pro Ala Asn Pro Gly Thr Thr Ala Thr Tyr Leu Glu Gly Asn Met<br>535                     540                     545 | 3847 |
| ctc atc acc agc gag agc gag acg cag ccg gtg aac cgc gtg gcg tac<br>Leu Ile Thr Ser Glu Ser Glu Thr Gln Pro Val Asn Arg Val Ala Tyr | 3895 |

```
                550                     555                     560
aac gtc ggc ggg cag atg gcc acc aac aac cag agc tcc acc act gcc    3943
Asn Val Gly Gly Gln Met Ala Thr Asn Asn Gln Ser Ser Thr Thr Ala
565                     570                     575 ccc gcg acc ggc acg tac aac ctc cag gaa atc gtg ccc ggc agc gtg    3991
Pro Ala Thr Gly Thr Tyr Asn Leu Gln Glu Ile Val Pro Gly Ser Val
580                     585                     590                 595 tgg atg gag agg gac gtg tac ctc caa gga ccc atc tgg gcc aag atc    4039
Trp Met Glu Arg Asp Val Tyr Leu Gln Gly Pro Ile Trp Ala Lys Ile
                600                     605                     610 cca gag acg ggg gcg cac ttt cac ccc tct ccg gcc atg ggc gga ttc    4087
Pro Glu Thr Gly Ala His Phe His Pro Ser Pro Ala Met Gly Gly Phe
615                     620                     625 gga ctc aaa cac cca ccg ccc atg atg ctc atc aag aac acg cct gtg    4135
Gly Leu Lys His Pro Pro Pro Met Met Leu Ile Lys Asn Thr Pro Val
630                     635                     640 ccc gga aat atc acc agc ttc tcg gac gtg ccc gtc agc agc ttc atc    4183
Pro Gly Asn Ile Thr Ser Phe Ser Asp Val Pro Val Ser Ser Phe Ile
645                     650                     655 acc cag tac agc acc ggg cag gtc acc gtg gag atg gag tgg gag ctc    4231
Thr Gln Tyr Ser Thr Gly Gln Val Thr Val Glu Met Glu Trp Glu Leu
660                     665                     670                 675 aag aag gaa aac tcc aag agg tgg aac cca gag atc cag tac aca aac    4279
Lys Lys Glu Asn Ser Lys Arg Trp Asn Pro Glu Ile Gln Tyr Thr Asn
                680                     685                     690 aac tac aac gac ccc cag ttt gtg gac ttt gcc ccg gac agc acc ggg    4327
Asn Tyr Asn Asp Pro Gln Phe Val Asp Phe Ala Pro Asp Ser Thr Gly
                695                     700                     705 gaa tac aga acc acc aga cct atc gga acc cga tac ctt acc cga ccc    4375
Glu Tyr Arg Thr Thr Arg Pro Ile Gly Thr Arg Tyr Leu Thr Arg Pro
710                     715                     720 ctt taa cccattcatg tcgcataccc tcaataaacc gtgtattcgt gtcagtaaaa    4431
Leu tactgcctct tgtggtcatt caatgaataa cagcttacaa catctacaaa acctccttgc    4491
ttgagagtgt ggcactctcc cccctgtcgc gttcgctcgc tcgctggctc gtttgggggg    4551
gtggcagctc aaagagctgc cagacgacgg ccctctggcc gtcgcccccc caaacgagcc    4611
agcgagcgag cgaacgcgac aggggggaga g                                  4642

<210> SEQ ID NO 22
<211> LENGTH: 724
<212> TYPE: PRT
<213> ORGANISM: Artificial Sequence
<220> FEATURE:
<223> OTHER INFORMATION: Synthetic Construct

<400> SEQUENCE: 22

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
```

```
                85                  90                  95
Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
            130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Leu Gly Ala Asp Thr
            180                 185                 190

Met Ser Ala Gly Gly Gly Pro Leu Gly Asp Asn Asn Gln Gly Ala
            195                 200                 205

Asp Gly Val Gly Asn Ala Ser Gly Asp Trp His Cys Asp Ser Thr Trp
            210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
            370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Thr Gly Gly Val Gln
            435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510
```

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
        530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 23
<211> LENGTH: 4683
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 6
<220> FEATURE:
<221> NAME/KEY: CDS
<222> LOCATION: (2208)..(4418)
<223> OTHER INFORMATION: AAV6 VP1
<220> FEATURE:
<221> NAME/KEY: misc_feature
<222> LOCATION: (2619)..(4418)
<223> OTHER INFORMATION: AAV6 VP2
<220> FEATURE:
<221> NAME/KEY: misc_feature
<222> LOCATION: (2814)..(4418)
<223> OTHER INFORMATION: AAV6 VP3

<400> SEQUENCE: 23
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctggagg ggtggagtcg tgacgtgaat tacgtcatag   180
ggttagggag gtcctgtatt agaggtcacg tgagtgtttt gcgacatttt gcgacaccat   240
gtggtcacgc tgggtattta agcccgagtg agcacgcagg gtctccattt tgaagcggga   300
ggtttgaacg cgcagcgcca tgccgggggtt ttacgagatt gtgattaagg tccccagcga   360

```
ccttgacgag catctgcccg gcatttctga cagctttgtg aactgggtgg ccgagaagga      420
atgggagttg ccgccagatt ctgacatgga tctgaatctg attgagcagg caccectgac      480 cgtggccgag aagctgcagc gcgacttcct ggtccagtgg cgccgcgtga gtaaggcccc      540
ggaggccctc ttctttgttc agttcgagaa gggcgagtcc tacttccacc tccatattct      600
ggtggagacc acgggggtca atccatggt gctgggccgc ttcctgagtc agattaggga      660
caagctggtg cagaccatct accgcgggat cgagccgacc ctgcccaact ggttcgcggt      720
gaccaagacg cgtaatggcg ccggaggggg gaacaaggtg gtggacgagt gctacatccc      780
caactacctc ctgcccaaga ctcagcccga gctgcagtgg gcgtggacta acatggagga      840
gtatataagc gcgtgtttaa acctggccga gcgcaaacgg ctcgtggcgc acgacctgac      900
ccacgtcagc cagacccagg agcagaacaa ggagaatctg aaccccaatt ctgacgcgcc      960
tgtcatccgg tcaaaaacct ccgcacgcta catggagctg gtcgggtggc tggtggaccg     1020
gggcatcacc tccgagaagc agtggatcca ggaggaccag gcctcgtaca tctccttcaa     1080
cgccgcctcc aactcgcggt cccagatcaa ggccgctctg acaatgccg gcaagatcat      1140 ggcgctgacc aaatccgcgc cgactacct ggtaggcccc gctccgcccg ccgacattaa      1200
aaccaaccgc atttaccgca tcctggagct gaacggctac gaccctgcct acgccggctc     1260
cgtctttctc ggctgggccc agaaaaggtt cggaaaacgc aacaccatct ggctgtttgg     1320
gccggccacc acgggcaaga ccaacatcgc ggaagccatc gcccacgccg tgcccttcta     1380
cggctgcgtc aactggacca atgagaactt tcccttcaac gattgcgtcg acaagatggt     1440
gatctggtgg gaggagggca agatgacggc caaggtcgtg gagtccgcca aggccattct     1500
cggcggcagc aaggtgcgcg tggaccaaaa gtgcaagtcg tccgcccaga tcgatcccac     1560
ccccgtgatc gtcacctcca acaccaacat gtgcgccgtg attgacggga acagcaccac     1620
cttcgagcac cagcagccgt gcaggaccg gatgttcaaa tttgaactca cccgccgtct     1680
ggagcatgac tttggcaagg tgacaaagca ggaagtcaaa gagttcttcc gctgggcgca     1740
ggatcacgtg accgaggtgg cgcatgagtt ctacgtcaga aagggtggag ccaacaagag     1800
acccgccccc gatgacgcgg ataaaagcga gcccaagcgg gcctgcccct cagtcgcgga     1860
tccatcgacg tcagacgcgg aaggagctcc ggtggacttt gccgacaggt accaaaacaa     1920
atgttctcgt cacgcgggca tgcttcagat gctgttccc tgcaaaacat gcgagagaat      1980
gaatcagaat ttcaacattt gcttcacgca cgggaccaga gactgttcag aatgtttccc     2040
cggcgtgtca gaatctcaac cggtcgtcag aaagaggacg tatcggaaac tctgtgccat     2100
tcatcatctg ctggggcggg ctcccgagat tgcttgctcg gcctgcgatc tggtcaacgt     2160
ggatctggat gactgtgttt ctgagcaata aatgacttaa accaggt atg gct gcc      2216
                                                    Met Ala Ala
                                                    1 gat ggt tat ctt cca gat tgg ctc gag gac aac ctc tct gag ggc att      2264
Asp Gly Tyr Leu Pro Asp Trp Leu Glu Asp Asn Leu Ser Glu Gly Ile
    5                   10                  15 cgc gag tgg tgg gac ttg aaa cct gga gcc ccg aaa ccc aaa gcc aac      2312
Arg Glu Trp Trp Asp Leu Lys Pro Gly Ala Pro Lys Pro Lys Ala Asn
 20                  25                  30                  35 cag caa aag cag gac gac ggc cgg ggt ctg gtg ctt cct ggc tac aag      2360
Gln Gln Lys Gln Asp Asp Gly Arg Gly Leu Val Leu Pro Gly Tyr Lys
                40                  45                  50 tac ctc gga ccc ttc aac gga ctc gac aag ggg gag ccc gtc aac gcg      2408
Tyr Leu Gly Pro Phe Asn Gly Leu Asp Lys Gly Glu Pro Val Asn Ala
        55                  60                  65
```

-continued

```
gcg gat gca gcg gcc ctc gag cac gac aag gcc tac gac cag cag ctc      2456
Ala Asp Ala Ala Ala Leu Glu His Asp Lys Ala Tyr Asp Gln Gln Leu
         70                  75                  80 aaa gcg ggt gac aat ccg tac ctg cgg tat aac cac gcc gac gcc gag      2504
Lys Ala Gly Asp Asn Pro Tyr Leu Arg Tyr Asn His Ala Asp Ala Glu
 85                  90                  95 ttt cag gag cgt ctg caa gaa gat acg tct ttt ggg ggc aac ctc ggg      2552
Phe Gln Glu Arg Leu Gln Glu Asp Thr Ser Phe Gly Gly Asn Leu Gly
100                 105                 110                 115 cga gca gtc ttc cag gcc aag aag agg gtt ctc gaa cct ttt ggt ctg      2600
Arg Ala Val Phe Gln Ala Lys Lys Arg Val Leu Glu Pro Phe Gly Leu
                    120                 125                 130 gtt gag gaa ggt gct aag acg gct cct gga aag aaa cgt ccg gta gag      2648
Val Glu Glu Gly Ala Lys Thr Ala Pro Gly Lys Lys Arg Pro Val Glu
                135                 140                 145 cag tcg cca caa gag cca gac tcc tcc tcg ggc att ggc aag aca ggc      2696
Gln Ser Pro Gln Glu Pro Asp Ser Ser Ser Gly Ile Gly Lys Thr Gly
            150                 155                 160 cag cag ccc gct aaa aag aga ctc aat ttt ggt cag act ggc gac tca      2744
Gln Gln Pro Ala Lys Lys Arg Leu Asn Phe Gly Gln Thr Gly Asp Ser
        165                 170                 175 gag tca gtc ccc gac cca caa cct ctc gga gaa cct cca gca acc ccc      2792
Glu Ser Val Pro Asp Pro Gln Pro Leu Gly Glu Pro Pro Ala Thr Pro
180                 185                 190                 195 gct gct gtg gga cct act aca atg gct tca ggc ggt ggc gca cca atg      2840
Ala Ala Val Gly Pro Thr Thr Met Ala Ser Gly Gly Gly Ala Pro Met
                    200                 205                 210 gca gac aat aac gaa ggc gcc gac gga gtg ggt aat gcc tca gga aat      2888
Ala Asp Asn Asn Glu Gly Ala Asp Gly Val Gly Asn Ala Ser Gly Asn
                215                 220                 225 tgg cat tgc gat tcc aca tgg ctg ggc gac aga gtc atc acc acc agc      2936
Trp His Cys Asp Ser Thr Trp Leu Gly Asp Arg Val Ile Thr Thr Ser
            230                 235                 240 acc cga aca tgg gcc ttg ccc acc tat aac aac cac ctc tac aag caa      2984
Thr Arg Thr Trp Ala Leu Pro Thr Tyr Asn Asn His Leu Tyr Lys Gln
        245                 250                 255 atc tcc agt gct tca acg ggg gcc agc aac gac aac cac tac ttc ggc      3032
Ile Ser Ser Ala Ser Thr Gly Ala Ser Asn Asp Asn His Tyr Phe Gly
260                 265                 270                 275 tac agc acc ccc tgg ggg tat ttt gat ttc aac aga ttc cac tgc cat      3080
Tyr Ser Thr Pro Trp Gly Tyr Phe Asp Phe Asn Arg Phe His Cys His
                    280                 285                 290 ttc tca cca cgt gac tgg cag cga ctc atc aac aac aat tgg gga ttc      3128
Phe Ser Pro Arg Asp Trp Gln Arg Leu Ile Asn Asn Asn Trp Gly Phe
                295                 300                 305 cgg ccc aag aga ctc aac ttc aag ctc ttc aac atc caa gtc aag gag      3176
Arg Pro Lys Arg Leu Asn Phe Lys Leu Phe Asn Ile Gln Val Lys Glu
            310                 315                 320 gtc acg acg aat gat ggc gtc acg acc atc gct aat aac ctt acc agc      3224
Val Thr Thr Asn Asp Gly Val Thr Thr Ile Ala Asn Asn Leu Thr Ser
        325                 330                 335 acg gtt caa gtc ttc tcg gac tcg gag tac cag ttg ccg tac gtc ctc      3272
Thr Val Gln Val Phe Ser Asp Ser Glu Tyr Gln Leu Pro Tyr Val Leu
340                 345                 350                 355 ggc tct gcg cac cag ggc tgc ctc cct ccg ttc ccg gcg gac gtg ttc      3320
Gly Ser Ala His Gln Gly Cys Leu Pro Pro Phe Pro Ala Asp Val Phe
                    360                 365                 370 atg att ccg cag tac ggc tac cta acg ctc aac aat ggc agc cag gca      3368
Met Ile Pro Gln Tyr Gly Tyr Leu Thr Leu Asn Asn Gly Ser Gln Ala
```

-continued

```
              375                 380                 385
gtg gga cgg tca tcc ttt tac tgc ctg gaa tat ttc cca tcg cag atg    3416
Val Gly Arg Ser Ser Phe Tyr Cys Leu Glu Tyr Phe Pro Ser Gln Met
        390                 395                 400 ctg aga acg ggc aat aac ttt acc ttc agc tac acc ttc gag gac gtg    3464
Leu Arg Thr Gly Asn Asn Phe Thr Phe Ser Tyr Thr Phe Glu Asp Val
405                 410                 415 cct ttc cac agc agc tac gcg cac agc cag agc ctg gac cgg ctg atg    3512
Pro Phe His Ser Ser Tyr Ala His Ser Gln Ser Leu Asp Arg Leu Met
420                 425                 430                 435 aat cct ctc atc gac cag tac ctg tat tac ctg aac aga act cag aat    3560
Asn Pro Leu Ile Asp Gln Tyr Leu Tyr Tyr Leu Asn Arg Thr Gln Asn
                440                 445                 450 cag tcc gga agt gcc caa aac aag gac ttg ctg ttt agc cgg ggg tct    3608
Gln Ser Gly Ser Ala Gln Asn Lys Asp Leu Leu Phe Ser Arg Gly Ser
            455                 460                 465 cca gct ggc atg tct gtt cag ccc aaa aac tgg cta cct gga ccc tgt    3656
Pro Ala Gly Met Ser Val Gln Pro Lys Asn Trp Leu Pro Gly Pro Cys
        470                 475                 480 tac cgg cag cag cgc gtt tct aaa aca aaa aca gac aac aac aac agc    3704
Tyr Arg Gln Gln Arg Val Ser Lys Thr Lys Thr Asp Asn Asn Asn Ser
485                 490                 495 aac ttt acc tgg act ggt gct tca aaa tat aac ctt aat ggg cgt gaa    3752
Asn Phe Thr Trp Thr Gly Ala Ser Lys Tyr Asn Leu Asn Gly Arg Glu
500                 505                 510                 515 tct ata atc aac cct ggc act gct atg gcc tca cac aaa gac gac aaa    3800
Ser Ile Ile Asn Pro Gly Thr Ala Met Ala Ser His Lys Asp Asp Lys
                520                 525                 530 gac aag ttc ttt ccc atg agc ggt gtc atg att ttt gga aag gag agc    3848
Asp Lys Phe Phe Pro Met Ser Gly Val Met Ile Phe Gly Lys Glu Ser
            535                 540                 545 gcc gga gct tca aac act gca ttg gac aat gtc atg atc aca gac gaa    3896
Ala Gly Ala Ser Asn Thr Ala Leu Asp Asn Val Met Ile Thr Asp Glu
        550                 555                 560 gag gaa atc aaa gcc act aac ccc gtg gcc acc gaa aga ttt ggg act    3944
Glu Glu Ile Lys Ala Thr Asn Pro Val Ala Thr Glu Arg Phe Gly Thr
565                 570                 575 gtg gca gtc aat ctc cag agc agc agc aca gac cct gcg acc gga gat    3992
Val Ala Val Asn Leu Gln Ser Ser Ser Thr Asp Pro Ala Thr Gly Asp
580                 585                 590                 595 gtg cat gtt atg gga gcc tta cct gga atg gtg tgg caa gac aga gac    4040
Val His Val Met Gly Ala Leu Pro Gly Met Val Trp Gln Asp Arg Asp
                600                 605                 610 gta tac ctg cag ggt cct att tgg gcc aaa att cct cac acg gat gga    4088
Val Tyr Leu Gln Gly Pro Ile Trp Ala Lys Ile Pro His Thr Asp Gly
            615                 620                 625 cac ttt cac ccg tct cct ctc atg ggc ggc ttt gga ctt aag cac ccg    4136
His Phe His Pro Ser Pro Leu Met Gly Gly Phe Gly Leu Lys His Pro
        630                 635                 640 cct cct cag atc ctc atc aaa aac acg cct gtt cct gcg aat cct ccg    4184
Pro Pro Gln Ile Leu Ile Lys Asn Thr Pro Val Pro Ala Asn Pro Pro
645                 650                 655 gca gag ttt tcg gct aca aag ttt gct tca ttc atc acc cag tat tcc    4232
Ala Glu Phe Ser Ala Thr Lys Phe Ala Ser Phe Ile Thr Gln Tyr Ser
660                 665                 670                 675 aca gga caa gtg agc gtg gag att gaa tgg gag ctg cag aaa gaa aac    4280
Thr Gly Gln Val Ser Val Glu Ile Glu Trp Glu Leu Gln Lys Glu Asn
                680                 685                 690 agc aaa cgc tgg aat ccc gaa gtg cag tat aca tct aac tat gca aaa    4328
Ser Lys Arg Trp Asn Pro Glu Val Gln Tyr Thr Ser Asn Tyr Ala Lys
```

```
Ser Lys Arg Trp Asn Pro Glu Val Gln Tyr Thr Ser Asn Tyr Ala Lys
            695                 700                 705 tct gcc aac gtt gat ttc act gtg gac aac aat gga ctt tat act gag      4376
Ser Ala Asn Val Asp Phe Thr Val Asp Asn Asn Gly Leu Tyr Thr Glu
            710                 715                 720 cct cgc ccc att ggc acc cgt tac ctc acc cgt ccc ctg taa              4418
Pro Arg Pro Ile Gly Thr Arg Tyr Leu Thr Arg Pro Leu
725                 730                 735 ttgtgtgtta atcaataaac cggttaattc gtgtcagttg aactttggtc tcatgtcgtt    4478
attatcttat ctggtcacca tagcaaccgg ttacacatta actgcttagt tgcgcttcgc    4538 gaataccct agtgatggag ttgcccactc cctctatgcg cgctcgctcg ctcggtgggg     4598
ccggcagagc agagctctgc cgtctgcgga cctttggtcc gcaggcccca ccgagcgagc    4658
gagcgcgcat agagggagtg ggcaa                                          4683

<210> SEQ ID NO 24
<211> LENGTH: 736
<212> TYPE: PRT
<213> ORGANISM: Artificial Sequence
<220> FEATURE:
<223> OTHER INFORMATION: Synthetic Construct

<400> SEQUENCE: 24

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
```

|       | 675 |     |     |     | 680 |     |     |     |     | 685 |     |     |     |     |
|-------|-----|-----|-----|-----|-----|-----|-----|-----|-----|-----|-----|-----|-----|-----|
Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

```
<210> SEQ ID NO 25
<211> LENGTH: 4721
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 7
<220> FEATURE:
<221> NAME/KEY: CDS
<222> LOCATION: (2222)..(4435)
<223> OTHER INFORMATION: AAV7 VP1
<220> FEATURE:
<221> NAME/KEY: misc_feature
<222> LOCATION: (2633)..(4435)
<223> OTHER INFORMATION: AAV7 VP2
<220> FEATURE:
<221> NAME/KEY: misc_feature
<222> LOCATION: (2831)..(4435)
<223> OTHER INFORMATION: AAV7 VP3

<400> SEQUENCE: 25
ttggccactc cctctatgcg cgctcgctcg ctcggtgggg cctgcggacc aaaggtccgc    60
agacggcaga gctctgctct gccggcccca ccgagcgagc gagcgcgcat agagggagtg   120
gccaactcca tcactagggg taccgcgaag cgcctccac gctgccgcgt cagcgctgac    180
gtaaatcacg tcataggga gtggtcctgt attagctgtc acgtgagtgc ttttgcgaca    240
ttttgcgaca ccacgtggcc atttgaggta tatatggccg agtgagcgag caggatctcc   300
attttgaccg cgaaatttga acgagcagca gccatgccgg gtttctacga gatcgtgatc    360
aaggtgccga cgacctgga cgagcacctg ccgggcattt ctgactcgtt tgtgaactgg    420
gtggccgaga aggaatggga gctgccccg gattctgaca tggatctgaa tctgatcgag    480
caggcacccc tgaccgtggc cgagaagctg cagcgcgact cctggtcca atggcgccgc    540 gtgagtaagg ccccggaggc cctgttcttt gttcagttcg agaagggcga gagctacttc    600
caccttcacg ttctggtgga gaccacgggg tcaagtccca tggtgctagg ccgcttcctg    660
agtcagattc gggagaagct ggtccagacc atctaccgcg gggtcgagcc cacgctgccc    720
aactggttcg cggtgaccaa gacgcgtaat ggcgccggcg gggggaacaa ggtggtggac    780
gagtgctaca tccccaacta cctcctgccc aagacccagc ccgagctgca gtgggcgtgg    840
actaacatgg aggagtatat aagcgcgtgt ttgaacctgg ccgaacgcaa acggctcgtg    900
gcgcagcacc tgacccacgt cagccagacg caggagcaga acaaggagaa tctgaacccc    960
aattctgacg cgcccgtgat caggtcaaaa acctccgcgc gctacatgga gctggtcggg   1020
tggctggtgg accgggggat cacctccgag aagcagtgga tccaggagga ccaggcctcg   1080
tacatctcct tcaacgccgc ctccaactcg cggtcccaga tcaaggccgc gctggacaat   1140
gccggcaaga tcatggcgct gaccaaatcc gcgcccgact acctggtggg gcccgctgtg   1200
cccgcggaca ttaaaaccaa ccgcatctac cgcatcctgg agctgaacgg gtacgatcct   1260
gcctacgccg gctccgtctt tctcggctgg gcccagaaaa agttcgggaa gcgcaacacc   1320
```

```
atctggctgt ttgggcccgc caccaccggc aagaccaaca ttgcggaagc catcgcccac   1380
gccgtgccct tctacggctg cgtcaactgg accaatgaga actttccctt caacgattgc   1440
gtcgacaaga tggtgatctg gtgggaggag ggcaagatga cggccaaggt cgtggagtcc   1500
gccaaggcca ttctcggcgg cagcaaggtg cgcgtggacc aaaagtgcaa gtcgtccgcc   1560
cagatcgacc ccaccccgt gatcgtcacc tccaacacca acatgtgcgc cgtgattgac    1620
gggaacagca ccaccttcga gcaccagcag ccgttgcagg accggatgtt caaatttgaa   1680
ctcacccgcc gtctggagca cgactttggc aaggtgacga agcaggaagt caaagagttc   1740
ttccgctggg ccagtgatca cgtgaccgag gtggcgcatg agttctacgt cagaaagggc   1800
ggagccagca aaagacccgc ccccgatgac gcggatataa gcgagcccaa gcgggcctgc   1860
ccctcagtcg cggatccatc gacgtcagac gcggaaggag ctccggtgga ctttgccgac   1920
aggtaccaaa acaaatgttc tcgtcacgcg ggcatgattc agatgctgtt tccctgcaaa   1980
acgtgcgaga gaatgaatca gaatttcaac atttgcttca cacgggggt cagagactgt    2040
ttagagtgtt tccccggcgt gtcagaatct caaccggtcg tcagaaaaaa gacgtatcgg   2100
aaactctgcg cgattcatca tctgctgggg cgggcgcccg agattgcttg ctcggcctgc   2160
gacctggtca acgtggacct ggacgactgc gtttctgagc aataaatgac ttaaaccagg   2220
t atg gct gcc gat ggt tat ctt cca gat tgg ctc gag gac aac ctc tct   2269
  Met Ala Ala Asp Gly Tyr Leu Pro Asp Trp Leu Glu Asp Asn Leu Ser
  1               5                   10                  15 gag ggc att cgc gag tgg tgg gac ctg aaa cct gga gcc ccg aaa ccc     2317
Glu Gly Ile Arg Glu Trp Trp Asp Leu Lys Pro Gly Ala Pro Lys Pro
            20                  25                  30 aaa gcc aac cag caa aag cag gac aac ggc cgg ggt ctg gtg ctt cct     2365
Lys Ala Asn Gln Gln Lys Gln Asp Asn Gly Arg Gly Leu Val Leu Pro
        35                  40                  45 ggc tac aag tac ctc gga ccc ttc aac gga ctc gac aag ggg gag ccc     2413
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     2461
Val Asn Ala Ala Asp Ala Ala Ala Leu Glu His Asp Lys Ala Tyr Asp
65                  70                  75                  80 cag cag ctc aaa gcg ggt gac aat ccg tac ctg cgg tat aac cac gcc     2509
Gln Gln Leu Lys Ala Gly Asp Asn Pro Tyr Leu Arg Tyr Asn His Ala
            85                  90                  95 gac gcc gag ttt cag gag cgt ctg caa gaa gat acg tca ttt ggg ggc     2557
Asp Ala Glu Phe Gln Glu Arg Leu Gln Glu Asp Thr Ser Phe Gly Gly
        100                 105                 110 aac ctc ggg cga gca gtc ttc cag gcc aag aag cgg gtt ctc gaa cct     2605
Asn Leu Gly Arg Ala Val Phe Gln Ala Lys Lys Arg Val Leu Glu Pro
    115                 120                 125 ctc ggt ctg gtt gag gaa ggc gct aag acg gct cct gca aag aag aga     2653
Leu Gly Leu Val Glu Glu Gly Ala Lys Thr Ala Pro Ala Lys Lys Arg
130                 135                 140 ccg gta gag ccg tca cct cag cgt tcc ccc gac tcc tcc acg ggc atc     2701
Pro Val Glu Pro Ser Pro Gln Arg Ser Pro Asp Ser Ser Thr Gly Ile
145                 150                 155                 160 ggc aag aaa ggc cag cag ccc gcc aga aag aga ctc aat ttc ggt cag     2749
Gly Lys Lys Gly Gln Gln Pro Ala Arg Lys Arg Leu Asn Phe Gly Gln
            165                 170                 175 act ggc gac tca gag tca gtc ccc gac cct caa cct ctc gga gaa cct     2797
Thr Gly Asp Ser Glu Ser Val Pro Asp Pro Gln Pro Leu Gly Glu Pro
        180                 185                 190
```

| | | |
|---|---|---|
| cca gca gcg ccc tct agt gtg gga tct ggt aca gtg gct gca ggc ggt<br>Pro Ala Ala Pro Ser Ser Val Gly Ser Gly Thr Val Ala Ala Gly Gly<br>195 200 205 | | 2845 |
| ggc gca cca atg gca gac aat aac gaa ggt gcc gac gga gtg ggt aat<br>Gly Ala Pro Met Ala Asp Asn Asn Glu Gly Ala Asp Gly Val Gly Asn<br>210 215 220 | | 2893 |
| gcc tca gga aat tgg cat tgc gat tcc aca tgg ctg ggc gac aga gtc<br>Ala Ser Gly Asn Trp His Cys Asp Ser Thr Trp Leu Gly Asp Arg Val<br>225 230 235 240 | | 2941 |
| att acc acc agc acc cga acc tgg gcc ctg ccc acc tac aac aac cac<br>Ile Thr Thr Ser Thr Arg Thr Trp Ala Leu Pro Thr Tyr Asn Asn His<br>245 250 255 | | 2989 |
| ctc tac aag caa atc tcc agt gaa act gca ggt agt acc aac gac aac<br>Leu Tyr Lys Gln Ile Ser Ser Glu Thr Ala Gly Ser Thr Asn Asp Asn<br>260 265 270 | | 3037 |
| acc tac ttc ggc tac agc acc ccc tgg ggg tat ttt gac ttt aac aga<br>Thr Tyr Phe Gly Tyr Ser Thr Pro Trp Gly Tyr Phe Asp Phe Asn Arg<br>275 280 285 | | 3085 |
| ttc cac tgc cac ttc tca cca cgt gac tgg cag cga ctc atc aac aac<br>Phe His Cys His Phe Ser Pro Arg Asp Trp Gln Arg Leu Ile Asn Asn<br>290 295 300 | | 3133 |
| aac tgg gga ttc cgg ccc aag aag ctg cgg ttc aag ctc ttc aac atc<br>Asn Trp Gly Phe Arg Pro Lys Lys Leu Arg Phe Lys Leu Phe Asn Ile<br>305 310 315 320 | | 3181 |
| cag gtc aag gag gtc acg acg aat gac ggc gtt acg acc atc gct aat<br>Gln Val Lys Glu Val Thr Thr Asn Asp Gly Val Thr Thr Ile Ala Asn<br>325 330 335 | | 3229 |
| aac ctt acc agc acg att cag gta ttc tcg gac tcg gaa tac cag ctg<br>Asn Leu Thr Ser Thr Ile Gln Val Phe Ser Asp Ser Glu Tyr Gln Leu<br>340 345 350 | | 3277 |
| ccg tac gtc ctc ggc tct gcg cac cag ggc tgc ctg cct ccg ttc ccg<br>Pro Tyr Val Leu Gly Ser Ala His Gln Gly Cys Leu Pro Pro Phe Pro<br>355 360 365 | | 3325 |
| gcg gac gtc ttc atg att cct cag tac ggc tac ctg act ctc aac aat<br>Ala Asp Val Phe Met Ile Pro Gln Tyr Gly Tyr Leu Thr Leu Asn Asn<br>370 375 380 | | 3373 |
| ggc agt cag tct gtg gga cgt tcc tcc ttc tac tgc ctg gag tac ttc<br>Gly Ser Gln Ser Val Gly Arg Ser Ser Phe Tyr Cys Leu Glu Tyr Phe<br>385 390 395 400 | | 3421 |
| ccc tct cag atg ctg aga acg ggc aac aac ttt gag ttc agc tac agc<br>Pro Ser Gln Met Leu Arg Thr Gly Asn Asn Phe Glu Phe Ser Tyr Ser<br>405 410 415 | | 3469 |
| ttc gag gac gtg cct ttc cac agc agc tac gca cac agc cag agc ctg<br>Phe Glu Asp Val Pro Phe His Ser Ser Tyr Ala His Ser Gln Ser Leu<br>420 425 430 | | 3517 |
| gac cgg ctg atg aat ccc ctc atc gac cag tac ttg tac tac ctg gcc<br>Asp Arg Leu Met Asn Pro Leu Ile Asp Gln Tyr Leu Tyr Tyr Leu Ala<br>435 440 445 | | 3565 |
| aga aca cag agt aac cca gga ggc aca gct ggc aat cgg gaa ctg cag<br>Arg Thr Gln Ser Asn Pro Gly Gly Thr Ala Gly Asn Arg Glu Leu Gln<br>450 455 460 | | 3613 |
| ttt tac cag ggc ggg cct tca act atg gcc gaa caa gcc aag aat tgg<br>Phe Tyr Gln Gly Gly Pro Ser Thr Met Ala Glu Gln Ala Lys Asn Trp<br>465 470 475 480 | | 3661 |
| tta cct gga cct tgc ttc cgg caa caa aga gtc tcc aaa acg ctg gat<br>Leu Pro Gly Pro Cys Phe Arg Gln Gln Arg Val Ser Lys Thr Leu Asp<br>485 490 495 | | 3709 |
| caa aac aac aac agc aac ttt gct tgg act ggt gcc acc aaa tat cac<br>Gln Asn Asn Asn Ser Asn Phe Ala Trp Thr Gly Ala Thr Lys Tyr His<br>500 505 510 | | 3757 |

```
ctg aac ggc aga aac tcg ttg gtt aat ccc ggc gtc gcc atg gca act      3805
Leu Asn Gly Arg Asn Ser Leu Val Asn Pro Gly Val Ala Met Ala Thr
        515                 520                 525 cac aag gac gac gag gac cgc ttt ttc cca tcc agc gga gtc ctg att      3853
His Lys Asp Asp Glu Asp Arg Phe Phe Pro Ser Ser Gly Val Leu Ile
    530                 535                 540 ttt gga aaa act gga gca act aac aaa act aca ttg gaa aat gtg tta      3901
Phe Gly Lys Thr Gly Ala Thr Asn Lys Thr Thr Leu Glu Asn Val Leu
545                 550                 555                 560 atg aca aat gaa gaa gaa att cgt cct act aat cct gta gcc acg gaa      3949
Met Thr Asn Glu Glu Glu Ile Arg Pro Thr Asn Pro Val Ala Thr Glu
                565                 570                 575 gaa tac ggg ata gtc agc agc aac tta caa gcg gct aat act gca gcc      3997
Glu Tyr Gly Ile Val Ser Ser Asn Leu Gln Ala Ala Asn Thr Ala Ala
            580                 585                 590 cag aca caa gtt gtc aac aac cag gga gcc tta cct ggc atg gtc tgg      4045
Gln Thr Gln Val Val Asn Asn Gln Gly Ala Leu Pro Gly Met Val Trp
        595                 600                 605 cag aac cgg gac gtg tac ctg cag ggt ccc atc tgg gcc aag att cct      4093
Gln Asn Arg Asp Val Tyr Leu Gln Gly Pro Ile Trp Ala Lys Ile Pro
    610                 615                 620 cac acg gat ggc aac ttt cac ccg tct cct ttg atg ggc ggc ttt gga      4141
His Thr Asp Gly Asn Phe His Pro Ser Pro Leu Met Gly Gly Phe Gly
625                 630                 635                 640 ctt aaa cat ccg cct cct cag atc ctg atc aag aac act ccc gtt ccc      4189
Leu Lys His Pro Pro Pro Gln Ile Leu Ile Lys Asn Thr Pro Val Pro
                645                 650                 655 gct aat cct ccg gag gtg ttt act cct gcc aag ttt gct tcg ttc atc      4237
Ala Asn Pro Pro Glu Val Phe Thr Pro Ala Lys Phe Ala Ser Phe Ile
            660                 665                 670 aca cag tac agc acc gga caa gtc agc gtg gaa atc gag tgg gag ctg      4285
Thr Gln Tyr Ser Thr Gly Gln Val Ser Val Glu Ile Glu Trp Glu Leu
        675                 680                 685 cag aag gaa aac agc aag cgc tgg aac ccg gag att cag tac acc tcc      4333
Gln Lys Glu Asn Ser Lys Arg Trp Asn Pro Glu Ile Gln Tyr Thr Ser
    690                 695                 700 aac ttt gaa aag cag act ggt gtg gac ttt gcc gtt gac agc cag ggt      4381
Asn Phe Glu Lys Gln Thr Gly Val Asp Phe Ala Val Asp Ser Gln Gly
705                 710                 715                 720 gtt tac tct gag cct cgc cct att ggc act cgt tac ctc acc cgt aat      4429
Val Tyr Ser Glu Pro Arg Pro Ile Gly Thr Arg Tyr Leu Thr Arg Asn
                725                 730                 735 ctg taa ttgcatgtta atcaataaac cggttgattc gtttcagttg aactttggtc      4485
Leu tcctgtgctt cttatcttat cggtttccat agcaactggt tacacattaa ctgcttgggt      4545
gcgcttcacg ataagaacac tgacgtcacc gcggtacccc tagtgatgga gttggccact      4605
ccctctatgc gcgctcgctc gctcggtggg gcctgcggac caaaggtccg cagacggcag      4665
agctctgctc tgccggcccc accgagcgag cgagcgcgca tagagggagt ggccaa          4721

<210> SEQ ID NO 26
<211> LENGTH: 737
<212> TYPE: PRT
<213> ORGANISM: Artificial Sequence
<220> FEATURE:
<223> OTHER INFORMATION: Synthetic Construct

<400> SEQUENCE: 26

Met Ala Ala Asp Gly Tyr Leu Pro Asp Trp Leu Glu Asp Asn Leu Ser
```

-continued

```
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asn Gly Arg Gly Leu Val Leu Pro
                35                  40                  45
Gly Tyr Lys Tyr Leu Gly Pro Phe Asn Gly Leu Asp Lys Gly Glu Pro
                50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Gly Ala Lys Thr Ala Pro Ala Lys Lys Arg
                130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
                180                 185                 190
Pro Ala Ala Pro Ser Ser Val Gly Ser Gly Thr Val Ala Ala Gly Gly
                195                 200                 205
Gly Ala Pro Met Ala Asp Asn Asn Glu Gly Ala Asp Gly Val Gly Asn
                210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Glu Thr Ala Gly Ser Thr Asn Asp Asn
                260                 265                 270
Thr Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Ile Gln Val Phe Ser Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
                370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
                405                 410                 415
Phe Glu Asp Val Pro Phe His Ser Ser Tyr Ala His Ser Gln Ser Leu
                420                 425                 430
```

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
        530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 27
<211> LENGTH: 4393
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 8
<220> FEATURE:
<221> NAME/KEY: CDS
<222> LOCATION: (2121)..(4337)
<223> OTHER INFORMATION: AAV8 VP1
<220> FEATURE:
<221> NAME/KEY: misc_feature
<222> LOCATION: (2532)..(4337)
<223> OTHER INFORMATION: AAV8 VP2
<220> FEATURE:

```
<221> NAME/KEY: misc_feature
<222> LOCATION: (2730)..(4337)
<223> OTHER INFORMATION: AAV8 VP3

<400> SEQUENCE: 27
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180
gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc cgcgtgagta aggccccgga ggccctcttc tttgttcagt tcgagaaggg     480
cgagagctac tttcacctgc acgttctggt cgagaccacg ggggtcaagt ccatggtgct     540
aggccgcttc ctgagtcaga ttcggaaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca agactcagcc     720
cgagctgcag tgggcgtgga ctaacatgga ggagtatata agcgcgtgct gaacctggc      780 cgagcgcaaa cggctcgtgg cgcagcacct gacccacgtc agccagacgc aggagcagaa     840
caaggagaat ctgaacccca attctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc ccgcggacat tacccagaac cgcatctacc gcatcctcgc    1140
tctcaacggc tacgaccctg cctacgccgg ctccgtcttt ctcggctggg ctcagaaaaa    1200
gttcgggaaa cgcaacacca tctggctgtt tggacccgcc accaccggca agaccaacat    1260
tgcggaagcc atcgcccacg ccgtgccctt ctacggctgc gtcaactgga ccaatgagaa    1320 cttcccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc caccccgtg atcgtcacct ccaacaccaa    1500
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa aagacccgcc ccgatgacg cggataaaag    1740 cgagcccaag cgggcctgcc cctcagtcgc ggatccatcg acgtcagacg cggaaggagc    1800
tccggtggac tttgccgaca ggtaccaaaa caaatgttct cgtcacgcgg gcatgcttca    1860
gatgctgttt ccctgcaaaa cgtgcgagag aatgaatcag aatttcaaca tttgcttcac    1920 acacgggtc agagactgct cagagtgttt ccccggcgtg tcagaatctc aaccggtcgt    1980
cagaaagagg acgtatcgga aactctgtgc gattcatcat ctgctggggc gggctcccga    2040
gattgcttgc tcggcctgcg atctggtcaa cgtggacctg atgactgtg tttctgagca    2100 ataaatgact taaaccaggt atg gct gcc gat ggt tat ctt cca gat tgg ctc    2153
                      Met Ala Ala Asp Gly Tyr Leu Pro Asp Trp Leu
                       1               5                  10
```

```
gag gac aac ctc tct gag ggc att cgc gag tgg tgg gcg ctg aaa cct    2201
Glu Asp Asn Leu Ser Glu Gly Ile Arg Glu Trp Trp Ala Leu Lys Pro
            15                  20                  25 gga gcc ccg aag ccc aaa gcc aac cag caa aag cag gac gac ggc cgg    2249
Gly Ala Pro Lys Pro Lys Ala Asn Gln Gln Lys Gln Asp Asp Gly Arg
        30                  35                  40 ggt ctg gtg ctt cct ggc tac aag tac ctc gga ccc ttc aac gga ctc    2297
Gly Leu Val Leu Pro Gly Tyr Lys Tyr Leu Gly Pro Phe Asn Gly Leu
    45                  50                  55 gac aag ggg gag ccc gtc aac gcg gcg gac gca gcg gcc ctc gag cac    2345
Asp Lys Gly Glu Pro Val Asn Ala Ala Asp Ala Ala Ala Leu Glu His
60                  65                  70                  75 gac aag gcc tac gac cag cag ctg cag gcg ggt gac aat ccg tac ctg    2393
Asp Lys Ala Tyr Asp Gln Gln Leu Gln Ala Gly Asp Asn Pro Tyr Leu
                80                  85                  90 cgg tat aac cac gcc gac gcc gag ttt cag gag cgt ctg caa gaa gat    2441
Arg Tyr Asn His Ala Asp Ala Glu Phe Gln Glu Arg Leu Gln Glu Asp
            95                  100                 105 acg tct ttt ggg ggc aac ctc ggg cga gca gtc ttc cag gcc aag aag    2489
Thr Ser Phe Gly Gly Asn Leu Gly Arg Ala Val Phe Gln Ala Lys Lys
        110                 115                 120 cgg gtt ctc gaa cct ctc ggt ctg gtt gag gaa ggc gct aag acg gct    2537
Arg Val Leu Glu Pro Leu Gly Leu Val Glu Glu Gly Ala Lys Thr Ala
    125                 130                 135 cct gga aag aag aga ccg gta gag cca tca ccc cag cgt tct cca gac    2585
Pro Gly Lys Lys Arg Pro Val Glu Pro Ser Pro Gln Arg Ser Pro Asp
140                 145                 150                 155 tcc tct acg ggc atc ggc aag aaa ggc caa cag ccc gcc aga aaa aga    2633
Ser Ser Thr Gly Ile Gly Lys Lys Gly Gln Gln Pro Ala Arg Lys Arg
                160                 165                 170 ctc aat ttt ggt cag act ggc gac tca gag tca gtt cca gac cct caa    2681
Leu Asn Phe Gly Gln Thr Gly Asp Ser Glu Ser Val Pro Asp Pro Gln
            175                 180                 185 cct ctc gga gaa cct cca gca gcg ccc tct ggt gtg gga cct aat aca    2729
Pro Leu Gly Glu Pro Pro Ala Ala Pro Ser Gly Val Gly Pro Asn Thr
        190                 195                 200 atg gct gca ggc ggt ggc gca cca atg gca gac aat aac gaa ggc gcc    2777
Met Ala Ala Gly Gly Gly Ala Pro Met Ala Asp Asn Asn Glu Gly Ala
    205                 210                 215 gac gga gtg ggt agt tcc tcg gga aat tgg cat tgc gat tcc aca tgg    2825
Asp Gly Val Gly Ser Ser Ser Gly Asn Trp His Cys Asp Ser Thr Trp
220                 225                 230                 235 ctg ggc gac aga gtc atc acc acc agc acc cga acc tgg gcc ctg ccc    2873
Leu Gly Asp Arg Val Ile Thr Thr Ser Thr Arg Thr Trp Ala Leu Pro
                240                 245                 250 acc tac aac aac cac ctc tac aag caa atc tcc aac ggg aca tcg gga    2921
Thr Tyr Asn Asn His Leu Tyr Lys Gln Ile Ser Asn Gly Thr Ser Gly
            255                 260                 265 gga gcc acc aac gac aac acc tac ttc ggc tac agc acc ccc tgg ggg    2969
Gly Ala Thr Asn Asp Asn Thr Tyr Phe Gly Tyr Ser Thr Pro Trp Gly
        270                 275                 280 tat ttt gac ttt aac aga ttc cac tgc cac ttt tca cca cgt gac tgg    3017
Tyr Phe Asp Phe Asn Arg Phe His Cys His Phe Ser Pro Arg Asp Trp
    285                 290                 295 cag cga ctc atc aac aac aac tgg gga ttc cgg ccc aag aga ctc agc    3065
Gln Arg Leu Ile Asn Asn Asn Trp Gly Phe Arg Pro Lys Arg Leu Ser
300                 305                 310                 315 ttc aag ctc ttc aac atc cag gtc aag gag gtc acg cag aat gaa ggc    3113
Phe Lys Leu Phe Asn Ile Gln Val Lys Glu Val Thr Gln Asn Glu Gly
```

```
                     320                 325                 330
acc aag acc atc gcc aat aac ctc acc agc acc atc cag gtg ttt acg    3161
Thr Lys Thr Ile Ala Asn Asn Leu Thr Ser Thr Ile Gln Val Phe Thr
            335                 340                 345 gac tcg gag tac cag ctg ccg tac gtt ctc ggc tct gcc cac cag ggc    3209
Asp Ser Glu Tyr Gln Leu Pro Tyr Val Leu Gly Ser Ala His Gln Gly
        350                 355                 360 tgc ctg cct ccg ttc ccg gcg gac gtg ttc atg att ccc cag tac ggc    3257
Cys Leu Pro Pro Phe Pro Ala Asp Val Phe Met Ile Pro Gln Tyr Gly
365                 370                 375 tac cta aca ctc aac aac ggt agt cag gcc gtg gga cgc tcc tcc ttc    3305
Tyr Leu Thr Leu Asn Asn Gly Ser Gln Ala Val Gly Arg Ser Ser Phe
380                 385                 390                 395 tac tgc ctg gaa tac ttt cct tcg cag atg ctg aga acc ggc aac aac    3353
Tyr Cys Leu Glu Tyr Phe Pro Ser Gln Met Leu Arg Thr Gly Asn Asn
                400                 405                 410 ttc cag ttt act tac acc ttc gag gac gtg cct ttc cac agc agc tac    3401
Phe Gln Phe Thr Tyr Thr Phe Glu Asp Val Pro Phe His Ser Ser Tyr
            415                 420                 425 gcc cac agc cag agc ttg gac cgg ctg atg aat cct ctg att gac cag    3449
Ala His Ser Gln Ser Leu Asp Arg Leu Met Asn Pro Leu Ile Asp Gln
        430                 435                 440 tac ctg tac tac ttg tct cgg act caa aca aca gga ggc acg gca aat    3497
Tyr Leu Tyr Tyr Leu Ser Arg Thr Gln Thr Thr Gly Gly Thr Ala Asn
445                 450                 455 acg cag act ctg ggc ttc agc caa ggt ggg cct aat aca atg gcc aat    3545
Thr Gln Thr Leu Gly Phe Ser Gln Gly Gly Pro Asn Thr Met Ala Asn
460                 465                 470                 475 cag gca aag aac tgg ctg cca gga ccc tgt tac cgc caa caa cgc gtc    3593
Gln Ala Lys Asn Trp Leu Pro Gly Pro Cys Tyr Arg Gln Gln Arg Val
                480                 485                 490 tca acg aca acc ggg caa aac aac aat agc aac ttt gcc tgg act gct    3641
Ser Thr Thr Thr Gly Gln Asn Asn Asn Ser Asn Phe Ala Trp Thr Ala
            495                 500                 505 ggg acc aaa tac cat ctg aat gga aga aat tca ttg gct aat cct ggc    3689
Gly Thr Lys Tyr His Leu Asn Gly Arg Asn Ser Leu Ala Asn Pro Gly
        510                 515                 520 atc gct atg gca aca cac aaa gac gac gag gag cgt ttt ttt ccc agt    3737
Ile Ala Met Ala Thr His Lys Asp Asp Glu Glu Arg Phe Phe Pro Ser
525                 530                 535 aac ggg atc ctg att ttt ggc aaa caa aat gct gcc aga gac aat gcg    3785
Asn Gly Ile Leu Ile Phe Gly Lys Gln Asn Ala Ala Arg Asp Asn Ala
540                 545                 550                 555 gat tac agc gat gtc atg ctc acc agc gag gaa gaa atc aaa acc act    3833
Asp Tyr Ser Asp Val Met Leu Thr Ser Glu Glu Glu Ile Lys Thr Thr
                560                 565                 570 aac cct gtg gct aca gag gaa tac ggt atc gtg gca gat aac ttg cag    3881
Asn Pro Val Ala Thr Glu Glu Tyr Gly Ile Val Ala Asp Asn Leu Gln
            575                 580                 585 cag caa aac acg gct cct caa att gga act gtc aac agc cag ggg gcc    3929
Gln Gln Asn Thr Ala Pro Gln Ile Gly Thr Val Asn Ser Gln Gly Ala
        590                 595                 600 tta ccc ggt atg gtc tgg cag aac cgg gac gtg tac ctg cag ggt ccc    3977
Leu Pro Gly Met Val Trp Gln Asn Arg Asp Val Tyr Leu Gln Gly Pro
605                 610                 615 atc tgg gcc aag att cct cac acg gac ggc aac ttc cac ccg tct ccg    4025
Ile Trp Ala Lys Ile Pro His Thr Asp Gly Asn Phe His Pro Ser Pro
620                 625                 630                 635 ctg atg ggc ggc ttt ggc ctg aaa cat cct ccg cct cag atc ctg atc    4073
```

```
Leu Met Gly Gly Phe Gly Leu Lys His Pro Pro Gln Ile Leu Ile
            640                 645                 650 aag aac acg cct gta cct gcg gat cct ccg acc acc ttc aac cag tca     4121
Lys Asn Thr Pro Val Pro Ala Asp Pro Pro Thr Thr Phe Asn Gln Ser
            655                 660                 665 aag ctg aac tct ttc atc acg caa tac agc acc gga cag gtc agc gtg     4169
Lys Leu Asn Ser Phe Ile Thr Gln Tyr Ser Thr Gly Gln Val Ser Val
            670                 675                 680 gaa att gaa tgg gag ctg cag aag gaa aac agc aag cgc tgg aac ccc     4217
Glu Ile Glu Trp Glu Leu Gln Lys Glu Asn Ser Lys Arg Trp Asn Pro
        685                 690                 695 gag atc cag tac acc tcc aac tac tac aaa tct aca agt gtg gac ttt     4265
Glu Ile Gln Tyr Thr Ser Asn Tyr Tyr Lys Ser Thr Ser Val Asp Phe
700                 705                 710                 715 gct gtt aat aca gaa ggc gtg tac tct gaa ccc cgc ccc att ggc acc     4313
Ala Val Asn Thr Glu Gly Val Tyr Ser Glu Pro Arg Pro Ile Gly Thr
                720                 725                 730 cgt tac ctc acc cgt aat ctg taa ttgcctgtta atcaataaac cggttgattc    4367
Arg Tyr Leu Thr Arg Asn Leu
                735 gtttcagttg aactttggtc tctgcg                                        4393

<210> SEQ ID NO 28
<211> LENGTH: 738
<212> TYPE: PRT
<213> ORGANISM: Artificial Sequence
<220> FEATURE:
<223> OTHER INFORMATION: Synthetic Construct

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
```

-continued

```
            210                 215                 220
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                    245                 250                 255

Leu Tyr Lys Gln Ile Ser Asn Gly Thr Ser Gly Gly Ala Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                    325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                    405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                    485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                    565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640
```

```
Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 29
<211> LENGTH: 4385
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 9
<220> FEATURE:
<221> NAME/KEY: CDS
<222> LOCATION: (2116)..(4329)
<223> OTHER INFORMATION: AAV9 VP1
<220> FEATURE:
<221> NAME/KEY: misc_feature
<222> LOCATION: (2527)..(4329)
<223> OTHER INFORMATION: AAV9 VP2
<220> FEATURE:
<221> NAME/KEY: misc_feature
<222> LOCATION: (2725)..(4329)
<223> OTHER INFORMATION: AAV9 VP3

<400> SEQUENCE: 29
cagagaggga gtggccaact ccatcactag gggtaatcgc gaagcgcctc ccacgctgcc      60
gcgtcagcgc tgacgtagat tacgtcatag gggagtggtc ctgtattagc tgtcacgtga     120
gtgcttttgc gacattttgc gacaccacat ggccatttga ggtatatatg gccgagtgag     180
cgagcaggat ctccattttg accgcgaaat ttgaacgagc agcagccatg ccgggcttct     240
acgagattgt gatcaaggtg ccgagcgacc tggacgagca cctgccgggc atttctgact     300
cttttgtgaa ctgggtggcc gagaaggaat gggagctgcc cccggattct gacatggatc     360
ggaatctgat cgagcaggca cccctgaccg tggccgagaa gctgcagcgc gacttcctgg     420
tccaatggcg ccgcgtgagt aaggccccgg aggccctctt ctttgttcag ttcgagaagg     480
gcgagagcta ctttcacctg cacgttctgg tcgagaccac gggggtcaag tccatggtgc     540
taggccgctt cctgagtcag attcgggaga agctggtcca gaccatctac gcgggatcg      600 agccgacct gcccaactgg ttcgcggtga ccaagacgcg taatggcgcc ggcgggggga     660
acaaggtggt ggacgagtgc tacatcccca actacctcct gcccaagact cagcccgagc     720
tgcagtgggc gtggactaac atggaggagt atataagcgc gtgcttgaac ctggccgagc     780
gcaaacggct cgtggcgcag cacctgaccc acgtcagcca gacgcaggag cagaacaagg     840
agaatctgaa ccccaattct gacgcgcccg tgatcaggtc aaaaacctcc gcgcgctaca     900
tggagctggt cgggtggctg gtggaccggg gcatcacctc cgagaagcag tggatccagg     960
aggaccaggc ctcgtacatc tccttcaacg ccgcctccaa ctcgcggtcc cagatcaagg    1020
```

```
ccgcgctgga caatgccggc aagatcatgg cgctgaccaa atccgcgccc gactacctgg    1080
taggcccttc acttccggtg acattacgc agaaccgcat ctaccgcatc ctgcagctca     1140
acggctacga ccctgcctac gccggctccg tctttctcgg ctgggcacaa agaagttcg     1200 ggaaacgcaa caccatctgg ctgtttgggc cggccaccac gggaaagacc aacatcgcag    1260
aagccattgc ccacgccgtg cccttctacg gctgcgtcaa ctggaccaat gagaactttc    1320
ccttcaacga ttgcgtcgac aagatggtga tctggtggga ggagggcaag atgacggcca    1380
aggtcgtgga gtccgccaag gccattctcg gcggcagcaa ggtgcgcgtg gaccaaaagt    1440
gcaagtcgtc cgcccagatc gaccccactc ccgtgatcgt cacctccaac accaacatgt    1500
gcgccgtgat tgacgggaac agcaccacct tcgagcacca gcagcctctc caggaccgga    1560
tgtttaagtt cgaactcacc cgccgtctgg agcacgactt tggcaaggtg acaaagcagg    1620
aagtcaaaga gttcttccgc tgggccagtg atcacgtgac cgaggtggcg catgagtttt    1680
acgtcagaaa gggcggagcc agcaaaagac ccgcccccga tgacgcggat aaaagcgagc    1740
ccaagcgggc ctgcccctca gtcgcggatc catcgacgtc agacgcggaa ggagctccgg    1800
tggactttgc cgacaggtac caaaacaaat gttctcgtca cgcgggcatg cttcagatgc    1860
tgcttccctg caaaacgtgc gagagaatga atcagaattt caacatttgc ttcacacacg    1920
gggtcagaga ctgctcagag tgtttccccg gcgtgtcaga atctcaaccg gtcgtcagaa    1980
agaggacgta tcggaaactc tgtgcgattc atcatctgct ggggcgggct cccgagattg    2040
cttgctcggc ctgcgatctg gtcaacgtgg acctggatga ctgtgtttct gagcaataaa    2100
tgacttaaac caggt atg gct gcc gat ggt tat ctt cca gat tgg ctc gag    2151
              Met Ala Ala Asp Gly Tyr Leu Pro Asp Trp Leu Glu
                1               5                  10 gac aac ctc tct gag ggc att cgc gag tgg tgg gcg ctg aaa cct gga    2199
Asp Asn Leu Ser Glu Gly Ile Arg Glu Trp Trp Ala Leu Lys Pro Gly
         15                  20                  25 gcc ccg aag ccc aaa gcc aac cag caa aag cag gac gac ggc cgg ggt    2247
Ala Pro Lys Pro Lys Ala Asn Gln Gln Lys Gln Asp Asp Gly Arg Gly
 30                  35                  40 ctg gtg ctt cct ggc tac aag tac ctc gga ccc ttc aac gga ctc gac    2295
Leu Val Leu Pro Gly Tyr Lys Tyr Leu Gly Pro Phe Asn Gly Leu Asp
45                  50                  55                  60 aag ggg gag ccc gtc aac gcg gcg gac gca gcg gcc ctc gag cac ggc    2343
Lys Gly Glu Pro Val Asn Ala Ala Asp Ala Ala Ala Leu Glu His Gly
                 65                  70                  75 aag gcc tac gac cag cag ctg cag gcg ggt gac aat ccg tac ctg cgg    2391
Lys Ala Tyr Asp Gln Gln Leu Gln Ala Gly Asp Asn Pro Tyr Leu Arg
         80                  85                  90 tat aac cac gcc gac gcc gag ttt cag gag cgt ctg caa gaa gat acg    2439
Tyr Asn His Ala Asp Ala Glu Phe Gln Glu Arg Leu Gln Glu Asp Thr
             95                 100                 105 tct ttt ggg ggc aac ctc ggg cga gca gtc ttc cag gcc aag aag cgg    2487
Ser Phe Gly Gly Asn Leu Gly Arg Ala Val Phe Gln Ala Lys Lys Arg
        110                 115                 120 gtt ctc gaa cct ctc ggt ctg gtt gag gaa ggc gct aag acg gct cct    2535
Val Leu Glu Pro Leu Gly Leu Val Glu Glu Gly Ala Lys Thr Ala Pro
125                 130                 135                 140 gga aag aag aga ccg gta gag cca tca ccc cag cgt tct cca gac tcc    2583
Gly Lys Lys Arg Pro Val Glu Pro Ser Pro Gln Arg Ser Pro Asp Ser
                145                 150                 155 tct acg ggc atc ggc aag aaa ggc caa cag ccc gcc aga aaa aga ctc    2631
Ser Thr Gly Ile Gly Lys Lys Gly Gln Gln Pro Ala Arg Lys Arg Leu
```

-continued

```
                    160                 165                 170
aat ttt ggt cag act ggc gac tca gag tca gtt cca gac cct caa cct    2679
Asn Phe Gly Gln Thr Gly Asp Ser Glu Ser Val Pro Asp Pro Gln Pro
        175                 180                 185 ctc gga gaa cct cca gca gcg ccc tct ggt gtg gga cct aat aca atg    2727
Leu Gly Glu Pro Pro Ala Ala Pro Ser Gly Val Gly Pro Asn Thr Met
190                 195                 200 gct gca ggc ggt ggc gca cca atg gca gac aat aac gaa ggc gcc gac    2775
Ala Ala Gly Gly Gly Ala Pro Met Ala Asp Asn Asn Glu Gly Ala Asp
205                 210                 215                 220 gga gtg ggt aat tcc tcg gga aat tgg cat tgc gat tcc aca tgg ctg    2823
Gly Val Gly Asn Ser Ser Gly Asn Trp His Cys Asp Ser Thr Trp Leu
                225                 230                 235 ggg gac aga gtc atc acc acc agc acc cga acc tgg gca ttg ccc acc    2871
Gly Asp Arg Val Ile Thr Thr Ser Thr Arg Thr Trp Ala Leu Pro Thr
        240                 245                 250 tac aac aac cac ctc tac aag caa atc tcc aat gga aca tcg gga gga    2919
Tyr Asn Asn His Leu Tyr Lys Gln Ile Ser Asn Gly Thr Ser Gly Gly
                255                 260                 265 agc acc aac gac aac acc tac ttt ggc tac agc acc ccc tgg ggg tat    2967
Ser Thr Asn Asp Asn Thr Tyr Phe Gly Tyr Ser Thr Pro Trp Gly Tyr
270                 275                 280 ttt gac ttc aac aga ttc cac tgc cac ttc tca cca cgt gac tgg cag    3015
Phe Asp Phe Asn Arg Phe His Cys His Phe Ser Pro Arg Asp Trp Gln
285                 290                 295                 300 cga ctc atc aac aac aac tgg gga ttc cgg cca aag aga ctc aac ttc    3063
Arg Leu Ile Asn Asn Asn Trp Gly Phe Arg Pro Lys Arg Leu Asn Phe
                305                 310                 315 aag ctg ttc aac atc cag gtc aag gag gtt acg acg aac gaa ggc acc    3111
Lys Leu Phe Asn Ile Gln Val Lys Glu Val Thr Thr Asn Glu Gly Thr
        320                 325                 330 aag acc atc gcc aat aac ctt acc agc acc gtc cag gtc ttt acg gac    3159
Lys Thr Ile Ala Asn Asn Leu Thr Ser Thr Val Gln Val Phe Thr Asp
                335                 340                 345 tcg gag tac cag cta ccg tac gtc cta ggc tct gcc cac caa gga tgc    3207
Ser Glu Tyr Gln Leu Pro Tyr Val Leu Gly Ser Ala His Gln Gly Cys
350                 355                 360 ctg cca ccg ttt cct gca gac gtc ttc atg gtt cct cag tac ggc tac    3255
Leu Pro Pro Phe Pro Ala Asp Val Phe Met Val Pro Gln Tyr Gly Tyr
365                 370                 375                 380 ctg acg ctc aac aat gga agt caa gcg tta gga cgt tct tct ttc tac    3303
Leu Thr Leu Asn Asn Gly Ser Gln Ala Leu Gly Arg Ser Ser Phe Tyr
                385                 390                 395 tgt ctg gaa tac ttc cct tct cag atg ctg aga acc ggc aac aac ttt    3351
Cys Leu Glu Tyr Phe Pro Ser Gln Met Leu Arg Thr Gly Asn Asn Phe
        400                 405                 410 cag ttc agc tac act ttc gag gac gtg cct ttc cac agc agc tac gca    3399
Gln Phe Ser Tyr Thr Phe Glu Asp Val Pro Phe His Ser Ser Tyr Ala
                415                 420                 425 cac agc cag agt cta gat cga ctg atg aac ccc ctc atc gac cag tac    3447
His Ser Gln Ser Leu Asp Arg Leu Met Asn Pro Leu Ile Asp Gln Tyr
430                 435                 440 cta tac tac ctg tca aga aca cag aca act gga act ggg gga act caa    3495
Leu Tyr Tyr Leu Val Arg Thr Gln Thr Thr Gly Thr Gly Gly Thr Gln
445                 450                 455                 460 act ttg gca ttc agc caa gca ggc cct agc tca atg gcc aat cag gct    3543
Thr Leu Ala Phe Ser Gln Ala Gly Pro Ser Ser Met Ala Asn Gln Ala
                465                 470                 475 aga aac tgg gta ccc ggg cct tgc tac cgt cag cag cgc gtc tcc aca    3591
```

```
                Arg Asn Trp Val Pro Gly Pro Cys Tyr Arg Gln Gln Arg Val Ser Thr
                            480                 485                 490 acc acc aac caa aat aac aac agc aac ttt gcg tgg acg gga gct gct                 3639
Thr Thr Asn Gln Asn Asn Asn Ser Asn Phe Ala Trp Thr Gly Ala Ala
            495                 500                 505 aaa ttc aag ctg aac ggg aga gac tcg cta atg aat cct ggc gtg gct                 3687
Lys Phe Lys Leu Asn Gly Arg Asp Ser Leu Met Asn Pro Gly Val Ala
510                 515                 520 atg gca tcg cac aaa gac gac gag gac cgc ttc ttt cca tca agt ggc                 3735
Met Ala Ser His Lys Asp Asp Glu Asp Arg Phe Phe Pro Ser Ser Gly
525                 530                 535                 540 gtt ctc ata ttt ggc aag caa gga gcc ggg aac gat gga gtc gac tac                 3783
Val Leu Ile Phe Gly Lys Gln Gly Ala Gly Asn Asp Gly Val Asp Tyr
                545                 550                 555 agc cag gtg ctg att aca gat gag gaa gaa att aaa gcc acc aac cct                 3831
Ser Gln Val Leu Ile Thr Asp Glu Glu Glu Ile Lys Ala Thr Asn Pro
            560                 565                 570 gta gcc aca gag gaa tac gga gca gtg gcc atc aac aac cag gcc gct                 3879
Val Ala Thr Glu Glu Tyr Gly Ala Val Ala Ile Asn Asn Gln Ala Ala
        575                 580                 585 aac acg cag gcg caa act gga ctt gtg cat aac cag gga gtt att cct                 3927
Asn Thr Gln Ala Gln Thr Gly Leu Val His Asn Gln Gly Val Ile Pro
590                 595                 600 ggt atg gtc tgg cag aac cgg gac gtg tac ctg cag ggc cct att tgg                 3975
Gly Met Val Trp Gln Asn Arg Asp Val Tyr Leu Gln Gly Pro Ile Trp
605                 610                 615                 620 gct aaa ata cct cac aca gat ggc aac ttt cac ccg tct cct ctg atg                 4023
Ala Lys Ile Pro His Thr Asp Gly Asn Phe His Pro Ser Pro Leu Met
                625                 630                 635 ggt gga ttt gga ctg aaa cac cca cct cca cag att cta att aaa aat                 4071
Gly Gly Phe Gly Leu Lys His Pro Pro Pro Gln Ile Leu Ile Lys Asn
            640                 645                 650 aca cca gtg ccg gca gat cct cct ctt acc ttc aat caa gcc aag ctg                 4119
Thr Pro Val Pro Ala Asp Pro Pro Leu Thr Phe Asn Gln Ala Lys Leu
        655                 660                 665 aac tct ttc atc acg cag tac agc acg gga caa gtc agc gtg gaa atc                 4167
Asn Ser Phe Ile Thr Gln Tyr Ser Thr Gly Gln Val Ser Val Glu Ile
670                 675                 680 gag tgg gag ctg cag aaa gaa aac agc aag cgc tgg aat cca gag atc                 4215
Glu Trp Glu Leu Gln Lys Glu Asn Ser Lys Arg Trp Asn Pro Glu Ile
685                 690                 695                 700 cag tat act tca aac tac tac aaa tct aca aat gtg gac ttt gct gtc                 4263
Gln Tyr Thr Ser Asn Tyr Tyr Lys Ser Thr Asn Val Asp Phe Ala Val
                705                 710                 715 aat acc aaa ggt gtt tac tct gag cct cgc ccc att ggt act cgt tac                 4311
Asn Thr Lys Gly Val Tyr Ser Glu Pro Arg Pro Ile Gly Thr Arg Tyr
            720                 725                 730 ctc acc cgt aat ttg taa ttgcctgtta atcaataaac cggttaattc                        4359
Leu Thr Arg Asn Leu
            735 gtttcagttg aactttggtc tctgcg                                                    4385

<210> SEQ ID NO 30
<211> LENGTH: 737
<212> TYPE: PRT
<213> ORGANISM: Artificial Sequence
<220> FEATURE:
<223> OTHER INFORMATION: Synthetic Construct

<400> SEQUENCE: 30
```

```
Met Ala Ala Asp Gly Tyr Leu Pro Asp Trp Leu Glu Asp Asn Leu Ser
1               5                  10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Gly Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Asn
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Thr Asn Glu Gly Thr Lys Thr Ile Ala
                325                 330                 335
Asn Asn Leu Thr Ser Thr Val Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Val Pro Gln Tyr Gly Tyr Leu Thr Leu Asn
    370                 375                 380
Asn Gly Ser Gln Ala Leu Gly Arg Ser Ser Phe Tyr Cys Leu Glu Tyr
385                 390                 395                 400
Phe Pro Ser Gln Met Leu Arg Thr Gly Asn Asn Phe Gln Phe Ser Tyr
                405                 410                 415
Thr Phe Glu Asp Val Pro Phe His Ser Ser Tyr Ala His Ser Gln Ser
```

-continued

```
                420                 425                 430
Leu Asp Arg Leu Met Asn Pro Leu Ile Asp Gln Tyr Leu Tyr Tyr Leu
            435                 440                 445
Val Arg Thr Gln Thr Thr Gly Thr Gly Gly Thr Gln Thr Leu Ala Phe
    450                 455                 460
Ser Gln Ala Gly Pro Ser Ser Met Ala Asn Gln Ala Arg Asn Trp Val
465                 470                 475                 480
Pro Gly Pro Cys Tyr Arg Gln Gln Arg Val Ser Thr Thr Thr Asn Gln
                485                 490                 495
Asn Asn Asn Ser Asn Phe Ala Trp Thr Gly Ala Ala Lys Phe Lys Leu
            500                 505                 510
Asn Gly Arg Asp Ser Leu Met Asn Pro Gly Val Ala Met Ala Ser His
    515                 520                 525
Lys Asp Asp Glu Asp Arg Phe Phe Pro Ser Ser Gly Val Leu Ile Phe
530                 535                 540
Gly Lys Gln Gly Ala Gly Asn Asp Gly Val Asp Tyr Ser Gln Val Leu
545                 550                 555                 560
Ile Thr Asp Glu Glu Glu Ile Lys Ala Thr Asn Pro Val Ala Thr Glu
                565                 570                 575
Glu Tyr Gly Ala Val Ala Ile Asn Asn Gln Ala Ala Asn Thr Gln Ala
            580                 585                 590
Gln Thr Gly Leu Val His Asn Gln Gly Val Ile Pro Gly Met Val Trp
    595                 600                 605
Gln Asn Arg Asp Val Tyr Leu Gln Gly Pro Ile Trp Ala Lys Ile Pro
610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asp Pro Pro Leu Thr Phe Asn Gln Ala Lys Leu Asn Ser Phe Ile
            660                 665                 670
Thr Gln Tyr Ser Thr Gly Gln Val Ser Val Glu Ile Glu Trp Glu Leu
    675                 680                 685
Gln Lys Glu Asn Ser Lys Arg Trp Asn Pro Glu Ile Gln Tyr Thr Ser
690                 695                 700
Asn Tyr Tyr Lys Ser Thr Asn Val Asp Phe Ala Val Asn Thr Lys Gly
705                 710                 715                 720
Val Tyr Ser Glu Pro Arg Pro Ile Gly Thr Arg Tyr Leu Thr Arg Asn
                725                 730                 735
Leu

<210> SEQ ID NO 31
<211> LENGTH: 4102
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 10
<220> FEATURE:
<221> NAME/KEY: CDS
<222> LOCATION: (1886)..(4102)
<223> OTHER INFORMATION: AAV10 VP1
<220> FEATURE:
<221> NAME/KEY: misc_feature
<222> LOCATION: (2297)..(4102)
<223> OTHER INFORMATION: AAV10 VP2
```

<220> FEATURE:
<221> NAME/KEY: misc_feature
<222> LOCATION: (2495)..(4102)
<223> OTHER INFORMATION: AAV10 VP3

<400> SEQUENCE: 31

| | |
|---|---:|
| atgccgggct tctacgagat cgtgatcaag gtgccgagcg acctggacga gcacctgccg | 60 |
| ggcatttctg actcgtttgt gaactgggtg gccgagaagg aatgggagct gccccggat | 120 |
| tctgacatgg atcggaatct gatcgagcag gcacccctga ccgtggccga gaagctgcag | 180 |
| cgcgacttcc tggtccactg gcgccgcgtg agtaaggccc ggaggccct cttctttgtt | 240 |
| cagttcgaga gggcgagtc ctactttcac ctgcacgttc tggtcgagac cacggggtc | 300 |
| aagtccatgg tcctgggccg cttcctgagt cagatcagag acaggctggt gcagaccatc | 360 |
| taccgcgggg tagagcccac gctgcccaac tggttcgcgg tgaccaagac gcgaaatggc | 420 |
| gccggcgggg ggaacaaggt ggtggacgag tgctacatcc ccaactacct cctgcccaag | 480 |
| acgcagcccg agctgcagtg ggcgtggact aacatggagg agtatataag cgcgtgtctg | 540 |
| aacctcgcgg agcgtaaacg gctcgtggcg cagcacctga cccacgtcag ccagacgcag | 600 |
| gagcagaaca aggagaatct gaacccgaat tctgacgcgc ccgtgatcag gtcaaaaacc | 660 |
| tccgcgcgct acatggagct ggtcgggtgg ctggtggacc ggggcatcac ctccgagaag | 720 |
| cagtggatcc aggaggacca ggcctcgtac atctccttca cgccgcctc caactcgcgg | 780 |
| tcccagatca aggccgcgct ggacaatgcc ggaaagatca tggcgctgac caaatccgcg | 840 |
| cccgactacc tggtaggccc gtccttaccc gcggacatta aggccaaccg catctaccgc | 900 |
| atcctggagc tcaacggcta cgaccccgcc tacgccggct ccgtcttcct gggctgggcg | 960 |
| cagaaaaagt tcggtaaaag gaatacaatt tggctgttcg ggcccgccac caccggcaag | 1020 |
| accaacatcg cggaagccat cgcccacgcc gtgcccttct acggctgcgt caactggacc | 1080 |
| aatgagaact ttccttcaa cgattgcgtc gacaagatgg tgatctggtg ggaggagggc | 1140 |
| aagatgaccg ccaaggtcgt ggagtccgcc aaggccattc gggcggaag caaggtgcgc | 1200 |
| gtcgaccaaa agtgcaagtc ctcggcccag atcgaccca cgcccgtgat cgtcacctcc | 1260 |
| aacaccaaca tgtgcgccgt gatcgacggg aacagcacca ccttcgagca ccagcagccc | 1320 |
| ctgcaggacc gcatgttcaa gttcgagctc acccgccgtc tggagcacga ctttggcaag | 1380 |
| gtgaccaagc aggaagtcaa agagttcttc cgctgggctc aggatcacgt gactgaggtg | 1440 |
| acgcatgagt tctacgtcag aaagggcgga gccaccaaaa gacccgcccc cagtgacgcg | 1500 |
| gatataagcg agcccaagcg ggcctgcccc tcagttgcgg agccatcgac gtcagacgcg | 1560 |
| gaagcaccgg tggactttgc ggacaggtac caaaacaaat gttctcgtca cgcgggcatg | 1620 |
| cttcagatgc tgtttccctg caagacatgc gagagaatga atcagaattt caacgtctgc | 1680 |
| ttcacgcacg gggtcagaga ctgctcagag tgcttcccg gcgcgtcaga atctcaacct | 1740 |
| gtcgtcagaa aaagacgta tcagaaactg tgcgcgattc atcatctgct ggggcgggca | 1800 |
| cccgagattg cgtgttcggc ctgcgatctc gtcaacgtgg acttggatga ctgtgtttct | 1860 |

| | | | | | | | | | | | | | |
|---|---|---|---|---|---|---|---|---|---|---|---|---|---:|
| gagcaataaa tgacttaaac caggt | atg | gct | gct | gac | ggt | tat | ctt | cca | gat | | | | 1912 |
| | Met | Ala | Ala | Asp | Gly | Tyr | Leu | Pro | Asp | | | | |
| | 1 | | | | 5 | | | | | | | | |

| | | | | | | | | | | | | |
|---|---|---|---|---|---|---|---|---|---|---|---|---:|
| tgg | ctc | gag | gac | aac | ctc | tct | gag | ggc | att | cgc | gag | tgg | tgg | gac | ctg | 1960 |
| Trp | Leu | Glu | Asp | Asn | Leu | Ser | Glu | Gly | Ile | Arg | Glu | Trp | Trp | Asp | Leu | |
| 10 | | | | 15 | | | | | 20 | | | | | 25 | | |

| | | | | | | | | | | | | |
|---|---|---|---|---|---|---|---|---|---|---|---|---:|
| aaa | cct | gga | gcc | ccc | aag | ccc | aag | gcc | aac | cag | cag | aag | cag | gac | gac | 2008 |
| Lys | Pro | Gly | Ala | Pro | Lys | Pro | Lys | Ala | Asn | Gln | Gln | Lys | Gln | Asp | Asp | |

30                    35                    40
ggc cgg ggt ctg gtg ctt cct ggc tac aag tac ctc gga ccc ttc aac     2056
Gly Arg Gly Leu Val Leu Pro Gly Tyr Lys Tyr Leu Gly Pro Phe Asn
             45                    50                    55 gga ctc gac aag ggg gag ccc gtc aac gcg gcg gac gca gcg gcc ctc     2104
Gly Leu Asp Lys Gly Glu Pro Val Asn Ala Ala Asp Ala Ala Ala Leu
         60                    65                    70 gag cac gac aag gcc tac gac cag cag ctc aaa gcg ggt gac aat ccg     2152
Glu His Asp Lys Ala Tyr Asp Gln Gln Leu Lys Ala Gly Asp Asn Pro
     75                    80                    85 tac ctg cgg tat aac cac gcc gac gcc gag ttt cag gag cgt ctg caa     2200
Tyr Leu Arg Tyr Asn His Ala Asp Ala Glu Phe Gln Glu Arg Leu Gln
 90                    95                   100                   105 gaa gat acg tct ttt ggg ggc aac ctc ggg cga gca gtc ttc cag gcc     2248
Glu Asp Thr Ser Phe Gly Gly Asn Leu Gly Arg Ala Val Phe Gln Ala
                    110                   115                   120 aag aag cgg gtt ctc gaa cct ctc ggt ctg gtt gag gaa gct gct aag     2296
Lys Lys Arg Val Leu Glu Pro Leu Gly Leu Val Glu Glu Ala Ala Lys
                125                   130                   135 acg gct cct gga aag aag aga ccg gta gaa ccg tca cct cag cgt tcc     2344
Thr Ala Pro Gly Lys Lys Arg Pro Val Glu Pro Ser Pro Gln Arg Ser
            140                   145                   150 ccc gac tcc tcc acg ggc atc ggc aag aaa ggc cag cag ccc gct aaa     2392
Pro Asp Ser Ser Thr Gly Ile Gly Lys Lys Gly Gln Gln Pro Ala Lys
        155                   160                   165 aag aga ctg aac ttt ggg cag act ggc gag tca gag tca gtc ccc gac     2440
Lys Arg Leu Asn Phe Gly Gln Thr Gly Glu Ser Glu Ser Val Pro Asp
170                   175                   180                   185 cct caa cca atc gga gaa cca cca gca ggc ccc tct ggt ctg gga tct     2488
Pro Gln Pro Ile Gly Glu Pro Pro Ala Gly Pro Ser Gly Leu Gly Ser
                190                   195                   200 ggt aca atg gct gca ggc ggt ggc gct cca atg gca gac aat aac gaa     2536
Gly Thr Met Ala Ala Gly Gly Gly Ala Pro Met Ala Asp Asn Asn Glu
            205                   210                   215 ggc gcc gac gga gtg ggt agt tcc tca gga aat tgg cat tgc gat tcc     2584
Gly Ala Asp Gly Val Gly Ser Ser Ser Gly Asn Trp His Cys Asp Ser
        220                   225                   230 aca tgg ctg ggc gac aga gtc atc acc acc agc acc cga acc tgg gcc     2632
Thr Trp Leu Gly Asp Arg Val Ile Thr Thr Ser Thr Arg Thr Trp Ala
235                   240                   245 ctg ccc acc tac aac aac cac ctc tac aag caa atc tcc aac ggg aca     2680
Leu Pro Thr Tyr Asn Asn His Leu Tyr Lys Gln Ile Ser Asn Gly Thr
250                   255                   260                   265 tcg gga gga agc acc aac gac aac acc tac ttc ggc tac agc acc ccc     2728
Ser Gly Gly Ser Thr Asn Asp Asn Thr Tyr Phe Gly Tyr Ser Thr Pro
                270                   275                   280 tgg ggg tat ttt gac ttc aac aga ttc cac tgc cac ttc tca cca cgt     2776
Trp Gly Tyr Phe Asp Phe Asn Arg Phe His Cys His Phe Ser Pro Arg
            285                   290                   295 gac tgg cag cga ctc atc aac aac aac tgg gga ttc cgg cca aaa aga     2824
Asp Trp Gln Arg Leu Ile Asn Asn Asn Trp Gly Phe Arg Pro Lys Arg
        300                   305                   310 ctc agc ttc aag ctc ttc aac atc cag gtc aag gag gtc acg cag aat     2872
Leu Ser Phe Lys Leu Phe Asn Ile Gln Val Lys Glu Val Thr Gln Asn
    315                   320                   325 gaa ggc acc aag acc atc gcc aat aac ctt acc agc acg att cag gta     2920
Glu Gly Thr Lys Thr Ile Ala Asn Asn Leu Thr Ser Thr Ile Gln Val
330                   335                   340                   345 ttt acg gac tcg gaa tac cag ctg ccg tac gtc ctc ggc tcc gcg cac     2968

```
Phe Thr Asp Ser Glu Tyr Gln Leu Pro Tyr Val Leu Gly Ser Ala His
                350                 355                 360 cag ggc tgc ctg cct ccg ttc ccg gcg gat gtc ttc atg att ccc cag           3016
Gln Gly Cys Leu Pro Pro Phe Pro Ala Asp Val Phe Met Ile Pro Gln
            365                 370                 375 tac ggc tac ctg aca ctg aac aat gga agt caa gcc gta ggc cgt tcc           3064
Tyr Gly Tyr Leu Thr Leu Asn Asn Gly Ser Gln Ala Val Gly Arg Ser
        380                 385                 390 tcc ttc tac tgc ctg gaa tat ttt cca tct caa atg ctg cga act gga           3112
Ser Phe Tyr Cys Leu Glu Tyr Phe Pro Ser Gln Met Leu Arg Thr Gly
    395                 400                 405 aac aat ttt gaa ttc agc tac acc ttc gag gac gtg cct ttc cac agc           3160
Asn Asn Phe Glu Phe Ser Tyr Thr Phe Glu Asp Val Pro Phe His Ser
410                 415                 420                 425 agc tac gca cac agc cag agc ttg gac cga ctg atg aat cct ctc att           3208
Ser Tyr Ala His Ser Gln Ser Leu Asp Arg Leu Met Asn Pro Leu Ile
                430                 435                 440 gac cag tac ctg tac tac tta tcc aga act cag tcc aca gga gga act           3256
Asp Gln Tyr Leu Tyr Tyr Leu Ser Arg Thr Gln Ser Thr Gly Gly Thr
            445                 450                 455 caa ggt acc cag caa ttg tta ttt tct caa gct ggg cct gca aac atg           3304
Gln Gly Thr Gln Gln Leu Leu Phe Ser Gln Ala Gly Pro Ala Asn Met
        460                 465                 470 tcg gct cag gcc aag aac tgg ctg cct gga cct tgc tac cgg cag cag           3352
Ser Ala Gln Ala Lys Asn Trp Leu Pro Gly Pro Cys Tyr Arg Gln Gln
    475                 480                 485 cga gtc tcc acg aca ctg tcg caa aac aac aac agc aac ttt gct tgg           3400
Arg Val Ser Thr Thr Leu Ser Gln Asn Asn Asn Ser Asn Phe Ala Trp
490                 495                 500                 505 act ggt gcc acc aaa tat cac ctg aac gga aga gac tct ctg gtg aat           3448
Thr Gly Ala Thr Lys Tyr His Leu Asn Gly Arg Asp Ser Leu Val Asn
                510                 515                 520 ccc ggt gtc gcc atg gca acc cac aag gac gac gag gaa cgc ttc ttc           3496
Pro Gly Val Ala Met Ala Thr His Lys Asp Asp Glu Glu Arg Phe Phe
            525                 530                 535 ccg tcg agc gga gtc ctg atg ttt gga aaa cag ggt gct gga aga gac           3544
Pro Ser Ser Gly Val Leu Met Phe Gly Lys Gln Gly Ala Gly Arg Asp
        540                 545                 550 aat gtg gac tac agc agc gtt atg cta aca agc gaa gaa gaa att aaa           3592
Asn Val Asp Tyr Ser Ser Val Met Leu Thr Ser Glu Glu Glu Ile Lys
    555                 560                 565 acc act aac cct gta gcc aca gaa caa tac ggc gtg gtg gct gac aac           3640
Thr Thr Asn Pro Val Ala Thr Glu Gln Tyr Gly Val Val Ala Asp Asn
570                 575                 580                 585 ttg cag caa gcc aat aca ggg cct att gtg gga aat gtc aac agc caa           3688
Leu Gln Gln Ala Asn Thr Gly Pro Ile Val Gly Asn Val Asn Ser Gln
                590                 595                 600 gga gcc tta cct ggc atg gtc tgg cag aac cga gac gtg tac ctg cag           3736
Gly Ala Leu Pro Gly Met Val Trp Gln Asn Arg Asp Val Tyr Leu Gln
            605                 610                 615 ggt ccc atc tgg gcc aag att cct cac acg gac ggc aac ttt cac ccg           3784
Gly Pro Ile Trp Ala Lys Ile Pro His Thr Asp Gly Asn Phe His Pro
        620                 625                 630 tct cct ctg atg ggc ggc ttt gga ctt aaa cac ccg cct cca cag atc           3832
Ser Pro Leu Met Gly Gly Phe Gly Leu Lys His Pro Pro Pro Gln Ile
    635                 640                 645 ctg atc aag aac acg ccg gta cct gcg gat cct cca aca acg ttc agc           3880
Leu Ile Lys Asn Thr Pro Val Pro Ala Asp Pro Pro Thr Thr Phe Ser
650                 655                 660                 665
```

```
cag gcg aaa ttg gct tcc ttc atc acg cag tac agc acc gga cag gtc      3928
Gln Ala Lys Leu Ala Ser Phe Ile Thr Gln Tyr Ser Thr Gly Gln Val
            670                 675                 680 agc gtg gaa atc gag tgg gag ctg cag aag gag aac agc aaa cgc tgg      3976
Ser Val Glu Ile Glu Trp Glu Leu Gln Lys Glu Asn Ser Lys Arg Trp
685                 690                 695 aac cca gag att cag tac act tca aac tac tac aaa tct aca aat gtg      4024
Asn Pro Glu Ile Gln Tyr Thr Ser Asn Tyr Tyr Lys Ser Thr Asn Val
        700                 705                 710 gac ttt gct gtc aat aca gag gga act tat tct gag cct cgc ccc att      4072
Asp Phe Ala Val Asn Thr Glu Gly Thr Tyr Ser Glu Pro Arg Pro Ile
    715                 720                 725 ggt act cgt tat ctg aca cgt aat ctg taa                              4102
Gly Thr Arg Tyr Leu Thr Arg Asn Leu
730                 735

<210> SEQ ID NO 32
<211> LENGTH: 738
<212> TYPE: PRT
<213> ORGANISM: Artificial Sequence
<220> FEATURE:
<223> OTHER INFORMATION: Synthetic Construct

<400> SEQUENCE: 32

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Glu Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
```

```
              260                 265                 270
Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
            450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685
```

```
Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 33
<211> LENGTH: 4087
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 11
<220> FEATURE:
<221> NAME/KEY: CDS
<222> LOCATION: (1886)..(4087)
<223> OTHER INFORMATION: AAV11 VP1
<220> FEATURE:
<221> NAME/KEY: misc_feature
<222> LOCATION: (2297)..(4087)
<223> OTHER INFORMATION: AAV11 VP2
<220> FEATURE:
<221> NAME/KEY: misc_feature
<222> LOCATION: (2474)..(4087)
<223> OTHER INFORMATION: AAV11 VP3

<400> SEQUENCE: 33
atgccgggct ctacgagat cgtgatcaag gtgccgagcg acctggacga gcacctgccg      60
ggcatttctg actcgtttgt gaactgggtg gccgagaagg aatgggagct gcccccggat    120
tctgacatgg atcggaatct gatcgagcag gcacccctga ccgtggccga aagctgcag    180 cgcgacttcc tggtccactg cgccgcgtg agtaaggccc cggaggccct cttctttgtt    240
cagttcgaga agggcgagtc ctacttccac ctccacgttc tcgtcgagac cacggggtc    300 aagtccatgg tcctgggccg cttcctgagt cagatcagag acaggctggt gcagaccatc    360
taccgcgggg tcgagcccac gctgcccaac tggttcgcgg tgaccaagac gcgaaatggc    420
gccggcgggg ggaacaaggt ggtggacgag tgctacatcc ccaactacct cctgcccaag    480
acccagcccg agctgcagtg ggcgtggact aacatggagg agtatataag gcgtgtgtcta    540 aacctcgcgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca cgccgcctc caactcgcgg    780 tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgaccccgcc tacgccggct ccgtcttcct gggctgggcg    960
cagaaaaagt tcggtaaacg caacaccatc tggctgtttg gcccgccac caccggcaag   1020 accaacatcg cggaagccat agcccacgcc gtgcccttct acggctgcgt gaactggacc   1080
aatgagaact tccccttcaa cgattgcgtc gacaagatgg tgatctggtg gaggagggc   1140 aagatgaccg ccaaggtcgt ggagtccgcc aaggccattc tgggcggaag caaggtcgcg   1200
gtggaccaaa agtgcaagtc ctcggcccag atcgacccca cgcccgtgat cgtcacctcc   1260
```

```
aacaccaaca tgtgcgccgt gatcgacggg aacagcacca ccttcgagca ccagcagccg    1320
ctgcaggacc gcatgttcaa gttcgagctc acccgccgtc tggagcacga ctttggcaag    1380
gtgaccaagc aggaagtcaa agagttcttc cgctgggctc aggatcacgt gactgaggtg    1440
gcgcatgagt tctacgtcag aaagggcgga gccaccaaaa gacccgcccc cagtgacgcg    1500
gatataagcg agcccaagcg ggcctgcccc tcagttccgg agccatcgac gtcagacgcg    1560
gaagcaccgg tggactttgc ggacaggtac caaaacaaat gttctcgtca cgcgggcatg    1620
cttcagatgc tgtttccctg caagacatgc gagagaatga atcagaattt caacgtctgc    1680
ttcacgcacg gggtcagaga ctgctcagag tgcttccccg gcgcgtcaga atctcaaccc    1740
gtcgtcagaa aaagacgta tcagaaactg tgcgcgattc atcatctgct ggggcgggca    1800
cccgagattg cgtgttcggc ctgcgatctc gtcaacgtgg acttggatga ctgtgtttct    1860
gagcaataaa tgacttaaac caggt atg gct gct gac ggt tat ctt cca gat      1912
                             Met Ala Ala Asp Gly Tyr Leu Pro Asp
                             1               5 tgg ctc gag gac aac ctc tct gag ggc att cgc gag tgg tgg gac ctg      1960
Trp Leu Glu Asp Asn Leu Ser Glu Gly Ile Arg Glu Trp Trp Asp Leu
10              15                  20                  25 aaa cct gga gcc ccg aag ccc aag gcc aac cag cag aag cag gac gac      2008
Lys Pro Gly Ala Pro Lys Pro Lys Ala Asn Gln Gln Lys Gln Asp Asp
            30                  35                  40 ggc cgg ggt ctg gtg ctt cct ggc tac aag tac ctc gga ccc ttc aac      2056
Gly Arg Gly Leu Val Leu Pro Gly Tyr Lys Tyr Leu Gly Pro Phe Asn
        45                  50                  55 gga ctc gac aag ggg gag ccc gtc aac gcg gcg gac gca gcg gcc ctc      2104
Gly Leu Asp Lys Gly Glu Pro Val Asn Ala Ala Asp Ala Ala Ala Leu
    60                  65                  70 gag cac gac aag gcc tac gac cag cag ctc aaa gcg ggt gac aat ccg      2152
Glu His Asp Lys Ala Tyr Asp Gln Gln Leu Lys Ala Gly Asp Asn Pro
75                  80                  85 tac ctg cgg tat aac cac gcc gac gcc gag ttt cag gag cgt ctg caa      2200
Tyr Leu Arg Tyr Asn His Ala Asp Ala Glu Phe Gln Glu Arg Leu Gln
90                  95                  100                 105 gaa gat acg tct ttt ggg ggc aac ctc ggg cga gca gtc ttc cag gcc      2248
Glu Asp Thr Ser Phe Gly Gly Asn Leu Gly Arg Ala Val Phe Gln Ala
            110                 115                 120 aag aag agg gta ctc gaa cct ctg ggc ctg gtt gaa gaa ggt gct aaa      2296
Lys Lys Arg Val Leu Glu Pro Leu Gly Leu Val Glu Glu Gly Ala Lys
        125                 130                 135 acg gct cct gga aag aag aga ccg tta gag tca cca caa gag ccc gac      2344
Thr Ala Pro Gly Lys Lys Arg Pro Leu Glu Ser Pro Gln Glu Pro Asp
    140                 145                 150 tcc tcc tcg ggc atc ggc aaa aaa ggc aaa caa cca gcc aga aag agg      2392
Ser Ser Ser Gly Ile Gly Lys Lys Gly Lys Gln Pro Ala Arg Lys Arg
155                 160                 165 ctc aac ttt gaa gag gac act gga gcc gga gac gga ccc cct gaa gga      2440
Leu Asn Phe Glu Glu Asp Thr Gly Ala Gly Asp Gly Pro Pro Glu Gly
170                 175                 180                 185 tca gat acc agc gcc atg tct tca gac att gaa atg cgt gca gca ccg      2488
Ser Asp Thr Ser Ala Met Ser Ser Asp Ile Glu Met Arg Ala Ala Pro
            190                 195                 200 ggc gga aat gct gtc gat gcg gga caa ggt tcc gat gga gtg ggt aat      2536
Gly Gly Asn Ala Val Asp Ala Gly Gln Gly Ser Asp Gly Val Gly Asn
        205                 210                 215 gcc tcg ggt gat tgg cat tgc gat tcc acc tgg tct gag ggc aag gtc      2584
Ala Ser Gly Asp Trp His Cys Asp Ser Thr Trp Ser Glu Gly Lys Val
    220                 225                 230
```

```
aca aca acc tcg acc aga acc tgg gtc ttg ccc acc tac aac aac cac    2632
Thr Thr Thr Ser Thr Arg Thr Trp Val Leu Pro Thr Tyr Asn Asn His
    235                 240                 245 ttg tac ctg cgt ctc gga aca aca tca agc agc aac acc tac aac gga    2680
Leu Tyr Leu Arg Leu Gly Thr Thr Ser Ser Ser Asn Thr Tyr Asn Gly
250                 255                 260                 265 ttc tcc acc ccc tgg gga tat ttt gac ttc aac aga ttc cac tgt cac    2728
Phe Ser Thr Pro Trp Gly Tyr Phe Asp Phe Asn Arg Phe His Cys His
                270                 275                 280 ttc tca cca cgt gac tgg caa aga ctc atc aac aac aac tgg gga cta    2776
Phe Ser Pro Arg Asp Trp Gln Arg Leu Ile Asn Asn Asn Trp Gly Leu
            285                 290                 295 cga cca aaa gcc atg cgc gtt aaa atc ttc aat atc caa gtt aag gag    2824
Arg Pro Lys Ala Met Arg Val Lys Ile Phe Asn Ile Gln Val Lys Glu
        300                 305                 310 gtc aca acg tcg aac ggc gag act acg gtc gct aat aac ctt acc agc    2872
Val Thr Thr Ser Asn Gly Glu Thr Thr Val Ala Asn Asn Leu Thr Ser
    315                 320                 325 acg gtt cag ata ttt gcg gac tcg tcg tat gag ctc ccg tac gtg atg    2920
Thr Val Gln Ile Phe Ala Asp Ser Ser Tyr Glu Leu Pro Tyr Val Met
330                 335                 340                 345 gac gct gga caa gag ggg agc ctg cct cct ttc ccc aat gac gtg ttc    2968
Asp Ala Gly Gln Glu Gly Ser Leu Pro Pro Phe Pro Asn Asp Val Phe
                350                 355                 360 atg gtg cct caa tat ggc tac tgt ggc atc gtg act ggc gag aat cag    3016
Met Val Pro Gln Tyr Gly Tyr Cys Gly Ile Val Thr Gly Glu Asn Gln
            365                 370                 375 aac caa acg gac aga aac gct ttc tac tgc ctg gag tat ttt cct tcg    3064
Asn Gln Thr Asp Arg Asn Ala Phe Tyr Cys Leu Glu Tyr Phe Pro Ser
        380                 385                 390 caa atg ttg aga act ggc aac aac ttt gaa atg gct tac aac ttt gag    3112
Gln Met Leu Arg Thr Gly Asn Asn Phe Glu Met Ala Tyr Asn Phe Glu
    395                 400                 405 aag gtg ccg ttc cac tca atg tat gct cac agc cag agc ctg gac aga    3160
Lys Val Pro Phe His Ser Met Tyr Ala His Ser Gln Ser Leu Asp Arg
410                 415                 420                 425 ctg atg aat ccc ctc ctg gac cag tac ctg tgg cac tta cag tcg act    3208
Leu Met Asn Pro Leu Leu Asp Gln Tyr Leu Trp His Leu Gln Ser Thr
                430                 435                 440 acc tct gga gag act ctg aat caa ggc aat gca gca aca aca ttt gga    3256
Thr Ser Gly Glu Thr Leu Asn Gln Gly Asn Ala Ala Thr Thr Phe Gly
            445                 450                 455 aaa atc agg agt gga gac ttt gcc ttt tac aga aag aac tgg ctg cct    3304
Lys Ile Arg Ser Gly Asp Phe Ala Phe Tyr Arg Lys Asn Trp Leu Pro
        460                 465                 470 ggg cct tgt gtt aaa cag cag aga ttc tca aaa act gcc agt caa aat    3352
Gly Pro Cys Val Lys Gln Gln Arg Phe Ser Lys Thr Ala Ser Gln Asn
    475                 480                 485 tac aag att cct gcc agc ggg ggc aac gct ctg tta aag tat gac acc    3400
Tyr Lys Ile Pro Ala Ser Gly Gly Asn Ala Leu Leu Lys Tyr Asp Thr
490                 495                 500                 505 cac tat acc tta aac aac cgc tgg agc aac atc gcg ccc gga cct cca    3448
His Tyr Thr Leu Asn Asn Arg Trp Ser Asn Ile Ala Pro Gly Pro Pro
                510                 515                 520 atg gcc aca gcc gga cct tcg gat ggg gac ttc agt aac gcc cag ctt    3496
Met Ala Thr Ala Gly Pro Ser Asp Gly Asp Phe Ser Asn Ala Gln Leu
            525                 530                 535 ata ttc cct gga cca tct gtt acc gga aat aca aca act tca gcc aac    3544
Ile Phe Pro Gly Pro Ser Val Thr Gly Asn Thr Thr Thr Ser Ala Asn
```

```
                540                 545                 550
aat ctg ttg ttt aca tca gaa gaa gaa att gct gcc acc aac cca aga   3592
Asn Leu Leu Phe Thr Ser Glu Glu Glu Ile Ala Ala Thr Asn Pro Arg
        555                 560                 565 gac acg gac atg ttt ggc cag att gct gac aat aat cag aat gct aca   3640
Asp Thr Asp Met Phe Gly Gln Ile Ala Asp Asn Asn Gln Asn Ala Thr
570                 575                 580                 585 act gct ccc ata acc ggc aac gtg act gct atg gga gtg ctg cct ggc   3688
Thr Ala Pro Ile Thr Gly Asn Val Thr Ala Met Gly Val Leu Pro Gly
                590                 595                 600 atg gtg tgg caa aac aga gac att tac tac caa ggg cca att tgg gcc   3736
Met Val Trp Gln Asn Arg Asp Ile Tyr Tyr Gln Gly Pro Ile Trp Ala
        605                 610                 615 aag atc cca cac gcg gac gga cat ttt cat cct tca ccg ctg att ggt   3784
Lys Ile Pro His Ala Asp Gly His Phe His Pro Ser Pro Leu Ile Gly
620                 625                 630 ggg ttt gga ctg aaa cac ccg cct ccc cag ata ttc atc aag aac act   3832
Gly Phe Gly Leu Lys His Pro Pro Pro Gln Ile Phe Ile Lys Asn Thr
                635                 640                 645 ccc gta cct gcc aat cct gcg aca acc ttc act gca gcc aga gtg gac   3880
Pro Val Pro Ala Asn Pro Ala Thr Thr Phe Thr Ala Ala Arg Val Asp
650                 655                 660                 665 tct ttc atc aca caa tac agc acc ggc cag gtc gct gtt cag att gaa   3928
Ser Phe Ile Thr Gln Tyr Ser Thr Gly Gln Val Ala Val Gln Ile Glu
                670                 675                 680 tgg gaa att gaa aag gaa cgc tcc aaa cgc tgg aat cct gaa gtg cag   3976
Trp Glu Ile Glu Lys Glu Arg Ser Lys Arg Trp Asn Pro Glu Val Gln
        685                 690                 695 ttt act tca aac tat ggg aac cag tct tct atg ttg tgg gct cct gat   4024
Phe Thr Ser Asn Tyr Gly Asn Gln Ser Ser Met Leu Trp Ala Pro Asp
                700                 705                 710 aca act ggg aag tat aca gag ccg cgg gtt att ggc tct cgt tat ttg   4072
Thr Thr Gly Lys Tyr Thr Glu Pro Arg Val Ile Gly Ser Arg Tyr Leu
        715                 720                 725 act aat cat ttg taa                                              4087
Thr Asn His Leu
730

<210> SEQ ID NO 34
<211> LENGTH: 733
<212> TYPE: PRT
<213> ORGANISM: Artificial Sequence
<220> FEATURE:
<223> OTHER INFORMATION: Synthetic Construct

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
```

```
              100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
            130                 135             140
Pro Leu Glu Ser Pro Gln Glu Pro Asp Ser Ser Gly Ile Gly Lys
145                 150                 155                 160
Lys Gly Lys Gln Pro Ala Arg Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
            195                 200                 205
Gly Gln Gly Ser Asp Gly Val Gly Asn Ala Ser Gly Asp Trp His Cys
            210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Ser Ser Asn Thr Tyr Asn Gly Phe Ser Thr Pro Trp Gly Tyr
                260                 265                 270
Phe Asp Phe Asn Arg Phe His Cys His Phe Ser Pro Arg Asp Trp Gln
            275                 280                 285
Arg Leu Ile Asn Asn Asn Trp Gly Leu Arg Pro Lys Ala Met Arg Val
            290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
            355                 360                 365
Cys Gly Ile Val Thr Gly Glu Asn Gln Asn Gln Thr Asp Arg Asn Ala
            370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Glu Lys Val Pro Phe His Ser Met
                405                 410                 415
Tyr Ala His Ser Gln Ser Leu Asp Arg Leu Met Asn Pro Leu Leu Asp
            420                 425                 430
Gln Tyr Leu Trp His Leu Gln Ser Thr Thr Ser Gly Glu Thr Leu Asn
            435                 440                 445
Gln Gly Asn Ala Ala Thr Thr Phe Gly Lys Ile Arg Ser Gly Asp Phe
            450                 455                 460
Ala Phe Tyr Arg Lys Asn Trp Leu Pro Gly Pro Cys Val Lys Gln Gln
465                 470                 475                 480
Arg Phe Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
            500                 505                 510
Trp Ser Asn Ile Ala Pro Gly Pro Pro Met Ala Thr Ala Gly Pro Ser
            515                 520                 525
```

```
Asp Gly Asp Phe Ser Asn Ala Gln Leu Ile Phe Pro Gly Pro Ser Val
        530                 535                 540
Thr Gly Asn Thr Thr Thr Ser Ala Asn Asn Leu Leu Phe Thr Ser Glu
545                 550                 555                 560
Glu Glu Ile Ala Ala Thr Asn Pro Arg Asp Thr Asp Met Phe Gly Gln
                565                 570                 575
Ile Ala Asp Asn Asn Gln Asn Ala Thr Thr Ala Pro Ile Thr Gly Asn
            580                 585                 590
Val Thr Ala Met Gly Val Leu Pro Gly Met Val Trp Gln Asn Arg Asp
        595                 600                 605
Ile Tyr Tyr Gln Gly Pro Ile Trp Ala Lys Ile Pro His Ala Asp Gly
    610                 615                 620
His Phe His Pro Ser Pro Leu Ile Gly Gly Phe Gly Leu Lys His Pro
625                 630                 635                 640
Pro Pro Gln Ile Phe Ile Lys Asn Thr Pro Val Pro Ala Asn Pro Ala
                645                 650                 655
Thr Thr Phe Thr Ala Ala Arg Val Asp Ser Phe Ile Thr Gln Tyr Ser
            660                 665                 670
Thr Gly Gln Val Ala Val Gln Ile Glu Trp Glu Ile Glu Lys Glu Arg
        675                 680                 685
Ser Lys Arg Trp Asn Pro Glu Val Gln Phe Thr Ser Asn Tyr Gly Asn
    690                 695                 700
Gln Ser Ser Met Leu Trp Ala Pro Asp Thr Thr Gly Lys Tyr Thr Glu
705                 710                 715                 720
Pro Arg Val Ile Gly Ser Arg Tyr Leu Thr Asn His Leu
                725                 730

<210> SEQ ID NO 35
<211> LENGTH: 4213
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 12
<220> FEATURE:
<221> NAME/KEY: CDS
<222> LOCATION: (1985)..(4213)
<223> OTHER INFORMATION: AAV12 VP1
<220> FEATURE:
<221> NAME/KEY: misc_feature
<222> LOCATION: (2396)..(4213)
<223> OTHER INFORMATION: AAV12 VP2
<220> FEATURE:
<221> NAME/KEY: misc_feature
<222> LOCATION: (2600)..(4213)
<223> OTHER INFORMATION: AAV12 VP3

<400> SEQUENCE: 35
ttgcgacagt tgcgacacc atgtggtcac aagaggtata taaccgcgag tgagccagcg      60
aggagctcca ttttgcccgc gaagtttgaa cgagcagcag ccatgccggg gttctacgag     120
gtggtgatca aggtgcccag cgacctggac gagcacctgc ccggcatttc tgactccttt     180
gtgaactggg tggccgagaa ggaatgggag ttgccccgg attctgacat ggatcagaat     240
ctgattgagc aggcacccct gaccgtggcc gagaagctgc agcgcgagtt cctggtggaa     300
tggcgccgag tgagtaaatt tctggaggcc aagtttttg tgcagtttga aaaggggggac     360 tcgtactttc atttgcatat tctgattgaa attaccggcg tgaaatccat ggtggtgggc     420
```

```
cgctacgtga gtcagattag ggataaactg atccagcgca tctaccgcgg ggtcgagccc      480
cagctgccca actggttcgc ggtcacaaag acccgaaatg cgccggagg cgggaacaag       540 gtggtggacg agtgctacat ccccaactac ctgctcccca aggtccagcc cgagcttcag      600
tgggcgtgga ctaacatgga ggagtatata agcgcctgtt tgaacctcgc ggagcgtaaa     660
cggctcgtgg cgcagcacct gacgcacgtc tcccagaccc aggagggcga caaggagaat     720
ctgaacccga attctgacgc gccggtgatc cggtcaaaaa cctccgccag gtacatggag      780
ctggtcgggt ggctggtgga caagggcatc acgtccgaga agcagtggat ccaggaggac     840
caggcctcgt acatctcctt caacgcggcc tccaactccc ggtcgcagat caaggcggcc     900
ctggacaatg cctccaaaat catgagcctc accaaaacgg ctccggacta tctcatcggg     960
cagcagcccg tgggggacat taccaccaac cggatctaca aaatcctgga actgaacggg    1020
tacgaccccc agtacgccgc ctccgtcttt ctcggctggg cccagaaaaa gtttggaaag    1080
cgcaacacca tctggctgtt tgggcccgcc accaccggca agaccaacat cgcggaagcc    1140
atcgcccacg cggtccccttt ctacggctgc gtcaactgga ccaatgagaa ctttcccttc   1200
aacgactgcg tcgacaaaat ggtgatttgg tgggaggagg gcaagatgac cgccaaggtc    1260
gtagagtccg ccaaggccat tctgggcggc agcaaggtgc gcgtggacca aaaatgcaag    1320
gcctctgcgc agatcgaccc cacccccgtg atcgtcacct ccaacaccaa catgtgcgcc   1380
gtgattgacg gaacagcac caccttcgag caccagcagc cctgcagga ccggatgttc     1440 aagtttgaac tcacccgccg cctcgaccac gactttggca aggtcaccaa gcaggaagtc     1500
aaggactttt tccggtgggc ggctgatcac gtgactgacg tggctcatga gttttacgtc    1560
acaaagggtg gagctaagaa aaggcccgcc ccctctgacg aggatataag cgagcccaag    1620
cggccgcgcg tgtcatttgc gcagccggag acgtcagacg cggaagctcc cggagacttc    1680
gccgacaggt accaaaacaa atgttctcgt cacgcgggta tgctgcagat gctctttccc    1740
tgcaagacgt gcgagagaat gaatcagaat tccaacgtct gcttcacgca cggtcagaaa    1800
gattgcgggg agtgctttcc cgggtcagaa tctcaaccgg tttctgtcgt cagaaaaacg    1860
tatcagaaac tgtgcatcct tcatcagctc cgggggggcac ccgagatcgc ctgctctgct    1920
tgcgaccaac tcaaccccga tttggacgat tgccaatttg agcaataaat gactgaaatc   1980
```

| | | |
|---|---|---|
| aggt atg gct gct gac ggt tat ctt cca gat tgg ctc gag gac aac ctc | | 2029 |
| Met Ala Ala Asp Gly Tyr Leu Pro Asp Trp Leu Glu Asp Asn Leu | | |
| 1 5 10 15 | | |

| | | |
|---|---|---|
| tct gaa ggc att cgc gag tgg tgg gcg ctg aaa cct gga gct cca caa | | 2077 |
| Ser Glu Gly Ile Arg Glu Trp Trp Ala Leu Lys Pro Gly Ala Pro Gln | | |
| 20 25 30 | | |

| | | |
|---|---|---|
| ccc aag gcc aac caa cag cat cag gac aac ggc agg ggt ctt gtg ctt | | 2125 |
| Pro Lys Ala Asn Gln Gln His Gln Asp Asn Gly Arg Gly Leu Val Leu | | |
| 35 40 45 | | |

| | | |
|---|---|---|
| cct ggg tac aag tac ctc gga ccc ttc aac gga ctc gac aag gga gag | | 2173 |
| Pro Gly Tyr Lys Tyr Leu Gly Pro Phe Asn Gly Leu Asp Lys Gly Glu | | |
| 50 55 60 | | |

| | | |
|---|---|---|
| ccg gtc aac gag gca gac gcc gcg gcc ctc gag cac gac aag gcc tac | | 2221 |
| Pro Val Asn Glu Ala Asp Ala Ala Ala Leu Glu His Asp Lys Ala Tyr | | |
| 65 70 75 | | |

| | | |
|---|---|---|
| gac aag cag ctc gag cag ggg gac aac ccg tat ctc aag tac aac cac | | 2269 |
| Asp Lys Gln Leu Glu Gln Gly Asp Asn Pro Tyr Leu Lys Tyr Asn His | | |
| 80 85 90 95 | | |

| | | |
|---|---|---|
| gcc gac gcc gag ttc cag cag cgc ttg gcg acc gac acc tct ttt ggg | | 2317 |
| Ala Asp Ala Glu Phe Gln Gln Arg Leu Ala Thr Asp Thr Ser Phe Gly | | |
| 100 105 110 | | |

|  |  |
|---|---:|
| ggc aac ctc ggg cga gca gtc ttc cag gcc aaa aag agg att ctc gag<br>Gly Asn Leu Gly Arg Ala Val Phe Gln Ala Lys Lys Arg Ile Leu Glu<br>115                       120                      125 | 2365 |
| cct ctg ggt ctg gtt gaa gag ggc gtt aaa acg gct cct gga aag aaa<br>Pro Leu Gly Leu Val Glu Glu Gly Val Lys Thr Ala Pro Gly Lys Lys<br>    130                   135                     140 | 2413 |
| cgc cca tta gaa aag act cca aat cgg ccg acc aac ccg gac tct ggg<br>Arg Pro Leu Glu Lys Thr Pro Asn Arg Pro Thr Asn Pro Asp Ser Gly<br>145                   150                   155 | 2461 |
| aag gcc ccg gcc aag aaa aag caa aaa gac ggc gaa cca gcc gac tct<br>Lys Ala Pro Ala Lys Lys Lys Gln Lys Asp Gly Glu Pro Ala Asp Ser<br>160                165                170                175 | 2509 |
| gct aga agg aca ctc gac ttt gaa gac tct gga gca gga gac gga ccc<br>Ala Arg Arg Thr Leu Asp Phe Glu Asp Ser Gly Ala Gly Asp Gly Pro<br>         180                  185                 190 | 2557 |
| cct gag gga tca tct tcc gga gaa atg tct cat gat gct gag atg cgt<br>Pro Glu Gly Ser Ser Ser Gly Glu Met Ser His Asp Ala Glu Met Arg<br>195                   200                   205 | 2605 |
| gcg gcg cca ggc gga aat gct gtc gag gcg gga caa ggt gcc gat gga<br>Ala Ala Pro Gly Gly Asn Ala Val Glu Ala Gly Gln Gly Ala Asp Gly<br>    210                   215                     220 | 2653 |
| gtg ggt aat gcc tcc ggt gat tgg cat tgc gat tcc acc tgg tca gag<br>Val Gly Asn Ala Ser Gly Asp Trp His Cys Asp Ser Thr Trp Ser Glu<br>225                   230                   235 | 2701 |
| ggc cga gtc acc acc acc agc acc cga acc tgg gtc cta ccc acg tac<br>Gly Arg Val Thr Thr Thr Ser Thr Arg Thr Trp Val Leu Pro Thr Tyr<br>240                   245                   250                255 | 2749 |
| aac aac cac ctg tac ctg cga atc gga aca acg gcc aac agc aac acc<br>Asn Asn His Leu Tyr Leu Arg Ile Gly Thr Thr Ala Asn Ser Asn Thr<br>                  260                   265                270 | 2797 |
| tac aac gga ttc tcc acc ccc tgg gga tac ttt gac ttt aac cgc ttc<br>Tyr Asn Gly Phe Ser Thr Pro Trp Gly Tyr Phe Asp Phe Asn Arg Phe<br>             275                   280                285 | 2845 |
| cac tgc cac ttt tcc cca cgc gac tgg cag cga ctc atc aac aac aac<br>His Cys His Phe Ser Pro Arg Asp Trp Gln Arg Leu Ile Asn Asn Asn<br>    290                   295                     300 | 2893 |
| tgg gga ctc agg ccg aaa tcg atg cgt gtt aaa atc ttc aac ata cag<br>Trp Gly Leu Arg Pro Lys Ser Met Arg Val Lys Ile Phe Asn Ile Gln<br>305                   310                   315 | 2941 |
| gtc aag gag gtc acg acg tca aac ggc gag act acg gtc gct aat aac<br>Val Lys Glu Val Thr Thr Ser Asn Gly Glu Thr Thr Val Ala Asn Asn<br>320                   325                   330                335 | 2989 |
| ctt acc agc acg gtt cag atc ttt gcg gat tcg acg tat gaa ctc cca<br>Leu Thr Ser Thr Val Gln Ile Phe Ala Asp Ser Thr Tyr Glu Leu Pro<br>                 340                   345                350 | 3037 |
| tac gtg atg gac gcc ggt cag gag ggg agc ttt cct ccg ttt ccc aac<br>Tyr Val Met Asp Ala Gly Gln Glu Gly Ser Phe Pro Pro Phe Pro Asn<br>             355                   360                365 | 3085 |
| gac gtc ttt atg gtt ccc caa tac gga tac tgc gga gtt gtc act gga<br>Asp Val Phe Met Val Pro Gln Tyr Gly Tyr Cys Gly Val Val Thr Gly<br>    370                   375                     380 | 3133 |
| aaa aac cag aac cag aca gac aga aat gcc ttt tac tgc ctg gaa tac<br>Lys Asn Gln Asn Gln Thr Asp Arg Asn Ala Phe Tyr Cys Leu Glu Tyr<br>385                   390                   395 | 3181 |
| ttt cca tcc caa atg cta aga act ggc aac aat ttt gaa gtc agt tac<br>Phe Pro Ser Gln Met Leu Arg Thr Gly Asn Asn Phe Glu Val Ser Tyr<br>400                   405                   410                415 | 3229 |
| caa ttt gaa aaa gtt cct ttc cat tca atg tac gcg cac agc cag agc<br>Gln Phe Glu Lys Val Pro Phe His Ser Met Tyr Ala His Ser Gln Ser | 3277 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 420 |     |     |     |     | 425 |     |     |     |     | 430 |     |     |      |
| ctg | gac | aga | atg | atg | aat | cct | tta | ctg | gat | cag | tac | ctg | tgg | cat | ctg | 3325 |
| Leu | Asp | Arg | Met | Met | Asn | Pro | Leu | Leu | Asp | Gln | Tyr | Leu | Trp | His | Leu |      |
|     |     |     | 435 |     |     |     | 440 |     |     |     |     | 445 |     |     |     |      |
| caa | tcg | acc | act | acc | gga | aat | tcc | ctt | aat | caa | gga | aca | gct | acc | acc | 3373 |
| Gln | Ser | Thr | Thr | Thr | Gly | Asn | Ser | Leu | Asn | Gln | Gly | Thr | Ala | Thr | Thr |      |
|     |     | 450 |     |     |     |     | 455 |     |     |     |     | 460 |     |     |     |      |
| acg | tac | ggg | aaa | att | acc | act | gga | gac | ttt | gcc | tac | tac | agg | aaa | aac | 3421 |
| Thr | Tyr | Gly | Lys | Ile | Thr | Thr | Gly | Asp | Phe | Ala | Tyr | Tyr | Arg | Lys | Asn |      |
|     | 465 |     |     |     |     | 470 |     |     |     |     | 475 |     |     |     |     |      |
| tgg | ttg | cct | gga | gcc | tgc | att | aaa | caa | caa | aaa | ttt | tca | aag | aat | gcc | 3469 |
| Trp | Leu | Pro | Gly | Ala | Cys | Ile | Lys | Gln | Gln | Lys | Phe | Ser | Lys | Asn | Ala |      |
| 480 |     |     |     |     | 485 |     |     |     |     | 490 |     |     |     |     | 495 |      |
| aat | caa | aac | tac | aag | att | ccc | gcc | agc | ggg | gga | gac | gcc | ctt | tta | aag | 3517 |
| Asn | Gln | Asn | Tyr | Lys | Ile | Pro | Ala | Ser | Gly | Gly | Asp | Ala | Leu | Leu | Lys |      |
|     |     |     |     | 500 |     |     |     |     | 505 |     |     |     |     | 510 |     |      |
| tat | gac | acg | cat | acc | act | cta | aat | ggg | cga | tgg | agt | aac | atg | gct | cct | 3565 |
| Tyr | Asp | Thr | His | Thr | Thr | Leu | Asn | Gly | Arg | Trp | Ser | Asn | Met | Ala | Pro |      |
|     |     |     | 515 |     |     |     | 520 |     |     |     |     | 525 |     |     |     |      |
| gga | cct | cca | atg | gca | acc | gca | ggt | gcc | ggg | gac | tcg | gat | ttt | agc | aac | 3613 |
| Gly | Pro | Pro | Met | Ala | Thr | Ala | Gly | Ala | Gly | Asp | Ser | Asp | Phe | Ser | Asn |      |
|     |     | 530 |     |     |     |     | 535 |     |     |     |     | 540 |     |     |     |      |
| agc | cag | ctg | atc | ttt | gcc | gga | ccc | aat | ccg | agc | ggt | aac | acg | acc | aca | 3661 |
| Ser | Gln | Leu | Ile | Phe | Ala | Gly | Pro | Asn | Pro | Ser | Gly | Asn | Thr | Thr | Thr |      |
|     | 545 |     |     |     |     | 550 |     |     |     |     | 555 |     |     |     |     |      |
| tct | tca | aac | aat | ttg | ttg | ttt | acc | tca | gaa | gag | gag | att | gcc | aca | aca | 3709 |
| Ser | Ser | Asn | Asn | Leu | Leu | Phe | Thr | Ser | Glu | Glu | Glu | Ile | Ala | Thr | Thr |      |
| 560 |     |     |     |     | 565 |     |     |     |     | 570 |     |     |     |     | 575 |      |
| aac | cca | cga | gac | acg | gac | atg | ttt | gga | cag | att | gca | gat | aat | aat | caa | 3757 |
| Asn | Pro | Arg | Asp | Thr | Asp | Met | Phe | Gly | Gln | Ile | Ala | Asp | Asn | Asn | Gln |      |
|     |     |     |     | 580 |     |     |     |     | 585 |     |     |     |     | 590 |     |      |
| aat | gcc | acc | acc | gcc | cct | cac | atc | gct | aac | ctg | gac | gct | atg | gga | att | 3805 |
| Asn | Ala | Thr | Thr | Ala | Pro | His | Ile | Ala | Asn | Leu | Asp | Ala | Met | Gly | Ile |      |
|     |     |     | 595 |     |     |     | 600 |     |     |     |     | 605 |     |     |     |      |
| gtt | ccc | gga | atg | gtc | tgg | caa | aac | aga | gac | atc | tac | tac | cag | ggc | cct | 3853 |
| Val | Pro | Gly | Met | Val | Trp | Gln | Asn | Arg | Asp | Ile | Tyr | Tyr | Gln | Gly | Pro |      |
|     |     | 610 |     |     |     |     | 615 |     |     |     |     | 620 |     |     |     |      |
| att | tgg | gcc | aag | gtc | cct | cac | acg | gac | gga | cac | ttt | cac | cct | tcg | ccg | 3901 |
| Ile | Trp | Ala | Lys | Val | Pro | His | Thr | Asp | Gly | His | Phe | His | Pro | Ser | Pro |      |
|     | 625 |     |     |     |     | 630 |     |     |     |     | 635 |     |     |     |     |      |
| ctg | atg | gga | gga | ttt | gga | ctg | aaa | cac | ccg | cct | cca | cag | att | ttc | atc | 3949 |
| Leu | Met | Gly | Gly | Phe | Gly | Leu | Lys | His | Pro | Pro | Pro | Gln | Ile | Phe | Ile |      |
| 640 |     |     |     |     | 645 |     |     |     |     | 650 |     |     |     |     | 655 |      |
| aaa | aac | acc | ccc | gta | ccc | gcc | aat | ccc | aat | act | acc | ttt | agc | gct | gca | 3997 |
| Lys | Asn | Thr | Pro | Val | Pro | Ala | Asn | Pro | Asn | Thr | Thr | Phe | Ser | Ala | Ala |      |
|     |     |     | 660 |     |     |     | 665 |     |     |     |     | 670 |     |     |     |      |
| agg | att | aat | tct | ttt | ctg | acg | cag | tac | agc | acc | gga | caa | gtt | gcc | gtt | 4045 |
| Arg | Ile | Asn | Ser | Phe | Leu | Thr | Gln | Tyr | Ser | Thr | Gly | Gln | Val | Ala | Val |      |
|     |     | 675 |     |     |     |     | 680 |     |     |     |     | 685 |     |     |     |      |
| cag | atc | gac | tgg | gaa | att | cag | aag | gag | cat | tcc | aaa | cgc | tgg | aat | ccc | 4093 |
| Gln | Ile | Asp | Trp | Glu | Ile | Gln | Lys | Glu | His | Ser | Lys | Arg | Trp | Asn | Pro |      |
|     | 690 |     |     |     |     | 695 |     |     |     |     | 700 |     |     |     |     |      |
| gaa | gtt | caa | ttt | act | tca | aac | tac | ggc | act | caa | aat | tct | atg | ctg | tgg | 4141 |
| Glu | Val | Gln | Phe | Thr | Ser | Asn | Tyr | Gly | Thr | Gln | Asn | Ser | Met | Leu | Trp |      |
| 705 |     |     |     |     | 710 |     |     |     |     | 715 |     |     |     |     |     |      |
| gct | ccc | gac | aat | gct | ggc | aac | tac | cac | gaa | ctc | cgg | gct | att | ggg | tcc | 4189 |
| Ala | Pro | Asp | Asn | Ala | Gly | Asn | Tyr | His | Glu | Leu | Arg | Ala | Ile | Gly | Ser |      |
| 720 |     |     |     | 725 |     |     |     |     | 730 |     |     |     |     | 735 |     |      |
| cgt | ttc | ctc | acc | cac | cac | ttg | taa |     |     |     |     |     |     |     |     | 4213 |

Arg Phe Leu Thr His His Leu
                740

<210> SEQ ID NO 36
<211> LENGTH: 742
<212> TYPE: PRT
<213> ORGANISM: Artificial Sequence
<220> FEATURE:
<223> OTHER INFORMATION: Synthetic Construct

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

-continued

Val Met Asp Ala Gly Gln Glu Gly Ser Phe Pro Phe Pro Asn Asp
            355                 360                 365

Val Phe Met Val Pro Gln Tyr Gly Tyr Cys Gly Val Val Thr Gly Lys
370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
            405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
            530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Ile Ala Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
            610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
            675                 680                 685

Ile Asp Trp Glu Ile Gln Lys Glu His Ser Lys Arg Trp Asn Pro Glu
690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740

<210> SEQ ID NO 37
<211> LENGTH: 4180
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 13
<220> FEATURE:
<221> NAME/KEY: CDS
<222> LOCATION: (1948)..(4149)
<223> OTHER INFORMATION: AAV13 VP1
<220> FEATURE:
<221> NAME/KEY: misc_feature
<222> LOCATION: (2356)..(4149)
<223> OTHER INFORMATION: AAV13 VP2
<220> FEATURE:
<221> NAME/KEY: misc_feature
<222> LOCATION: (2551)..(4149)
<223> OTHER INFORMATION: AAV13 VP3
```

<400> SEQUENCE: 37

| | | | | | |
|---|---|---|---|---|---|
| ccgcgagtga | gcgaaccagg | agctccattt | tgcccgcgaa | ttttgaacga | gcagcagcca | 60 |
| tgccgggatt | ctacgagatt | gtcctgaagg | tgcccagcga | cctggacgag | cacctgcctg | 120 |
| gcatttctga | ctcttttgta | aactgggtgg | cggagaagga | atgggagctg | ccgccggatt | 180 |
| ctgacatgga | tctgaatctg | attgagcagg | caccccctaac | cgtggccgaa | aagctgcaac | 240 |
| gcgaattcct | ggtcgagtgg | cgccgcgtga | gtaaggcccc | ggaggccctc | ttctttgttc | 300 |
| agttcgagaa | gggggacagc | tacttccacc | tacacattct | ggtggagacc | gtgggcgtga | 360 |
| aatccatggt | ggtgggccgc | tacgtgagcc | agattaaaga | gaagctggtg | acccgcatct | 420 |
| accgcgggt | cgagccgcag | cttccgaact | ggttcgcggt | gaccaagacg | cgtaatggcg | 480 |
| ccggaggcgg | gaacaaggtg | gtggacgact | gctacatccc | caactacctg | ctccccaaga | 540 |
| cccagcccga | gctccagtgg | gcgtggacta | atatggacca | gtatttaagc | gcctgtttga | 600 |
| atctcgcgga | gcgtaaacgg | ctggtggcgc | agcatctgac | gcacgtgtcg | cagacgcagg | 660 |
| agcagaacaa | agagaaccag | aatcccaatt | ctgacgcgcc | ggtgatcaga | tcaaaaacct | 720 |
| ccgcgaggta | catggagctg | gtcgggtggc | tggtggaccg | cggatcacg | tcagaaaagc | 780 |
| aatggatcca | ggaggaccag | gcctcttaca | tctccttcaa | cgccgcctcc | aactcgcggt | 840 |
| cacaaatcaa | ggccgcactg | gacaatgcct | ccaaatttat | gagcctgaca | aaaacggctc | 900 |
| cggactacct | ggtgggaaac | aacccgccgg | aggacattac | cagcaaccgg | atctacaaaa | 960 |
| tcctcgagat | gaacgggtac | gatccgcagt | acgcggcctc | cgtcttcctg | ggctgggcgc | 1020 |
| aaaagaagtt | cgggaagagg | aacaccatct | ggctctttgg | gccggccacg | acgggtaaaa | 1080 |
| ccaacatcgc | tgaagctatc | gcccacgccg | tgcccttta | cggctgcgtg | aactggacca | 1140 |
| atgagaactt | tccgttcaac | gattgcgtcg | acaagatggt | gatctggtgg | gaggagggca | 1200 |
| agatgacggc | caaggtcgtg | gagtccgcca | aggccattct | gggcggaagc | aaggtgcgcg | 1260 |
| tggaccaaaa | gtgcaagtca | tcggcccaga | tcgacccaac | tcccgtcatc | gtcacctcca | 1320 |
| acaccaacat | gtgcgcggtc | atcgacggaa | attccaccac | cttcgagcac | caacaaccac | 1380 |
| tccaagaccg | gatgttcaag | ttcgagctca | ccaagcgcct | ggagcacgac | tttggcaagg | 1440 |
| tcaccaagca | ggaagtcaag | gactttttcc | ggtgggcgtc | agatcacgtg | actgaggtgt | 1500 |
| ctcacgagtt | ttacgtcaga | aagggtggag | ctagaaagag | gccgcccccc | aatgacgcag | 1560 |
| atataagtga | gcccaagcgg | gcctgtccgt | cagttgcgca | gccatcgacg | tcagacgcgg | 1620 |
| aagctccggt | ggactacgcg | gacaggtacc | aaaacaaatg | ttctcgtcac | gtgggcatga | 1680 |
| atctgatgct | ttttccctgc | cggcaatgcg | agagaatgaa | tcagaatgtg | gacatttgct | 1740 |

```
tcacgcacgg ggtcatggac tgtgccgagt gcttccccgt gtcagaatct caacccgtgt    1800
ctgtcgtcag aaagcggaca tatcagaaac tgtgtccgat tcatcacatc atggggaggg    1860
cgcccgaggt ggcttgttcg gcctgcgatc tggccaatgt ggacttggat gactgtgaca    1920
tggagcaata aatgactcaa accagat atg act gac ggt tac ctt cca gat tgg    1974
                              Met Thr Asp Gly Tyr Leu Pro Asp Trp
                              1                5 cta gag gac aac ctc tct gaa ggc gtt cga gag tgg tgg gcg ctg caa       2022
Leu Glu Asp Asn Leu Ser Glu Gly Val Arg Glu Trp Trp Ala Leu Gln
10              15                  20                  25 cct gga gcc cct aaa ccc aag gca aat caa caa cat cag gac aac gct       2070
Pro Gly Ala Pro Lys Pro Lys Ala Asn Gln Gln His Gln Asp Asn Ala
            30                  35                  40 cgg ggt ctt gtg ctt ccg ggt tac aaa tac ctc gga ccc ggc aac gga       2118
Arg Gly Leu Val Leu Pro Gly Tyr Lys Tyr Leu Gly Pro Gly Asn Gly
        45                  50                  55 ctt gac aag ggg gaa ccc gtc aac gca gcg gac gcg gca gcc ctc gaa       2166
Leu Asp Lys Gly Glu Pro Val Asn Ala Ala Asp Ala Ala Ala Leu Glu
    60                  65                  70 cac gac aag gcc tac gac cag cag ctc aag gcc ggt gac aac ccc tac       2214
His Asp Lys Ala Tyr Asp Gln Gln Leu Lys Ala Gly Asp Asn Pro Tyr
75                  80                  85 ctc aag tac aac cac gcc gac gcc gag ttt cag gag cgt ctt caa gaa       2262
Leu Lys Tyr Asn His Ala Asp Ala Glu Phe Gln Glu Arg Leu Gln Glu
90                  95                  100                 105 gat acg tct ttt ggg ggc aac ctc gga cga gca gtc ttc cag gcc aaa       2310
Asp Thr Ser Phe Gly Gly Asn Leu Gly Arg Ala Val Phe Gln Ala Lys
                110                 115                 120 aag agg atc ctt gag cct ctg ggt ctg gtt gag gaa gcg gct aag acg       2358
Lys Arg Ile Leu Glu Pro Leu Gly Leu Val Glu Glu Ala Ala Lys Thr
            125                 130                 135 gct cct gga aaa aag aga cct gta gag caa tct cca gca gaa ccg gac       2406
Ala Pro Gly Lys Lys Arg Pro Val Glu Gln Ser Pro Ala Glu Pro Asp
        140                 145                 150 tcc tct tcg ggc atc ggc aaa tca ggc cag cag ccc gct aga aaa aga       2454
Ser Ser Ser Gly Ile Gly Lys Ser Gly Gln Gln Pro Ala Arg Lys Arg
    155                 160                 165 ctg aat ttt ggt cag act ggc gac aca gag tca gtc cca gac cct caa       2502
Leu Asn Phe Gly Gln Thr Gly Asp Thr Glu Ser Val Pro Asp Pro Gln
170                 175                 180                 185 cca ctc gga caa cct ccc gca gcc ccc tct ggt gtg gga tct act aca       2550
Pro Leu Gly Gln Pro Pro Ala Ala Pro Ser Gly Val Gly Ser Thr Thr
                190                 195                 200 atg gct tca ggc ggt ggc gca cca atg gca gac aat aac gag ggt gcc       2598
Met Ala Ser Gly Gly Gly Ala Pro Met Ala Asp Asn Asn Glu Gly Ala
            205                 210                 215 gat gga gtg ggt aat tcc tca gga aat tgg cat tgc gat tcc caa tgg       2646
Asp Gly Val Gly Asn Ser Ser Gly Asn Trp His Cys Asp Ser Gln Trp
        220                 225                 230 ctg ggc gac aga gtc atc acc acc agc acc cgc acc tgg gcc ctg ccc       2694
Leu Gly Asp Arg Val Ile Thr Thr Ser Thr Arg Thr Trp Ala Leu Pro
    235                 240                 245 acc tac aac aat cac ctc tac aag caa atc tcc agc caa tca gga gcc       2742
Thr Tyr Asn Asn His Leu Tyr Lys Gln Ile Ser Ser Gln Ser Gly Ala
250                 255                 260                 265 acc aac gac aac cac tac ttt ggc tac agc acc ccc tgg ggg tat ttt       2790
Thr Asn Asp Asn His Tyr Phe Gly Tyr Ser Thr Pro Trp Gly Tyr Phe
                270                 275                 280 gac ttc aac aga ttc cac tgc cac ttt tca cca cgt gac tgg caa aga       2838
Asp Phe Asn Arg Phe His Cys His Phe Ser Pro Arg Asp Trp Gln Arg
```

-continued

```
                Asp Phe Asn Arg Phe His Cys His Phe Ser Pro Arg Asp Trp Gln Arg
                                285                 290                 295 ctc atc aac aac aac tgg gga ttc cga ccc aag aga ctc aac ttc aag           2886
Leu Ile Asn Asn Asn Trp Gly Phe Arg Pro Lys Arg Leu Asn Phe Lys
            300                 305                 310 ctc ttt aac att caa gtc aaa gag gtc acg cag aat gac ggt acg acg           2934
Leu Phe Asn Ile Gln Val Lys Glu Val Thr Gln Asn Asp Gly Thr Thr
315                 320                 325 acg att gcc aat aac ctt acc agc acg gtt cag gtg ttt act gac tcc           2982
Thr Ile Ala Asn Asn Leu Thr Ser Thr Val Gln Val Phe Thr Asp Ser
330                 335                 340                 345 gag tac cag ctc ccg tac gtc ctc ggc tcg gcg cat cag gga tgc ctc           3030
Glu Tyr Gln Leu Pro Tyr Val Leu Gly Ser Ala His Gln Gly Cys Leu
                350                 355                 360 ccg ccg ttc cca gca gac gtc ttc atg gtc cca cag tat gga tac ctc           3078
Pro Pro Phe Pro Ala Asp Val Phe Met Val Pro Gln Tyr Gly Tyr Leu
            365                 370                 375 acc ctg aac aac ggg agt cag gcg gta gga cgc tct tcc ttt tac tgc           3126
Thr Leu Asn Asn Gly Ser Gln Ala Val Gly Arg Ser Ser Phe Tyr Cys
380                 385                 390 ctg gag tac ttt cct tct cag atg ctg cgt act gga aac aac ttt cag           3174
Leu Glu Tyr Phe Pro Ser Gln Met Leu Arg Thr Gly Asn Asn Phe Gln
395                 400                 405 ttt agc tac act ttt gaa gac gtg cct ttc cac agc agc tac gct cac           3222
Phe Ser Tyr Thr Phe Glu Asp Val Pro Phe His Ser Ser Tyr Ala His
410                 415                 420                 425 agc caa agt ctg gac cgt ctc atg aat cct ctg atc gac cag tac ctg           3270
Ser Gln Ser Leu Asp Arg Leu Met Asn Pro Leu Ile Asp Gln Tyr Leu
                430                 435                 440 tac tat ctg aac agg aca caa aca gcc agt gga act cag cag tct cgg           3318
Tyr Tyr Leu Asn Arg Thr Gln Thr Ala Ser Gly Thr Gln Gln Ser Arg
            445                 450                 455 cta ctg ttt agc caa gct gga ccc acc agt atg tct ctt caa gct aaa           3366
Leu Leu Phe Ser Gln Ala Gly Pro Thr Ser Met Ser Leu Gln Ala Lys
460                 465                 470 aac tgg ctg cct gga cct tgc tac aga cag cag cgt ctg tca aag cag           3414
Asn Trp Leu Pro Gly Pro Cys Tyr Arg Gln Gln Arg Leu Ser Lys Gln
475                 480                 485 gca aac gac aac aac aac agc aac ttt ccc tgg act ggt gcc acc aaa           3462
Ala Asn Asp Asn Asn Asn Ser Asn Phe Pro Trp Thr Gly Ala Thr Lys
490                 495                 500                 505 tat cat ctg aat ggc cgg gac tca ttg gtg aac ccg ggc cct gct atg           3510
Tyr His Leu Asn Gly Arg Asp Ser Leu Val Asn Pro Gly Pro Ala Met
                510                 515                 520 gcc agt cac aag gat gac aaa gaa aag ttt ttc ccc atg cat gga acc           3558
Ala Ser His Lys Asp Asp Lys Glu Lys Phe Phe Pro Met His Gly Thr
            525                 530                 535 ctg ata ttt ggt aaa gaa gga aca aat gcc aac aac gcg gat ttg gaa           3606
Leu Ile Phe Gly Lys Glu Gly Thr Asn Ala Asn Asn Ala Asp Leu Glu
540                 545                 550 aat gtc atg att aca gat gaa gaa gaa atc cgc acc acc aat ccc gtg           3654
Asn Val Met Ile Thr Asp Glu Glu Glu Ile Arg Thr Thr Asn Pro Val
555                 560                 565 gct acg gag cag tac ggg act gtg tca aat aat ttg caa aac tca aac           3702
Ala Thr Glu Gln Tyr Gly Thr Val Ser Asn Asn Leu Gln Asn Ser Asn
570                 575                 580                 585 gct ggt cca act act gga act gtc aat cac caa gga gcg tta cct ggt           3750
Ala Gly Pro Thr Thr Gly Thr Val Asn His Gln Gly Ala Leu Pro Gly
                590                 595                 600
```

| | |
|---|---|
| atg gtg tgg cag gat cga gac gtg tac ctg cag gga ccc att tgg gcc<br>Met Val Trp Gln Asp Arg Asp Val Tyr Leu Gln Gly Pro Ile Trp Ala<br>605 610 615 | 3798 |
| aag att cct cac acc gat gga cac ttt cat cct tct cca ctg atg gga<br>Lys Ile Pro His Thr Asp Gly His Phe His Pro Ser Pro Leu Met Gly<br>620 625 630 | 3846 |
| ggt ttt ggg ctc aaa cac ccg cct cct cag atc atg atc aaa aac act<br>Gly Phe Gly Leu Lys His Pro Pro Pro Gln Ile Met Ile Lys Asn Thr<br>635 640 645 | 3894 |
| ccc gtt cca gcc aat cct ccc aca aac ttt agt gcg gca aag ttt gct<br>Pro Val Pro Ala Asn Pro Pro Thr Asn Phe Ser Ala Ala Lys Phe Ala<br>650 655 660 665 | 3942 |
| tcc ttc atc aca cag tac tcc acg ggg cag gtc agc gtg gag atc gag<br>Ser Phe Ile Thr Gln Tyr Ser Thr Gly Gln Val Ser Val Glu Ile Glu<br>670 675 680 | 3990 |
| tgg gag ctg cag aag gag aac agc aaa cgc tgg aat ccc gaa att cag<br>Trp Glu Leu Gln Lys Glu Asn Ser Lys Arg Trp Asn Pro Glu Ile Gln<br>685 690 695 | 4038 |
| tac act tcc aac tac aac aaa tct gtt aat gtg gac ttt act gtg gac<br>Tyr Thr Ser Asn Tyr Asn Lys Ser Val Asn Val Asp Phe Thr Val Asp<br>700 705 710 | 4086 |
| act aat ggt gtg tat tca gag cct cgc ccc att ggc acc aga tac ctg<br>Thr Asn Gly Val Tyr Ser Glu Pro Arg Pro Ile Gly Thr Arg Tyr Leu<br>715 720 725 | 4134 |
| act cgt aat ctg taa ttgcttgtta atcaataaac cggttaattc g<br>Thr Arg Asn Leu<br>730 | 4180 |

```
<210> SEQ ID NO 38
<211> LENGTH: 733
<212> TYPE: PRT
<213> ORGANISM: Artificial Sequence
<220> FEATURE:
<223> OTHER INFORMATION: Synthetic Construct

<400> SEQUENCE: 38
```

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Gly Ile Gly Lys
145                 150                 155                 160

Ser Gly Gln Gln Pro Ala Arg Lys Arg Leu Asn Phe Gly Gln Thr Gly
                165                 170                 175

```
Asp Thr Glu Ser Val Pro Asp Pro Gln Pro Leu Gly Gln Pro Pro Ala
            180                 185                 190

Ala Pro Ser Gly Val Gly Ser Thr Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Thr Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365

Phe Met Val Pro Gln Tyr Gly Tyr Leu Thr Leu Asn Asn Gly Ser Gln
    370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
        435                 440                 445

Thr Ala Ser Gly Thr Gln Gln Ser Arg Leu Leu Phe Ser Gln Ala Gly
    450                 455                 460

Pro Thr Ser Met Ser Leu Gln Ala Lys Asn Trp Leu Pro Gly Pro Cys
465                 470                 475                 480

Tyr Arg Gln Gln Arg Leu Ser Lys Gln Ala Asn Asp Asn Asn Asn Ser
                485                 490                 495

Asn Phe Pro Trp Thr Gly Ala Thr Lys Tyr His Leu Asn Gly Arg Asp
            500                 505                 510

Ser Leu Val Asn Pro Gly Pro Ala Met Ala Ser His Lys Asp Asp Lys
        515                 520                 525

Glu Lys Phe Phe Pro Met His Gly Thr Leu Ile Phe Gly Lys Glu Gly
    530                 535                 540

Thr Asn Ala Asn Asn Ala Asp Leu Glu Asn Val Met Ile Thr Asp Glu
545                 550                 555                 560

Glu Glu Ile Arg Thr Thr Asn Pro Val Ala Thr Glu Gln Tyr Gly Thr
                565                 570                 575

Val Ser Asn Asn Leu Gln Asn Ser Asn Ala Gly Pro Thr Thr Gly Thr
            580                 585                 590

Val Asn His Gln Gly Ala Leu Pro Gly Met Val Trp Gln Asp Arg Asp
```

```
                    595                 600                 605
Val Tyr Leu Gln Gly Pro Ile Trp Ala Lys Ile Pro His Thr Asp Gly
    610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
                645                 650                 655

Thr Asn Phe Ser Ala Ala Lys Phe Ala Ser Phe Ile Thr Gln Tyr Ser
                660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Asn Lys
        690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
                725                 730

<210> SEQ ID NO 39
<211> LENGTH: 2175
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 5
<220> FEATURE:
<221> NAME/KEY: CDS
<222> LOCATION: (1)..(2175)
<223> OTHER INFORMATION: AAV5 VP1

<400> SEQUENCE: 39 atg tct ttt gtt gat cac cca ccc gat tgg ttg gaa gaa gtt ggt gaa      48
Met Ser Phe Val Asp His Pro Pro Asp Trp Leu Glu Glu Val Gly Glu
1               5                   10                  15 ggt ctt cgc gag ttt ttg ggc ctt gaa gcg ggc cca ccg aaa cca aaa      96
Gly Leu Arg Glu Phe Leu Gly Leu Glu Ala Gly Pro Pro Lys Pro Lys
            20                  25                  30 ccc aat cag cag cat caa gat caa gcc cgt ggt ctt gtg ctg cct ggt     144
Pro Asn Gln Gln His Gln Asp Gln Ala Arg Gly Leu Val Leu Pro Gly
        35                  40                  45 tat aac tat ctc gga ccc gga aac ggt ctc gat cga gga gag cct gtc     192
Tyr Asn Tyr Leu Gly Pro Gly Asn Gly Leu Asp Arg Gly Glu Pro Val
    50                  55                  60 aac agg gca gac gag gtc gcg cga gag cac gac atc tcg tac aac gag     240
Asn Arg Ala Asp Glu Val Ala Arg Glu His Asp Ile Ser Tyr Asn Glu
65                  70                  75                  80 cag ctt gag gcg gga gac aac ccc tac ctc aag tac aac cac gcg gac     288
Gln Leu Glu Ala Gly Asp Asn Pro Tyr Leu Lys Tyr Asn His Ala Asp
                85                  90                  95 gcc gag ttt cag gag aag ctc gcc gac gac aca tcc ttc ggg gga aac     336
Ala Glu Phe Gln Glu Lys Leu Ala Asp Asp Thr Ser Phe Gly Gly Asn
            100                 105                 110 ctc gga aag gca gtc ttt cag gcc aag aaa agg gtt ctc gaa cct ttt     384
Leu Gly Lys Ala Val Phe Gln Ala Lys Lys Arg Val Leu Glu Pro Phe
        115                 120                 125 ggc ctg gtt gaa gag ggt gct aag acg gcc cct acc gga aag cgg ata     432
Gly Leu Val Glu Glu Gly Ala Lys Thr Ala Pro Thr Gly Lys Arg Ile
    130                 135                 140
```

```
gac gac cac ttt cca aaa aga aag aag gct cgg acc gaa gag gac tcc         480
Asp Asp His Phe Pro Lys Arg Lys Lys Ala Arg Thr Glu Glu Asp Ser
145                 150                 155                 160 aag cct tcc acc tcg tca gac gcc gaa gct gga ccc agc gga tcc cag         528
Lys Pro Ser Thr Ser Ser Asp Ala Glu Ala Gly Pro Ser Gly Ser Gln
                165                 170                 175 cag ctg caa atc cca gcc caa cca gcc tca agt ttg gga gct gat aca         576
Gln Leu Gln Ile Pro Ala Gln Pro Ala Ser Ser Leu Gly Ala Asp Thr
            180                 185                 190 atg tct gcg gga ggt ggc ggc cca ttg ggc gac aat aac caa ggt gcc         624
Met Ser Ala Gly Gly Gly Gly Pro Leu Gly Asp Asn Asn Gln Gly Ala
        195                 200                 205 gat gga gtg ggc aat gcc tcg gga gat tgg cat tgc gat tcc acg tgg         672
Asp Gly Val Gly Asn Ala Ser Gly Asp Trp His Cys Asp Ser Thr Trp
    210                 215                 220 atg ggg gac aga gtc gtc acc aag tcc acc cga acc tgg gtg ctg ccc         720
Met Gly Asp Arg Val Val Thr Lys Ser Thr Arg Thr Trp Val Leu Pro
225                 230                 235                 240 agc tac aac aac cac cag tac cga gag atc aaa agc ggc tcc gtc gac         768
Ser Tyr Asn Asn His Gln Tyr Arg Glu Ile Lys Ser Gly Ser Val Asp
                245                 250                 255 gga agc aac gcc aac gcc tac ttt gga tac agc acc ccc tgg ggg tac         816
Gly Ser Asn Ala Asn Ala Tyr Phe Gly Tyr Ser Thr Pro Trp Gly Tyr
            260                 265                 270 ttt gac ttt aac cgc ttc cac agc cac tgg agc ccc cga gac tgg caa         864
Phe Asp Phe Asn Arg Phe His Ser His Trp Ser Pro Arg Asp Trp Gln
        275                 280                 285 aga ctc atc aac aac tac tgg ggc ttc aga ccc cgg tcc ctc aga gtc         912
Arg Leu Ile Asn Asn Tyr Trp Gly Phe Arg Pro Arg Ser Leu Arg Val
    290                 295                 300 aaa atc ttc aac att caa gtc aaa gag gtc acg gtg cag gac tcc acc         960
Lys Ile Phe Asn Ile Gln Val Lys Glu Val Thr Val Gln Asp Ser Thr
305                 310                 315                 320 acc acc atc gcc aac aac ctc acc tcc acc gtc caa gtg ttt acg gac        1008
Thr Thr Ile Ala Asn Asn Leu Thr Ser Thr Val Gln Val Phe Thr Asp
                325                 330                 335 gac gac tac cag ctg ccc tac gtc gtc ggc aac ggg acc gag gga tgc        1056
Asp Asp Tyr Gln Leu Pro Tyr Val Val Gly Asn Gly Thr Glu Gly Cys
            340                 345                 350 ctg ccg gcc ttc cct ccg cag gtc ttt acg ctg ccg cag tac ggt tac        1104
Leu Pro Ala Phe Pro Pro Gln Val Phe Thr Leu Pro Gln Tyr Gly Tyr
        355                 360                 365 gcg acg ctg aac cgc gac aac aca gaa aat ccc acc gag agg agc agc        1152
Ala Thr Leu Asn Arg Asp Asn Thr Glu Asn Pro Thr Glu Arg Ser Ser
    370                 375                 380 ttc ttc tgc cta gag tac ttt ccc agc aag atg ctg aga acg ggc aac        1200
Phe Phe Cys Leu Glu Tyr Phe Pro Ser Lys Met Leu Arg Thr Gly Asn
385                 390                 395                 400 aac ttt gag ttt acc tac aac ttt gag gag gtg ccc ttc cac tcc agc        1248
Asn Phe Glu Phe Thr Tyr Asn Phe Glu Glu Val Pro Phe His Ser Ser
                405                 410                 415 ttc gct ccc agt cag aac ctg ttc aag ctg gcc aac ccg ctg gtg gac        1296
Phe Ala Pro Ser Gln Asn Leu Phe Lys Leu Ala Asn Pro Leu Val Asp
            420                 425                 430 cag tac ttg tac cgc ttc gtg agc aca aat aac act ggc gga gtc cag        1344
Gln Tyr Leu Tyr Arg Phe Val Ser Thr Asn Asn Thr Gly Gly Val Gln
        435                 440                 445 ttc aac aag aac ctg gcc ggg aga tac gcc aac acc tac aaa aac tgg        1392
Phe Asn Lys Asn Leu Ala Gly Arg Tyr Ala Asn Thr Tyr Lys Asn Trp
    450                 455                 460
```

```
ttc ccg ggg ccc atg ggc cga acc cag ggc tgg aac ctg ggc tcc ggg      1440
Phe Pro Gly Pro Met Gly Arg Thr Gln Gly Trp Asn Leu Gly Ser Gly
465                 470                 475                 480 gtc aac cgc gcc agt gtc agc gcc ttc gcc acg acc aat agg atg gag      1488
Val Asn Arg Ala Ser Val Ser Ala Phe Ala Thr Thr Asn Arg Met Glu
                485                 490                 495 ctc gag ggc gcg agt tac cag gtg ccc ccg cag ccg aac ggc atg acc      1536
Leu Glu Gly Ala Ser Tyr Gln Val Pro Pro Gln Pro Asn Gly Met Thr
            500                 505                 510 aac aac ctc cag ggc agc aac acc tat gcc ctg gag aac act atg atc      1584
Asn Asn Leu Gln Gly Ser Asn Thr Tyr Ala Leu Glu Asn Thr Met Ile
        515                 520                 525 ttc aac agc cag ccg gcg aac ccg ggc acc acc gcc acg tac ctc gag      1632
Phe Asn Ser Gln Pro Ala Asn Pro Gly Thr Thr Ala Thr Tyr Leu Glu
    530                 535                 540 ggc aac atg ctc atc acc agc gag agc gag acg cag ccg gtg aac cgc      1680
Gly Asn Met Leu Ile Thr Ser Glu Ser Glu Thr Gln Pro Val Asn Arg
545                 550                 555                 560 gtg gcg tac aac gtc ggc ggg cag atg gcc acc aac aac cag agc tcc      1728
Val Ala Tyr Asn Val Gly Gly Gln Met Ala Thr Asn Asn Gln Ser Ser
                565                 570                 575 acc act gcc ccc gcg acc ggc acg tac aac ctc cag gaa atc gtg ccc      1776
Thr Thr Ala Pro Ala Thr Gly Thr Tyr Asn Leu Gln Glu Ile Val Pro
            580                 585                 590 ggc agc gtg tgg atg gag agg gac gtg tac ctc caa gga ccc atc tgg      1824
Gly Ser Val Trp Met Glu Arg Asp Val Tyr Leu Gln Gly Pro Ile Trp
        595                 600                 605 gcc aag atc cca gag acg ggg gcg cac ttt cac ccc tct ccg gcc atg      1872
Ala Lys Ile Pro Glu Thr Gly Ala His Phe His Pro Ser Pro Ala Met
    610                 615                 620 ggc gga ttc gga ctc aaa cac cca ccg ccc atg atg ctc atc aag aac      1920
Gly Gly Phe Gly Leu Lys His Pro Pro Pro Met Met Leu Ile Lys Asn
625                 630                 635                 640 acg cct gtg ccc gga aat atc acc agc ttc tcg gac gtg ccc gtc agc      1968
Thr Pro Val Pro Gly Asn Ile Thr Ser Phe Ser Asp Val Pro Val Ser
                645                 650                 655 agc ttc atc acc cag tac agc acc ggg cag gtc acc gtg gag atg gag      2016
Ser Phe Ile Thr Gln Tyr Ser Thr Gly Gln Val Thr Val Glu Met Glu
            660                 665                 670 tgg gag ctc aag aag gaa aac tcc aag agg tgg aac cca gag atc cag      2064
Trp Glu Leu Lys Lys Glu Asn Ser Lys Arg Trp Asn Pro Glu Ile Gln
        675                 680                 685 tac aca aac aac tac aac gac ccc cag ttt gtg gac ttt gcc ccg gac      2112
Tyr Thr Asn Asn Tyr Asn Asp Pro Gln Phe Val Asp Phe Ala Pro Asp
    690                 695                 700 agc acc ggg gaa tac aga acc acc aga cct atc gga acc cga tac ctt      2160
Ser Thr Gly Glu Tyr Arg Thr Thr Arg Pro Ile Gly Thr Arg Tyr Leu
705                 710                 715                 720 acc cga ccc ctt taa                                                  2175
Thr Arg Pro Leu <210> SEQ ID NO 40
<211> LENGTH: 724
<212> TYPE: PRT
<213> ORGANISM: Artificial Sequence
<220> FEATURE:
<223> OTHER INFORMATION: Synthetic Construct

<400> SEQUENCE: 40

Met Ser Phe Val Asp His Pro Pro Asp Trp Leu Glu Glu Val Gly Glu
```

```
1               5                   10                  15
Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
        130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
            195                 200                 205

Asp Gly Val Gly Asn Ala Ser Gly Asp Trp His Cys Asp Ser Thr Trp
        210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430
```

-continued

```
Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 41
<211> LENGTH: 2184
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: construct based on AAV5
<220> FEATURE:
<221> NAME/KEY: misc_feature
<222> LOCATION: (1)..(9)
<223> OTHER INFORMATION: VP2 initiatior context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: misc_feature
<222> LOCATION: (30)..(30)
<223> OTHER INFORMATION: splicing site
```

<220> FEATURE:
<221> NAME/KEY: misc_feature
<222> LOCATION: (33)..(33)
<223> OTHER INFORMATION: splicing site

<400> SEQUENCE: 41

| | | | | | |
|---|---|---|---|---|---|
| cctgttaaga | cgtcttttgt | tgatcaccca | cccgattggt | tggaagaagt | tggtgaaggt | 60 |
| cttcgcgagt | ttttgggcct | tgaagcgggc | ccaccgaaac | caaaacccaa | tcagcagcat | 120 |
| caagatcaag | cccgtggtct | tgtgctgcct | ggttataact | atctcggacc | cggaaacggt | 180 |
| ctcgatcgag | gagagcctgt | caacagggca | gacgaggtcg | cgcgagagca | cgacatctcg | 240 |
| tacaacgagc | agcttgaggc | gggagacaac | ccctacctca | agtacaacca | cgcggacgcc | 300 |
| gagtttcagg | agaagctcgc | cgacgacaca | tccttcgggg | gaaacctcgg | aaaggcagtc | 360 |
| tttcaggcca | agaaaagggt | tctcgaacct | tttggcctgg | ttgaagaggg | tgctaagacg | 420 |
| gccccctaccg | gaaagcggat | agacgaccac | tttccaaaaa | gaaagaaggc | tcggaccgaa | 480 |
| gaggactcca | agccttccac | ctcgtcagac | gccgaagctg | gacccagcgg | atcccagcag | 540 |
| ctgcaaatcc | cagcccaacc | agcctcaagt | ttgggagctg | atacaatgtc | tgcgggaggt | 600 |
| ggcggcccat | tgggcgacaa | taaccaaggt | gccgatggag | tgggcaatgc | ctcgggagat | 660 |
| tggcattgcg | attccacgtg | gatggggggac | agagtcgtca | ccaagtccac | ccgaacctgg | 720 |
| gtgctgccca | gctacaacaa | ccaccagtac | cgagagatca | aaagcggctc | cgtcgacgga | 780 |
| agcaacgcca | acgcctactt | tggatacagc | acccccctggg | ggtactttga | ctttaaccgc | 840 |
| ttccacagcc | actggagccc | ccgagactgg | caaagactca | tcaacaacta | ctggggcttc | 900 |
| agacccccggt | ccctcagagt | caaaatcttc | aacattcaag | tcaaagaggt | cacggtgcag | 960 |
| gactccacca | ccaccatcgc | caacaacctc | acctccaccg | tccaagtgtt | tacggacgac | 1020 |
| gactaccagc | tgccctacgt | cgtcggcaac | gggaccgagg | gatgcctgcc | ggccttccct | 1080 |
| ccgcaggtct | ttacgctgcc | gcagtacggt | tacgcgacgc | tgaaccgcga | caacacagaa | 1140 |
| aatcccaccg | agaggagcag | cttcttctgc | ctagagtact | ttcccagcaa | gatgctgaga | 1200 |
| acgggcaaca | actttgagtt | tacctacaac | tttgaggagg | tgcccttcca | ctccagcttc | 1260 |
| gctcccagtc | agaacctctt | caagctggcc | aaccgctgg | tggaccagta | cttgtaccgc | 1320 |
| ttcgtgagca | caaataacac | tggcggagtc | cagttcaaca | agaacctggc | cgggagatac | 1380 |
| gccaacacct | acaaaaactg | gttcccgggg | cccatgggcc | gaacccaggg | ctggaacctg | 1440 |
| ggctccgggg | tcaaccgcgc | cagtgtcagc | gccttcgcca | cgaccaatag | gatggagctc | 1500 |
| gagggcgcga | gttaccaggt | gcccccgcag | ccgaacggca | tgaccaacaa | cctccagggc | 1560 |
| agcaacacct | atgccctgga | gaacactatg | atcttcaaca | gccagccggc | gaacccgggc | 1620 |
| accaccgcca | cgtacctcga | gggcaacatg | ctcatcacca | gcgagagcga | gacgcagccg | 1680 |
| gtgaaccgcg | tggcgtacaa | cgtcggcggg | cagatggcca | ccaacaacca | gagctccacc | 1740 |
| actgccccccg | cgaccggcac | gtacaacctc | caggaaatcg | tgcccggcag | cgtgtggatg | 1800 |
| gagagggacg | tgtacctcca | aggacccatc | tgggccaaga | tcccagagac | gggggcgcac | 1860 |
| tttcaccccct | ctccggccat | gggcggattc | ggactcaaac | acccaccgcc | catgatgctc | 1920 |
| atcaagaaca | cgcctgtgcc | cggaaatatc | accagcttct | cggacgtgcc | cgtcagcagc | 1980 |
| ttcatcaccc | agtacagcac | cgggcaggtc | accgtggaga | tggagtggga | gctcaagaag | 2040 |
| gaaaactcca | gaggtggaa | cccagagatc | cagtacacaa | caactacaa | cgaccccccag | 2100 |
| tttgtggact | ttgcccccgga | cagcaccggg | gaatacagaa | ccaccagacc | tatcggaacc | 2160 | cgataccttaa cccgaccct ttaa                                                   2184

<210> SEQ ID NO 42
<211> LENGTH: 2187
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: artificial sequence based on AAV5
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: misc_feature
<222> LOCATION: (13)..(15)
<223> OTHER INFORMATION: additional triplet added to sequence
<220> FEATURE:
<221> NAME/KEY: mutation
<222> LOCATION: (33)..(33)
<223> OTHER INFORMATION: remove splice site
<220> FEATURE:
<221> NAME/KEY: mutation
<222> LOCATION: (36)..(36)
<223> OTHER INFORMATION: remove splice site

<400> SEQUENCE: 42
cctgttaaga cggcttcttt tgttgatcac ccacccgatt ggttggaaga agttggtgaa    60
ggtcttcgcg agttttttggg ccttgaagcg ggcccaccga aaccaaaacc caatcagcag   120
catcaagatc aagcccgtgg tcttgtgctg cctggttata actatctcgg acccggaaac   180
ggtctcgatc gaggagagcc tgtcaacagg gcagacgagg tcgcgcgaga gcacgacatc   240
tcgtacaacg agcagcttga ggcgggagac aaccctacc tcaagtacaa ccacgcggac   300
gccgagtttc aggagaagct cgccgacgac acatccttcg ggggaaaccct cggaaaggca   360 gtcttttcagg ccaagaaaag ggttctcgaa ccttttggcc tggttgaaga gggtgctaag   420
acggccccta ccggaaagcg gatagacgac cactttccaa aaagaaagaa ggctcggacc   480
gaagaggact ccaagccttc cacctcgtca gacgccgaag ctggaccag cggatcccag   540 cagctgcaaa tcccagccca accagcctca gtttgggag ctgatacaat gtctgcggga   600
ggtggcggcc cattgggcga caataaccaa ggtgccgatg gagtgggcaa tgcctcggga   660
gattggcatt gcgattccac gtggatgggg gacagagtcg tcaccaagtc cacccgaacc   720
tgggtgctgc ccagctacaa caaccaccag taccgagaga tcaaaagcgg ctccgtcgac   780
ggaagcaacg ccaacgccta ctttggatac agcaccccct gggggtactt tgactttaac   840
cgcttccaca gccactggag cccccgagac tggcaaagac tcatcaacaa ctactgggc   900 ttcagacccc ggtccctcag agtcaaaatc ttcaacattc aagtcaaaga ggtcacggtg   960
caggactcca ccaccaccat cgccaacaac ctcacctcca ccgtccaagt gtttacggac  1020
gacgactacc agctgcccta cgtcgtcggc aacgggaccg agggatgcct gccggccttc  1080
cctccgcagg tctttacgct gccgcagtac ggttacgcga cgctgaaccg cgacaacaca  1140
gaaaatccca ccgagaggag cagcttcttc tgcctagagt actttcccag caagatgctg  1200
agaacgggca caactttga gttttaccac aactttgagg aggtgccctt ccactccagc  1260
ttcgctccca gtcagaacct cttcaagctg gccaacccgc tggtggacca gtacttgtac  1320

```
cgcttcgtga gcacaaataa cactggcgga gtccagttca acaagaacct ggccgggaga      1380
tacgccaaca cctacaaaaa ctggttcccg gggcccatgg gccgaaccca gggctggaac      1440
ctgggctccg gggtcaaccg cgccagtgtc agcgccttcg ccacgaccaa taggatggag      1500
ctcgagggcg cgagttacca ggtgcccccg cagccgaacg gcatgaccaa caacctccag      1560
ggcagcaaca cctatgccct ggagaacact atgatcttca acagccagcc ggcgaacccg      1620
ggcaccaccg ccacgtacct cgagggcaac atgctcatca ccagcgagag cgagacgcag      1680
ccggtgaacc gcgtggcgta caacgtcggc gggcagatgg ccaccaacaa ccagagctcc      1740
accactgccc ccgcgaccgg cacgtacaac ctccaggaaa tcgtgcccgg cagcgtgtgg      1800
atggagaggg acgtgtacct ccaaggaccc atctgggcca agatcccaga cggggggcg       1860 cactttcacc cctctccggc catgggcgga ttcggactca acacccacc gcccatgatg       1920 ctcatcaaga acacgcctgt gcccggaaat atcaccagct tctcggacgt gcccgtcagc      1980
agcttcatca cccagtacag caccgggcag gtcaccgtgg agatggagtg ggagctcaag      2040
aaggaaaact ccaagaggtg gaacccagag atccagtaca caaacaacta caacgacccc      2100
cagtttgtgg actttgcccc ggacagcacc ggggaataca gaaccaccag acctatcgga      2160
acccgatacc ttacccgacc cctttaa                                          2187

<210> SEQ ID NO 43
<211> LENGTH: 2184
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: artificial sequence based on AAV5
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: mutation
<222> LOCATION: (13)..(13)
<223> OTHER INFORMATION: point mutation to G
<220> FEATURE:
<221> NAME/KEY: mutation
<222> LOCATION: (30)..(30)
<223> OTHER INFORMATION: point mutation to remove splice site
<220> FEATURE:
<221> NAME/KEY: mutation
<222> LOCATION: (33)..(33)
<223> OTHER INFORMATION: point mutation to remove splice site

<400> SEQUENCE: 43
cctgttaaga cggcttttgt tgatcaccca cccgattggt tggaagaagt tggtgaaggt       60
cttcgcgagt ttttgggcct tgaagcgggc ccaccgaaac caaaacccaa tcagcagcat      120
caagatcaag cccgtggtct tgtgctgcct ggttataact atctcggacc cggaaacggt      180
ctcgatcgag gagagcctgt caacagggca gacgaggtcg cgcgagagca cgacatctcg      240
tacaacgagc agcttgaggc gggagacaac ccctacctca gtacaaccca gcggacgcc       300 gagtttcagg agaagctcgc cgacgacaca tccttcgggg gaaacctcgg aaaggcagtc      360
tttcaggcca agaaaagggt tctcgaacct tttggcctgg ttgagagggg tgctaagacg      420
gcccctaccg gaaagcggat agacgaccac tttccaaaaa gaagaaggc tcggaccgaa       480
```

```
gaggactcca agccttccac ctcgtcagac gccgaagctg acccagcgg atcccagcag      540 ctgcaaatcc cagcccaacc agcctcaagt ttgggagctg atacaatgtc tgcgggaggt      600
ggcggcccat tgggcgacaa taaccaaggt gccgatggag tgggcaatgc ctcgggagat      660
tggcattgcg attccacgtg gatgggggac agagtcgtca ccaagtccac ccgaacctgg      720
gtgctgccca gctacaacaa ccaccagtac cgagagatca aaagcggctc cgtcgacgga      780
agcaacgcca cgcctacttt ggatacagc acccccctgg ggtactttga ctttaaccgc      840
ttccacagcc actggagccc ccgagactgg caaagactca tcaacaacta ctggggcttc      900 agacccggt ccctcagagt caaaatcttc aacattcaag tcaaagaggt cacggtgcag      960
gactccacca ccaccatcgc caacaacctc acctccaccg tccaagtgtt tacggacgac     1020
gactaccagc tgccctacgt cgtcggcaac gggaccgagg gatgcctgcc ggccttccct     1080
ccgcaggtct ttacgctgcc gcagtacggt tacgcgacgc tgaaccgcga caacacagaa     1140
aatcccaccg agaggagcag cttcttctgc ctagagtact ttcccagcaa gatgctgaga     1200
acgggcaaca actttgagtt tacctacaac tttgaggagg tgcccttcca ctccagcttc     1260
gctcccagtc agaacctctt caagctggcc aacccgctgg tggaccagta cttgtaccgc     1320
ttcgtgagca caaataacac tggcggagtc cagttcaaca agaacctggc cgggagatac     1380
gccaacacct acaaaaactg gttcccgggg cccatgggcc gaacccaggg ctggaacctg     1440
ggctccgggg tcaaccgcgc cagtgtcagc gccttcgcca cgaccaatag gatggagctc     1500
gagggcgcga gttaccaggt gccccgcag ccgaacggca tgaccaacaa cctccagggc     1560
agcaacacct atgccctgga gaacactatg atcttcaaca ccagccggc gaacccgggc     1620 accaccgcca cgtacctcga gggcaacatg ctcatcacca gcgagagcga gacgcagccg     1680
gtgaaccgcg tggcgtacaa cgtcggcggg cagatggcca ccaacaacca gagctccacc     1740 actgccccg cgaccggcac gtacaacctc caggaaatcg tgcccggcag cgtgtggatg     1800
gagagggacg tgtacctcca aggacccatc tgggccaaga tcccagagac gggggcgcac     1860
tttcacccct ctccggccat gggcggattc ggactcaaac acccaccgcc catgatgctc     1920
atcaagaaca cgcctgtgcc cggaaatatc accagcttct cggacgtgcc cgtcagcagc     1980
ttcatcaccc agtacagcac cgggcaggtc accgtgagga tggagtggga gctcaagaag     2040
gaaaactcca gaggtggaa cccagagatc cagtacacaa acaactacaa cgaccccag     2100 tttgtggact tgccccgga cagcaccggg gaatacagaa ccaccagacc tatcggaacc     2160
cgatacctta cccgaccccct ttaa                                             2184
```

<210> SEQ ID NO 44
<211> LENGTH: 2184
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: artificial sequence based on AAV5
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: mutation
<222> LOCATION: (13)..(13)

<223> OTHER INFORMATION: piont mutation to threonine
<220> FEATURE:
<221> NAME/KEY: mutation
<222> LOCATION: (30)..(30)
<223> OTHER INFORMATION: point mutation to remove splice site
<220> FEATURE:
<221> NAME/KEY: mutation
<222> LOCATION: (33)..(33)
<223> OTHER INFORMATION: point mutation to remove splice site

<400> SEQUENCE: 44

```
cctgttaagc tgactttgt tgatcaccca cccgattggt tggaagaagt tggtgaaggt      60
cttcgcgagt ttttgggcct tgaagcgggc ccaccgaaac caaaacccaa tcagcagcat    120
caagatcaag cccgtggtct tgtgctgcct ggttataact atctcggacc cggaaacggt    180
ctcgatcgag gagagcctgt caacagggca gacgaggtcg cgcgagagca cgacatctcg    240
tacaacgagc agcttgaggc gggagacaac ccctacctca agtacaacca cgcggacgcc    300
gagtttcagg agaagctcgc cgacgacaca tccttcgggg gaaacctcgg aaaggcagtc    360
tttcaggcca agaaaagggt tctcgaacct tttggcctgg ttgaagaggg tgctaagacg    420
gccctaccg gaaagcggat agacgaccac tttccaaaaa gaaagaaggc tcggaccgaa     480
gaggactcca agccttccac ctcgtcagac gccgaagctg acccagcgg atcccagcag     540
ctgcaaatcc cagcccaacc agcctcaagt ttgggagctg atacaatgtc tgcgggaggt    600
ggcggcccat tgggcgacaa taaccaaggt gccgatgag tgggcaatgc ctcgggagat     660
tggcattgcg attccacgtg gatggggac agagtcgtca ccaagtccac ccgaacctgg     720
gtgctgccca gctacaacaa ccaccagtac cgagagatca aaagcggctc cgtcgacgga    780
agcaacgcca cgcctactt tggatacagc acccctggg ggtactttga ctttaaccgc      840
ttccacagcc actggagccc ccgagactgg caaagactca tcaacaacta ctggggcttc    900
agaccccggt ccctcagagt caaaatcttc aacattcaag tcaaagaggt cacggtgcag    960
gactccacca ccaccatcgc caacaacctc acctccaccg tccaagtgtt tacgacgac   1020
gactaccagc tgccctacgt cgtcggcaac gggaccgagg gatgcctgcc ggccttccct   1080
ccgcaggtct ttacgctgcc gcagtacggt tacgcgacgc tgaaccgcga caacacagaa   1140
aatcccaccg agaggagcag cttcttctgc ctagagtact ttcccagcaa gatgctgaga   1200
acgggcaaca actttgagtt tacctacaac tttgaggagg tgcccttcca ctccagcttc   1260
gctcccagtc agaacctctt caagctggcc aaccgctgg tggaccagta cttgtaccgc    1320
ttcgtgagca caaataacac tggcggagtc cagttcaaca agaacctggc cgggagatac   1380
gccaacacct acaaaaactg gttcccgggg cccatgggcc gaacccaggg ctggaacctg   1440
ggctccgggg tcaaccgcgc cagtgtcagc gccttcgcca cgaccaatag gatggagctc   1500
gagggcgcga gttaccaggt gccccgcag ccgaacggca tgaccaacaa cctccagggc    1560
agcaacacct atgccctgga gaacactatg atcttcaaca gccagccggc gaacccgggc   1620
accaccgcca cgtacctcga gggcaacatg ctcatcacca gcgagagcga gacgcagccg   1680
gtgaaccgcg tggcgtacaa cgtcggcggg cagatggcca ccaacaacca gagctccacc   1740
actgcccccg cgaccggcac gtacaacctc caggaaatcg tgcccggcag cgtgtggatg   1800
gagagggacg tgtacctcca aggacccatc tgggccaaga tcccagagac ggggcgcac    1860
tttcaccct ctccggccat gggcggattc ggactcaaac acccaccgcc catgatgctc    1920
atcaagaaca cgcctgtgcc cggaaatatc accagcttct cggacgtgcc cgtcagcagc   1980
ttcatcaccc agtacagcac cgggcaggtc accgtggaga tggagtggga gctcaagaag   2040
```

-continued

```
gaaaactcca agaggtggaa cccagagatc cagtacacaa acaactacaa cgaccccag      2100 tttgtggact tgccccgga cagcaccggg aatacagaa ccaccagacc tatcggaacc      2160 cgataccta cccgacccct ttaa                                              2184
```

<210> SEQ ID NO 45
<211> LENGTH: 2187
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: artificial sequence based on AAV5: construct 163
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: mutation
<222> LOCATION: (13)..(15)
<223> OTHER INFORMATION: insertion of triplet as compared to native AAV5 sequence
<220> FEATURE:
<221> NAME/KEY: mutation
<222> LOCATION: (16)..(18)
<223> OTHER INFORMATION: mutation of triplet as compared to native AAV5 sequence
<220> FEATURE:
<221> NAME/KEY: mutation
<222> LOCATION: (33)..(33)
<223> OTHER INFORMATION: point mutation to remove splice site
<220> FEATURE:
<221> NAME/KEY: mutation
<222> LOCATION: (36)..(36)
<223> OTHER INFORMATION: point mutation to remove splice site

<400> SEQUENCE: 45

```
cctgttaagc tgactagctt tgttgatcac ccacccgatt ggttggaaga agttggtgaa      60
ggtcttcgcg agttttgggg ccttgaagcg ggcccaccga aaccaaaacc caatcagcag     120
catcaagatc aagcccgtgg tcttgtgctg cctggttata actatctcgg acccggaaac     180
ggtctcgatc gaggagagcc tgtcaacagg gcagacgagg tcgcgcgaga gcacgacatc     240
tcgtacaacg agcagcttga ggcgggagac aacccctacc tcaagtacaa ccacgcggac     300
gccgagtttc aggagaagct cgccgacgac acatccttcg ggggaaacct cggaaaggca     360
gtctttcagg ccaagaaaag ggttctcgaa cctttggcc tggttgaaga gggtgctaag     420
acggccccta ccggaaagcg gatagacgac cactttccaa aaagaaagaa ggctcggacc     480
gaagaggact ccaagccttc cacctcgtca gacgccgaag ctggacccag cggatcccag     540
cagctgcaaa tccagcccca accagcctca gtttgggag ctgatacaat gtctgcggga     600
ggtggcggcc cattgggcga caataaccaa ggtgccgatg gagtgggcaa tgcctcggga     660
gattggcatt gcgattccac gtggatgggg gacagagtcg tcaccaagtc cacccgaacc     720
tgggtgctgc ccagctacaa caaccaccag taccgagaga tcaaaagcgg ctccgtcgac     780
ggaagcaacg ccaacgccta ctttggatac agcacccccc tggggtactt tgactttaac     840
cgcttccaca gccactggag cccccgagac tggcaaagac tcatcaacaa ctactgggc     900 ttcagacccc ggtccctcag agtcaaaatc ttcaacatc aagtcaaaga ggtcacggtg     960
```

-continued

```
caggactcca ccaccaccat cgccaacaac ctcacctcca ccgtccaagt gtttacggac    1020
gacgactacc agctgcccta cgtcgtcggc aacgggaccg agggatgcct gccggccttc    1080
cctccgcagg tctttacgct gccgcagtac ggttacgcga cgctgaaccg cgacaacaca    1140
gaaaatccca ccgagaggag cagcttcttc tgcctagagt actttcccag caagatgctg    1200
agaacgggca acaactttga gtttacctac aactttgagg aggtgcccct ccactccagc    1260
ttcgctccca gtcagaacct cttcaagctg gccaacccgc tggtggacca gtacttgtac    1320
cgcttcgtga gcacaaataa cactggcgga gtccagttca acaagaacct ggccgggaga    1380
tacgccaaca cctacaaaaa ctggttcccg gggcccatgg gccgaaccca gggctggaac    1440
ctgggctccg gggtcaaccg cgccagtgtc agcgccttcg ccacgaccaa taggatggag    1500
ctcgagggcg cgagttacca ggtgcccccg cagccgaacg gcatgaccaa caacctccag    1560
ggcagcaaca cctatgccct ggagaacact atgatcttca cagccagcc ggcgaacccg    1620 ggcaccaccg ccacgtacct cgagggcaac atgctcatca ccagcgagag cgagacgcag    1680
ccggtgaacc gcgtggcgta caacgtcggc gggcagatgg ccaccaacaa ccagagctcc    1740
accactgccc ccgcgaccgg cacgtacaac ctccaggaaa tcgtgcccgg cagcgtgtgg    1800
atggagaggg acgtgtacct ccaaggaccc atctgggcca agatcccaga cggggggcg    1860 cactttcacc cctctccggc catgggcgga ttcggactca acacccacc gcccatgatg    1920 ctcatcaaga cacgcctgt gcccggaaat atcaccagct tctcggacgt gcccgtcagc    1980
agcttcatca cccagtacag caccgggcag gtcaccgtgg agatggagtg ggagctcaag    2040
aaggaaaact ccaagaggtg gaacccagag atccagtaca caaacaacta caacgacccc    2100
cagtttgtgg actttgcccc ggacagcacc ggggaataca gaaccaccag acctatcgga    2160
acccgatacc ttacccgacc cctttaa                                       2187
```

<210> SEQ ID NO 46
<211> LENGTH: 2184
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence based on AAV5: construct 164
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: mutation
<222> LOCATION: (13)..(15)
<223> OTHER INFORMATION: mutation of triplet to serine codon
<220> FEATURE:
<221> NAME/KEY: mutation
<222> LOCATION: (30)..(30)
<223> OTHER INFORMATION: point mutation to remove splice site
<220> FEATURE:
<221> NAME/KEY: mutation
<222> LOCATION: (33)..(33)
<223> OTHER INFORMATION: point mutation to remove splice site

<400> SEQUENCE: 46

```
cctgttaagc tgagttttgt tgatcaccca cccgattggt tggaagaagt tggtgaaggt      60
cttcgcgagt ttttgggcct tgaagcgggc ccaccgaaac caaaacccaa tcagcagcat     120
```

```
caagatcaag cccgtggtct tgtgctgcct ggttataact atctcggacc cggaaacggt    180
ctcgatcgag gagagcctgt caacagggca gacgaggtcg cgcgagagca cgacatctcg    240
tacaacgagc agcttgaggc gggagacaac ccctacctca agtacaacca cgcggacgcc    300
gagtttcagg agaagctcgc cgacgacaca tccttcgggg gaaacctcgg aaaggcagtc    360
tttcaggcca agaaaagggt tctcgaacct tttggcctgg ttgaagaggg tgctaagacg    420
gcccctaccg gaaagcggat agacgaccac tttccaaaaa gaaagaaggc tcggaccgaa    480
gaggactcca agccttccac ctcgtcagac gccgaagctg acccagcgg atcccagcag     540 ctgcaaatcc cagcccaacc agcctcaagt ttgggagctg atacaatgtc tgcgggaggt    600
ggcggcccat gggcgacaa taaccaaggt gccgatgag tgggcaatgc ctcgggagat      660
tggcattgcg attccacgtg gatggggac agagtcgtca ccaagtccac ccgaacctgg     720
gtgctgccca gctacaacaa ccaccagtac cgagagatca aaagcggctc cgtcgacgga    780
agcaacgcca cgcctactt tggatacagc accccctggg ggtactttga ctttaaccgc     840
ttccacagcc actggagccc ccgagactgg caaagactca tcaacaacta ctggggcttc    900 agacccggt ccctcagagt caaaatcttc aacattcaag tcaaagaggt cacggtgcag     960
gactccacca ccaccatcgc caacaacctc acctccaccg tccaagtgtt tacggacgac   1020
gactaccagc tgccctacgt cgtcggcaac gggaccgagg gatgcctgcc ggccttccct   1080
ccgcaggtct ttacgctgcc gcagtacggt tacgcgacgc tgaaccgcga caacacagaa   1140
aatcccaccg agaggagcag cttcttctgc ctagagtact ttcccagcaa gatgctgaga   1200
acgggcaaca actttgagtt tacctacaac tttgaggagg tgcccttcca ctccagcttc   1260
gctcccagtc agaacctctt caagctggcc aacccgctgg tggaccagta cttgtaccgc   1320
ttcgtgagca caaataacac tggcggagtc cagttcaaca gaacctggc cgggagatac    1380 gccaacacct acaaaaactg gttcccgggg cccatgggcc gaacccaggg ctggaacctg   1440
ggctccgggg tcaaccgcgc cagtgtcagc gccttcgcca cgaccaatag gatggagctc   1500
gagggcgcga gttaccaggt gccccgcag ccgaacggca tgaccaacaa cctccagggc    1560
agcaacacct atgccctgga gaacactatg atcttcaaca ccagccggc gaacccgggc    1620 accaccgcca cgtacctcga gggcaacatg ctcatcacca gcgagagcga gacgcagccg   1680
gtgaaccgcg tggcgtacaa cgtcggcggg cagatggcca ccaacaacca gagctccacc   1740
actgcccccg cgaccggcac gtacaacctc caggaaatcg tgcccggcag cgtgtggatg   1800
gagagggacg tgtacctcca aggacccatc tgggccaaga tcccagagac gggggcgcac   1860
tttcacccct ctccggccat gggcggattc ggactcaaac acccaccgcc catgatgctc   1920
atcaagaaca cgcctgtgcc cggaaatatc accagcttct cggacgtgcc cgtcagcagc   1980
ttcatcaccc agtacagcac cgggcaggtc accgtggaga tggagtggga gctcaagaag   2040
gaaaactcca gaggtggaa cccagagatc cagtacacaa caactacaa cgaccccag     2100 tttgtggact tgcccccgga cagcaccggg gaatacagaa ccaccagacc tatcggaacc   2160 cgataccta cccgacccct ttaa                                           2184
```

<210> SEQ ID NO 47
<211> LENGTH: 2187
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<223> OTHER INFORMATION: sequence based on AAV5: sequence 761
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: mutation
<222> LOCATION: (13)..(15)
<223> OTHER INFORMATION: insertion of triplet encoding alanine
<220> FEATURE:
<221> NAME/KEY: mutation
<222> LOCATION: (33)..(33)
<223> OTHER INFORMATION: point mutation to remove splice site
<220> FEATURE:
<221> NAME/KEY: mutation
<222> LOCATION: (36)..(36)
<223> OTHER INFORMATION: point mutation to remove splice site

<400> SEQUENCE: 47
cctgttaaga cggcttcttt tgttgatcac ccacccgatt ggttggaaga agttggtgaa      60
ggtcttcgcg agttttgggg ccttgaagcg ggcccaccga aaccaaaacc caatcagcag     120
catcaagatc aagcccgtgg tcttgtgctg cctggttata actatctcgg acccggaaac     180
ggtctcgatc gaggagagcc tgtcaacagg gcagacgagg tcgcgcgaga gcacgacatc     240
tcgtacaacg agcagcttga ggcgggagac aaccccctacc tcaagtacaa ccacgcggac     300
gccgagtttc aggagaagct cgccgacgac acatccttcg ggggaaacct cggaaaggca     360
gtctttcagg ccaagaaaag ggttctcgaa ccttttggcc tggttgaaga gggtgctaag     420
acggccccta ccggaaagcg gatagacgac cactttccaa aaagaaagaa ggctcggacc     480
gaagaggact ccaagccttc cacctcgtca gacgccgaag ctggacccag cggatcccag     540
cagctgcaaa tcccagccca accagcctca gtttgggag ctgatacaat gtctgcggga     600
ggtggcggcc cattgggcga caataaccaa ggtgccgatg gagtgggcaa tgcctcggga     660
gattggcatt gcgattccac gtggatgggg gacagagtcg tcaccaagtc caccccgaacc     720
tgggtgctgc ccagctacaa caaccaccag taccgagaga tcaaaagcgg ctccgtcgac     780
ggaagcaacg ccaacgccta ctttggatac agcaccccct gggggtactt tgactttaac     840
cgcttccaca gccactggag ccccccgaac tggcaaagac tcatcaacaa ctactggggc     900
ttcagacccc ggtccctcag agtcaaaatc ttcaacattc aagtcaaaga ggtcacggtg     960
caggactcca ccaccaccat cgccaacaac ctcacctcca ccgtccaagt gtttacggac    1020
gacgactacc agctgcccta cgtcgtcggc aacgggaccg agggatgcct gccggccttc    1080
cctccgcagg tctttacgct gccgcagtac ggttacgcga cgctgaaccg cgacaacaca    1140
gaaaatccca ccgagaggag cagcttcttc tgcctagagt actttcccag caagatgctg    1200
agaacgggca caactttga gtttacctac aactttgagg aggtgccctt ccactccagc    1260
ttcgctccca gtcagaacct gttcaagctg gccaacccgc tggtggacca gtacttgtac    1320
cgcttcgtga gcacaaataa cactggcgga gtccagttca caagaacct ggccgggaga    1380
tacgccaaca cctacaaaaa ctggttcccg gggcccatgg gccgaaccca gggctggaac    1440
ctgggctccg gggtcaaccg cgccagtgtc agcgccttcg ccacgaccaa taggatggag    1500
ctcgagggcg cgagttacca ggtgcccccg cagccgaacg gcatgaccaa caacctccag    1560
ggcagcaaca cctatgccct ggagaacact atgatcttca acagccagcc ggcgaacccg    1620
ggcaccaccg ccacgtacct cgagggcaac atgctcatca ccagcgagag cgagacgcag    1680
```

```
ccggtgaacc gcgtggcgta caacgtcggc gggcagatgg ccaccaacaa ccagagctcc    1740
accactgccc ccgcgaccgg cacgtacaac ctccaggaaa tcgtgcccgg cagcgtgtgg    1800
atggagaggg acgtgtacct ccaaggaccc atctgggcca agatcccaga cgggggcg      1860 cactttcacc cctctccggc catgggcgga ttcggactca acacccacc gcccatgatg     1920 ctcatcaaga acacgcctgt gcccggaaat atccaccagct tctcggacgt gcccgtcagc   1980
agcttcatca cccagtacag caccgggcag gtcaccgtgg agatggagtg ggagctcaag    2040
aaggaaaact ccaagaggtg gaacccagag atccagtaca caaacaacta caacgacccc   2100
cagtttgtgg actttgcccc ggacagcacc ggggaataca gaaccaccag acctatcgga   2160
acccgatacc ttacccgacc cctttaa                                       2187

<210> SEQ ID NO 48
<211> LENGTH: 2178
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence based on AAV5: sequence 762
<220> FEATURE:
<221> NAME/KEY: misc_feature
<222> LOCATION: (1)..(3)
<223> OTHER INFORMATION: suboptimal translation initiation codon
<220> FEATURE:
<221> NAME/KEY: mutation
<222> LOCATION: (4)..(6)
<223> OTHER INFORMATION: insertion of triplet encoding alanine
<220> FEATURE:
<221> NAME/KEY: mutation
<222> LOCATION: (24)..(24)
<223> OTHER INFORMATION: point mutation to remove splice site
<220> FEATURE:
<221> NAME/KEY: mutation
<222> LOCATION: (27)..(27)
<223> OTHER INFORMATION: point mutation to remove splice site

<400> SEQUENCE: 48
acggcttctt tgttgatca cccacccgat tggttggaag aagttggtga aggtcttcgc      60
gagtttttgg gccttgaagc gggcccaccg aaaccaaaac ccaatcagca gcatcaagat    120
caagcccgtg gtcttgtgct gcctggttat aactatctcg gacccggaaa cggtctcgat    180
cgaggagagc ctgtcaacag ggcagacgag gtcgcgcgag agcacgacat ctcgtacaac    240
gagcagcttg aggcgggaga caaccctac ctcaagtaca accacgcgga cgccgagttt    300
caggagaagc tcgccgacga cacatccttc gggggaaacc tcggaaaggc agtctttcag    360
gccaagaaaa gggttctcga acctttggc ctggttgaag agggtgctaa gacggccct     420 accggaaagc ggatagacga ccactttcca aaaagaaaga aggctcggac cgaagaggac   480
tccaagcctt ccacctcgtc agacgccgaa gctggaccca gcggatccca gcagctgcaa   540
atcccagccc aaccagcctc aagtttggga gctgatacaa tgtctgcggg aggtggcggc   600
ccattgggcg acaataacca aggtgccgat ggagtgggca atgcctcggg agattggcat   660
tgcgattcca cgtggatggg ggacagagtc gtcaccaagt ccaccgaac ctgggtgctg    720 cccagctaca acaaccacca gtaccgagag atcaaaagcg gctccgtcga cggaagcaac   780
gccaacgcct actttggata cagcaccccc tgggggtact ttgactttaa ccgcttccac   840
agccactgga gccccgaga ctggcaaaga ctcatcaaca actactgggg cttcagaccc   900
cggtccctca gagtcaaaat cttcaacatt caagtcaaag aggtcacggt gcaggactcc    960
```

```
accaccacca tcgccaacaa cctcacctcc accgtccaag tgtttacgga cgacgactac    1020
cagctgccct acgtcgtcgg caacgggacc gagggatgcc tgccggcctt ccctccgcag    1080
gtctttacgc tgccgcagta cggttacgcg acgctgaacc gcgacaacac agaaaatccc    1140
accgagagga gcagcttctt ctgcctagaa tactttccca gcaagatgct gagaacgggc    1200
aacaactttg agtttaccta caactttgag gaggtgccct ccactccag cttcgctccc    1260 agtcagaacc tgttcaagct ggccaacccg ctggtggacc agtacttgta ccgcttcgtg    1320
agcacaaata cactggcgg agtccagttc aacaagaacc tggccgggag atacgccaac    1380
acctacaaaa actggttccc ggggcccatg ggccgaaccc agggctggaa cctgggctcc    1440
ggggtcaacc gcgccagtgt cagcgccttc gccacgacca ataggatgga gctcgagggc    1500
gcgagttacc aggtgccccc gcagccgaac ggcatgacca caacctcca gggcagcaac    1560 acctatgccc tggagaacac tatgatcttc aacagccagc cggcgaaccc gggcaccacc    1620
gccacgtacc tcgagggcaa catgctcatc accagcgaga gcgagacgca gccggtgaac    1680
cgcgtggcgt acaacgtcgg cgggcagatg gccaccaaca accagagctc caccactgcc    1740
cccgcgaccg gcacgtacaa cctccaggaa atcgtgcccg gcagcgtgtg gatggagagg    1800
gacgtgtacc tccaaggacc catctgggcc aagatcccag agacgggggc gcactttcac    1860
ccctctccgg ccatgggcgg attcggactc aaacacccac cgccatgat gctcatcaag    1920 aacacgcctg tgcccggaaa tatcaccagc ttctcggacg tgcccgtcag cagcttcatc    1980
acccagtaca gcaccgggca ggtcaccgtg gagatggagt gggagctcaa gaaggaaaac    2040
tccaagaggt ggaacccaga gatccagtac acaaacaact acaacgaccc ccagtttgtg    2100
gactttgccc cggacagcac cggggaatac agaaccacca gacctatcgg aacccgatac    2160
cttacccgac ccctttaa                                                 2178

<210> SEQ ID NO 49
<211> LENGTH: 2175
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 5
<220> FEATURE:
<221> NAME/KEY: misc_feature
<222> LOCATION: (1)..(3)
<223> OTHER INFORMATION: start codon

<400> SEQUENCE: 49 atgtctttg ttgatcaccc tccagattgg ttggaagaag ttggtgaagg tcttcgcgag    60
tttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cgggagacaa ccccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgagagg gtgctaagac ggcccctacc    420
ggaaagcgga tagacgacca cttttccaaaa agaaagaagg ctcggaccga agaggactcc    480
aagccttcca cctcgtcaga cgccgaagct ggacccagcg atcccagca gctgcaaatc    540 ccagcccaac cagcctcaag tttgggagct gatacaatgt ctgcgggagg tggcggccca    600
```

```
ttgggcgaca ataaccaagg tgccgatgga gtgggcaatg cctcgggaga ttggcattgc      660
gattccacgt ggatggggga cagagtcgtc accaagtcca cccgaacctg ggtgctgccc      720
agctacaaca accaccagta ccgagagatc aaaagcggct ccgtcgacgg aagcaacgcc      780
aacgcctact tggatacag cacccctgg gggtactttg actttaaccg cttccacagc       840
cactggagcc cccgagactg gcaaagactc atcaacaact actggggctt cagaccccgg      900
tccctcagag tcaaaatctt caacattcaa gtcaaagagg tcacggtgca ggactccacc      960
accaccatcg ccaacaacct cacctccacc gtccaagtgt ttacggacga cgactaccag     1020
ctgccctacg tcgtcggcaa cgggaccgag ggatgcctgc cggccttccc tcgcagggtc     1080
tttacgctgc cgcagtacgg ttacgcgacg ctgaaccgcg acaacacaga aatcccacc     1140 gagaggagca gcttcttctg cctagagtac tttcccagca agatgctgag aacgggcaac     1200
aactttgagt ttacctacaa ctttgaggag gtgcccttcc actccagctt cgctcccagt     1260
cagaacctgt tcaagctggc caacccgctg gtggaccagt acttgtaccg cttcgtgagc     1320
acaaataaca ctggcggagt ccagttcaac aagaacctgg ccgggagata cgccaacacc     1380
tacaaaaact ggttcccggg gcccatgggc cgaacccagg gctggaacct gggctccggg     1440
gtcaaccgcg ccagtgtcag cgccttcgcc acgaccaata ggatggagct cgagggcgcg     1500
agttaccagg tgccccgca gccgaacggc atgaccaaca cctccaggg cagcaacacc     1560 tatgccctgg agaacactat gatcttcaac agccagccgg cgaacccggg caccaccgcc     1620
acgtacctcg agggcaacat gctcatcacc agcgagagcg agacgcagcc ggtgaaccgc     1680
gtggcgtaca acgtcggcgg gcagatggcc accaacaacc agagctccac cactgccccc     1740
gcgaccggca cgtacaacct ccaggaaatc gtgcccggca gcgtgtggat ggagagggac     1800
gtgtacctcc aaggacccat ctgggccaag atcccagaga cggggcgca ctttcaccccc     1860 tctccggcca tgggcggatt cggactcaaa cacccaccgc ccatgatgct catcaagaac     1920
acgcctgtgc ccggaaatat caccagcttc tcggacgtgc ccgtcagcag cttcatcacc     1980
cagtacagca ccgggcaggt caccgtggag atggagtggg agctcaagaa ggaaaactcc     2040
aagaggtgga acccagagat ccagtacaca aacaactaca acgaccccca gtttgtggac     2100
tttgccccgg acagcaccgg ggaatacaga accaccagac ctatcggaac ccgatacctt     2160
acccgacccc tttaa                                                      2175
```

<210> SEQ ID NO 50
<211> LENGTH: 2178
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence based on AAV5: sequence 764
<220> FEATURE:
<221> NAME/KEY: misc_feature
<222> LOCATION: (1)..(3)
<223> OTHER INFORMATION: suboptimal translation initiation codon
<220> FEATURE:
<221> NAME/KEY: mutation
<222> LOCATION: (4)..(6)
<223> OTHER INFORMATION: insertion of triplet encoding alanine
<220> FEATURE:
<221> NAME/KEY: mutation
<222> LOCATION: (24)..(24)
<223> OTHER INFORMATION: point mutation to remove splice site
<220> FEATURE:
<221> NAME/KEY: mutation
<222> LOCATION: (27)..(27)
<223> OTHER INFORMATION: point mutation to remove splice site

<400> SEQUENCE: 50

```
ttggcttctt tgttgatca cccacccgat tggttggaag aagttggtga aggtcttcgc        60
gagttttgg gccttgaagc gggcccaccg aaaccaaaac ccaatcagca gcatcaagat       120
caagcccgtg gtcttgtgct gcctggttat aactatctcg gacccggaaa cggtctcgat       180
cgaggagagc ctgtcaacag gcagacgag gtcgcgcgag agcacgacat ctcgtacaac       240
gagcagcttg aggcgggaga caaccccctac ctcaagtaca accacgcgga cgccgagttt      300
caggagaagc tcgccgacga cacatccttc gggggaaacc tcggaaaggc agtctttcag      360
gccaagaaaa gggttctcga accttttggc ctggttgaag agggtgctaa gacggcccct      420
accggaaagc ggatagacga ccactttcca aaaagaaaga aggctcggac cgaagaggac      480
tccaagcctt ccacctcgtc agacgccgaa gctggaccca gcggatccca gcagctgcaa      540
atcccagccc aaccagcctc aagtttggga gctgatacaa tgtctgcggg aggtggcggc      600
ccattgggcg acaataacca aggtgccgat ggagtgggca atgcctcggg agattggcat      660
tgcgattcca cgtggatggg ggacagagtc gtcaccaagt ccacccgaac ctgggtgctg      720
cccagctaca acaaccacca gtaccgagag atcaaaagcg gctccgtcga cggaagcaac      780
gccaacgcct actttggata cagcaccccc tggggtact ttgactttaa ccgcttccac       840
agccactgga gcccccgaga ctggcaaaga ctcatcaaca actactgggg cttcagaccc      900
cggtccctca gagtcaaaat cttcaacatt caagtcaaag aggtcacggt gcaggactcc      960
accaccacca tcgccaacaa cctcacctcc accgtccaag tgtttacgga cgacgactac     1020
cagctgccct acgtcgtcgg caacgggacc gagggatgcc tgccggcctt ccctccgcag     1080
gtctttacgc tgccgcagta cggttacgcg acgctgaacc gcgacaacac agaaaatccc     1140
accgagagga gcagcttctt ctgcctagag tactttccca gcaagatgct gagaacgggc     1200
aacaactttg agtttaccta caactttgag gaggtgccct tccactccag cttcgctccc     1260
agtcagaacc tgttcaagct ggccaacccc ctggtggacc agtacttgta ccgcttcgtg     1320
agcacaaata cacactggcgg agtccagttc aacaagaacc tggccgggag atacgccaac     1380
acctacaaaa actggttccc ggggcccatg ggccgaaccc agggctggaa cctgggctcc     1440
ggggtcaacc gcgccagtgt cagcgccttc gccacgacca ataggatgga gctcgagggc     1500
gcgagttacc aggtgccccc gcagccgaac ggcatgacca caacctcca gggcagcaac    1560
acctatgccc tggagaacac tatgatcttc aacagccagc cggcgaaccc gggcaccacc    1620
gccacgtacc tcgagggcaa catgctcatc accagcgaga gcgagacgca gccggtgaac    1680
cgcgtggcgt acaacgtcgg cgggcagatg gccaccaaca accagagctc caccactgcc    1740
cccgcgaccg gcacgtacaa cctccaggaa atcgtgcccg gcagcgtgtg gatggagagg    1800
gacgtgtacc tccaaggacc catctgggcc aagatcccag agacggggc gcactttcac    1860
ccctctccgg ccatgggcgg attcggactc aaacacccac cgcccatgat gctcatcaag    1920
aacacgcctg tgcccggaaa tatcaccagc ttctcggacg tgcccgtcag cagcttcatc    1980
acccagtaca gcaccgggca ggtcaccgtg gagatggagt gggagctcaa gaaggaaaac    2040
tccaagaggt ggaacccaga gatccagtac acaaacaact acaacgaccc ccagtttgtg    2100
gactttgccc cggacagcac cggggaatac agaaccacca gacctatcgg aacccgatac    2160
cttacccgac ccctttaa                                                  2178
```

<210> SEQ ID NO 51
<211> LENGTH: 2178
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence based on AAV5: sequence 765
<220> FEATURE:
<221> NAME/KEY: misc_feature
<222> LOCATION: (1)..(3)
<223> OTHER INFORMATION: suboptimal translation initiation codon
<220> FEATURE:
<221> NAME/KEY: mutation
<222> LOCATION: (4)..(6)
<223> OTHER INFORMATION: insertion of triplet encoding alanine
<220> FEATURE:
<221> NAME/KEY: mutation
<222> LOCATION: (24)..(24)
<223> OTHER INFORMATION: point mutation to remove splice site
<220> FEATURE:
<221> NAME/KEY: mutation
<222> LOCATION: (27)..(27)
<223> OTHER INFORMATION: point mutation to remove splice site

<400> SEQUENCE: 51

```
ctggcttctt tgttgatca cccacccgat tggttggaag aagttggtga aggtcttcgc      60
gagttttttgg gccttgaagc gggcccaccg aaaccaaaac ccaatcagca gcatcaagat    120
caagcccgtg gtcttgtgct gcctggttat aactatctcg gacccggaaa cggtctcgat    180
cgaggagagc ctgtcaacag gcagacgag gtcgcgcgag agcacgacat ctcgtacaac     240
gagcagcttg aggcgggaga caaccccctac ctcaagtaca ccacgcgga cgccgagttt    300
caggagaagc tcgccgacga cacatccttc gggggaaacc tcggaaaggc agtcttttcag  360
gccaagaaaa gggttctcga accttttggc ctggttgaag agggtgctaa gacggcccct    420
accggaaagc ggatagacga ccactttcca aaaagaaaga aggctcggac cgaagaggac    480
tccaagcctt ccacctcgtc agacgccgaa gctggaccca gcggatccca gcagctgcaa    540
atcccagccc aaccagcctc aagtttggga gctgatacaa tgtctgcggg aggtggcggc    600
ccattgggcg acaataacca aggtgccgat ggagtgggca atgcctcggg agattggcat    660
tgcgattcca cgtggatggg ggacagagtc gtcaccaagt ccacccgaac ctgggtgctg    720
cccagctaca acaaccacca gtaccgagag atcaaaagcg gctccgtcga cggaagcaac    780
gccaacgcct actttggata cagcaccccc tggggggtact ttgactttaa ccgcttccac    840
agccactgga gcccccgaga ctggcaaaga ctcatcaaca actactgggg cttcagaccc    900
cggtccctca gagtcaaaat cttcaacatt caagtcaaag aggtcacggt gcaggactcc    960
accaccacca tcgccaacaa cctcacctcc accgtccaag tgtttacgga cgacgactac   1020
cagctgccct acgtcgtcgg caacgggacc gagggatgcc tgccggcctt ccctccgcag   1080
gtctttacgc tgccgcagta cggttacgcg acgctgaacc gcgacaacac agaaaatccc   1140
accgagagga gcagcttctt ctgcctagag tactttccca gcaagatgct gagaacgggc   1200
aacaactttg agtttaccta caactttgag gaggtgccct ccactccag cttcgctccc   1260
agtcagaacc tgttcaagct ggccaacccg ctggtggacc agtacttgta ccgcttcgtg   1320
agcacaaata cactggcgg agtccagttc aacaagaacc tggccgggag atacgccaac   1380
acctacaaaa actggttccc ggggcccatg ggccgaaccc agggctggaa cctgggctcc   1440
ggggtcaacc gcgccagtgt cagcgccttc gccacgacca ataggatgga gctcgagggc   1500
```

```
gcgagttacc aggtgccccc gcagccgaac ggcatgacca acaacctcca gggcagcaac    1560
acctatgccc tggagaacac tatgatcttc aacagccagc cggcgaaccc gggcaccacc    1620
gccacgtacc tcgagggcaa catgctcatc accagcgaga gcgagacgca gccggtgaac    1680
cgcgtggcgt acaacgtcgg cgggcagatg gccaccaaca accagagctc caccactgcc    1740
cccgcgaccg gcacgtacaa cctccaggaa atcgtgcccg gcagcgtgtg gatggagagg    1800
gacgtgtacc tccaaggacc catctgggcc aagatcccag agacggggc gcactttcac     1860 ccctctccgg ccatgggcgg attcggactc aaacacccac cgcccatgat gctcatcaag    1920
aacacgcctg tgcccggaaa tatcaccagc ttctcggacg tgcccgtcag cagcttcatc    1980
acccagtaca gcaccgggca ggtcaccgtg agatggagt gggagctcaa gaaggaaaac    2040
tccaagaggt ggaacccaga gatccagtac acaaacaact acaacgaccc ccagtttgtg    2100
gactttgccc cggacagcac cggggaatac agaaccacca gacctatcgg aacccgatac    2160
cttacccgac ccctttaa                                                  2178
```

<210> SEQ ID NO 52
<211> LENGTH: 2178
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sequence based on AAV5: sequence 766
<220> FEATURE:
<221> NAME/KEY: misc_feature
<222> LOCATION: (1)..(3)
<223> OTHER INFORMATION: suboptimal translation initiation codon
<220> FEATURE:
<221> NAME/KEY: mutation
<222> LOCATION: (4)..(6)
<223> OTHER INFORMATION: insertion of triplet encoding alanine
<220> FEATURE:
<221> NAME/KEY: mutation
<222> LOCATION: (24)..(24)
<223> OTHER INFORMATION: point mutation to remove splice site
<220> FEATURE:
<221> NAME/KEY: mutation
<222> LOCATION: (27)..(27)
<223> OTHER INFORMATION: point mutation to remove splice site

<400> SEQUENCE: 52

```
gtggcttctt ttgttgatca cccacccgat tggttggaag aagttggtga aggtcttcgc     60
gagttttggg gccttgaagc gggcccaccg aaaccaaaac ccaatcagca gcatcaagat    120
caagcccgtg gtcttgtgct gcctggttat aactatctcg gacccggaaa cggtctcgat    180
cgaggagagc ctgtcaacag ggcagacgag gtcgcgcgag agcacgacat ctcgtacaac    240
gagcagcttg aggcgggaga caaccccta ctcaagtaca ccacgcgga cgccgagttt     300 caggagaagc tcgccgacga cacatccttc ggggaaaacc tcggaaaggc agtctttcag    360
gccaagaaaa gggttctcga acctttggc ctggttgaag agggtgctaa gacggcccct    420
accggaaagc ggatagacga ccactttcca aaagaaaga aggctcggac cgaagaggac    480
tccaagcctt ccacctcgtc agacgccgaa gctggaccca gcggatccca gcagctgcaa    540
atcccagccc aaccagcctc aagtttggga gctgatacaa tgtctgcggg aggtggcggc    600
ccattgggcg acaataacca aggtgccgat ggagtgggca atgcctcggg agattggcat    660
tgcgattcca cgtggatggg ggacagagtc gtcaccaagt ccaccgaac ctgggtgctg    720 cccagctaca acaaccacca gtaccgagag atcaaaagcg gctccgtcga cggaagcaac    780
```

```
gccaacgcct actttggata cagcaccccc tggggtact ttgactttaa ccgcttccac      840
agccactgga gccccgaga ctggcaaaga ctcatcaaca actactgggg cttcagaccc      900
cggtccctca gagtcaaaat cttcaacatt caagtcaaag aggtcacggt gcaggactcc    960
accaccacca tcgccaacaa cctcacctcc accgtccaag tgtttacgga cgacgactac   1020
cagctgccct acgtcgtcgg caacgggacc gagggatgcc tgccggcctt ccctccgcag   1080
gtctttacgc tgccgcagta cggttacgcg acgctgaacc gcgacaacac agaaaatccc   1140
accgagagga gcagcttctt ctgcctagag tactttccca gcaagatgct gagaacgggc   1200
aacaactttg agtttaccta caactttgag gaggtgccct tccactccag cttcgctccc   1260
agtcagaacc tgttcaagct ggccaacccg ctggtggacc agtacttgta ccgcttcgtg   1320
agcacaaata acactggcgg agtccagttc aacaagaacc tggccgggag atacgccaac   1380
acctacaaaa actggttccc ggggcccatg ggccgaaccc agggctggaa cctgggctcc   1440
ggggtcaacc gcgccagtgt cagcgccttc gccacgacca ataggatgga gctcgagggc   1500
gcgagttacc aggtgccccc gcagccgaac ggcatgacca acaacctcca gggcagcaac   1560
acctatgccc tggagaacac tatgatcttc aacagccagc cggcgaaccc gggcaccacc   1620
gccacgtacc tcgagggcaa catgctcatc accagcgaga gcgagacgca gccggtgaac   1680
cgcgtggcgt acaacgtcgg cgggcagatg gccaccaaca accagagctc caccactgcc   1740
cccgcgaccg gcacgtacaa cctccaggaa atcgtgcccg gcagcgtgtg gatggagagg   1800
gacgtgtacc tccaaggacc catctgggcc aagatcccag agacgggggc gcactttcac   1860
ccctctccgg ccatgggcgg attcggactc aaacacccac cgcccatgat gctcatcaag   1920
aacacgcctg tgcccggaaa tatcaccagc ttctcggacg tgcccgtcag cagcttcatc   1980
acccagtaca gcaccgggca ggtcaccgtg gagatggagt gggagctcaa gaaggaaaac   2040
tccaagaggt ggaacccaga gatccagtac acaaacaact acaacgaccc ccagtttgtg   2100
gactttgccc cggacagcac cggggaatac agaaccacca gacctatcgg aacccgatac   2160
cttacccgac ccctttaa                                                 2178

<210> SEQ ID NO 53
<211> LENGTH: 250
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polH promoter long

<400> SEQUENCE: 53
tgtaatgaga cgcacaaact aatatcacaa actggaaatg tctatcaata tatagttgct      60
gatctatgca tcagctgcta gtactccgga atattaatag atcatggaga taattaaaat     120
gataaccatc tcgcaaataa ataagtattt tactgttttc gtaacagttt tgtaataaaa     180
aaacctataa atattccgga ttattcatac cgtcccacca tcgggcgcgg atcgtaccgg     240
gcccaagctt                                                            250

<210> SEQ ID NO 54
<211> LENGTH: 155
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: polH promoter short

<400> SEQUENCE: 54
tgtaatgaga cgcacaaact aatatcacaa actggaaatg tctatcaata tatagttgct    60
gatatcatgg agataattaa aatgataacc atctcgcaaa taaataagta ttttactgtt   120
ttcgtaacag ttttgtaata aaaaaaccta taaat                              155

<210> SEQ ID NO 55
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: primer

<400> SEQUENCE: 55
aatgggcggt aggcgtgta                                                 19

<210> SEQ ID NO 56
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: primer

<400> SEQUENCE: 56
aggcgatctg acggttcact aa                                             22

<210> SEQ ID NO 57
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: probe

<400> SEQUENCE: 57
tgggaggtct atataagcag                                                20

<210> SEQ ID NO 58
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: primer

<400> SEQUENCE: 58
caagtatggc atctacacca aagtct                                         26

<210> SEQ ID NO 59
<211> LENGTH: 25
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: primer

<400> SEQUENCE: 59
gcaatagcat cacaaatttc acaaa                                           25

<210> SEQ ID NO 60
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: probe

<400> SEQUENCE: 60
tgtgaactgg atcaaggaga agaccaagc                                       29

<210> SEQ ID NO 61
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence
<220> FEATURE:
<221> NAME/KEY: CDS
<222> LOCATION: (1)..(27)

<400> SEQUENCE: 61 tct ttt gtt gat cac cct cca gat tgg t                                 28
Ser Phe Val Asp His Pro Pro Asp Trp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Ser Phe Val Asp His Pro Pro Asp Trp
1               5

<210> SEQ ID NO 63
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence with splice
      sites removed
<220> FEATURE:
<221> NAME/KEY: CDS
<222> LOCATION: (1)..(27)

<400> SEQUENCE: 63 tct ttt gtt gat cac cca ccc gat tgg t                                 28
Ser Phe Val Asp His Pro Pro Asp Trp
1               5

<210> SEQ ID NO 64
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 64

Ser Phe Val Asp His Pro Pro Asp Trp
1               5

<210> SEQ ID NO 65
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence with splice
      sites removed and alanine substitution

<400> SEQUENCE: 65
gcttttgttg atcacccacc cgattggt                                              28

<210> SEQ ID NO 66
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence with splice
      sites removed and threonine substitution

<400> SEQUENCE: 66
acttttgttg atcacccacc cgattggt                                              28

<210> SEQ ID NO 67
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence with splice
      sites removed and point mutations at positions 4-6

<400> SEQUENCE: 67
agctttgttg atcacccacc cgattggt                                              28

<210> SEQ ID NO 68
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' part of AAV5 capsid sequence with splice
      sites removed and point mutations at positions 4 and 5

<400> SEQUENCE: 68
agttttgttg atcacccacc cgattggt                                              28

<210> SEQ ID NO 69
<211> LENGTH: 2187
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: artificial sequence based on AAV5
<220> FEATURE:
<221> NAME/KEY: misc_feature
<222> LOCATION: (1)..(9)
<223> OTHER INFORMATION: VP2 initiator context
<220> FEATURE:
<221> NAME/KEY: misc_feature
<222> LOCATION: (10)..(12)
<223> OTHER INFORMATION: suboptimal translation initiation codon
<220> FEATURE:
<221> NAME/KEY: misc_feature
<222> LOCATION: (13)..(15)
<223> OTHER INFORMATION: additional triplet added to sequence
<220> FEATURE:
<221> NAME/KEY: mutation
<222> LOCATION: (33)..(33)
<223> OTHER INFORMATION: remove splice site
<220> FEATURE:
<221> NAME/KEY: mutation
<222> LOCATION: (36)..(36)
<223> OTHER INFORMATION: remove splice site

<400> SEQUENCE: 69
cctgttaagc tggcttcttt tgttgatcac ccacccgatt ggttggaaga agttggtgaa      60
ggtcttcgcg agtttttggg ccttgaagcg ggcccaccga aaccaaaacc caatcagcag     120
catcaagatc aagcccgtgg tcttgtgctg cctggttata actatctcgg acccggaaac     180
ggtctcgatc gaggagagcc tgtcaacagg gcagacgagg tcgcgcgaga gcacgacatc     240
tcgtacaacg agcagcttga ggcgggagac aaccctacc tcaagtacaa ccacgcggac     300
gccgagtttc aggagaagct cgccgacgac acatccttcg ggggaaacct cggaaaggca     360
gtctttcagg ccaagaaaag ggttctcgaa ccttttggcc tggttgaaga gggtgctaag     420
acggccccta ccggaaagcg gatagacgac cactttccaa aaagaaagaa ggctcggacc     480
gaagaggact ccaagccttc cacctcgtca gacgccgaag ctggaccag cggatcccag     540 cagctgcaaa tcccagccca accagcctca gtttgggag ctgatacaat gtctgcggga     600
ggtggcggcc cattgggcga caataaccaa ggtgccgatg gagtgggcaa tgcctcggga     660
gattggcatt gcgattccac gtggatgggg gacagagtcg tcaccaagtc cacccgaacc     720
tgggtgctgc ccagctacaa caaccaccag taccgagaga tcaaaagcgg ctccgtcgac     780
ggaagcaacg ccaacgccta ctttggatac agcaccccct gggggtactt tgactttaac     840
cgcttccaca gccactggag cccccgagac tggcaaagac tcatcaacaa ctactggggc     900
ttcagacccc ggtccctcag agtcaaaatc ttcaacattc aagtcaaaga ggtcacggtg     960
caggactcca ccaccaccat cgccaacaac ctcacctcca ccgtccaagt gtttacggac    1020
gacgactacc agctgcccta cgtcgtcggc aacgggaccg agggatgcct gccggccttc    1080
cctccgcagg tctttacgct gccgcagtac ggttacgcga cgctgaaccg cgacaacaca    1140
gaaaatccca ccgagaggag cagcttcttc tgcctagagt actttccag caagatgctg    1200 agaacgggca caactttga gtttaccta aactttgagg aggtgccctt ccactccagc    1260
ttcgctccca gtcagaacct cttcaagctg ccaacccgc tggtgaccg gtacttgtac    1320 cgcttcgtga gcacaaataa cactggcgga gtccagttca caagaacct ggccgggaga    1380 tacgccaaca cctacaaaaa ctggttcccg gggcccatgg gccgaaccca gggctggaac    1440
ctgggctccg ggtcaaccg cgccagtgtc agcgccttcg ccacgaccaa taggatggag    1500
ctcgagggcg cgagttacca ggtgccccg cagccgaacg gcatgaccaa caacctccag    1560
```

```
ggcagcaaca cctatgccct ggagaacact atgatcttca acagccagcc ggcgaacccg      1620
ggcaccaccg ccacgtacct cgagggcaac atgctcatca ccagcgagag cgagacgcag      1680
ccggtgaacc gcgtggcgta caacgtcggc gggcagatgg ccaccaacaa ccagagctcc      1740
accactgccc ccgcgaccgg cacgtacaac ctccaggaaa tcgtgcccgg cagcgtgtgg      1800
atggagaggg acgtgtacct ccaaggaccc atctgggcca agatcccaga cggggggcg       1860 cactttcacc cctctccggc catgggcgga ttcggactca acacccacc gcccatgatg       1920 ctcatcaaga acacgcctgt gcccggaaat atcaccagct tctcggacgt gcccgtcagc      1980
agcttcatca cccagtacag cacccgggcag gtcaccgtgg agatggagtg ggagctcaag     2040
aaggaaaact ccaagaggtg gaacccagag atccagtaca caaacaacta caacgacccc     2100
cagtttgtgg actttgcccc ggacagcacc ggggaataca aaccaccag acctatcgga      2160 acccgatacc ttacccgacc cctttaa                                         2187

<210> SEQ ID NO 70
<211> LENGTH: 4382
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus 9
<220> FEATURE:
<221> NAME/KEY: CDS
<222> LOCATION: (2116)..(4326)
<223> OTHER INFORMATION: coding sequence for VP1
<220> FEATURE:
<221> NAME/KEY: misc_feature
<222> LOCATION: (2527)..(4326)
<223> OTHER INFORMATION: coding sequence for VP2
<220> FEATURE:
<221> NAME/KEY: misc_feature
<222> LOCATION: (2722)..(4326)
<223> OTHER INFORMATION: coding sequence for VP3

<400> SEQUENCE: 70
cagagaggga gtggccaact ccatcactag gggtaatcgc gaagcgcctc ccacgctgcc       60
gcgtcagcgc tgacgtagat tacgtcatag gggagtggtc ctgtattagc tgtcacgtga      120
gtgcttttgc gacattttgc gacaccacat ggccatttga ggtatatatg gccgagtgag      180
cgagcaggat ctccattttg accgcgaaat ttgaacgagc agcagccatg ccgggcttct      240
acgagattgt gatcaaggtg ccgagcgacc tggacgagca cctgccgggc atttctgact      300
cttttgtgaa ctgggtggcc gagaaggaat gggagctgcc cccggattct gacatggatc      360
ggaatctgat cgagcaggca cccctgaccg tggccgagaa gctgtagcgc gacttcctgg      420
tccaatggcg ccgcgtgagt aaggccccgg aggccctctt ctttgttcag ttcgagaagg      480
gcgagagcta ctttcacctg cacgttctgg tcgagaccac gggggtcaag tccatggtgc      540
taggccgctt cctgagtcag attcgggaga agctggtcca gaccatctac cgcgggatcg      600 agccgacct gcccaactgg ttcgcggtga ccaagacgcg taatgcgcc ggcggggga       660 acaaggtggt ggacgagtgc tacatcccca actacctcct gcccaagact cagcccgagc      720
tgcagtgggc gtggactaac atggaggagt atataagcgc gtgcttgaac ctggccgagc      780
gcaaacggct cgtggcgcag cacctgaccc acgtcagcca gacgcaggag cagaacaagg      840
agaatctgaa ccccaattct gacgcgcccg tgatcaggtc aaaaaccttcc gcgcgctaca     900 tggagctggt cgggtggctg gtggaccggg gcatcacctc cgagaagcag tggatccagg      960
```

```
aggaccaggc ctcgtacatc tccttcaacg ccgcctccaa ctcgcggtcc cagatcaagg      1020
ccgcgctgga caatgccggc aagatcatgg cgctgaccaa atccgcgccc gactacctgg      1080
taggcccttc acttccggtg acattacgc agaaccgcat ctaccgcatc ctgcagctca       1140
acggctacga ccctgcctac gccggctccg tctttctcgg ctgggcacaa aagaagttcg      1200
ggaaacgcaa caccatctgg ctgtttgggc cggccaccac gggaaagacc aacatcgcag      1260
aagccattgc ccacgccgtg cccttctacg gctgcgtcaa ctggaccaat gagaactttc      1320
ccttcaacga ttgcgtcgac aagatggtga tctggtggga ggagggcaag atgacggcca      1380
aggtcgtgga gtccgccaag gccattctcg cggcagcaa ggtgcgcgtg gaccaaaagt       1440
gcaagtcgtc cgcccagatc gaccccactc ccgtgatcgt cacctccaac accaacatgt      1500
gcgccgtgat tgacgggaac agcaccacct tcgagcacca gcagcctctc caggaccgga      1560
tgtttaagtt cgaactcacc cgccgtctgg agcacgactt tggcaaggtg acaaagcagg      1620
aagtcaaaga gttcttccgc tgggccagtg atcacgtgac cgaggtggcg catgagtttt      1680
acgtcagaaa gggcggagcc agcaaaagac ccgcccccga tgacgcggat aaaagcgagc      1740
ccaagcgggc ctgcccctca gtcgcggatc catcgacgtc agacgcggaa ggagctccgg      1800
tggactttgc cgacaggtac caaaacaaat gttctcgtca cgcgggcatg cttcagatgc      1860
tgcttccctg caaacgtgc gagagaatga atcagaattt caacatttgc ttcacacacg       1920
gggtcagaga ctgctcagag tgtttccccg gcgtgtcaga atctcaaccg gtcgtcagaa      1980
agaggacgta tcggaaactc tgtgcgattc atcatctgct ggggcgggct cccgagattg      2040
cttgctcggc ctgcgatctg gtcaacgtgg acctggatga ctgtgtttct gagcaataaa      2100
tgacttaaac caggt atg gct gcc gat ggt tat ctt cca gat tgg ctc gag      2151
              Met Ala Ala Asp Gly Tyr Leu Pro Asp Trp Leu Glu
                1               5                   10 gac aac ctc tct gag ggc att cgc gag tgg tgg gac ctg aaa cct gga       2199
Asp Asn Leu Ser Glu Gly Ile Arg Glu Trp Trp Asp Leu Lys Pro Gly
         15                  20                  25 gcc ccg aaa ccc aaa gcc aac cag caa aag cag gac gac ggc cgg ggt       2247
Ala Pro Lys Pro Lys Ala Asn Gln Gln Lys Gln Asp Asp Gly Arg Gly
 30                  35                  40 ctg gtg ctt cct ggc tac aag tac ctc gga ccc ttc aac gga ctc gac       2295
Leu Val Leu Pro Gly Tyr Lys Tyr Leu Gly Pro Phe Asn Gly Leu Asp
45                  50                  55                  60 aag ggg gag ccc gtc aac gcg gcg gac gca gcg gcc ctc gag cac gac       2343
Lys Gly Glu Pro Val Asn Ala Ala Asp Ala Ala Ala Leu Glu His Asp
                 65                  70                  75 aag gcc tac gac cag cag ctc aaa gcg ggt gac aat ccg tac ctg cgg       2391
Lys Ala Tyr Asp Gln Gln Leu Lys Ala Gly Asp Asn Pro Tyr Leu Arg
             80                  85                  90 tat aac cac gcc gac gcc gag ttt cag gag cgt ctg caa gaa gat acg       2439
Tyr Asn His Ala Asp Ala Glu Phe Gln Glu Arg Leu Gln Glu Asp Thr
         95                  100                 105 tct ttt ggg ggc aac ctc ggg cga gca gtc ttc cag gcc aag aag cgg       2487
Ser Phe Gly Gly Asn Leu Gly Arg Ala Val Phe Gln Ala Lys Lys Arg
    110                 115                 120 gtt ctc gaa cct ctc ggt ctg gtt gag gaa ggc gct aag acg gct cct       2535
Val Leu Glu Pro Leu Gly Leu Val Glu Glu Gly Ala Lys Thr Ala Pro
125                 130                 135                 140 gga aag aag aga ccg gta gag cag tca ccc caa gaa cca gac tca tcc       2583
Gly Lys Lys Arg Pro Val Glu Gln Ser Pro Gln Glu Pro Asp Ser Ser
                145                 150                 155
```

-continued

| | | |
|---|---|---|
| tcg ggc atc ggc aaa tca ggc cag cag ccc gct aaa aag aga ctc aat<br>Ser Gly Ile Gly Lys Ser Gly Gln Gln Pro Ala Lys Lys Arg Leu Asn<br>160                        165                       170 | 2631 |
| ttt ggt cag act ggc gac tca gag tca gtc ccc gac cca caa cct ctc<br>Phe Gly Gln Thr Gly Asp Ser Glu Ser Val Pro Asp Pro Gln Pro Leu<br>175                       180                       185 | 2679 |
| gga gaa cct cca gaa gcc ccc tca ggt ctg gga cct aat aca atg gct<br>Gly Glu Pro Pro Glu Ala Pro Ser Gly Leu Gly Pro Asn Thr Met Ala<br>190                       195                       200 | 2727 |
| tca ggc ggt ggc gct cca atg gca gac aat aac gaa ggc gcc gac gga<br>Ser Gly Gly Gly Ala Pro Met Ala Asp Asn Asn Glu Gly Ala Asp Gly<br>205                       210                       215                       220 | 2775 |
| gtg ggt aat tcc tcg gga aat tgg cat tgc gat tcc aca tgg ctg ggg<br>Val Gly Asn Ser Ser Gly Asn Trp His Cys Asp Ser Thr Trp Leu Gly<br>225                       230                       235 | 2823 |
| gac aga gtc atc acc acc agc acc cga acc tgg gca ttg ccc acc tac<br>Asp Arg Val Ile Thr Thr Ser Thr Arg Thr Trp Ala Leu Pro Thr Tyr<br>240                       245                       250 | 2871 |
| aac aac cac ctc tac aag caa atc tcc aat gga aca tcg gga gga agc<br>Asn Asn His Leu Tyr Lys Gln Ile Ser Asn Gly Thr Ser Gly Gly Ser<br>255                       260                       265 | 2919 |
| acc aac gac aac acc tac ttt ggc tac agc acc ccc tgg ggg tat ttt<br>Thr Asn Asp Asn Thr Tyr Phe Gly Tyr Ser Thr Pro Trp Gly Tyr Phe<br>270                       275                       280 | 2967 |
| gac ttc aac aga ttc cac tgc cac ttc tca cca cgt gac tgg cag cga<br>Asp Phe Asn Arg Phe His Cys His Phe Ser Pro Arg Asp Trp Gln Arg<br>285                       290                       295                       300 | 3015 |
| ctc atc aac aac aac tgg gga ttc cgg cca aag aga ctc aac ttc aag<br>Leu Ile Asn Asn Asn Trp Gly Phe Arg Pro Lys Arg Leu Asn Phe Lys<br>305                       310                       315 | 3063 |
| ctg ttc aac atc cag gtc aag gag gtt acg acg aac gaa ggc acc aag<br>Leu Phe Asn Ile Gln Val Lys Glu Val Thr Thr Asn Glu Gly Thr Lys<br>320                       325                       330 | 3111 |
| acc atc gcc aat aac ctt acc agc acc gtc cag gtc ttt acg gac tcg<br>Thr Ile Ala Asn Asn Leu Thr Ser Thr Val Gln Val Phe Thr Asp Ser<br>335                       340                       345 | 3159 |
| gag tac cag cta ccg tac gtc cta ggc tct gcc cac caa gga tgc ctg<br>Glu Tyr Gln Leu Pro Tyr Val Leu Gly Ser Ala His Gln Gly Cys Leu<br>350                       355                       360 | 3207 |
| cca ccg ttt cct gca gac gtc ttc atg gtt cct cag tac ggc tac ctg<br>Pro Pro Phe Pro Ala Asp Val Phe Met Val Pro Gln Tyr Gly Tyr Leu<br>365                       370                       375                       380 | 3255 |
| acg ctc aac aat gga agt caa gcg tta gga cgt tct tct ttc tac tgt<br>Thr Leu Asn Asn Gly Ser Gln Ala Leu Gly Arg Ser Ser Phe Tyr Cys<br>385                       390                       395 | 3303 |
| ctg gaa tac ttc cct tct cag atg ctg aga acc ggc aac aac ttt cag<br>Leu Glu Tyr Phe Pro Ser Gln Met Leu Arg Thr Gly Asn Asn Phe Gln<br>400                       405                       410 | 3351 |
| ttc agc tac act ttc gag gac gtg cct ttc cac agc agc tac gca cac<br>Phe Ser Tyr Thr Phe Glu Asp Val Pro Phe His Ser Ser Tyr Ala His<br>415                       420                       425 | 3399 |
| agc cag agt cta gat cga ctg atg aac ccc ctc atc gac cag tac cta<br>Ser Gln Ser Leu Asp Arg Leu Met Asn Pro Leu Ile Asp Gln Tyr Leu<br>430                       435                       440 | 3447 |
| tac tac ctg gtc aga aca cag aca act gga act ggg gga act caa act<br>Tyr Tyr Leu Val Arg Thr Gln Thr Thr Gly Thr Gly Gly Thr Gln Thr<br>445                       450                       455                       460 | 3495 |
| ttg gca ttc agc caa gca ggc cct agc tca atg gcc aat cag gct aga<br>Leu Ala Phe Ser Gln Ala Gly Pro Ser Ser Met Ala Asn Gln Ala Arg<br>465                       470                       475 | 3543 |

```
aac tgg gta ccc ggg cct tgc tac cgt cag cag cgc gtc tcc aca acc      3591
Asn Trp Val Pro Gly Pro Cys Tyr Arg Gln Gln Arg Val Ser Thr Thr
            480                 485                 490 acc aac caa aat aac aac agc aac ttt gcg tgg acg gga gct gct aaa      3639
Thr Asn Gln Asn Asn Asn Ser Asn Phe Ala Trp Thr Gly Ala Ala Lys
            495                 500                 505 ttc aag ctg aac ggg aga gac tcg cta atg aat cct ggc gtg gct atg      3687
Phe Lys Leu Asn Gly Arg Asp Ser Leu Met Asn Pro Gly Val Ala Met
510                 515                 520 gca tcg cac aaa gac gac gag gac cgc ttc ttt cca tca agt ggc gtt      3735
Ala Ser His Lys Asp Asp Glu Asp Arg Phe Phe Pro Ser Ser Gly Val
525                 530                 535                 540 ctc ata ttt ggc aag caa gga gcc ggg aac gat gga gtc gac tac agc      3783
Leu Ile Phe Gly Lys Gln Gly Ala Gly Asn Asp Gly Val Asp Tyr Ser
            545                 550                 555 cag gtg ctg att aca gat gag gaa gaa att aaa gcc acc aac cct gta      3831
Gln Val Leu Ile Thr Asp Glu Glu Glu Ile Lys Ala Thr Asn Pro Val
            560                 565                 570 gcc aca gag gaa tac gga gca gtg gcc atc aac aac cag gcc gct aac      3879
Ala Thr Glu Glu Tyr Gly Ala Val Ala Ile Asn Asn Gln Ala Ala Asn
            575                 580                 585 acg cag gcg caa act gga ctt gtg cat aac cag gga gtt att cct ggt      3927
Thr Gln Ala Gln Thr Gly Leu Val His Asn Gln Gly Val Ile Pro Gly
590                 595                 600 atg gtc tgg cag aac cgg gac gtg tac ctg cag ggc cct att tgg gct      3975
Met Val Trp Gln Asn Arg Asp Val Tyr Leu Gln Gly Pro Ile Trp Ala
605                 610                 615                 620 aaa ata cct cac aca gat ggc aac ttt cac ccg tct cct ctg atg ggt      4023
Lys Ile Pro His Thr Asp Gly Asn Phe His Pro Ser Pro Leu Met Gly
            625                 630                 635 gga ttt gga ctg aaa cac cca cct cca cag att cta att aaa aat aca      4071
Gly Phe Gly Leu Lys His Pro Pro Pro Gln Ile Leu Ile Lys Asn Thr
            640                 645                 650 cca gtg ccg gca gat cct cct ctt acc ttc aat caa gcc aag ctg aac      4119
Pro Val Pro Ala Asp Pro Pro Leu Thr Phe Asn Gln Ala Lys Leu Asn
            655                 660                 665 tct ttc atc acg cag tac agc acg gga caa gtc agc gtg gaa atc gag      4167
Ser Phe Ile Thr Gln Tyr Ser Thr Gly Gln Val Ser Val Glu Ile Glu
670                 675                 680 tgg gag ctg cag aaa gaa aac agc aag cgc tgg aat cca gag atc cag      4215
Trp Glu Leu Gln Lys Glu Asn Ser Lys Arg Trp Asn Pro Glu Ile Gln
685                 690                 695                 700 tat act tca aac tac tac aaa tct aca aat gtg gac ttt gct gtc aat      4263
Tyr Thr Ser Asn Tyr Tyr Lys Ser Thr Asn Val Asp Phe Ala Val Asn
            705                 710                 715 acc gaa ggt gtt tac tct gag cct cgc ccc att ggt act cgt tac ctc      4311
Thr Glu Gly Val Tyr Ser Glu Pro Arg Pro Ile Gly Thr Arg Tyr Leu
            720                 725                 730 acc cgt aat ttg taa ttgcctgtta atcaataaac cggttaattc gtttcagttg      4366
Thr Arg Asn Leu
            735 aactttggtc tctgcg                                                    4382

<210> SEQ ID NO 71
<211> LENGTH: 736
<212> TYPE: PRT
<213> ORGANISM: Artificial Sequence
<220> FEATURE:
<223> OTHER INFORMATION: Synthetic Construct
```

<400> SEQUENCE: 71

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415
```

```
Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Thr Gln Thr Leu Ala Phe Ser
450                     455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Glu Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 72
<211> LENGTH: 2211
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: adeno-associated virus AAV9
<220> FEATURE:
<221> NAME/KEY: CDS
<222> LOCATION: (1)..(2211)
<223> OTHER INFORMATION: coding sequence for VP1
<220> FEATURE:
<221> NAME/KEY: misc_feature
<222> LOCATION: (412)..(2211)
<223> OTHER INFORMATION: coding sequence for VP2
```

```
<220> FEATURE:
<221> NAME/KEY: misc_feature
<222> LOCATION: (607)..(2211)
<223> OTHER INFORMATION: coding sequence for VP3

<400> SEQUENCE: 72 atg gct gcc gat ggt tat ctt cca gat tgg ctc gag gac aac ctt agt      48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc     336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct     384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg     432
Leu Gly Leu Val Glu Glu Ala Ala Lys Thr Ala Pro Gly Lys Lys Arg
    130                 135                 140 cct gta gag cag tct cct cag gaa ccg gac tcc tcc gcg ggt att ggc     480
Pro Val Glu Gln Ser Pro Gln Glu Pro Asp Ser Ser Ala Gly Ile Gly
145                 150                 155                 160 aaa tcg ggt gca cag ccc gct aaa aag aga ctc aat ttc ggt cag act     528
Lys Ser Gly Ala Gln Pro Ala Lys Lys Arg Leu Asn Phe Gly Gln Thr
                165                 170                 175 ggc gac aca gag tca gtc cca gac cct caa cca atc gga gaa cct ccc     576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc     624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc     672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc     720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc     768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac     816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga     864
Ala Tyr Phe Gly Tyr Ser Thr Pro Trp Gly Tyr Phe Asp Phe Asn Arg
        275                 280                 285
```

| | | |
|---|---|---|
| ttc cac tgc cac ttc tca cca cgt gac tgg cag cga ctc atc aac aac<br>Phe His Cys His Phe Ser Pro Arg Asp Trp Gln Arg Leu Ile Asn Asn<br>290                            295                        300 | | 912 |
| aac tgg gga ttc cgg cct aag cga ctc aac ttc aag ctc ttc aac att<br>Asn Trp Gly Phe Arg Pro Lys Arg Leu Asn Phe Lys Leu Phe Asn Ile<br>305                            310                        315                  320 | | 960 |
| cag gtc aaa gag gtt acg gac aac aat gga gtc aag acc atc gcc aat<br>Gln Val Lys Glu Val Thr Asp Asn Asn Gly Val Lys Thr Ile Ala Asn<br>                        325                        330                        335 | | 1008 |
| aac ctt acc agc acg gtc cag gtc ttc acg gac tca gac tat cag ctc<br>Asn Leu Thr Ser Thr Val Gln Val Phe Thr Asp Ser Asp Tyr Gln Leu<br>                        340                        345                        350 | | 1056 |
| ccg tac gtg ctc ggg tcg gct cac gag ggc tgc ctc ccg ccg ttc cca<br>Pro Tyr Val Leu Gly Ser Ala His Glu Gly Cys Leu Pro Pro Phe Pro<br>                    355                        360                        365 | | 1104 |
| gcg gac gtt ttc atg att cct cag tac ggg tat ctg acg ctt aat gat<br>Ala Asp Val Phe Met Ile Pro Gln Tyr Gly Tyr Leu Thr Leu Asn Asp<br>370                            375                        380 | | 1152 |
| gga agc cag gcc gtg ggt cgt tcc ttt tac tgc ctg gaa tat ttc<br>Gly Ser Gln Ala Val Gly Arg Ser Ser Phe Tyr Cys Leu Glu Tyr Phe<br>385                            390                        395                  400 | | 1200 |
| ccg tcg caa atg cta aga acg ggt aac aac ttc cag ttc agc tac gag<br>Pro Ser Gln Met Leu Arg Thr Gly Asn Asn Phe Gln Phe Ser Tyr Glu<br>                    405                        410                        415 | | 1248 |
| ttt gag aac gta cct ttc cat agc agc tac gct cac agc caa agc ctg<br>Phe Glu Asn Val Pro Phe His Ser Ser Tyr Ala His Ser Gln Ser Leu<br>                    420                        425                        430 | | 1296 |
| gac cga cta atg aat cca ctc atc gac caa tac ttg tac tat ctc tca<br>Asp Arg Leu Met Asn Pro Leu Ile Asp Gln Tyr Leu Tyr Tyr Leu Ser<br>                        435                        440                        445 | | 1344 |
| aag act att aac ggt tct gga cag aat caa caa acg cta aaa ttc agt<br>Lys Thr Ile Asn Gly Ser Gly Gln Asn Gln Gln Thr Leu Lys Phe Ser<br>450                            455                        460 | | 1392 |
| gtg gcc gga ccc agc aac atg gct gtc cag gga aga aac tac ata cct<br>Val Ala Gly Pro Ser Asn Met Ala Val Gln Gly Arg Asn Tyr Ile Pro<br>465                            470                        475                  480 | | 1440 |
| gga ccc agc tac cga caa caa cgt gtc tca acc act gtg act caa aac<br>Gly Pro Ser Tyr Arg Gln Gln Arg Val Ser Thr Thr Val Thr Gln Asn<br>                    485                        490                        495 | | 1488 |
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>                    500                        505                        510 | | 1536 |
| gga cgt aat agc ttg atg aat cct gga cct gct atg gcc agc cac aaa<br>Gly Arg Asn Ser Leu Met Asn Pro Gly Pro Ala Met Ala Ser His Lys<br>                    515                        520                        525 | | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>                  530                        535                        540 | | 1632 |
| aaa caa gga act gga aga gac aac gtg gat gcg gac aaa gtc atg ata<br>Lys Gln Gly Thr Gly Arg Asp Asn Val Asp Ala Asp Lys Val Met Ile<br>545                            550                        555                  560 | | 1680 |
| acc aac gaa gaa gaa att aaa act act aac ccg gta gca acg gag tcc<br>Thr Asn Glu Glu Glu Ile Lys Thr Thr Asn Pro Val Ala Thr Glu Ser<br>                        565                        570                        575 | | 1728 |
| tat gga caa gtg gcc aca aac cac cag agt gcc caa gca cag gcg cag<br>Tyr Gly Gln Val Ala Thr Asn His Gln Ser Ala Gln Ala Gln Ala Gln<br>                    580                        585                        590 | | 1776 |
| acc ggc tgg gtt caa aac caa gga ata ctt ccg ggt atg gtt tgg cag<br>Thr Gly Trp Val Gln Asn Gln Gly Ile Leu Pro Gly Met Val Trp Gln<br>                    595                        600                        605 | | 1824 |

```
gac aga gat gtg tac ctg caa gga ccc att tgg gcc aaa att cct cac     1872
Asp Arg Asp Val Tyr Leu Gln Gly Pro Ile Trp Ala Lys Ile Pro His
    610                 615                 620 acg gac ggc aac ttt cac cct tct ccg ctg atg gga ggg ttt gga atg     1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg     1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc     2016
Asp Pro Pro Thr Ala Phe Asn Lys Asp Lys Leu Asn Ser Phe Ile Thr
            660                 665                 670 cag tat tct act ggc caa gtc agc gtg gag atc gag tgg gag ctg cag     2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac     2112
Lys Glu Asn Ser Lys Arg Trp Asn Pro Glu Ile Gln Tyr Thr Ser Asn
    690                 695                 700 tat tac aag tct aat aat gtt gaa ttt gct gtt aat act gaa ggt gta     2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg     2208
Tyr Ser Glu Pro Arg Pro Ile Gly Thr Arg Tyr Leu Thr Arg Asn Leu
                725                 730                 735 taa                                                                 2211

<210> SEQ ID NO 73
<211> LENGTH: 736
<212> TYPE: PRT
<213> ORGANISM: Artificial Sequence
<220> FEATURE:
<223> OTHER INFORMATION: Synthetic Construct

<400> SEQUENCE: 73

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
```

```
            180                 185                 190
Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605
```

```
Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```